US012662705B2

(12) United States Patent
Minn

(10) Patent No.: US 12,662,705 B2
(45) Date of Patent: Jun. 23, 2026

(54) INTERFERON PATHWAY GENES REGULATE AND PREDICT EFFICACY OF IMMUNOTHERAPY

(71) Applicant: THE TRUSTEES OF THE UNIVERSITY OF PENNSYLVANIA, Philadelphia, PA (US)

(72) Inventor: Andy J. Minn, Philadelphia, PA (US)

(73) Assignee: The Trustees of the University of Pennsylvania

( * ) Notice: Subject to any disclaimer, the term of this patent is extended or adjusted under 35 U.S.C. 154(b) by 1171 days.

(21) Appl. No.: 17/274,426

(22) PCT Filed: Sep. 13, 2019

(86) PCT No.: PCT/US2019/051137
§ 371 (c)(1),
(2) Date: Mar. 8, 2021

(87) PCT Pub. No.: WO2020/056346
PCT Pub. Date: Mar. 19, 2020

(65) Prior Publication Data
US 2021/0269886 A1      Sep. 2, 2021

Related U.S. Application Data

(60) Provisional application No. 62/884,073, filed on Aug. 7, 2019, provisional application No. 62/730,844, filed on Sep. 13, 2018.

(51) Int. Cl.
| | |
|---|---|
| *C12Q 1/6886* | (2018.01) |
| *A61K 40/11* | (2025.01) |
| *A61K 40/31* | (2025.01) |
| *A61K 40/42* | (2025.01) |
| *G01N 33/575* | (2026.01) |

(52) U.S. Cl.
CPC ........... *C12Q 1/6886* (2013.01); *A61K 40/11* (2025.01); *A61K 40/4211* (2025.01); *G01N 33/5758* (2026.01); *G01N 33/57595* (2026.01); *A61K 40/31* (2025.01); *A61K 2239/31* (2023.05); *A61K 2239/38* (2023.05); *A61K 2239/57* (2023.05); *C12Q 2600/106* (2013.01); *C12Q 2600/156* (2013.01); *C12Q 2600/158* (2013.01); *G01N 2800/52* (2013.01)

(58) Field of Classification Search
CPC ............ C12Q 1/6886; C12Q 2600/106; C12Q 2600/156; C12Q 2600/158; A61K 39/4611; A61K 39/4631; A61K 39/464412; A61K 2239/31; A61K 2239/38; A61K 2239/48; A61K 40/11; A61K 40/31; A61K 40/4211; A61K 2239/57; G01N 33/5758; G01N 33/57595; G01N 2800/52
See application file for complete search history.

(56) References Cited

U.S. PATENT DOCUMENTS

| | | | |
|---|---|---|---|
| 7,892,740 B2 * | 2/2011 | Weichselbaum ..... | C12Q 1/6886 435/6.14 |
| 2017/0268001 A1 | 9/2017 | Khodarev | |
| 2018/0051347 A1 | 2/2018 | Ribas | |

OTHER PUBLICATIONS

Vareki et al. (2017) Critical Reviews in Oncology/Hematology 116: 116-124. (Year: 2017).*
Hellmann et al. (2018) Cancer Cell 33(5): 843-852. (Year: 2018).*
Liberzon (Cell Systems (2015) 1: 417-425) (Year: 2015).*
Taube (Clinical Cancer Research (2015) 21(17): 3969-3976) (Year: 2015).*
Garg (Oncoimmunology (2016) 5(2): e1069938) (Year: 2016).*
Gao (Cell (2016) 167(2): P397-404.E9) (Year: 2016).*
Ayers (The Journal of Clinical Investigation (2017) 127(8): 2930-2940) (Year: 2017).*
Dagogo-Jack (Nature Reviews Clinical Oncology (2017) 15: 81-94) (Year: 2017).*
Ji (Frontiers in Immunology (2021) 12: 729359) (Year: 2021).*
Wolchok (New England Journal of Medicine (2017) 377: 1345-1356) (Year: 2017).*
Shin (Cancer Discovery (2017) 7(2): 188-201) (Year: 2017).*
Van't Veer (Nature (2002) 415: 530-536) (Year: 2002).*
Benci, J.L., et al., "Tumor Interferon Signaling Regulates a Multigenic Resistance Program to Immune Checkpoint Blockade", Cell, vol. 167, No. 6, pp. 1540-1554, 2016.
Gao et al.,"Tumor immunoevasion by the conversion of effector NK cells into type 1 innate lymphoid cells", Nature Immunology, vol. 18, pp. 1004-1015, 2017.
Garon, E.B., et al., "Pembrolizumab for the treatment of non-small-cell lung cancer", N Engl J Med, vol. 372, No. 21, pp. 2018-2028, 2015.
Hugo et al., "Genomic and Transcriptomic Features of Response to Anti-PD-1 Therapy in Metastatic Melanoma ", Cell, vol. 165, pp. 35-44, 2016.
International Search Report and Written Opinion issued Nov. 19, 2019 in International Application No. PCT/ US2019/051137. 16 pages.
Miller et al., "Subsets of exhausted CD8+ T cells differentially mediate tumor control and respond to checkpoint plockade ", Nature Immunology, vol. 20, No. 3, pp. 326-336, 2019.
Minn, AJ et al., "Interferons and the Immunogenic Effects of Cancer Therapy", Trends in Immunology, (Nov. 2015), vol. 36, No. 11, doi: 10.1016/j.it.2015.09.007, pp. 1-19, XP055360461.
Moshe Sade-Feldman et al, "Resistance to checkpoint blockade therapy through inactivation of antigen presentation", Nature Communications, (Oct. 26, 2017), vol. 8, No. 1, doi: 10.1038/s41467-017-01062-w, XP055514594.
Partial Supplementary European Search Report issued Sep. 22, 2022 in European Patent Application No. 19860463.9. 19 pages.
Reck et al., "Pembrolizumab versus Chemotherapy for PD-L1-Positive Non-Small-Cell Lung Cancer", N Engl J Med, vol. 375, No. 19, pp. 1823-1833, 2016.
(Continued)

*Primary Examiner* — Brad Duffy
*Assistant Examiner* — Elizabeth A Shupe
(74) *Attorney, Agent, or Firm* — Saul Ewing LLP; Kathryn Doyle; Valerie O'Shea Murray

(57) ABSTRACT

The present invention includes methods for treating cancer and selecting a patient for immunotherapy administration.

14 Claims, 125 Drawing Sheets

Specification includes a Sequence Listing.

(56) References Cited

OTHER PUBLICATIONS

Riaz et al., "Tumor and Microenvironment Evolution during Immunotherapy with Nivolumab", Cell, vol. 171, pp. 934-949, 2017.

Sachet A. Shukla et al, "Cancer-Germline Antigen Expression Discriminates Clinical Outcome to CTLA-4 Blockade", CELL, Amsterdam NL, (Apr. 1, 2018), vol. 173, No. 3, doi:10.1016/j.cell.2018.03.026, ISSN 0092-8674, pp. 624-633.e8, XP055505673.

Teijaro, J.R., et al., "Persistent LCMV infection is controlled by blockade of type I interferon signaling", Science, vol. 340, No. 6129. pp. 207-211, 2013.

Tirosh et al., "Dissecting the multicellular ecosystem of metastatic melanoma by single-cell RNA-seq", Science, vol. 352, No. 6282, pp. 189-196, 2016.

Topalian, S.L., et al., "Mechanism-driven biomarkers to guide immune checkpoint blockade in cancer therapy", Nat Rev Cancer, vol. 16, No. 5, pp. 275-287, 2016.

Weichselbaum, RR et al., "An Interferon-Related Gene Signature for DNA Damage Resistance is a Predictive Marker for Chemo-therapy and Radiation for Breast Cancer", Proceedings of the National Academy of Sciences of the United States of America, (Nov. 10, 2008), vol. 105, No. 47, doi:10.1073/pnas.0809242105, pp. 18490-18495, XP055230743.

Wilson, E.B., et al., "Blockade of chronic type I interferon signaling to control persistent LCMV infection", Science, vol. 340, No. 6129, pp. 202-207, 2013.

Zaretsky, JM et al., "Mutations Associated with Acquired Resistance to PD-1 Blockade in Melanoma", The New England Journal of Medicine, (Jul. 13, 2016), vol. 375, No. 9, pp. 1-17, XP055443416.

Hellmann, Matthew D., et al. "Genomic features of response to combination immunotherapy in patients with advanced non-small-cell lung cancer." Cancer cell 33.5 (2018): 843-852.

Maleki Vareki Saman et al., "Biomarkers of response to PD-1/PD-L1 inhibition", Critical Reviews in Oncology/Hematology, (2017), vol. 116, doi:10.1016/ J.CRITREVONC.2017.06.001, ISSN 1040-8428, pp. 116-124, XP085123371.

Medina, P.J., et al., "PD-1 Pathway Inhibitors: Immuno-Oncology Agents for Restoring Antitumor Immune Responses", Pharmacotherapy, 36(3), pp. 317-334, doi: 10.1002/phar.1714. PMID: 26822752, Mar. 2016 (Mar. 2016).

* cited by examiner

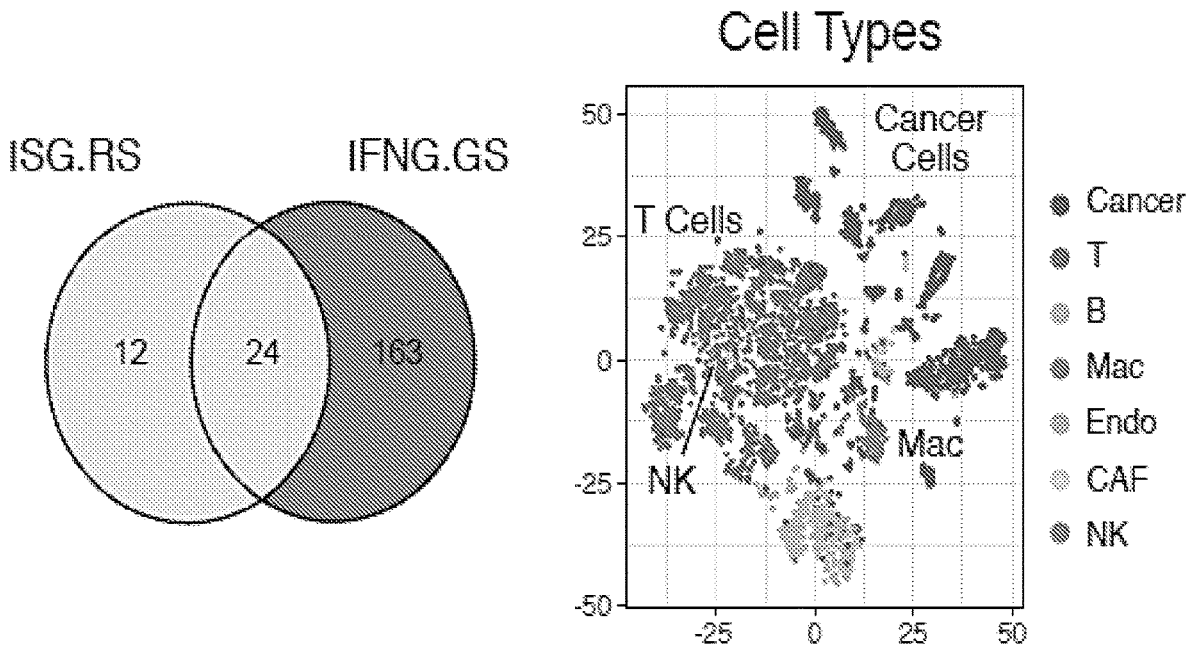
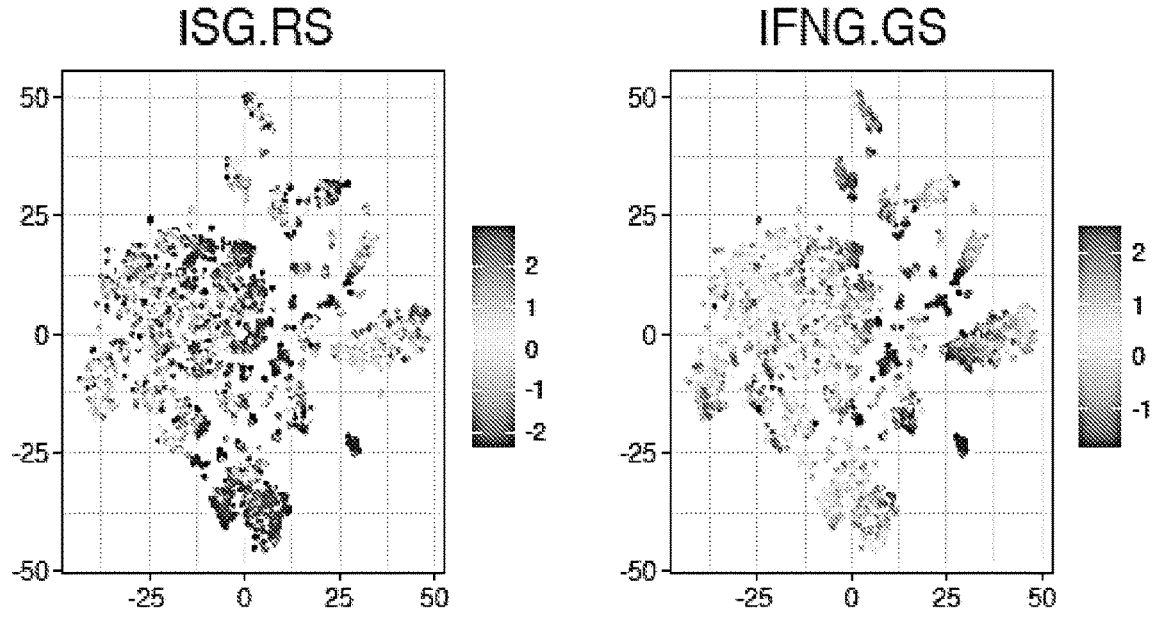
FIG. 1B

Res 499
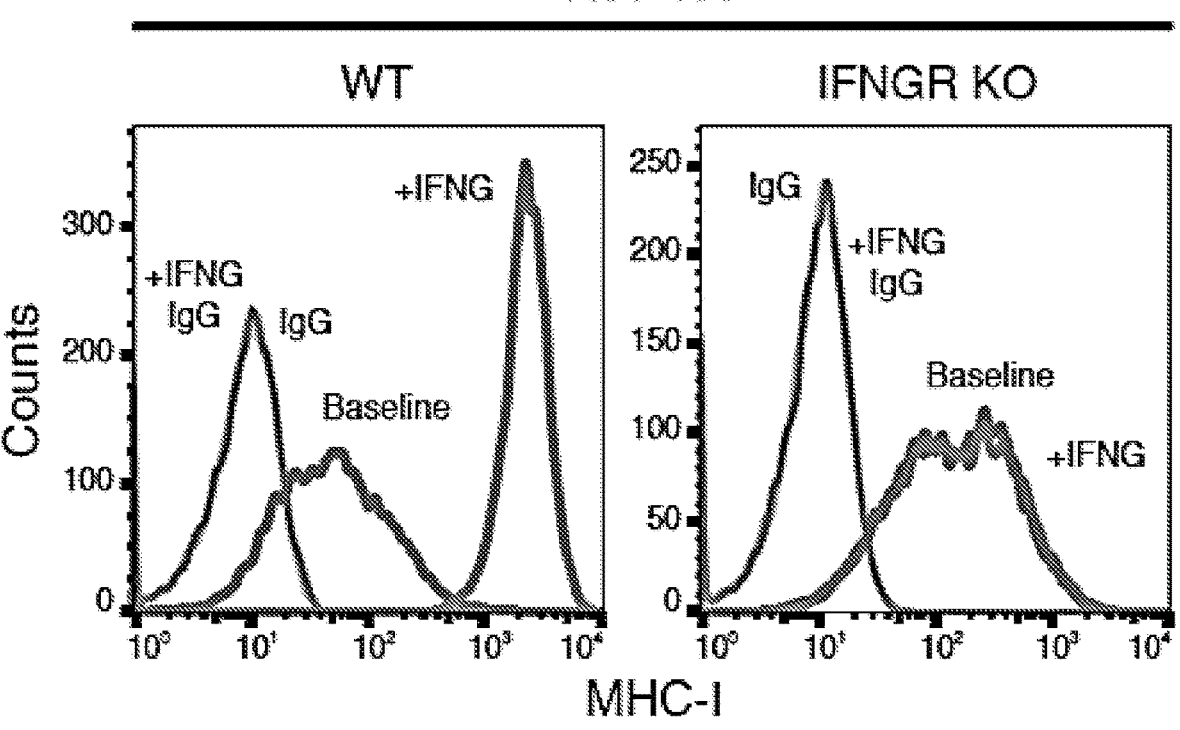
CT26
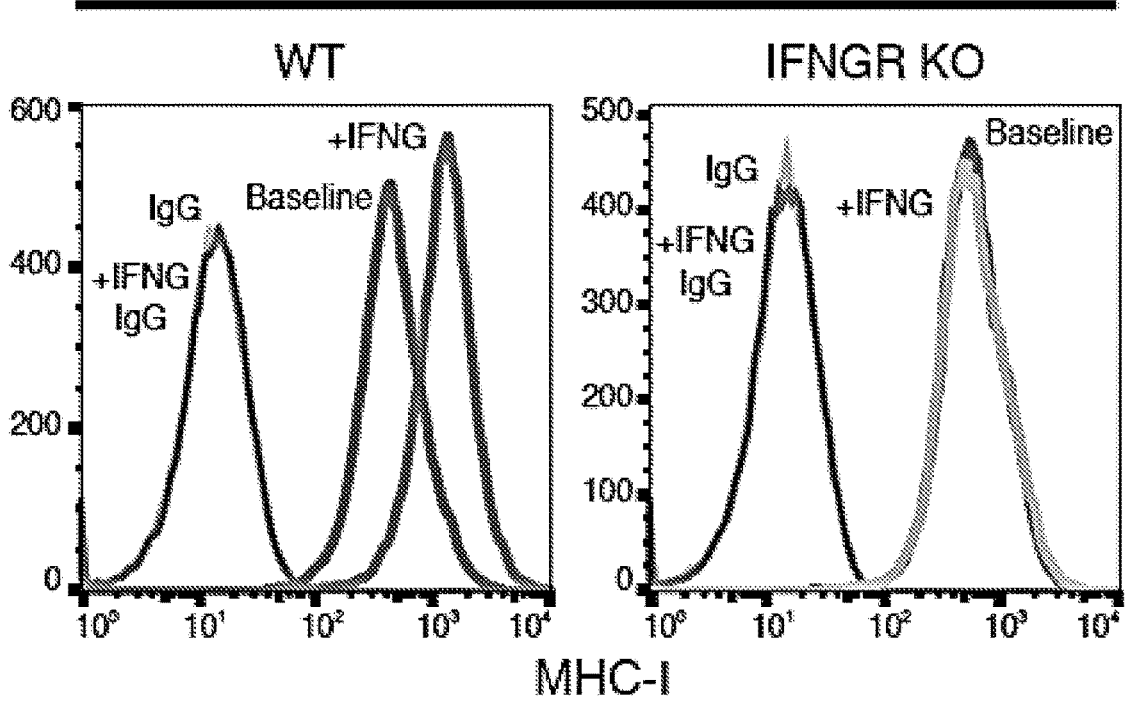
FIG. 2G

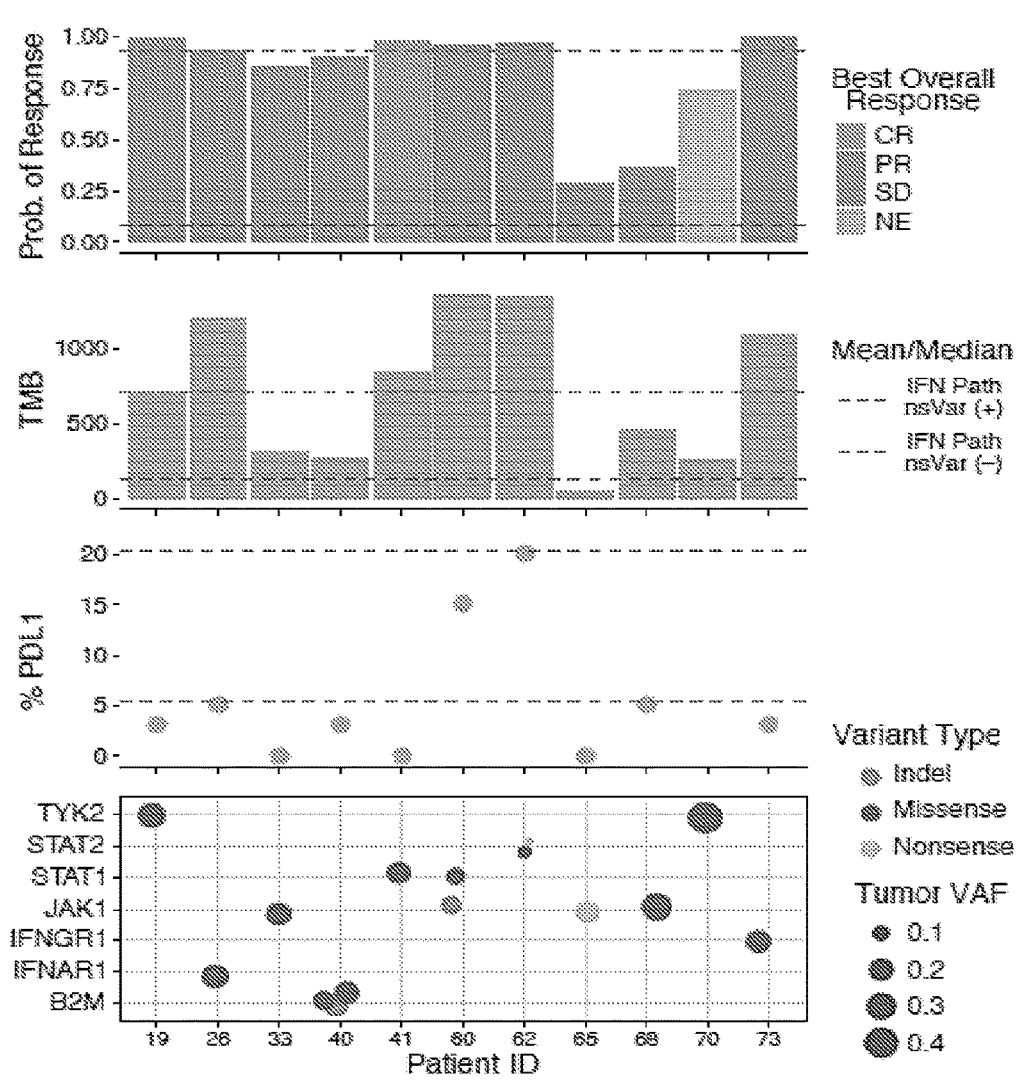
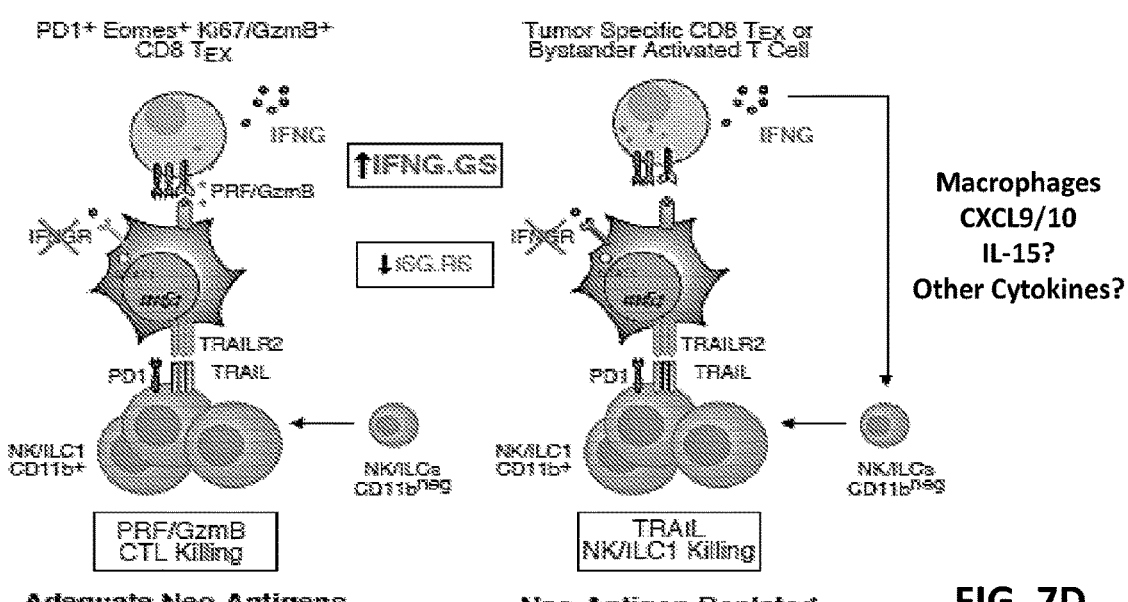
Blockade of Tumor IFN-Driven Resistance
Adequate Neo-Antigens         Neo-Antigen Depleted        FIG. 7D

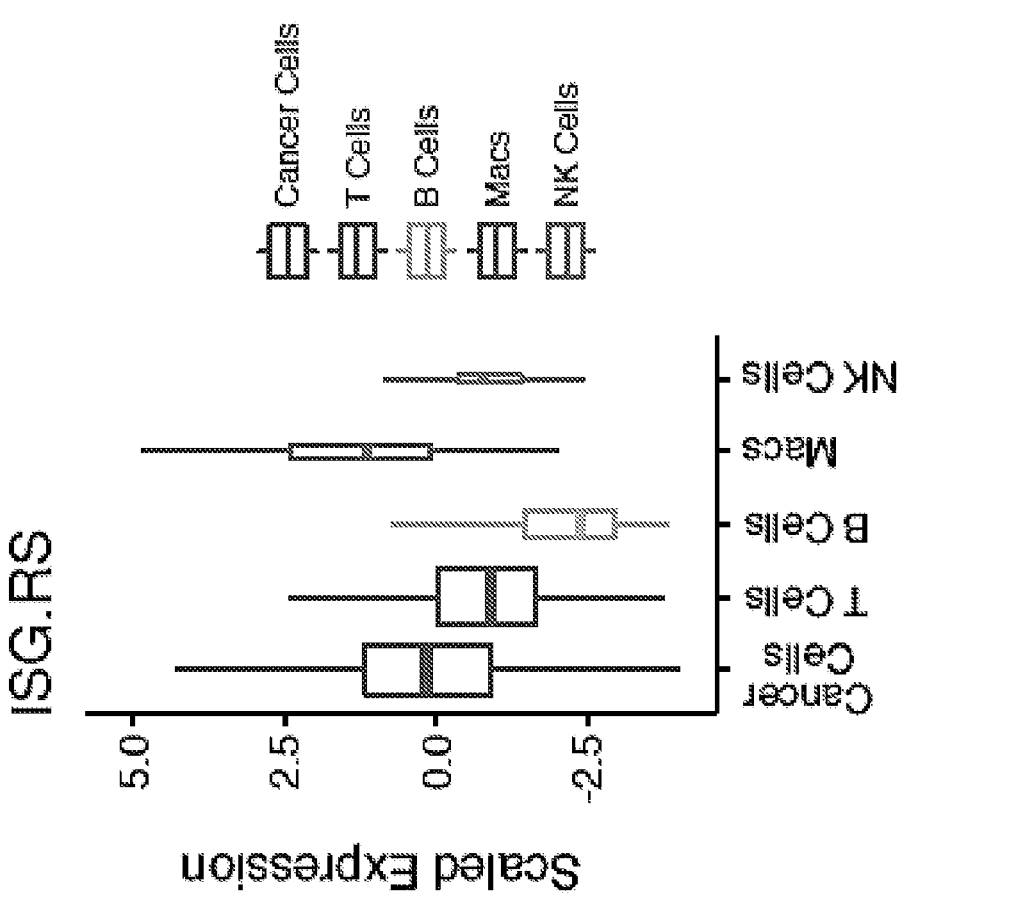
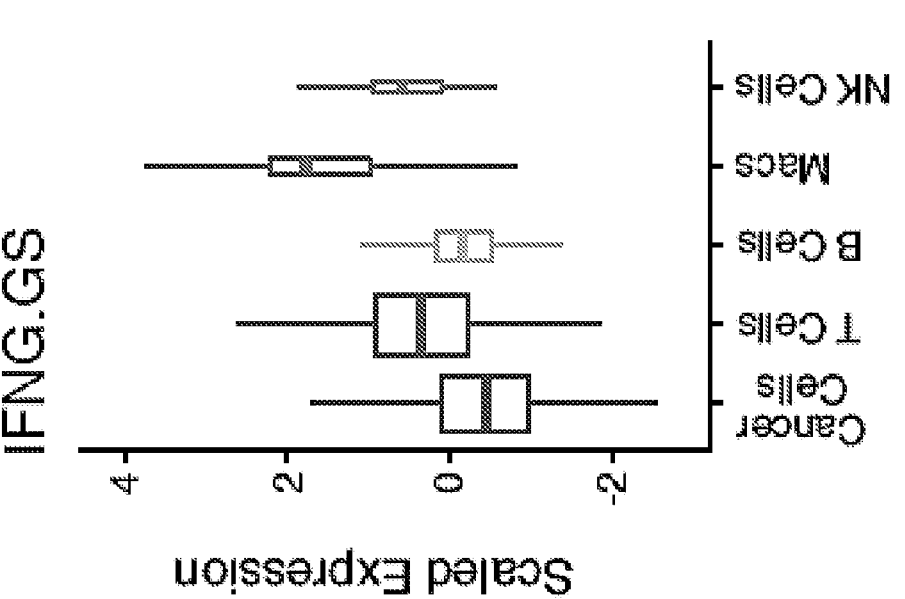
FIG. 8A

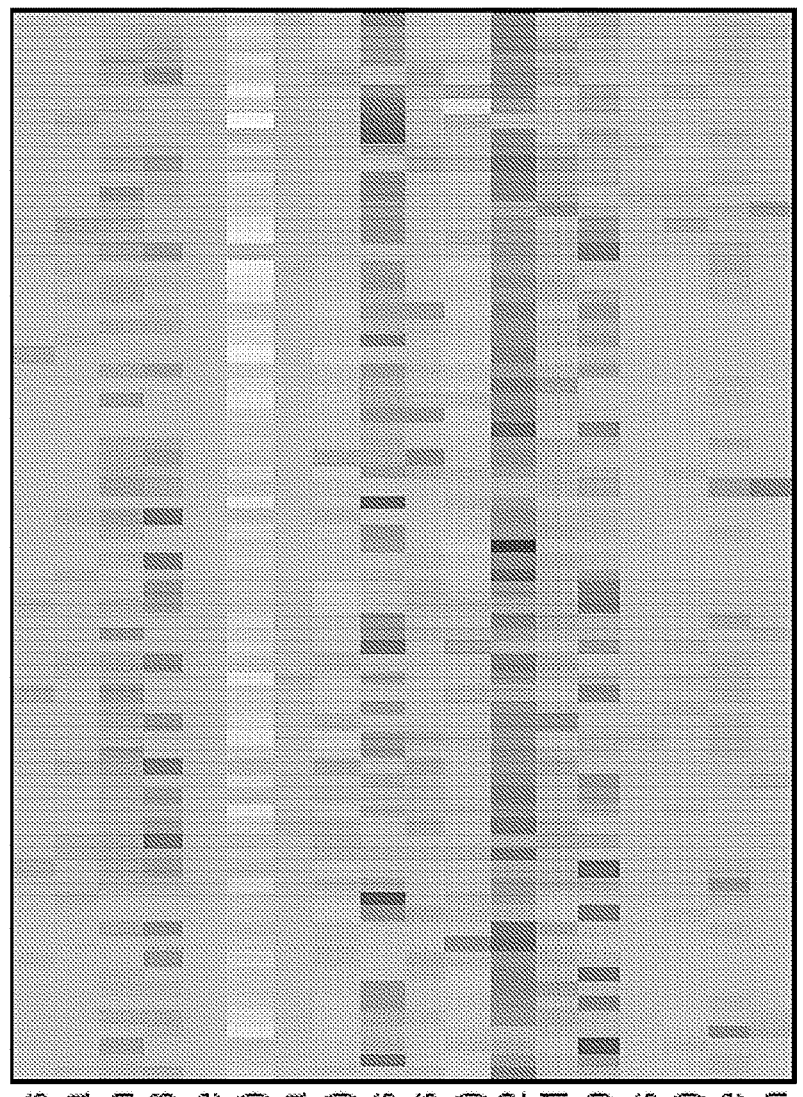
FIG. 8C

TSA/Res 237                    TSA/Res 237 IFNGR KO
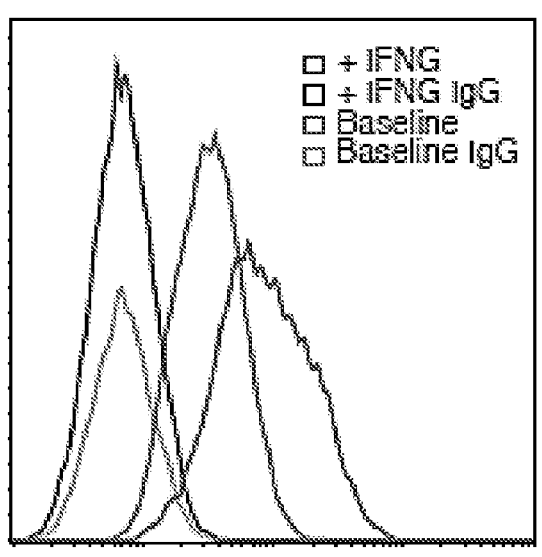
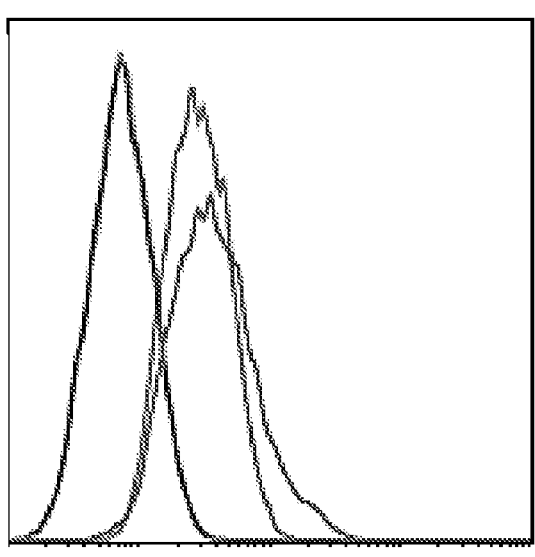
□ + IFNG
□ + IFNG IgG
□ Baseline
□ Baseline IgG
PDL1
FIG. 10C
Control                    Anti-AsialoGM1
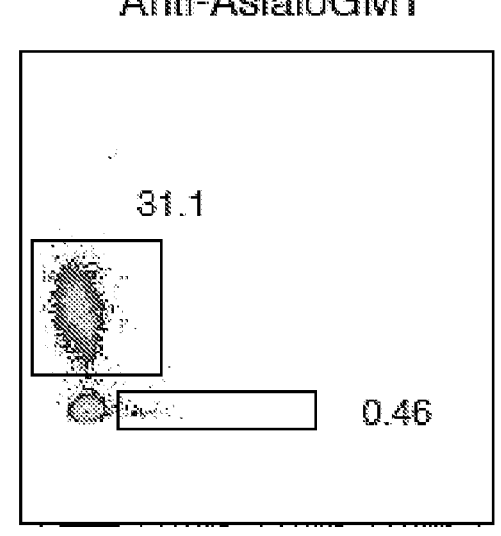
CD3
27.1                         31.1
3.23                         0.46
NKp46
FIG. 10D

FIG. 10F

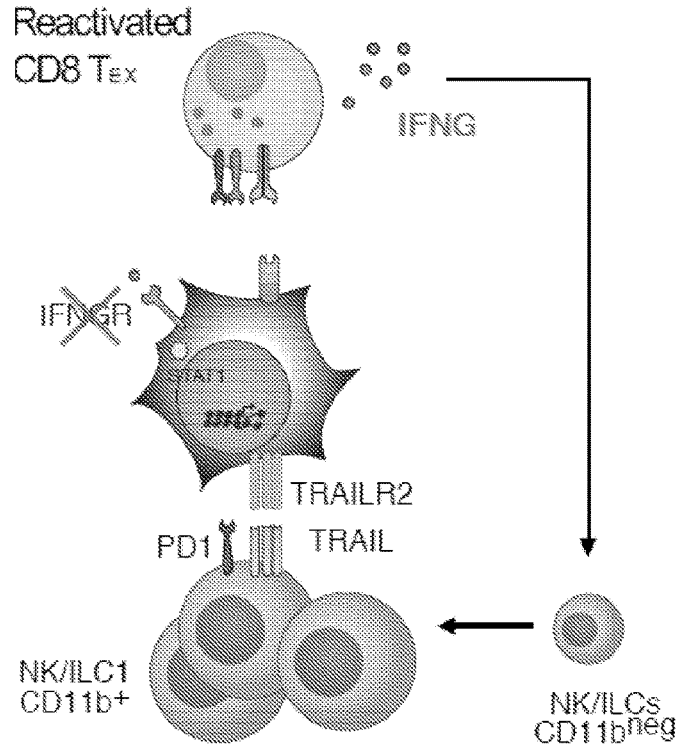
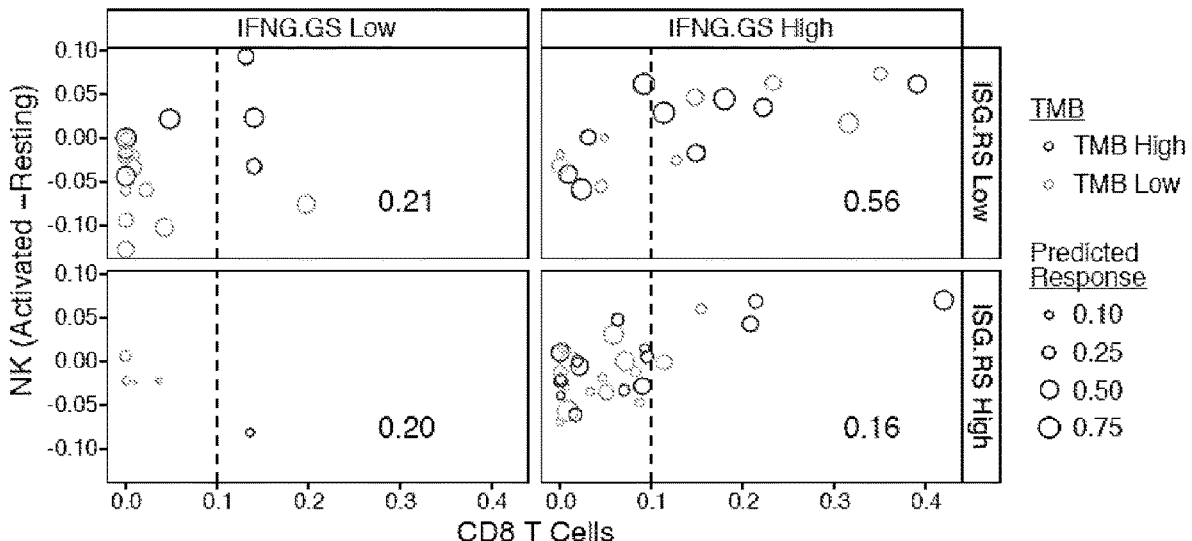
FIG. 17

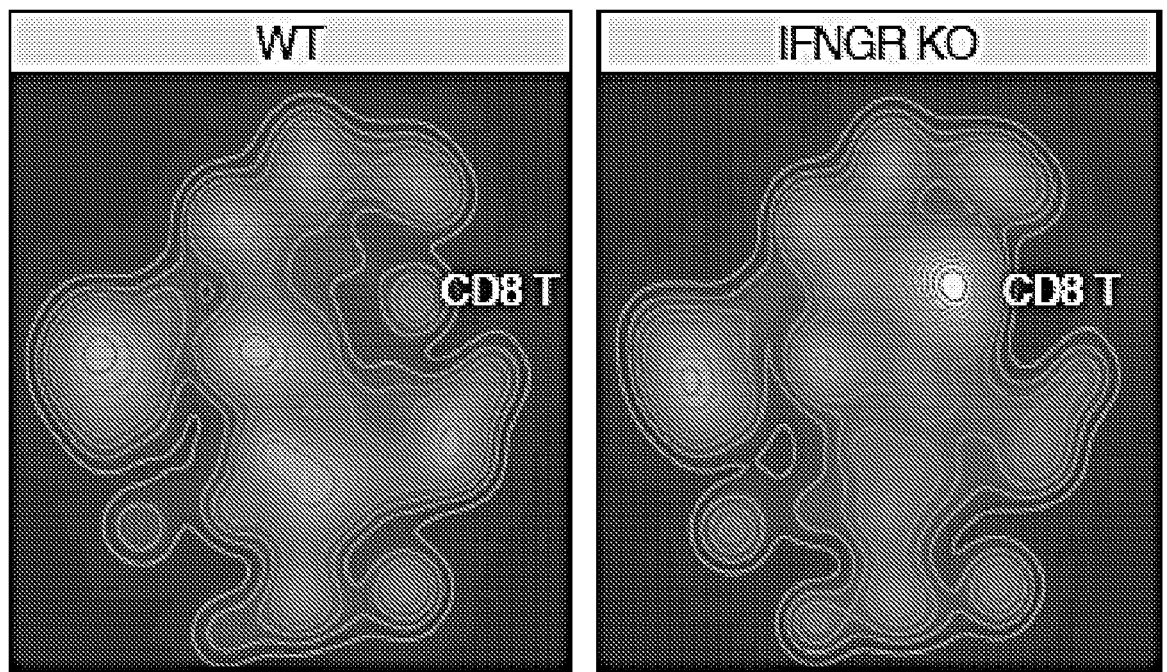
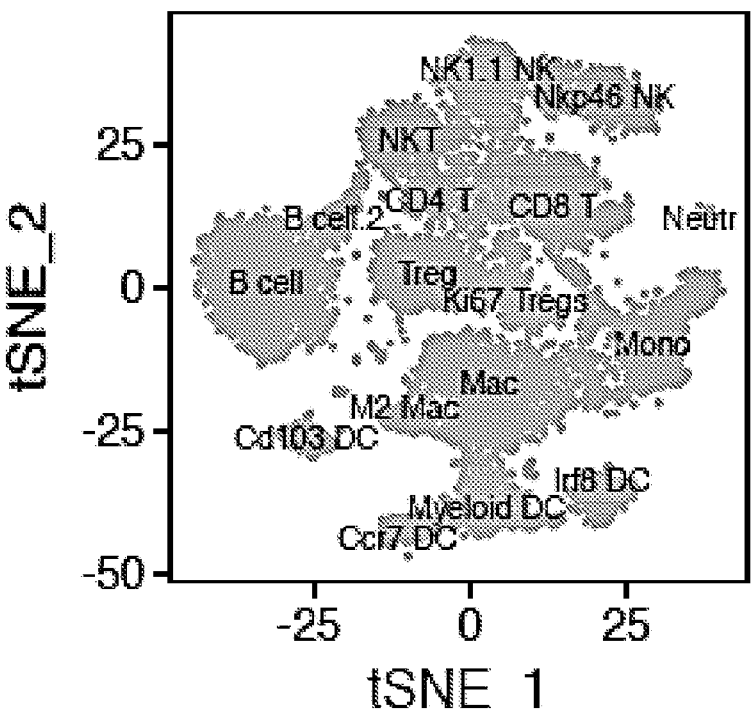
FIG. 19A

FIG. 19I

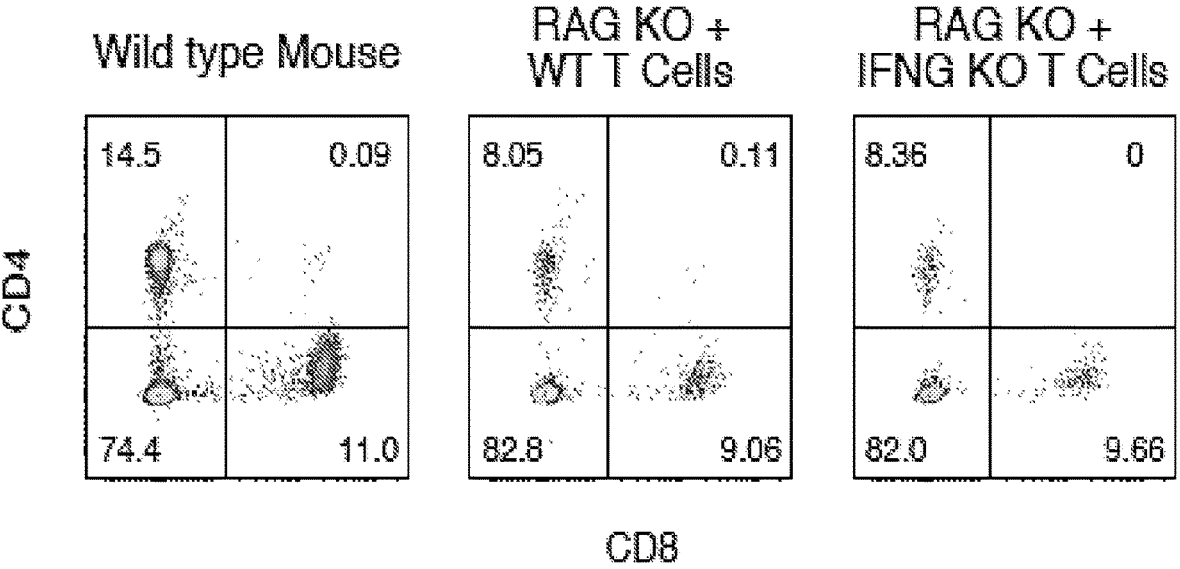
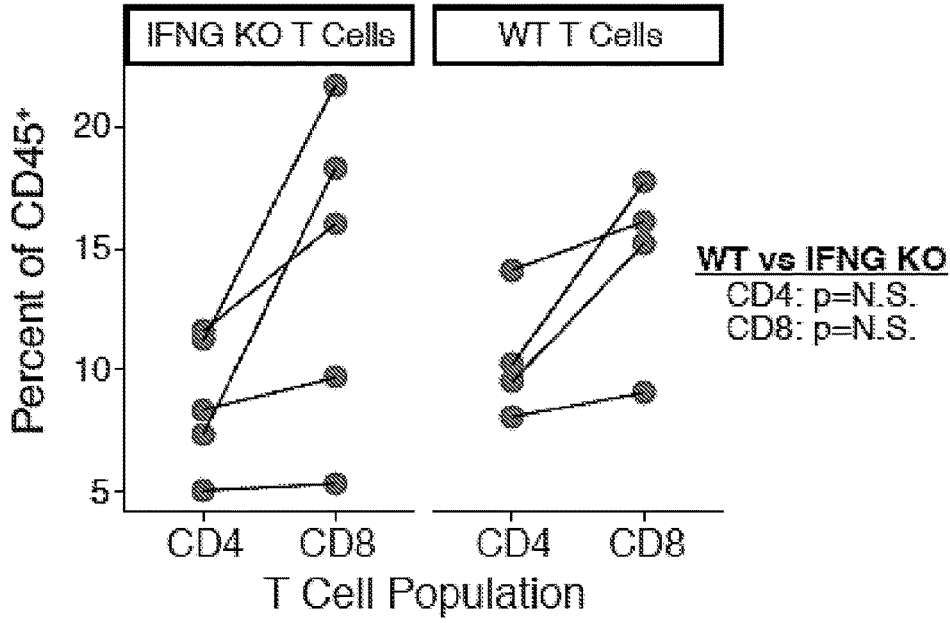
FIG. 21A

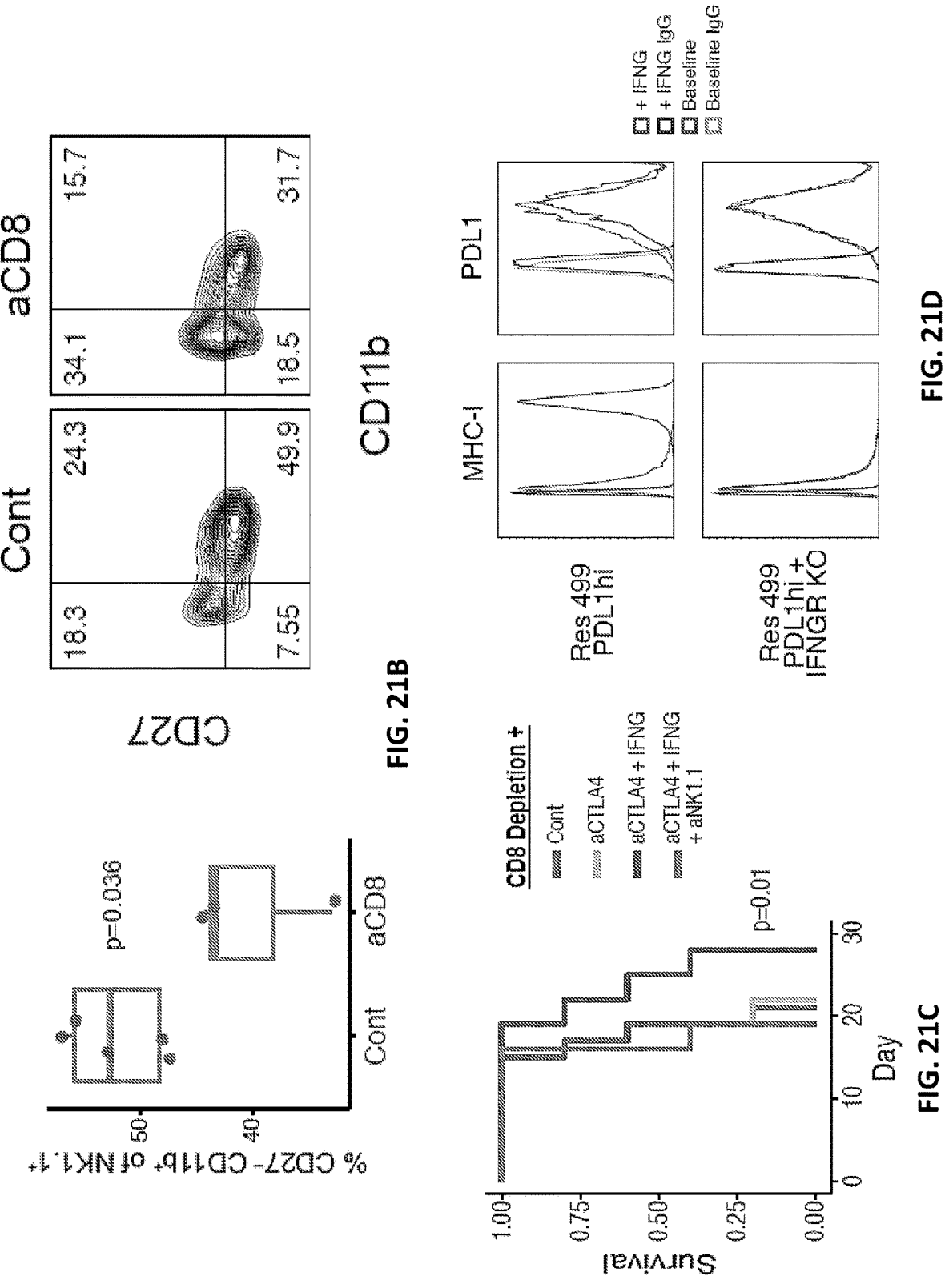

| ISG.RS | | | IFNG.GS | | |
|---|---|---|---|---|---|
| IFI27 | TNFSF10 | NLRC5 | CCL5 | PFKP | GZMA |
| IRF7 | IRF9 | NMI | RNF31 | CD38 | IFNAR2 |
| USP18 | PSMB9 | IDO1 | SOD2 | ZBP1 | CD74 |
| BST2 | EPSTI1 | PSMB10 | PSMA3 | BANK1 | RAPGEF6 |
| CXCL10 | PARP12 | CXCL11 | RNF213 | TOR1B | CASP4 |
| DDX60 | TRIM25 | ITGB7 | PELI1 | RBCK1 | FAS |
| HERC6 | LAP3 | SAMHD1 | CFB | PDE4B | OGFR |
| HLA-B | CASP7 | CMPK2 | CD86 | MVP | ARL4A |
| HLA-G | UPP1 | SAMD9L | TXNIP | IL7 | LYSMD2 |
| IFI35 | B2M | RTP4 | HLA-DQA1 | BPGM | CSF2RB |
| IFI44 | IRF4 | PTPN2 | GCH1 | FTSJD2 | ST3GAL5 |
| IFI44L | SRI | PARP14 | PNP | AUTS2 | C1R |
| IFIT1 | NFKBIA | TNFAIP2 | CCL7 | RIPK2 | CASP3 |
| IFIT3 | IFIT2 | IFITM2 | PTPN6 | CD69 | CMKLR1 |
| ISG15 | OAS2 | SOCS1 | SPPL2A | MYD88 | METTL7B |
| LGALS3BP | TAP1 | CASP1 | IL4R | PSMA2 | ST8SIA4 |
| LY6E | EIF2AK2 | ICAM1 | PNPT1 | PIM1 | XCL1 |
| MX1 | RSAD2 | WARS | DHX58 | NOD1 | IL2RB |
| MX2 | IRF1 | PSME1 | BTG1 | CFH | VAMP5 |
| OAS3 | XAF1 | ISG20 | CASP8 | TAPBP | IL18BP |
| OASL | SP110 | IRF2 | IFI30 | SLC25A28 | ZNFX1 |
| PLSCR1 | PSMB8 | FCGR1A | CCL2 | PTPN1 | ARID5B |
| STAT1 | IFITM3 | MARCH1 | FGL2 | TNFAIP3 | APOL6 |
| TRIM14 | GBP4 | SOCS3 | SECTM1 | SSPN | STAT4 |
| IRF8 | PML | JAK2 | IL15RA | NUP93 | |
| HSD17B1 | IFIH1 | HLA-DMA | CD40 | MTHFD2 | |
| OAS1 | UBE2L6 | TNFAIP6 | TRAFD1 | CDKN1A | |
| CA2 | ADAR | TRIM26 | HLA-DRB1 | NFKB1 | |
| CCNA1 | STAT2 | VCAM1 | GBP6 | BATF2 | |
| CXCL1 | CXCL9 | CD274 | LCP2 | LATS2 | |
| GALC | IL10RA | CIITA | MT2A | IRF5 | |
| IFI6 | PLA2G4A | NAMPT | RIPK1 | SLAMF7 | |
| IFITM1 | TRIM21 | SELP | KLRK1 | ISOC1 | |
| LAMP3 | PTGS2 | GPR18 | PSMB2 | P2RY14 | |
| MCL1 | CIS | FPR1 | TDRD7 | STAT3 | |
| ROBO1 | DDX58 | PRIC285 | HIF1A | NCOA3 | |
| SLC6A15 | IL15 | PSME2 | EIF4E3 | HLA-A | |
| THBS1 | | SERPING1 | VAMP8 | IL6 | |
| TIMP3 | | | | | |

FIG. 23

| | |
|---|---|
| Gzmb | Mrc1 |
| Mki67 | Cd68 |
| Sell | Csf1r |
| Klrg1 | Fcgr3 |
| Nkg7 | Mybl1 |
| Cd3d | Fcer1a |
| Cd3e | Fcgr1 |
| Cd3g | Cd24a |
| Cd8a | Batf3 |
| Prf1 | Itgae |
| Cd4 | Irf8 |
| Foxp3 | Ccr7 |
| Il17a | Zbtb46 |
| Icos | Flt3 |
| Ifngr1 | Xcr1 |
| Klrd1 | Clec9a |
| Cxcr3 | Cd209a |
| Bcl6 | Ccr2 |
| Il10 | Cx3cr1 |
| Ncr1 | Ms4a1 |
| Klrb1c | Cd19 |
| Itgax | Tlr2 |
| Itgam | C5ar1 |
| Ly6g | Csf3r |
| Ly6c1 | Cxcr1 |
| Adgre1 | Cxcr2 |
| Cd14 | Cd34 |
| Fcgr2b | Pdgfrb |
| Mertk | Pdgfra |
| Siglec1 | Kit |
| Mafb | Col1a1 |

FIG. 24

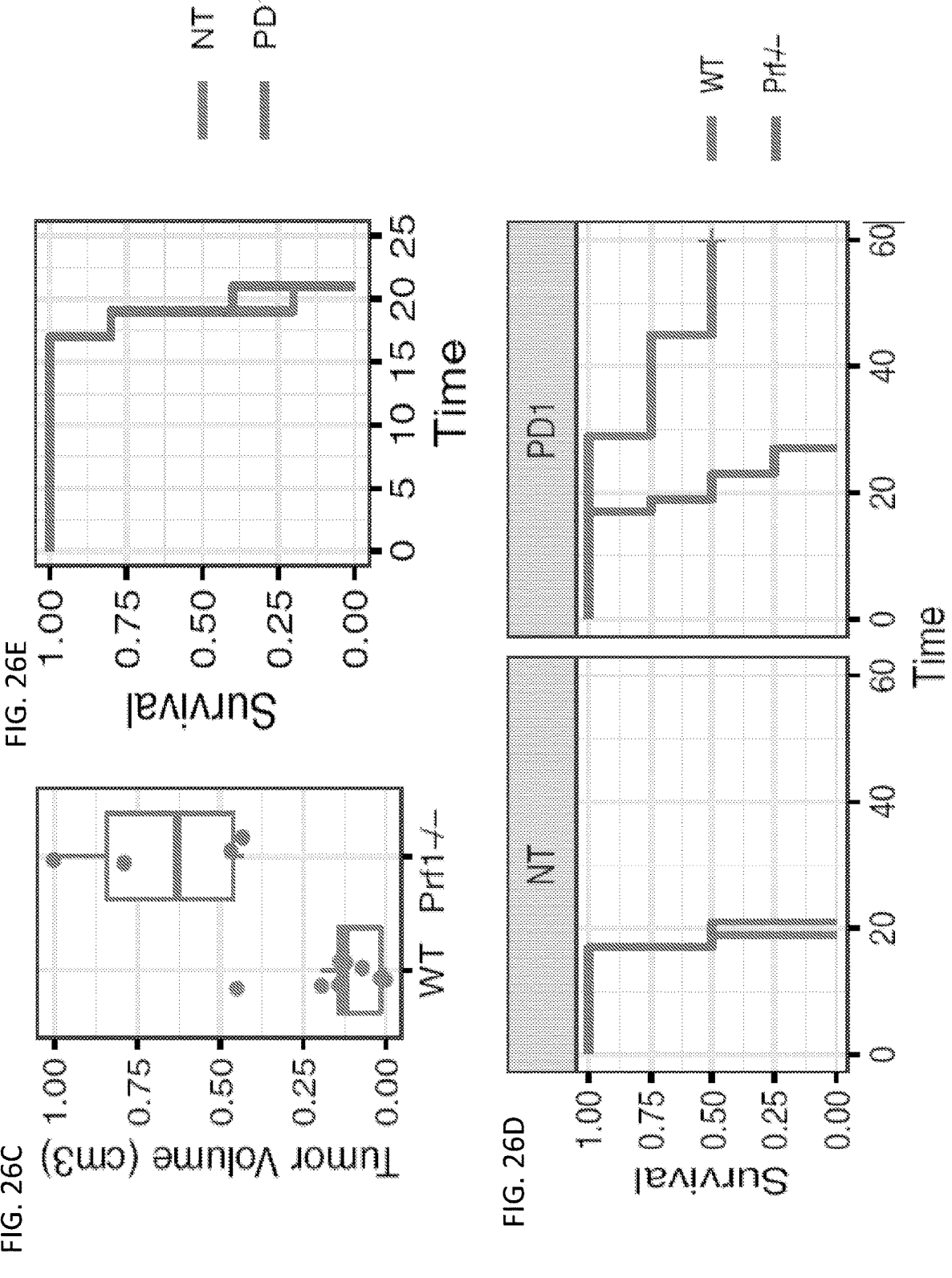

| Treatment Cycle Title — Scheduling Window (Days) | Screening Visit (-28 to -1) | 1 | 2 (±3) | 3 (±3) | 4 (±3) | 5 (±3) | 6 (±3) | 7 (±3) | 8 (±3) | Beyond 8 Cycles[13] 9+ (±3) | EOT (At time of Discontinuation[7]) | Safety Follow-up (30 days post EOT[8]) | Follow Up Visits (Every 8 weeks post discon of treatment[6]) | Survival Follow-Up (Every 12 weeks[5]) |
|---|---|---|---|---|---|---|---|---|---|---|---|---|---|---|
| Informed Consent | X | | | | | | | | | | | | | |
| Inclusion/Exclusion Criteria Assessment | X | | | | | | | | | | | | | |
| Demographics and Medical History | X | | | | | | | | | | | | | |
| Prior and Concomitant Medication Review | X | | | | | | | | | X | X | X | | |
| Pembrolizumab Administration | | X | X | X | X | X | X | X | X | X | | | | |
| Itacitinib Administration | | | X | X | | | | | | | | | | |
| Post-study anticancer therapy status | | | | | | | | | | | X | X | X | X |
| Survival Status | | | | | | | | | | | | | | X |
| Adverse Event Assessment | X | X | | | | | | | | X | X | X | | |
| Full Physical Examination | X | | | | | | | | X | X[5] | X | X | X | |
| Directed Physical Examination[4] | | X | X | X | X | X | X | X | | X | | | | |

FIG. 29A

| Trial Period | Screening | Treatment Cycles (q3 weeks) | | | | | | | | | End of Treatment | Post-Treatment | | Survival Follow-Up |
|---|---|---|---|---|---|---|---|---|---|---|---|---|---|---|
| Treatment Cycle/Title | Screening Visit | 1 | 2 | 3 | 4 | 5 | 6 | 7 | 8 | Beyond 8 Cycles 9+ | EOT | Safety Follow-up | Follow Up Visits | Survival Follow-Up |
| Scheduling Window (Days) | -28 to -1 | | ±3 | ±3 | ±3 | ±3 | ±3 | ±3 | ±3 | ±3 | At time of Discontinuation | 30 days post EOT[8] | Every 8 weeks post discon of treatment[6] | Every 12 weeks[4] |
| Vital Signs and Weight | X | X | X | X | X | X | X | X | X | X | X | X | X | |
| ECOG Performance Status | X | X | X | X | X | X | X | X | X | X | X | X | X | |
| Pregnancy Test – Urine or Serum β-HCG[3] | X | X[5] | | | | | | | | | | | | |
| PT/INR and aPTT[12] | X[12] | | | | | | | | | | | | | |
| CBC with Differential[11] | X[12] | X | X | X | X | X | X | X | X | X | X | X | X | |
| Comprehensive Serum Chemistry Panel[11] | X[12] | X | X | X | X | X | X | X | X | X | X | X | X | |
| TSH[11] | X[12] | X | | | | X | | | | | X | X | | |
| Tumor Imaging[7] | X[9] | | X[15] | | X[16] | | | X | | X[16] | | | X[14] | |
| Tumor Biopsies[1] | | | X[15] | | X[16] | | | | | | | | | |
| Archived Tumor Tissue Sample Collection | X[17] | | | | | | | | | | | | | |
| Research Blood Collection[2] | X | X | X | X | X | X | X | X | X | X | X | | | |

FIG. 29B

| Hematology | Chemistry | Other |
|---|---|---|
| Hematocrit | Albumin | Serum β-human chorionic gonadotropin (β-hCG)† |
| Hemoglobin | Alkaline phosphatase | Urine pregnancy test † |
| Platelet count | Alanine aminotransferase (ALT) | PT (INR) |
| WBC (total and differential) | Aspartate aminotransferase (AST) | aPTT |
| Red Blood Cell Count | Total protein | Total triiodothyronine (T3) |
| Absolute Neutrophil Count | Carbon Dioxide | Free tyroxine (T4) |
| | Blood Urea Nitrogen | Thyroid stimulating hormone (TSH) |
| | Calcium | |
| | Chloride | |
| | Creatinine | |
| | Glucose | |
| | Phosphorus | |
| | Potassium | |
| | Sodium | |
| | Magnesium | |
| | Total Bilirubin | |
| | Direct Bilirubin *(If total bilirubin is elevated above the upper limit of normal)* | |

† Performed on women of childbearing potential only. If urine pregnancy results cannot be confirmed as negative, a serum pregnancy test will be required.

After Cycle 1, pre-dose laboratory procedures can be conducted up to 72 hours prior to dosing. Results must be reviewed by the investigator or qualified designee and found to be acceptable prior to each dose of trial treatment.

INTERFERON PATHWAY GENES REGULATE AND PREDICT EFFICACY OF IMMUNOTHERAPY

CROSS-REFERENCE TO RELATED APPLICATION

The present application is a 35 U.S.C. § 371 national phase application from, and claims priority to, International Application No. PCT/US2019/051137, filed Sep. 13, 2019, and published under PCT Article 21(2) in English, which claims priority under 35 U.S.C. § 119(e) to U.S. Provisional Patent Application No. 62/730,844, filed Sep. 13, 2018, and U.S. Provisional Patent Application No. 62/884,073, filed Aug. 7, 2019, which are hereby incorporated by reference in their entireties herein.

STATEMENT REGARDING FEDERALLY SPONSORED RESEARCH OR DEVELOPMENT

This invention was made with government support under CA-163739-01 awarded by the National Institutes of Health. The government has certain rights in the invention.

REFERENCE TO AN ELECTRONIC SEQUENCE LISTING

The present application contains a Sequence Listing which has been submitted electronically in ASCII format and is hereby incorporated by reference in its entirety. Said ASCII copy, created on Mar. 8, 2021, is named 046483-7225US1-SequenceListing.TXT and is 4,096 bytes in size.

BACKGROUND OF THE INVENTION

Immune checkpoint blockade (ICB) of the inhibitory receptors CTLA4 and PD1 can result in durable responses in multiple cancer types. Resistance and relapse are common and can be influenced by factors inherent to immune cells, cancer cells, or both. Immune features that are important in ICB response include the status of the T cell infiltrate, the differentiation and activation state of these T cells, and the nature or functional status of innate immune cells such as myeloid and dendritic cell subsets. Features intrinsic to cancer cells that can impact ICB outcome include their repertoire of neoantigens, the ability to present antigens in major histocompatibility complex class one (MHC-I), and the expression of inhibitory receptor ligands such as PDL1. The clinical relevance of these immune and cancer cell factors is highlighted by common biomarkers for ICB response such as interferon (IFN) stimulated genes (ISGs), tumor mutational burden (TMB), and expression of PDL1. However, despite the biological and clinical relevance of these features, statistical models using these variables are generally poor at predicting ICB response. Undoubtedly, an incomplete understanding of the biological determinants controlling anti-tumor immunity contributes to this challenge.

A need exists for novel compositions and methods that predict whether an immunotherapy will be effective. The present invention addresses this need.

SUMMARY OF THE INVENTION

The present invention provides methods for treating cancer and selecting a patient for immunotherapy administration.

In one aspect, the invention provides a method for treating cancer in a subject in need thereof. The method comprises measuring the expression level of a panel of interferon stimulating genes (ISGs) in a cancer cell from the subject and measuring the expression level of the same panel of ISGs in an immune cell from the subject. The panel of ISGs comprises a first subpanel of ISGs and a second subpanel of ISGs. The first subpanel of ISGs comprises an ISG resistance signature (ISG.RS) and the second subpanel of ISGs comprises an interferon gene signature (IFNG.GS). When the expression level of the IFNG.GS is greater than the expression level of the ISG.RS, then the subject is administered an immunotherapy. When the expression level of the ISG.RS is greater than the expression level of the IFNG.GS, then the subject is not administered an immunotherapy, and an alternative treatment is administered to the subject. Thereby, the cancer is treated in the subject.

In another aspect, the invention provides a method for treating cancer in a subject in need thereof comprising measuring the expression level of a panel of interferon stimulating genes (ISGs) in a cancer cell from the subject and measuring the expression level of the same panel of ISGs in an immune cell from the subject. The panel of ISGs comprises a first subpanel of ISGs and a second subpanel of ISGs. The first subpanel of ISGs comprises an ISG resistance signature (ISG.RS) and the second subpanel of ISGs comprises an interferon gene signature (IFNG.GS) The ratio of the expression level of the IFNG.GS over the expression level of the ISG.RS is measured. When the ratio is increased in comparison to a reference sample, then the subject is administered an immunotherapy. When the ratio is not increased in comparison to a reference sample, then the subject is not administered an immunotherapy, and an alternative treatment is administered to the subject. Thereby, the cancer is treated in the subject.

In still another aspect, the invention provides a method for treating cancer in a subject in need thereof. The method comprises measuring the expression level of a panel of interferon stimulating genes (ISGs) in a cancer cell from the subject and measuring the expression level of the same panel of ISGs in an immune cell from the subject. The panel of ISGs comprises a first subpanel of ISGs and a second subpanel of ISGs. The expression level of the first subpanel of ISGs comprises an ISG resistance signature (ISG.RS) and the expression level of the second subpanel of ISGs comprises an interferon gene signature (IFNG.GS). When the ISG.RS from the cancer cell is decreased in comparison to a first reference sample, and the IFNG.GS from the immune cell is increased in comparison to a second reference sample, then the subject is administered an immunotherapy. When the ISG.RS from the cancer cell is not decreased in comparison to a reference sample and the IFNG.GS from the immune cell is not increased in comparison to a reference sample, then the subject is not administered an immunotherapy, and an alternative treatment is administered to the subject. Thereby, the cancer is treated in the subject.

Another aspect of the invention includes a method of selecting a patient for immunotherapy administration. The method comprises measuring the expression level of a panel of interferon stimulating genes (ISGs) in a cancer cell from the subject and measuring the expression level of the same panel of ISGs in an immune cell from the subject. The panel of ISGs comprises a first subpanel of ISGs and a second subpanel of ISGs. The expression level of the first subpanel of ISGs comprises an ISG resistance signature (ISG.RS) and the expression level of the second subpanel of ISGs comprises an interferon gene signature (IFNG.GS). When the ISG.RS from the cancer cell is decreased in comparison to a first reference sample, and the IFNG.GS from the immune cell is increased in comparison to a second reference sample, then the subject is selected for immunotherapy. When the ISG.RS from the cancer cell is not decreased in comparison to a reference sample and the IFNG.GS from the immune cell is not increased in comparison to a reference sample, then the subject is not selected for immunotherapy, and an alternative treatment is selected for the subject.

In various embodiments of the above aspects or any other aspect of the invention delineated herein, the first subpanel of ISGs is selected from one or more members of the group consisting of IFI27, IRF7, USP18, BST2, CXCL10, DDX60, HERC6, HLA-B, HLA-G, IFI35, IFI44, IFI44L, IFIT1, IFIT3, ISG15, LGALS3BP, LY6E, MX1, MX2, OAS3, OASL, PLSCR1, STAT1, TRIM14, HSD17B1, OAS1, CA2, CCNA1, CXCL1, GALC, IFI6, IFITM1, LAMP3, MCL1, ROBO1, SLC6A15, THBS1, and TIMP3, and/or the second subpanel of ISGs is selected from one or more members of the group consisting of TNFSF10, IRF9, EPSTI1, PARP12, TRIM25, CASP7, UPP1, B2M, IRF4, SRI, NFKBIA, OAS2, RSAD2, XAF1, SP110, IFITM3, GBP4, IRF8, IFIH1, UBE2L6, ADAR, STAT2, CXCL9, IL10RA, PLA2G4A, TRIM21, PTGS2, DDX58, IL15, NLRC5, NMI, IDO1, PSMB10, CXCL11, SAMD9L, RTP4, PTPN2, TNFAIP2, IFITM2, SOCS1, CASP1, ICAM1, WARS, PSME1, ISG20, FCGR1A, SOCS3, HLA-DMA, TNFAIP6, TRIM26, VCAM1, CD274, CIITA, NAMPT, GPR18, FPR1, PRIC285, PSME2, SERPING1, CCL5, RNF31, SOD2, PSMA3, RNF213, PELI1, CFB, CD86, HLA-DQA1, GCH1, PNP, CCL7, PTPN6, SPPL2A, IL4R, DHX58, CASP8, IFI30, CCL2, FGL2, SECTM1, IL15RA, CD40, HLA-DRB1, GBP6, LCP2, MT2A, RIPK1, PSMB2, TDRD7, HIF1A, PFKP, ZBP1, PDE4B, IL7, BPGM, FTSJD2, AUTS2, RIPK2, MYD88, PSMA2, NOD1, TAPBP, SLC25A28, PTPN1, SSPN, NUP93, MTHFD2, CDKN1A, NFKB1, BATF2, LATS2, IRF5, SLAMF7, ISOC1, P2RY14, STAT3, NCOA3, GZMA, IFNAR2, CD74, RAPGEF6, CASP4, OGFR, ARL4A, LYSMD2, CSF2RB, C1R, METTL7B, ST8SIA4, CD38, PSMB9, BANK1, TOR1B, ITGB7, RBCK1, FAS, LAP3, SAMHD1, CMPK2, MVP, TXNIP, ST3GAL5, PARP14, CASP3, IFIT2, CD69, CMKLR1, TAP1, EIF2AK2, PIM1, XCL1, IL2RB, IRF1, BTG1, CFH, VAMP5, IL18BP, IRF2, ZNFX1, PSMB8, ARID5B, MARCH1, TNFAIP3, APOL6, STAT4, JAK2, PML, TRAFD1, SELP, KLRK1, CIS, EIF4E3, HLA-A, PNPT1, VAMP8, and IL6.

In certain embodiments, when the subject is not selected for immunotherapy, an alternative treatment is administered to the subject.

In certain embodiments, the immunotherapy is selected from the group consisting of immune checkpoint blockade (ICB), adoptive cell therapy, and any combination thereof. In certain embodiments, the ICB is selected from the group consisting of anti-CTLA4, anti-PD1, anti-PDL1, and any combination thereof. In certain embodiments, the ICB comprises anti-PD1 and anti-CTLA4.

In certain embodiments, the adoptive cell therapy is selected from the group consisting of CAR T cell therapy and TCR engineered T cell therapy.

In certain embodiments, the immunotherapy or the alternative treatment modulates interferon or interferon stimulated genes. In certain embodiments, the immunotherapy or the alternative treatment comprises one or more selected from the group consisting of anti-TIM3, anti-LAG3, anti-2B4, anti-4-1BB, anti-GITR, anti-VISTA, anti-CD40, cGAS/STING agonists, RIG-I agonists, TLR agonists, MDA5 agonists, and any combination thereof.

In certain embodiments, the alternative treatment comprises one or more selected from the group consisting of chemotherapy, radiation, surgery, an alternative immune checkpoint blockade (ICB), an alternative adoptive cell therapy, an alternative immunotherapy, and any combination thereof.

In certain embodiments, the alternative treatment comprises a treatment that increases the IFNG.GS expression level and/or decreases the ISG.RS expression level. In certain embodiments, the treatment that decreases the ISG.RS comprises one or more selected from the group consisting of an IFN blocking agent, an IFN receptor blocking agent, a JAK inhibitor, a STAT inhibitor, an adoptive cell therapy, a small molecule, molecularly targeted agents, epigenetic therapies, and any combination thereof. In certain embodiments, the treatment that increases the IFNG.GS comprises one or more selected from the group consisting of anti-CTLA4, anti-PDL1, anti-TIM3, anti-LAG3, anti-2B4, anti-4-1BB, anti-GITR, anti-VISTA, anti-CD40, cGAS/STING agonists, RIG-I agonists, TLR agonists, MDA5 agonists, radiation, chemotherapy, molecularly targeted agents, epigenetic therapies, and any combination thereof.

In certain embodiments, the immune cell is selected from the group consisting of a T cell, an NK cell, a macrophage, a dendritic cell, a myeloid cell, an ILC cell, and a CD8+ cell.

In certain embodiments, the expression level is measured by a method selected from the group consisting of RNA-Seq, q-PCR, RT-PCR, sequencing, transcriptomics, and microarray.

In certain embodiments, the first reference sample comprises an IFNG.GS from an immune cell from the subject. In certain embodiments, the second reference sample comprises an ISG.RS from a cancer cell from the subject.

In certain embodiments, the cancer is a solid tumor. In certain embodiments, the cancer is melanoma, breast cancer, colorectal cancer, or lung cancer.

Another aspect of the invention includes a method of selecting a subject for immunotherapy administration. The method comprises analyzing a tumor sample from the subject, wherein when at least one gene selected from the group consisting of IFNGR1, IFNGR2, IFNAR1, IFNAR2, JAK1, JAK2, TYK2, STAT1, STAT2, IRF9, and B2M comprises a loss-of-function mutation, then the patient is selected for immunotherapy. In certain embodiments, the mutation is selected from the group consisting of a point mutation, an insertion, a deletion, a frameshift, and a gene knockout.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIGS. 1A-1M illustrate the finding that distinct ISGs are differentially expressed in cancer and immune cells and have opposing functions in predicting clinical ICB response. FIG. 1A shows results from gene set enrichment analysis of resistance-associated ISGs (ISG.RS) in Res 499 cells compared to parental B16 cells, both sorted from in vivo tumors. Heatmap and enrichment plot is shown along with the normalized enrichment score (NES) and p-value. FIG. 1B illustrates metagene expression in single cells from human melanoma tumors. Venn diagram shows genes in the ISG.RS along with hallmark IFNG-related genes (IFNG.GS) partitioned into non-overlapping gene sets and used to create individual metagenes. Cell types from the single-cell RNA-seq data of pooled tumors are shown in the tSNE plot along with expression of the metagenes. FIG. 1C illustrates genomic and clinical features associated with ICB response. Tumor mutational burden (TMB) and bulk tumor expression of the ISG metagenes were used to create a multivariable random forest model to predict response to anti-PD1. Partial plots of the adjusted effects of these variables on the probability of response is shown (bottom), along with one SD. Also shown are prior treatment with the anti-CTLA4 antibody ipilimumab (Ipi) and the relative frequency of CD8 T cells and activated NK cells inferred by CIBERSORT. FIG. 1D illustrates the balance between IFNG-related genes and cancer-associated ISGs is associated with anti-PD1 response. The ISG.RS is on the x-axis and IFNG.GS levels is on the y-axis. Circle color indicates response and circles size TMB. The dashed line goes through the origin with a slope of one. FIG. 1E shows variable importance scores of TMB and ISG metagenes from the random forest model for anti-PD1 response. FIG. 1F shows the relative frequency of activated NK cells (activated minus resting) vs. CD8 T cells among melanoma tumors stratified by low and high IFNG.GS and ISG.RS metagene expression. The frequency of tumors to the right of the dashed line is indicated. Responders and non-responders (circle color) and TMB (circle size) are also shown. FIG. 1G shows a summary of the relationships inferred by statistical modeling. FIG. 1H shows gene set enrichment analysis for ISG.RS genes after knockout of STAT1 or the indicated IFN receptor in Res 499 tumor cells. FIG. 1I illustrates the proportion of activated NK cells vs. CD8 T cells stratified by low/high IFNG.GS and ISG.RS expression. Regression line, Pearson correlation and p-value, and percent CD8 T cells in each quadrant are shown. FIG. 1J shows odds ratios and 95% confidence intervals from a multivariable model for clinical anti-PD1 response. FIG. 1K illustrates a multivariable random forest model for probability of response for melanoma patients treated with anti-PD1. Shown are the adjusted effects of model variables on the probability of response (left plots, boundaries indicate one standard error) and variable importance scores (right plot). Predictor values are metagene expression values for ISG.RS and IFNG.GS or log 10 frequency for TMB. Variable importance score represents the increase in classification error rate when the variable is perturbed. The classification error rate for the model is 36%. FIG. 1L shows expression of each metagene (left plot), and the predicted probability of anti-PD1 response (right plot) from a model using TMB and the ratio of IFNG.GS over ISG.RS (dISG). Odds ratios are shown in the inset. Circle color indicates response and size indicates TMB. FIG. 1M illustrates a random forest model with variable selection based on minimal depth performed on bootstrapped samples. Variables include inferred frequencies of various immune populations (based on CIBERSORT), the ratio of IFNG.GS to ISG.RS (dISG), TMB, and other control variables. Shown are the frequencies that each variable was selected based on minimal depth after resampling versus the average variable importance score (VIMP). The inset shows the distribution of the number of variables in each bootstrapped model. Similar results were also obtained with lasso and logistic regression.

FIGS. 2A-2M illustrate the finding that interfering with tumor IFN signaling restores ICB response to neoantigen depleted tumors and requires both T cells and NK/ILCs. FIG. 2A shows a summary of key properties of mouse tumor models. N.D. is not determined. FIG. 2B shows constitutive (baseline) and IFNG-inducible (+IFNG) MHC-I expression on CT26 tumor cells with or without IFNGR knockout. FIG. 2C illustrates tumor mutational burden measured by total non-synonymous somatic mutations for each of the indicated cell lines. The proportion of predicted high-affinity (<500 nM) neoantigens is also shown. FIG. 2D shows survival of mice bearing CT26 tumors with knockout of IFNGR or both IFNGR and IFNAR. Spontaneous tumor regression is shown (Control) in addition to response after anti-PD1 or depletion of CD8 T cells. FIG. 2E shows survival of mice bearing either B16 or Res 499 tumors with or without STAT1 knockout after treatment with radiation combined with anti-CTLA4. Control treated (Cont) mice are also shown. FIG. 2F shows response of B16 tumors expressing human CD19 (hCD19) after a single infusion with control transduced primary murine T cells (Cont) or T cells transduced with a chimeric antigen receptor against hCD19 (CART). Tumor volume is shown for tumors with control (WT) or combined knockout of IFNGR and IFNAR (IFNA/GR). FIG. 2G shows constitutive (baseline) and IFNG-inducible (+IFNG) MIC-I expression on Res 499 (left) and CT26 (right) tumor cells with or without IFNGR knockout. FIG. 2H shows allelic frequency (AF) of predicted high-affinity neoantigens (<100 nM) in B16 or Res 499 tumors. AF values are transformed onto a log 10 scale with a near-heterozygous value for a tetraploid genome indicated (dashed lines). Circle size corresponds to neoantigen affinity. Circle colors corresponds to sets of neoantigens (MutSet) predicted to be evolutionarily related and giving rise to FIG. 2I shows subclonal populations (Subclone 1-3) displayed in the phylogenetic tree. Frequencies of these subclonal populations in B16 and Res 499 cancer cells are shown. FIG. 2J illustrates Constitutive (baseline) MHC-I on indicated tumor cells with or without IFNGR KO. FIG. 2K illustrates a cumulative distribution function plot of the allelic frequencies for predicted high-affinity (<100 nM) neoantigens. The p-value is determined by an empirical distribution of the KS statistic from random variants. FIG. 2L illustrates allelic frequency of predicted high-affinity neoantigens in B16 and Res 499 tumors. Values are transformed onto a log 10 scale with a near-heterozygous value for a tetraploid genome indicated (dashed lines). Circle size corresponds to neoantigen affinity. Circle color corresponds to neoantigen clusters predicted to be evolutionarily related and giving rise to subclonal populations. FIG. 2M illustrate subclonal populations (Subclone 1-4) inferred from high quality variants and displayed using a phylogenetic tree. Frequencies of these subclonal populations are shown. See also FIG. 9B.

FIG. 3A illustrates survival of mice bearing IFNGR knockout Res 499 tumors following treatment with anti-CTLA4 (aCTLA4) or control (Cont). The effect of NK/ILC depletion with an anti-NK1.1 antibody (aNK1.1) or CD8 T cell depletion with an anti-CD8 antibody (aCD8) is indicated. Top shows the median (dot) and the 25th and 75th percentile survival. Bottom shows Kaplan-Meier survival. FIG. 3B shows abundance of NK/ILCs (top) or CD8 T cells (bottom) in wild type or IFNGR knockout Res 499 tumors after antibody-mediated depletion of CD8 T cells (aCD8) or depletion of NK/ILCs using an anti-NK1.1 antibody (aNK1.1). FIG. 3C shows survival of wild type (WT) or Perforin-deficient (Prf1 KO) mice bearing IFNGR knockout Res 499 tumors after treatment with anti-CTLA4 (aCTLA4) or control (Cont). FIG. 3D shows survival of mice bearing IFNGR knockout Res 499 tumors with or without concurrent B2M knockout after treatment with anti-CTLA4 (aCTLA4) or control (Cont). Effect of antibody-mediated depletion with anti-CD8 or anti-NK1.1 is shown. FIG. 3E shows in vitro NK-mediated cytotoxicity of Res 499 cells with B2M or IFNGR knockout after pre-treating tumor cells with IFNG prior to co-culture. CD107a expression by NK cells was used as a surrogate for engagement of cytotoxic function. FIG. 3F shows proportion of mature CD27⁻ CD11b+ NK/ILCs in Res 499 tumors after knockout of tumor IFNGR or FIG. 3G shows CD8 T cell depletion (aCD8). Representative flow cytometry contour plots are shown.

FIG. 4C shows fold-increase of CD8 T cells in PD1+Eomes+$T_{ex}$ clusters that show high expression of GzmB and Ki67 or (FIG. 4D) proportion of NK/ILCs that belong to CD11b$^{int/high}$ clusters in control untreated tumors (Cont) or after anti-CTLA4 (aCTLA4). Both wild type (WT) and IFNGR knockout (KO) Res 499 tumors were examined. FIG. 4E is a series of contour plots showing the distribution of CD8 T cells or NK/ILCs in wildtype or IFNGR knockout Res 499 tumors treated with or without anti-CTLA4. Contour plots are overlaid onto a tSNE map representing all CD8 T cell or NK/ILC clusters, as indicated. For CD8 T cells, clusters for PD1+Eomes+$T_{ex}$ with low or high expression of GzmB and Ki67 are color-coded. For NK/ILCs, clusters enriched for CD11b$^{int}$ cells or CD11b$^{high}$ PD1+TRAIL+ cells are color-coded. FIG. 4F is a series of contour plots showing the distribution of CD8 T cells after anti-CTLA4 or of NK/ILCs at baseline in either wildtype or IFNGR knockout Res 499 tumors. Individual cells corresponding to the contour plot are overlaid and colored according to the scaled MFI of the indicated markers.

FIG. 5A shows intracellular IFNG expression in tumor-infiltrating CD44+PD1+CD8+ T cells. FIG. 5B shows intratumoral IFNG protein levels from wild type or IFNGR knockout Res 499 tumors treated with or without anti-CTLA4. Effect of antibody-mediated CD8 T cell depletion (aCD8) on IFNG levels was also examined. Intratumoral IL-6 levels is shown for comparison. FIG. 5C shows mice bearing IFNGR knockout Res 499 tumors were depleted of CD8 T cells followed by intratumoral injection of PBS or the indicated cytokine. Shown is the percentage of intratumoral CD8 T cells and NK/ILCs. FIG. 5D shows survival of CD8 T cell-depleted mice after treatment with anti-CTLA4 with or without intratumoral injection of IFNG. Control and anti-NK1.1 treated mice to concurrently deplete NK/ILCs are also shown. FIG. 5E shows wild type or IFN-deficient CD8 T cells were adoptively transferred into RAG1 knockout mice. Shown is survival after implantation of IFNGR knockout Res 499 tumors and treatment with anti-CTLA4. FIG. 5F shows OT-1 mice bearing Res 499 tumors with combined IFNGR and B2M knockout were treated with anti-CTLA4 with or without intratumoral injection of OVA peptide. Wild type mice with or without CD8 T cell depletion were used as comparison. FIG. 5G shows tumor infiltration by CD8 T cells and NK/ILCs. FIG. 5H shows growth of IFNGR/B2M knockout Res 499 tumors.

FIG. 6C shows survival after anti-CTLA4 of mice bearing IFNGR knockout Res 499 tumors with or without concurrent knockout of TRAILR2. FIG. 6D shows survival benefit from anti-CTLA4 conferred by IFNGR knockout in Res 499 tumors. Shown are hazard ratios and standard errors for wild type tumors, tumors with ectopic expression of PDL1 (PDL1 hi), or concurrent knockout of B2M. FIG. 6E shows NK/ILC-dependent survival of mice bearing Res 499 tumors with concurrent knockout of PDL1 after treatment with anti-CTLA4. FIG. 6F shows effect of high constitutive PDL1 expression on NK/ILC-mediated response of Res 499 IFNGR knockout tumors after anti-CTLA4 (aC4). Schema showing CD8 T cell and NK/ILC depletion and restoration of NK/ILC function with intratumoral IFNG. Shown are tumor volumes relative to initial control tumor volume (V/Vi). FIG. 6G shows in vitro NK cell killing of Res 499 IFNGR knockout tumor cells with or without constitutive ectopic PDL1 expression. Both CD49a+PD1+ and CD49b+ PD1 populations were tested. Shown are relative proportions of CD107a+NK cells. For each biological replicate, data are normalized to results from Res 499 IFNGR knockout cells cultured with CD49a+PD1+NK cells. FIG. 6H shows tumor growth of Res 499 IFNGR knockout tumors implanted into wild type or FoxP3− DTR mice treated with anti-CTLA4 or diptheria toxin (DT). FIG. 6I shows top predictive features from a random forest model for proportion of activated NK cells in human melanoma tumors after anti-PD1 as a function of other CIBERSORT-inferred intratumoral immune populations. Top features were selected based on importance score and effect size.

FIGS. 7A-7I illustrate the finding that tumor mutations in IFN pathway genes predict decreased PDL1 but improved response and survival of lung cancer patients after anti-CTLA4 and anti-PD1. FIG. 7A shows predicted pathogenic non-synonymous variants in one of 11 core IFN pathway genes (IFN Path) from 75 NSCLC tumors. Variant type is indicated by color. Shown are scores from CADD and DANN, which predict deleterious missense/nonsense variants based on machine/deep learning approaches, and scores from GERP, which infers significance based on evolutionary conservation. Optimal cut points for classification as a pathogenic missense/nonsense variant (dashed line) is determined by ROC accuracy using benign vs. pathogenic variants from ClinVar. Missense/nonsense variants were selected as pathogenic if scores for any of the three methods exceeded the cut points. The mean value for benign ClinVar variants is shown (solid line). Frameshift indels were classified as deleterious based on SIFT. Shown are the associated SIFT confidence scores. FIG. 7B shows progression-free survival (PFS) of non-small cell lung cancer patients treated with anti-CTLA4 and anti-PD1 stratified according to the presence of cancer-associated non-synonymous variants (nsVar) in IFN pathway genes. FIG. 7C shows variable importance scores from a multivariable random forest model for clinical response (unbiased error rate of 30.1%). FIG. 7D shows clinical features associated with IFN pathway variants (bottom plot) and response (top plot). The mean/median values from IFN pathway variant positive and negative patients for each feature is indicated by dashed lines. For each variant, the predicted probability of response and observed response is shown on the top plot. Observed best overall response is color-coded (NE is nonevaluable). On the bottom plot, tumor variant allele frequency (VAF) is represented by circle size. FIG. 7E is a boxplot of % PDL1 staining for IFN pathway variant positive vs. negative patients. The best overall response to dual ICB for each patient is color coded. FIG. 7F is a model for how the opposing roles of IFN signaling in immune and tumor cells can regulate and predict ICB response in neoantigen high or low tumors. ISG levels and the primary mechanism of tumor killing upon blocking tumor IFNG signaling are boxed. In neoantigen depleted tumors, blocking IFNGR unleashes a feed-forward mechanism leading to NK/ILC-mediated killing. FIG. 7G illustrates a gene set enrichment analysis (GSEA) of ISG.RS genes comparing TCGA NSCLC patients with and without a predicted pathogenic variant in the IFN pathway (IFN Path Var). FIG. 7H illustrates odds ratios for response (with 95% confidence intervals) from multivariable logistic regression. FIG. 7I illustrates response (top plot), clinical features (middle two plots), and variant allele frequency (VAF; bottom plot) of tumors with IFN Path Vars. The mean/median values are indicated by dashed lines. Top plot shows predicted probability of response (from logistic regression) and observed best overall response (NE is nonevaluable).

FIGS. 8A-8D illustrate ISGs and immune cell populations expressed in human melanoma. FIG. 8A is a set of boxplots of ISG metagene expression in immune cell populations determined by single-cell RNA-seq of human melanoma. The width of the boxplots for the indicated cell types are proportional to the population size (of note, immune and cancer cells were sorted before sequencing). P-values for comparisons between cancer cells and each immune population are p<0.0001. FIG. 8B illustrates gene set enrichment analysis of cancer and resistance-associated ISGs (ISG.RS) and IFNG-related ISGs (IFNG.GS) in melanoma patient who fail to respond to anti-PD1. Shown are enrichment plots along with the normalized enrichment score (NES) and p-value. The leading edge for the ISG.RS is labeled. FIG. 8C shows relative frequencies of immune populations in the melanoma tumors inferred by CIBERSORT. For immune cell types with both resting and activated populations, the difference between activated and resting was used. FIG. 8D shows statistical interaction between immune cell types and the ISG.RS. Relative frequencies of intratumoral immune populations inferred by CIBERSORT were included in a random forest model for clinical response along with TMB, IFNG.GS, and the ISG.RS. Shown are the frequencies that each variable was selected based on minimal depth after bootstrap resampling (x-axis) versus the strength of the interaction with the ISG.RS (y-axis) as determined by the maximal subtree method. Circle size is proportional to the variable importance as measured by minimal depth. Grey circles are control variables.

FIG. 9A shows knockout of IFNGR in CT26 cells. IFNGR deficiency was confirmed by examining PDL1 expression after stimulation with IFNG. FIG. 9B shows constitutive and IFNG-inducible expression of MHC-I on B16. FIG. 9C shows expression of human CD19 on B16 cells. FIG. 9D shows survival of mice bearing Res 499 tumors with or without IFNAR and/or IFNGR knockout after treatment with anti-CTLA4+/− radiation. FIG. 9E shows survival after tumor rechallenge of mice with initial complete responses to anti-CTLA4+/− radiation. Res 499 cells with IFNGR knockout were used for both initial transplantation and rechallenge.

FIGS. 10A-10F illustrate immune cell requirements for response after IFNGR knockout. FIG. 10A show representative density plots of tumor infiltrating CD45+ lymphoid cells that are either NK1.1+ or CD8+ after control (top) or depletion with anti-NK1.1 (bottom left) or anti-CD8 (bottom right). FIG. 10B shows baseline and IFNG-inducible MHC-I expression on TSA/Res 237 breast cancer cells. FIG. 10C shows knockout of IFNGR in TSA/Res 237 cells. IFNGR deficiency was confirmed by examining PDL1 expression after stimulation with IFNG. FIG. 10D shows representative density plots of CD3⁻ NKp46+ intratumoral immune cells after control and depletion with anti-Asialo-GM1. FIG. 10E shows survival of mice bearing TSA/Res 237 tumors with IFNGR knockout after anti-CTLA4. Prior depletion of CD8 T cells or NK/ILCs with either anti-CD8 (aCD8) or anit-Asialo-GM1 (aAGM), respectively, is indicated. FIG. 10F shows baseline and IFNG-inducible expression of MHC-I and PDL1 on Res 499 cells with or without knockout of IFNGR and/or B2M.

FIG. 12A shows representative scatter plots for the frequency of peripheral CD8 and CD4 T cells after adoptive transfer of T cells from either wild type or IFNG-deficient mice into RAG1 knockout hosts. The plot on the far left is from a wild type mouse and is shown for comparison. Percentages relative to CD45+ cells are indicated. FIG. 12B shows the percentage of peripheral CD4 and CD8 T cells after adoptive transfer for all mice are shown. Values from the same mouse are connected.

FIG. 13A shows knockout of TRAILR2 and IFNGR in Res 499 cells. Baseline and IFNG-inducible expression of the indicated surface markers are shown. FIG. 13B shows constitutive high-level expression of PDL1 in Res 499 cells with or without IFNGR knockout. Expression of the indicated surface markers are shown with or without addition of IFNG. FIG. 13C shows expression of PD1 on CD49b⁻ CD49a+ or CD49b+CD49a⁻ liver NK cells. FIG. 13D shows survival of mice bearing Res 499 IFNGR knockout tumors treated with either a Treg-depleting or non-depleting anti-CTLA4 antibody.

FIG. 14A shows predicted pathogenic non-synonymous variants in one of 11 core IFN pathway genes (IFN Path) from 710 NSCLC tumors from TCGA. Variant type is indicated by color. Shown are scores from CADD and DANN, which predict deleterious missense/nonsense variants based on machine/deep learning approaches, and scores from GERP, which infers significance based on evolutionary conservation. Optimal cut points for classification as a pathogenic missense/nonsense variant (dashed line) is determined by ROC accuracy using benign vs. pathogenic variants from ClinVar. Missense/nonsense variants were selected as pathogenic if scores for any of the three methods exceeded the cut points. The mean value for benign ClinVar variants is shown (solid line). Frameshift indels were classified as deleterious based on SIFT. Shown are the associated SIFT confidence scores. SIFT information for two indels was not available. On the bottom plot, tumor variant allele frequency (VAF) is represented by circle size. FIG. 14B shows univariate hazard ratios and p-values for progression-free survival of NSCLC patients stratified by random variants. Patients were stratified by the presence or absence of a variant in at least one of 11 random genes. Density plots show results from 10,000 bootstrap samples. Dashed lines represent observed values from IFN pathway variant positive patients. The frequency of bootstrap samples that exceed these observed values is indicated. FIG. 14C is a set of boxplots showing predicted out-of-bag response rate and TMB for IFN pathway variant positive vs. negative patients. The best overall response to dual ICB for each patient is color coded. FIG. 14D shows odds ratio for response to dual ICB as determined by multivariable logistic regression. Odds ratios and standard errors are for % PDL1>1%, log 10 value for TMB, and IFN pathway variant status. The bootstrap p-value for each variable is shown. FIG. 14E shows percent PDL1 for NSCLC patients stratified by random variants. Patients were stratified by the presence or absence of a variant in at least one of 11 random genes. Density plots show results from 10,000 bootstrap samples. Dashed lines represent observed values from IFN pathway variant positive patients. The frequency of bootstrap samples that exceed these observed values is indicated. FIG. 14F illustrate CADD and DANN, which predict deleterious missense/nonsense variants, were used on ClinVar data to classify benign vs. pathogenic missense/nonsense variants. Shown is the ROC accuracy as a function of algorithm score. The cut point giving the highest accuracy (dashed line) is shown. FIG. 14G illustrate expression of IFNG.GS across TCGA patients. The IFN Path Var status is shown above the heatmap. FIG. 14H illustrates survival of TCGA NSCLC patients stratified by IFN Path Var status. FIG. 14I shows variable importance scores (left plot) from a multivariable random forest model for clinical response to anti-CTLA4+anti-PD1 (unbiased error rate of 30.1%) and predicted out-of-bag (OOB) probability of response (right plot). GOB predicted probabilities are from samples not used to generate the model. Actual observed response is color-coded.

FIG. 17 illustrates the finding that low ISGs in cancer cells and high ISGs in immune cells favor anti-PD1 response.

FIG. 18A illustrates survival of mice bearing CT26 tumors with KO of IFNGR[+/−] B2M or of both IFNGR and IFNAR (IFNA/GR) after no treatment (Cont), CD8 depletion (aCD8), or anti-PD1

(aPD1). For each group, n=5-15. FIG. 18B illustrates survival (top) and tumor volumes (bottom) after treatment with RT+anti-CTLA4 or control (Cont) for mice bearing B16 or Res 499 tumors with the indicated KO. Unless indicated, displayed p-values are for comparisons within each genotype (legend). For tumor volumes, only groups of interest are shown. Groups with no depletion: WT, n=20-28; IFNA/GR KO, n=10-20; IFNA/GR+B2M KO, n=4-5. For aNK1.1 groups, n=5. FIG. 18C illustrates tumor volumes for B16 and Res 499 tumors expressing human CD19 (hCD19) with or without IFNA/GR KO after a single infusion with primary murine T cells transduced with a CAR (CART) against hCD19. FIG. 18D illustrates survival of mice bearing IFNGR KO Res 499 tumors with or without concurrent B2M KO after treatment with anti-CTLA4. Effect of immune cell depletion with anti-CD8 or anti-NK1.1 is shown. IFNGR KO, n=5; B2M KO, n=5; IFNGR+B2M KO, n=10-20. FIG. 18E illustrates tumor growth of B16 and Res 499 tumors expressing human CD19 with (IFNA/GR KO) and without (Cont) concurrent IFNGR+IFNAR knockout. FIG. 18F illustrates survival after tumor rechallenge of mice with initial complete responses to anti-CTLA4 (n=7). Res 499 cells with IFNGR knockout were used for both initial transplantation and rechallenge. FIG. 18G illustrates in vitro NK-mediated cytotoxicity of Res 499 cells with B2M or IFNGR knockout after pre-treating tumor cells with IFNG prior to co-culture. CD107a expression by NK cells was used as a surrogate for engagement of cytotoxic function. FIG. 18H illustrates the median (dot) and the 25th and 75th percentile survival of mice bearing IFNGR knockout Res 499 tumors following treatment with anti-CTLA4 (aCTLA4) or control (Cont). Shown are effects of NK/ILC1 depletion with an anti-NK1.1 antibody (aNK1.1) and of CD4 or CD8 T cell depletion with an anti-CD4 (aCD4) or anti-CD8 antibody (aCD8).

FIGS. 19A-19I illustrate blockade of tumor IFNG signaling promotes CD8 Tex expansion, IFNG production, immune cell IFNG signaling, and maturation of NK and PD1 TRAIL[+] ILC1 cells. CD45[+] immune cells from Res 499 tumors with or without IFNGR KO were profiled by scRNA-seq. FIG. 19A shows a tSNE plot with identified immune populations (left) and corresponding density plots (right). The percent of CD8 T cells is 6.4% and 16.8% in wild type (WT) and IFNGR KO tumors, respectively. FIG. 19B illustrates GSEA on CD8 T cell clusters using T cell terminal exhaustion and progenitor exhaustion gene sets. FIG. 19C illustrates intratumoral IFNG protein levels from wild type or IFNGR KO Res 499 tumors treated with or without anti-CTLA4. Effect of CD8 T cell depletion (aCD8) is also shown. FIGS. 19D-19E illustrate expression of IFNG.GS (FIG. 19D) or average expression of Cxcl9 and Cxcl10 (FIG. 19E) across intratumoral immune cells from wildtype or IFNGR KO tumors overlaid on the tSNE map shown in FIG. 19A. FIG. 19F illustrates NK1.1[+] and NKp46[+] NK cell clusters from FIG. 19A re-clustered. Shown is a tSNE plot with identified NK and ILC1 populations (left) and corresponding density plots (right). FIG. 19G illustrates the average expression of select NK/ILC1 genes for each of the indicated NK or ILC1 maturation stages. FIG. 19H illustrates CD8 T cells and NK/ILC1 populations identified by 28-color flow cytometry. Shown is ratio of PD1[+] Eomes[+] CD8 Tex that belong to Ki67[+] GzmB[+] clusters over total PD1[+] Eomes[+] CD8 Tex (left) or the proportion of CD11b[hi] NK and PD1+ TRAIL+ILC1 cells relative to total NK/ILC1s (right). FIG. 19I shows density plots of NK/ILC1 clusters and expression of indicated markers overlaid onto a tSNE plot. Points are colored by scaled MFI and overlaid with a contour plot. Clusters 3, 9, 10, and 11 are CD11b$^{hi}$ NK cells, and cluster 4 is PD1$^{+}$ TRAIL+ILC1 cells.

FIG. 20A is a series of violin plots showing expression of the indicated genes in CD8 T cells from Res 499 wild type (WT) or IFNGR knockout (KO) tumors. FIG. 20B illustrates intracellular IFNG expression in tumor-infiltrating CD44$^{+}$ PD1$^{+}$ CD8$^{+}$ T cells from wild type or IFNGR knockout Res 499 tumors. FIG. 20C illustrates intratumoral IL6 protein levels from wild type or IFNGR knockout Res 499 tumors treated with or without anti-CTLA4. Effect of antibody-mediated CD8 T cell depletion (aCD8) on IL6 levels was also examined. FIG. 20D depicts a GSEA comparing ILC1 cluster to other NK cell clusters using genes increased or decreased in ILC1s relative to conventional NK cells. FIG. 20E illustrates dimensionality reduction and cluster identification performed on TCRB+CD8+ T cells or TCRB$^{-}$ NK1.1+NK/ILC1s. Shown are heatmaps of the scaled MFI for each of the indicated markers across the identified clusters (labels below heatmap). For CD8 T cells, clusters representing PD1$^{+}$ Eomes+T$_{ex}$ are denoted with an *. For NK/ILC1s, clusters denoted with an * indicate CD11b$^{high}$ innate immune cells. FIG. 20F is a series of contour plots showing the distribution of CD8 T cells after anti-CTLA4 (top) or of NK/ILC1s at baseline (bottom) in either wildtype or IFNGR knockout Res 499 tumors. Individual cells corresponding to the contour plot are overlaid and colored by the scaled MFI of the indicated marker. FIG. 20G shows density plots of CD8 T cells or NK/ILC1s in wildtype or IFNGR knockout Res 499 tumors treated with or without anti-CTLA4. The left plot is a tSNE map. For CD8 T cells, clusters for PD1+Eomes+T$_{ex}$ with low or high expression of GzmB and Ki67 are color-coded and numbered. For NK/ILC1s, clusters enriched for CD11b$^{high}$ NK cells or PD1$^{+}$ TRAIL$^{+}$ ILC1 cells are color-coded and numbered. The cluster numbers correspond to the cluster labels shown in the heatmap from FIG. 20E.

FIGS. 21A-21I illustrate regulatory roles for IFNG, PD1/PDL1, and TRAIL/TRAILR2 after tumor IFNGR knockout. FIG. 21A Representative scatter plots for the percent of peripheral CD8 and CD4 T cells after adoptive transfer of T cells from either wild type or IFNG-deficient mice into Rag1 knockout hosts. The plot on the far left is from a wild type mouse and is shown for comparison. Percentages relative to CD45+ cells are indicated. The percentage of peripheral CD4 and CD8 T cells after adoptive transfer for all mice are also shown (right plot). Values from the same mouse are connected. FIG. 21B Proportion of mature CD27$^{-}$ CD11b+ NK/ILC1s in Res 499 tumors after CD8 T cell depletion (aCD8). Representative flow cytometry contour plots are shown. FIG. 21C Survival of CD8 T cell-depleted mice after treatment with anti-CTLA4 with or without intratumoral injection of IFNG. Effect of anti-NK1.1 treatment to deplete NK/ILC1s is also shown. For each group, n=5. FIG. 21D Expression of ectopic PDL1 and baseline or IFNG-induced MHC-I in Res 499 cells with or without IFNGR knockout. FIG. 21E Survival benefit from anti-CTLA4 conferred by IFNGR knockout in Res 499 tumors. Shown are hazard ratios and standard errors for wild type tumors, tumors with ectopic expression of PDL1 (PDLhi), or concurrent knockout of B2M. FIG. 21F Expression of PD1 on CD49b$^{-}$ CD49a+ or CD49b+CD49a$^{-}$ liver NK cells. FIG. 21G In vitro TRAIL receptor (TRAILR2) expression after IFNG treatment on Res 499 cells with or without IFNGR knockout. FIG. 21H Expression of TRAILR2, MHC-I, and PDL1 in Res 499 cells with or without concurrent knockout of TRAILR2 and IFNGR. Baseline and IFNG-inducible expression are shown. FIG. 21I illustrates in vivo TRAILR2 and PDL1 expression on Res 499 tumors with or without IFNGR KO.

FIGS. 22A-22D illustrate the role of T$_{reg}$ depletion in response after tumor IFNGR knockout. FIG. 22A depicts proliferation status of T$_{regs}$ and other intratumoral immune cells in control (WT) or Res 499 IFNGR KO tumors measured by average expression of Ki67 and Top2a. FIG. 22B illustrates survival of mice bearing Res 499 IFNGR knockout tumors treated with either a T$_{reg}$-depleting (9H10) or non-depleting (4F10) anti-CTLA4 antibody. For each group, n=5. FIG. 22C illustrates expression of MHC-I on CT26 cells after IFNGR+B2M double knockout. FIG. 22D illustrates survival of mice bearing CT26 tumors with IFNGR+/−B2M KO after treatment with anti-PD1 or anti-CTLA4. For all groups, n=5.

FIG. 23 is a table listing ISG.RS and IFN.GS genes.

FIG. 24 is a table listing marker genes used for identifying intratumoral immune cell clusters in single-cell RNA-sequencing data.

FIG. 25A shows GSEA of sorted Res499 Ifnar knockout vs Res499 Ifngr knockout tumor cells using ISG.RS genes. FIG. 25P shows averaged percentage of cells in macrophage subsets by condition.

FIGS. 26A-26O illustrate sensitization of Ifnar knockout to aPD1 is dependent on CD8 T cells and DCs. FIGS. 26A-26B illustrate day 15 tumor volumes of Res499 Ifnar knockout cell lines treated with or without aPD1, depleted with or without aCD8 or aNK1.1 antibody (FIG. 26A) and survival of mice (FIG. 26B) (n=7-15). FIG. 26C illustrates day 15 tumor volumes of Res499 Ifnar knockout cell line injected in WT or Perforin knockout mice treated with aPD1 (n=4 for Prf−/− and 9 for WT). FIG. 26D illustrates survival of mice injected with Res499 Ifnar knockout cell line injected in WT or Perforin knockout mice treated with or without aPD1 (n=2-4). FIG. 26E illustrates survival of mice injected with Res499 Ifnar/B2m double knockout cell line treated with or without aPD1 (n=5). FIG. 26O illustrates expression of Cd86, Cd40 and Tap1 in dendritic cells subsetted on CD45+ single cells by condition.

FIGS. 27A-27J illustrate the quality of TCR in CD8 T cells from Ifnar knockout tumors differs from that in Res499 control tumors. FIG. 27A shows Nr4a1 (Nur77) expression of single CD8 T cells across phenotype clusters by condition. FIG. 27B shows UMAP of CDR3 clusters as determined by amino acid properties from scTCR-seq TCRα and TCRβ pairs. FIG. 27C illustrates the random forest error rate of each CDR3 clusters classifying TCR coming from WT or Ifnar knockout tumors. FIG. 27D shows UMAP of CDR3 clusters that are predicted to recognize Trp2 arranged by conditions and phenotype clusters overlaid with number of clones. Box indicates CDR3 cluster 2. FIG. 27E shows the distribution of expanded TCR clones across CDR3 clusters as grouped by phenotype clusters across conditions. FIG. 27F shows a UMAP of CD8 T cell subsets. FIG. 27G shows the distribution of phenotype clusters in CD8 T cells from each condition. FIG. 27H is a heatmap of normalized expression of selected markers across CD8 T cell subsets. FIG. 27I shows the percentage of Trp2. Dashed line indicates the average number sampled against a known Trp2 library. FIGS. 27J-27K show GSEA of CDR3 cluster 2 from Ifnar knockout treated tumors vs CDR3 cluster 4 from Res499 control treated tumors using terminal exhausted signature (FIG. 27J) and Hallmark IFN gamma signature FIG. 27K.

FIGS. 29A-29B illustrate the clinical trial Study Flow Chart.

FIG. 30 is a table illustrating the details regarding specific laboratory procedures/assessments performed in the clinical trial.

DETAILED DESCRIPTION

Definitions

Figure 1A:
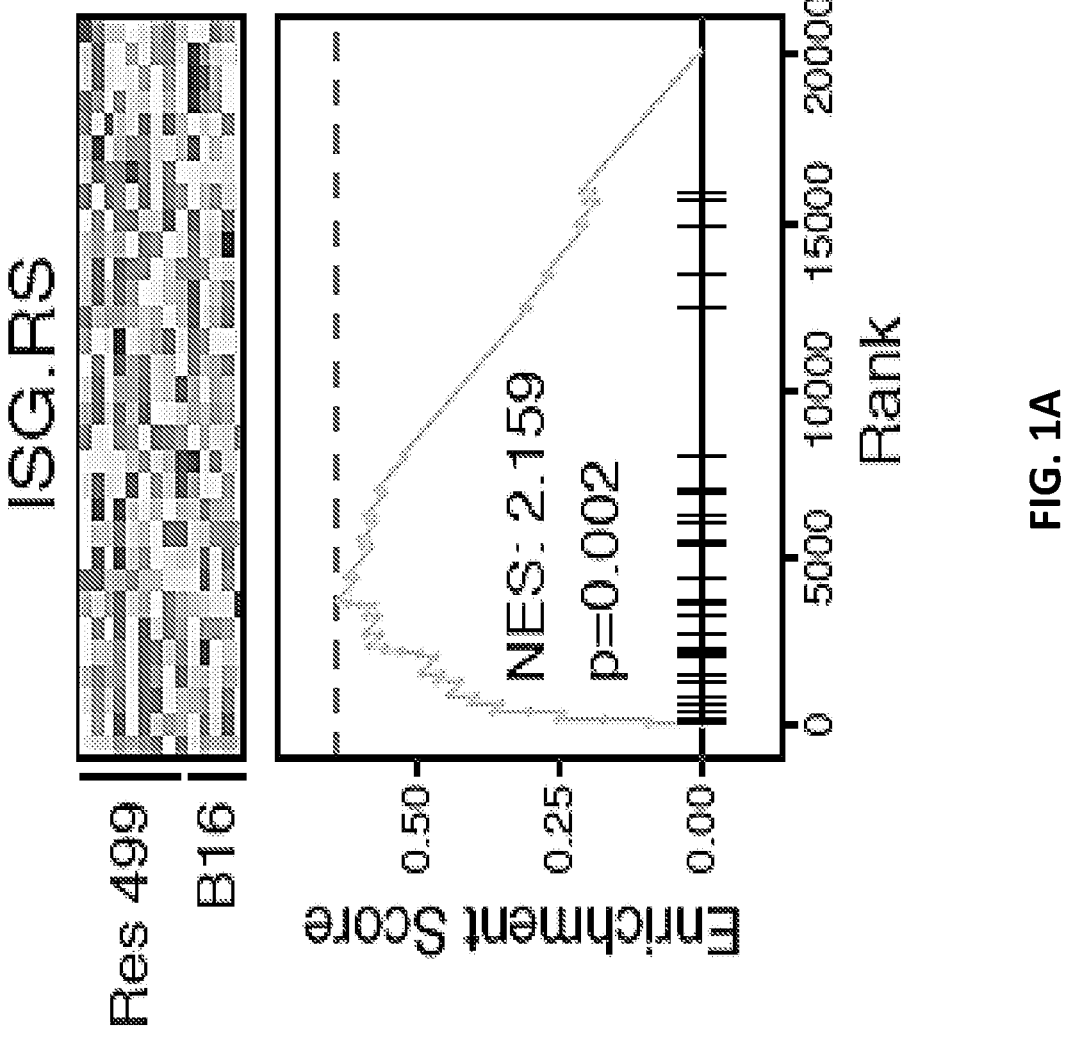

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species.

"Xenogeneic" refers to any material derived from an animal of a different species.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs has specificity to a selected target, for example a B cell surface receptor. CARs may also comprise an intracellular activation domain, a transmembrane domain and an extracellular domain comprising a tumor associated antigen binding region. In some aspects, CARs comprise an extracellular domain comprising an anti-B cell binding domain fused to CD3-zeta transmembrane and intracellular domain The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

The term "immune response" as used herein is defined as a cellular response to an antigen that occurs when lymphocytes identify antigenic molecules as foreign and induce the formation of antibodies and/or activate lymphocytes to remove the antigen.

"Ifnar" refers to the interferon-α/β receptor, which binds type I interferons including interferon-α and -β. It is a heteromeric cell surface receptor composed of one chain with two subunits referred to as IFNAR1 and IFNAR2. Upon binding of type I IFNs, IFNAR activates the JAK-STAT signaling pathway. Type I IFNs share a common receptor consisting of two subunits, IFNAR1 and IFNAR2, which associate upon IFN binding. IFNAR2 is the major ligand binding component of the receptor complex, exhibiting nanomolar affinity to both IFNα and IFNβ subtypes. IFNAR1 and IFNAR2 belong to the class II helical cytokine receptor (hCR) family.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides methods for treating cancer and selecting a patient for immunotherapy administration.

In this study, the molecular and cellular mechanisms for how tumor IFN signaling governs ICB response and resistance was investigated. In particular, given the opposing roles of IFN signaling in anti-tumor immunity, an important goal was to gain insight into whether distinct ISGs could represent either immune stimulatory or inhibitory functions of IFN and whether differentiating these orthogonal ISGs could improve prediction of clinical ICB response. By computationally modeling both the impact of these ISGs on clinical response and their interactions with other variables, mechanistic underpinnings of the statistical findings—namely, how IFN signaling dichotomously controls ICB efficacy, and whether blocking tumor IFN signaling can improve response despite MHC-I and neoantigen status were investigated.

Interferon-gamma augments immune cell functions and MHC-I yet promotes T cell exhaustion through inhibitory pathways like PDL1. How these opposing functions are integrated to broadly impact immune checkpoint blockade (ICB) is unclear. Herein it was demonstrated that blocking tumor IFNG signaling promotes ICB response in neoantigen high and low tumors. Inhibiting tumor IFNG signaling reactivates exhausted T cells ($T_{ex}$) to improve cytolytic potential and IFNG production. In tumors with favorable antigenicity, these T cells mediate rejection. In tumors with neoantigen depletion or MHC-I loss, reactivated $T_{ex}$ instead generate IFNG to drive maturation of NK and innate lymphoid cells (ILCs), including a PD1+ TRAIL+ILC1-like subset. Decreased PDL1 from blocking tumor IFNG signaling then enables TRAIL-dependent NK/ILC killing, especially when Tregs are inhibited. In melanoma patients, deconvoluting the opposing functions of IFN improves ICB prediction. In lung cancer, IFN pathway mutations correlate with response. In both cancers, these clinical associations are independent of mutational burden.

Additionally, it was discovered that the ISG.RS to IFNG.GS ratio can be used as a predictor of response to ICB and altering this ratio in a favorable or unfavorable manner can affect a patients outcome.
Methods
Certain aspects of the invention include methods for treating cancer in a subject in need thereof. In certain embodiments, the method comprises measuring the expression level of a panel of interferon stimulating genes (ISGs) in a cancer cell from the subject and measuring the expression level of the same panel of ISGs in an immune cell from the subject. The panel of ISGs comprises a first subpanel of ISGs and a second subpanel of ISGs. The first subpanel of ISGs comprises an ISG resistance signature (ISG.RS) and the second subpanel of ISGs comprises an interferon gene signature (IFNG.GS). When the expression level of the IFNG.GS is greater than the expression level of the ISG.RS, then the subject is administered an immunotherapy. When the expression level of the ISG.RS is greater than the expression level of the IFNG.GS, then the subject is not administered an immunotherapy, and an alternative treatment is administered to the subject. Thereby the cancer is treated in the subject.

In certain embodiments, the method comprises measuring the expression level of a panel of interferon stimulating genes (ISGs) in a cancer cell from the subject and measuring the expression level of the same panel of ISGs in an immune cell from the subject, wherein the panel of ISGs comprises a first subpanel of ISGs and a second subpanel of ISGs. The first subpanel of ISGs comprises an ISG resistance signature (ISG.RS) and the second subpanel of ISGs comprises an interferon gene signature (IFNG.GS). The ratio of the expression level of the IFNG.GS over the expression level of the ISG.RS is measured. When the ratio is increased in comparison to a reference sample, then the subject is administered an immunotherapy. When the ratio is not increased in comparison to a reference sample, then the subject is not administered an immunotherapy, and an alternative treatment is administered to the subject. Thereby, the cancer is treated in the subject. An examples of a reference sample that may be used includes, but is not limited to, a predefined value for the ratio determined by an appropriate training set (e.g., same cancer type as test subject matched for stage, treatment, and other clinical/pathological features) to give a positive and negative predictive value (or sensitivity and specificity) appropriate for the clinical scenario. Here, appropriateness may be determined by an estimated likelihood that the immunotherapy will fail that is deemed appropriate to withhold the therapy in favor of another (e.g., 90%).

In certain embodiments, the method comprises measuring the gene expression level of a panel of interferon stimulating genes (ISGs) in a cancer cell and in an immune cell from the subject. The panel of ISGs comprises a first subpanel of ISGs and a second subpanel of ISGs. The expression level of the first subpanel of ISGs comprises an ISG resistance signature (ISG.RS). The expression level of the second subpanel of ISGs comprises an interferon gene signature (IFNG.GS). When the ISG.RS from the cancer cell is decreased in comparison to a first reference sample, and the IFNG.GS from the immune cell is increased in comparison to a second reference sample, then the subject is administered an immunotherapy, thereby treating the cancer in the subject. When the ISG.RS from the cancer cell is not decreased in comparison to a reference sample and the IFNG.GS from the immune cell is not increased in comparison to a reference sample, then the subject is not administered an immunotherapy, and an alternative treatment is administered to the subject.

Another aspect of the invention includes a method of selecting a patient for immunotherapy administration. The method comprises measuring the gene expression level of a panel of interferon stimulating genes (ISGs) in a cancer cell and in an immune cell from the subject. The panel of ISGs comprises a first subpanel of ISGs and a second subpanel of ISGs. The expression level of the first subpanel of ISGs comprises an ISG resistance signature (ISG.RS) and the expression level of the second subpanel of ISGs comprises an interferon gene signature (IFNG.GS). In certain embodiments, when the ISG.RS from the cancer cell is decreased in comparison to a first reference sample, and the IFNG.GS from the immune cell is increased in comparison to a second reference sample, then the subject is selected for immunotherapy. When the ISG.RS from the cancer cell is not decreased in comparison to a reference sample and the IFNG.GS from the immune cell is not increased in comparison to a reference sample, then the subject is not selected for immunotherapy. In some embodiments, an alternative treatment is then selected for the subject.

In certain embodiments, of the method for selecting a patient for immunotherapy administration, the expression level of the IFNG.GS and the expression level of the ISG.RS are compared. When the expression level of the IFNG.GS is greater than the expression level of the ISG.RS, then the subject is administered an immunotherapy, and when the expression level of the ISG.RS is greater than the expression level of the IFNG.GS, then the subject is not administered an immunotherapy, and an alternative treatment is administered to the subject.

In certain embodiments of the method for selecting a patient for immunotherapy administration, a ratio of the expression level of the IFNG.GS over the expression level of the ISG.RS is measured. The ratio may be compared to a reference sample and when the ratio is increased in comparison to a reference sample, then the subject is administered an immunotherapy. When the ratio is not increased in comparison to a reference sample, then the subject is not administered an immunotherapy, and an alternative treatment is administered to the subject.

In some embodiments, the panel of ISGs is a set of ISGs. In some embodiments, the subpanel of ISGs is a subset of ISGs.

In certain embodiments, the first subpanel of ISGs are selected from the group consisting of IFI27, IRF7, USP18, BST2, DDX60, HERC6, HLA-B, HLA-G, IFI35, IFI44, IFI44L, IFIT1, IFIT3, ISG15, LGALS3BP, LY6E, MX1, MX2, TRIM14, HSD17B1, OAS1, CCNA1, CXCL1, GALC, IFI6, ROBO1, SLC6A15, CXCL10, OAS3, OASL, PLSCR1, STAT1, CA2, IFITM1, LAMP3, MCL1, THBS1, TIMP3, any homologs thereof, or any highly correlated genes that may be substituted for the aforementioned. In certain embodiments, the expression level of these genes comprises an ISG resistance signature (ISG.RS).

In certain embodiments the second subpanel of ISGs are selected from the group consisting of TNFSF10, IRF9, EPSTI1, PARP12, TRIM25, CASP7, UPP1, B2M, IRF4, SRI, NFKBIA, OAS2, RSAD2, XAF1, SP110, IFITM3, GBP4, IRF8, IFIH1, UBE2L6, ADAR, STAT2, CXCL9, IL10RA, PLA2G4A, TRIM21, PTGS2, DDX58, IL15, NLRC5, NMI, IDO1, PSMB10, CXCL11, SAMD9L, RTP4, PTPN2, TNFAIP2, IFITM2, SOCS1, CASP1, ICAM1, WARS, PSME1, ISG20, FCGR1A, SOCS3, HLA-DMA, TNFAIP6, TRIM26, VCAM1, CD274, CIITA, NAMPT, GPR18, FPR1, PRIC285, PSME2, SERPING1, CCL5, RNF31, SOD2, PSMA3, RNF213, PELI1, CFB, CD86, HLA-DQA1, GCH1, PNP, CCL7, PTPN6, SPPL2A, IL4R, DHX58, CASP8, IFI30, CCL2, FGL2, SECTM1, IL15RA, CD40, HLA-DRB1, GBP6, LCP2, MT2A, RIPK1, PSMB2, TDRD7, HIF1A, PFKP, ZBP1, PDE4B, IL7, BPGM, FTSJD2, AUTS2, RIPK2, MYD88, PSMA2, NOD1, TAPBP, SLC25A28, PTPN1, SSPN, NUP93, MTH1FD2, CDKN1A, NFKB1, BATF2, LATS2, IRF5, SLAMF7, ISOC1, P2RY14, STAT3, NCOA3, GZMA, IFNAR2, CD74, RAPGEF6, CASP4, OGFR, ARL4A, LYSMD2, CSF2RB, C1R, METTL7B, ST8SIA4, CD38, PSMB9, BANK1, TOR1B, ITGB7, RBCK1, FAS, LAP3, SAMIHD1, CMPK2, MVP, TXNIP, ST3GAL5, PARP14, CASP3, IFIT2, CD69, CMKLR1, TAP1, EIF2AK2, PIM1, XCL1, IL2RB, IRF1, BTG1, CFH, VAMP5, IL18BP, IRF2, ZNFX1, PSMB8, ARID5B, MARCH1, TNFAIP3, APOL6, STAT4, JAK2, PML, TRAFD1, SELP, KLRK1, CIS, EIF4E3, HLA-A, PNPT1, VAMP8, IL6, any homologs thereof, or any highly correlated genes that may be substituted for the aforementioned. In certain embodiments, the expression level of these genes comprises an interferon gene signature (IFNG.GS).

In some embodiments, the panel of ISGs is a set of ISGs. In some embodiments, the subpanel of ISGs is a subset of ISGs.

Yet another aspect of the invention includes a method for treating cancer in a subject in need thereof comprising administering (e.g. intratumorally injecting or oral administration of) an agent capable of mutating/inhibiting/disabling/knocking out a gene in the interferon pathway. In certain embodiments, the gene is selected from the group consisting of IFNGR1, IFNGR2, IFNAR1, IFNAR2, JAK1, JAK2, TYK2, STAT1, STAT2, IRF9, and B2M. In certain embodiments, the method decrease the ISG.RS and/or increases the IFNG.GS. Any agent capable of mutating or knocking out a gene can be used, including but not limited to RNAi, CRISPR/Cas9, TALENs, Zn-finger nucleases, meganucleases, drugs, small molecule inhibitors, etc.

Still another aspect of the invention includes method of selecting a subject for immunotherapy administration. The method comprises analyzing a tumor sample from the subject. When at least one gene selected from the group consisting of IFNGR1, IFNGR2, IFNAR1, IFNAR2, JAK1, JAK2, TYK2, STAT1, STAT2, IRF9, and B2M comprises a mutation, then the patient is selected for immunotherapy. The mutation may comprise a point mutation, an insertion, a deletion, a frameshift, and/or a gene knockout. In certain embodiments, the mutation is a loss of function mutation. Gene variants may be predicted to have a loss of function using machine/deep learning methods such DANN, CADD, or SIFT.

The immunotherapy utilized in any of the methods disclosed herein can be any type of immunotherapy known in the art. In certain embodiments, the immunotherapy is selected from the group consisting of immune checkpoint blockade (ICB), anti-CTLA4, anti-PD1, anti-PDL1, adoptive cell therapy, CAR T cell therapy, TCR engineered T cell therapy, anti-TIM3, anti-LAG3, anti-2B4, anti-4-1BB, anti-GITR, anti-VISTA, anti-CD40, cGAS/STING agonists, RIG-I agonists, TLR agonists, MDA5 agonists, any agent that modulates the interferon pathway or interferon stimulated genes including but not limited to radiation, chemotherapy, molecularly targeted agents, and epigenetic therapies, and any combination thereof. The immunotherapy may comprise a single type of treatment or a combination of different treatments. In certain embodiments, the immunotherapy comprises a combination of anti-PD1 and anti-CTLA4. The immunotherapy may be given at a single time point or over multiple time points. At any given time, a single dose may be given or multiple doses may be given. If a combination of two (or more) immunotherapies are administered, the two or more immunotherapies can be administered at the same time. Alternatively, the two or more immunotherapies can be administered at different times. For example, one immunotherapy can be administered at one time point, then after a certain time period delay, a second immunotherapy can be administered.

In certain embodiments, the alternative treatment is selected from the group consisting of chemotherapy, radiation, surgery, an alternative immune checkpoint blockade (ICB) (e.g., anti-CTLA4, anti-PD1, anti-PDL1), an alternative adoptive cell therapy, an alternative immunotherapy, and any combination thereof. For example, an "alternative ICB" could be an ICB different from one originally administered. However, any suitable alternative treatment can be administered to the subject. The alternative treatment may comprise a single type of treatment or a combination of different treatments. The alternative treatment may be given at a single time point or over multiple time points. At any given time, a single dose may be given or multiple doses may be given. If a combination of two (or more) alternative treatments are administered, the two or more alternative treatments can be administered at the same time. Alternatively, the two or more alternative treatments can be administered at different times. For example, one alternative treatments can be administered at one time point, then after a certain time period delay, a second alternative treatments can be administered.

The invention also includes embodiments in which an immunotherapy (one or more) is administered in combination with an alternative treatment (one or more). In certain embodiments, a subject is administered an immunotherapy (e.g. anti-PDI) then later administered an alternative treatment (e.g. JAK inhibitor). In certain embodiments, a subject is administered an alternative treatment then later administered an immunotherapy. In certain embodiments, a subject is administered an immunotherapy in combination with an alternative treatment. In certain embodiments, a combination of an immunotherapy and an alternative treatment is administered to a subject to treat cancer.

In certain embodiments, the alternative treatment comprises a treatment that increases the IFNG.GS expression level and/or decreases the ISG.RS expression level. This in turn would alter the ratio of IFNG.GS over ISG.RS (IFNG.GS/ISG.RS). Administering a treatment that alters the IFNG.GS/ISG.RS ratio may improve the response to immunotherapy in multiple ways including through both adaptive (e.g., CD8 T cell killing) and/or innate immunity (e.g., NK/ILC1 cells). Such a treatment can be any agent that modulates the interferon pathway or interferon stimulating genes. Examples of such treatments that decrease the ISG.RS include but are not limited to an IFN blocking agent, an IFN receptor blocking agent, a JAK inhibitor, a STAT inhibitor, an adoptive cell therapy, a small molecule, and any combination thereof. Examples of such treatments that can increase the IFNG.GS include but are not limited to anti-CTLA4, anti-PDL1, anti-TIM3, anti-LAG3, anti-2B4, anti-4-1BB, anti-GITR, anti-VISTA, anti-CD40, cGAS/STING agonists, RIG-I agonists, TLR agonists, MDA5 agonists, or other agents that increase the IFNG.GS including radiation, chemotherapy, molecularly targeted agents, and epigenetic therapies.

The IFNG.GS/ISG.RS ratio may serve as a means of establishing the likelihood a subject will respond to immunotherapy (e.g. ICB). For example, the methods disclosed herein may be used to measure the ratio pre-treatment (e.g. from a pre-treatment biopsy sample) in order to determine whether a certain immunotherapy (e.g. ICB) should be administered to a patient. Alternatively, the ratio may be used as a means to determine a subsequent treatment once the subject had already been receiving an immunotherapy. For example, if the subject is responding favorably to a particular immunotherapy (the IFNG.GS/ISG.RS ratio is high), then that immunotherapy would be continued. Alternatively if the subject is not responding favorably to a particular immunotherapy (the IFNG.GS/ISG.RS ratio is low), then an alternative treatment is administered.

Any of the methods disclosed herein may be repeated multiple times on the same subject. For example, the method may be performed on a subject before administering an immunotherapy, then performed again after a treatment (e.g.

an immunotherapy or an alternative treatment) has been given, then performed again any number of times throughout the course of treatment.

Any type of immune cell may be used in the methods disclosed herein. In certain embodiments, the immune cell is selected from the group consisting of a T cell, an NK cell, a macrophage, a monocyte, a dendritic cell, a myeloid cell, an ILC cell, and a CD8+ cell.

Gene expression levels can be measured by any method known to one of ordinary skill in the art (e.g. RNA-Seq, q-PCR, RT-PCR, sequencing, transcriptomics, microarray). Expression levels are compared to a reference sample. In certain embodiments, the first reference sample and the second reference sample are the same. In certain embodiments, the first reference sample and the second reference sample are different. In certain embodiments, the first reference sample comprises an IFNG.GS from an immune cell from the subject. In certain embodiments, the second reference sample comprises an ISG.RS from a cancer cell from the subject. In certain embodiments, the reference sample is a standardized curve.

In certain embodiments, the ISG.RS genes are selected by a method comprising creating a single feature from the expression values of ISG.RS genes by measuring the expression values of ISG.RS genes, selecting from the ISG.RS genes a subpanel of genes that are upregulated, applying a SAM statistic or similar statistic (e.g. a t-statistic or z-score), and taking the average value of all SAM statistics >0 to create a single score for each patient. The IFNG.GS genes are selected by a method comprising creating a single feature from the expression values of IFNG.GS genes by measuring the expression values of IFNG-related genes, omitting the genes that overlap with the ISG.RS genes, applying a SAM statistic or similar statistic (e.g. a t-statistic or z-score) for these remaining IFNG.GS genes, and taking the average value of all SAM statistics >0 to create a single score for each patient. A multivariable classifier is created for predicting probability of response using the ISG.RS, IFNG.GS (or a ratio comprised of the IFNG.GS and ISG.RS), and tumor mutational burden (TMB) to model clinical response using random forest machine learning and an imbalanced forest algorithm or any other multivariable statistical model (e.g., logistic regression) or univariate statistical model.

In certain embodiments, the ISG.RS genes and/or IFNG.GS genes are calculated based on the average of the scaled expression of the genes in each gene set. Weights may be assigned to the genes.

In some embodiments, gene expression for a panel or subpanel of genes may be measured in a single cell.

The SAM statistic, or Significance Analysis of Microarrays, measures the difference in average expression of gene i between states I and U, divided by the standard deviation+a constant meant to ensure that the variance is independent of gene expression. The SAM statistic is described in Tusher et al. (2001) PNAS, 99: 5116-5121, the contents of which are incorporated by reference in their entirety herein.

Cancer Therapies

The methods described herein may be used to treat cancer. The methods described herein may also improve existing cancer therapeutics to increase bioavailability and/or reduce toxicokinetics. Cancer or neoplasm includes solid or liquid cancer and includes benign or malignant tumors, and hyperplasias, including gastrointestinal cancer (such as non-metastatic or metastatic colorectal cancer, pancreatic cancer, gastric cancer, esophageal cancer, hepatocellular cancer, cholangiocellular cancer, oral cancer, lip cancer); urogenital cancer (such as hormone sensitive or hormone refractory prostate cancer, renal cell cancer, bladder cancer, penile cancer); gynecological cancer (such as ovarian cancer, cervical cancer, endometrial cancer); lung cancer (such as small-cell lung cancer and non-small-cell lung cancer); head and neck cancer (e.g. head and neck squamous cell cancer); CNS cancer including malignant glioma, astrocytomas, retinoblastomas and brain metastases; malignant mesothelioma; non-metastatic or metastatic breast cancer (e.g. hormone refractory metastatic breast cancer); skin cancer (such as malignant melanoma, basal and squamous cell skin cancers, Merkel Cell Carcinoma, lymphoma of the skin, Kaposi Sarcoma); thyroid cancer; bone and soft tissue sarcoma; and hematologic neoplasias (such as multiple myeloma, acute myelogenous leukemia, chronic myelogenous leukemia, myelodysplastic syndrome, acute lymphoblastic leukemia, Hodgkin's lymphoma). In certain embodiments, the cancer is melanoma. In certain embodiments, the cancer is breast cancer.

Administration of the immunotherapies and/or alternative treatments may be carried out in any convenient manner known to those of skill in the art. Treatment may be administered to a subject, for example, by aerosol inhalation, injection, ingestion, transfusion, implantation or transplantation, transarterially, subcutaneously, intradermally, intratumorally, intranodally, intramedullary, intramuscularly, by intravenous (i.v.) injection, or intraperitoneally. In other instances, treatment may be administered directly into a site of inflammation in the subject, a local disease site in the subject, a lymph node, an organ, a tumor, and the like. The optimal dosage and treatment regime for a particular subject can readily be determined by one skilled in the art of medicine by monitoring the subject for signs of disease and adjusting the treatment accordingly. Administration of the immunotherapy or alternative treatment may be combined with other methods/compositions useful to treat the desired disease or condition as determined by those of skill in the art.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described.

Mice: Five to seven week old C57BL/6 (stock #027) and BALB/c (stock #28) were obtained from Charles River Laboratory. Five to seven week old female C57BL/6 (stock #000664), Perforin knockout (C57BL/6-Prf1$^{tm1sdz}$/J; stock #002407), IFNG knockout (B6.129SJ-Ifng$^{tm1Ts}$/J; stock #002287), RAG1 knockout (B6.129S7-Rag1$^{tm1Mom}$/J; stock #002216), OT1 (C57BL/6-Tg(TcraTcrb)1100Mjb/J; stock #003831), FoxP3-DTR (B6.129(Cg)-Foxp3$^{tm3(DTR/GFP)Ayr}$/J; stock #016958) were ordered from Jackson Laboratory (Bar Harbor, ME). Mice were maintained under pathogen free conditions.

Cell Lines: B16-F10 melanoma cells, TSA breast cancer cells, and resistant sublines were derived and cultured as previously described (Twyman-Saint Victor et al., (2015) Nature 520, 373-377). CT26 colorectal cancer cell lines were purchased from ATCC and similarly cultured.

CRISPR gene targeting: Gene targeting by CRISPR/Cas9 was accomplished by co-transfection of a Cas9 plasmid (Addgene, 41815), the guide sequence (selected using ZiFit Targeter) cloned into the gBlock plasmid, and a plasmid with the puromycin selection marker. Gene blocks used contained a 20 bp target size (N), U6 promoter, gRNA scaffold, and termination signal. The common gene block sequence is:

(SEQ ID NO: 1)
```
TGTACAAAAAAGCAGGCTTTAAAGGAACCAATTCAGTCGACTGGATCCG

GTACCAAGGTCGGGCAGGAAGAGGGCCTATTTCCCATGATTCCTTCATA

TTTGCATATACGATACAAGGCTGTTAGAGAGATAATTAGAATTAATTTG

ACTGTAAACACAAAGATATTAGTACAAAATACGTGACGTAGAAAGTAAT

AATTTCTTGGGTAGTTTGCAGTTTTAAAATTATGTTTTAAAATGGACTA

TCATATGCTTACCGTAACTTGAAAGTATTTCGATTTCTTGGCTTTATAT

ATCTTGTGGAAAGGACGAAACACCGNNNNNNNNNNNNNNNNNNNNGTTTT

AGAGCTAGAAATAGCAAGTTAAAATAAGGCTAGTCCGTTATCAACTTGA

AAAAGTGGCACCGAGTCGGTGCTTTTTTTCTAGACCCAGCTTTCTTGTA

CAAAGTTGGCATTA.
```

```
STAT1 g1:
                                    (SEQ ID NO: 2)
GACTCCAAGTTCCTGGAGCG;

STAT1 g2:
                                    (SEQ ID NO: 3)
CAGCTGGACTCCAAGTTCCG;

STAT1 g3:
                                    (SEQ ID NO: 4)
TACGATGACAGTTTCCCCAG;
```

-continued

```
B2M g1:
                                    (SEQ ID NO: 5)
GACAAGCACCAGAAAGACCA;

B2M g2:
                                    (SEQ ID NO: 6)
GTGAGTATACTTGAATTTGA;

TRAILR g1:
                                    (SEQ ID NO: 7)
GTGGGCGTGCTGGGTCCTGG;

TRAILR g2:
                                    (SEQ ID NO: 8)
ATCGTCCAGCTGGCCTACAG.
```

Successful targeting of the gene(s) of interest was determined by treating cells with and with out 100 ng/mL of interferon (IFN)-gamma (PeproTech), 1000 units/mL IFN-beta (PBL Assay Science), or both depending on the target gene, and examining PDL1, B2M, or TRAILR2 surface expression by flow cytometry. Knockout cells were sorted from a bulk knockout population using Fluorescence Activated Cell Sorting (FACS) on the Aria (BD) or FACSJazz (BD) to maintain the diversity of the parent cells.

In vivo mouse studies: Tumor injection and treatment schedule were done as previously described (Twyman-Saint Victor et al., (2015) Nature 520, 373-377). Except for some experiments to measure immune cell infiltration, both flanks were implanted. Blocking antibodies were given on days 5, 8, and 11 unless otherwise specified. Anti-CD8, anti-NK1.1, and anti-Asialo-GM1 were given on days −2, 0, 4, 8, 12, and 16. Antibodies against CTLA4 (9H10), PDL1 (10F.9G2) or PD1 (RMP1-14) were all administered intraperitoneally at 200 ug/dose. Isotype controls were used to confirm the lack of non-specific effects and a similar response and survival to untreated mice.

Whole exome sequencing: Genomic DNA was isolated and purified from tumor cell lines in vitro using Purelink Genomic DNA Kit (Fisher) and exome libraries were prepared using the SureSelectQXT Kit (Agilent) with SureSelectXT Mouse All Exon bait. Libraries were sequenced on an Illumina HiSeq 2500 with 100 base paired end reads.

Single CellSequencing Preparation: Tumors were harvested on day 17 and viable CD45+ cells were FACS sorted. Single-cell emulsions were obtained using the 10x Genomics Controller and the v2 Library and Gel Bead kit (10x Genomics). RNA-sequencing libraries were prepared as instructed by the 10x3' v2 kit protocol. Resulting libraries were sequenced on an Illumina NextSeq using a NextSeq 500/550 v2.5 High Output Kit.

Flow cytometry: Tumors were harvested at day 13-15 post tumor implantation. Single-cell suspensions were prepared and red blood cells were lysed using ACK Lysis Buffer (Life Technologies). For in vitro cell lines, untreated or sub-confluent cells treated for 16 hours with 100 ng/mL of interferon gamma (PeproTech) were harvested and single-cell suspensions prepared. Live/dead cell discrimination was performed using Live/Dead Fixable Aqua Dead Cell Stain Kit (Life Technologies). Cell surface staining was done for 30 min at 4 degrees. Intracellular staining was performed using a fixation/permeabilization kit (eBioscience). Data acquisition was done using an LSR II (BD) or FACSCalibur (BD) and analysis was performed using FlowJo (TreeStar) or the FlowCore package in the R language and environment for statistical computing. For high-dimensional flow cytometry, a FACSymphony (BD) was used for data acquisition and data analysis was done using the cytofkit R package and a custom analysis pipeline described in Quantification and Statistical Analysis. For quantitation of immune infiltration, tumors were harvested and weighed and the entire tumor section was dissociated and stained. All events were collected on a flow cytometer and the total number of events of a given immune cell type were divided by the weight of the tumor.

Intratumoral cytokine assay: Approximately 200 ug of tumor was harvested, weighed, and placed in complete RPMI media for 4 hours at 37 degrees. The media was then harvested, spun to remove any remaining cells, and analyzed for cytokine expression (Luminex) according to the manufacturer's instructions. Resulting cytokine levels were then divided by the initial tumor weight for each sample.

In vivo cytokine rescue studies: All mice were pre-treated with anti-CD8 two days before tumor injection. Either 1 μg IFNg or 100 ng CXCL10 was mixed in the PBS/tumor cell suspension prior to injection of the tumor. Mice then continued receiving 500-1000 ng IFNG or 100 ng CXCL10 intra/peritumorally every 3 days post-tumor implantation. For flow cytometry experiments, mice were harvested at day 13 to examine the effects of cytokine addback on immune recruitment in the absence of CD8 T cells. For survival experiments, intra/peritumoral injections continued every 3 days for the remainder of the experiment.

OT1 and FoxP3-DTR mice studies: Transgenic OT1 mice or littermate wild type mice were implanted with tumors using Res 499 cells with IFNGR and B2M knockout. Groups receiving Ova peptide had 50 ng of peptide mixed into the suspension prior to tumor injection and continued to receive intra/peritumoral injections on days 3, 6, 9, and 12. For flow cytometry experiments, mice were harvested on day 13. For FoxP3− DTR mice studies, mice were implanted with Res 499 IFNGR knockout tumors and diptheria toxin was administered intraperitoneally at 1 ug/dose/mouse on days 5, 8, and 11 post-injection.

Murine chimeric antigen receptor T cells: B16-F10 tumor cells were transduced with pCLPs-hCD19 lentivirus to express a truncated human CD19 antigen that is unable to drive intracellular signaling. Cells were double sorted for stable expression. $5 \times 10^4$ tumor cells in log phase growth were implanted into flanks of B6 mice, and treated with murine CAR T cells 5 days later. Murine T cells were stimulated with CD3/CD28 Dynabeads (Invitrogen) for 24 hours, and then transduced with pMSCV-h19BBz retrovirus. 48 hours after transduction, CAR+ T cells were quantified and $5 \times 10^6$ CAR+ T cells were injected i.v. in mice bearing B16- or Res499-hCD19 tumors.

Adoptive transfer of mouse T cells: T cells from spleens of wild type or IFNG knockout mice were isolated by negative selection, and $8 \times 10^6$ cells were adoptively transferred i.v. into RAG1$^{-/-}$ mice. Recipient mice were allowed to reconstitute for 4 weeks, verified for reconstitution, and then were injected with flank tumors and treated with ICB as described above.

In vitro NK cell assays: Mice were injected i.p. with poly I:C 18 hours prior to NK cell isolation from mouse spleens or livers by negative selection. NK cells were then cultured with tumor cells for 6 hours. Flow cytometry was performed to assess the effector function and activation status of NK cells by examining Cd49a, Cd49b, PD1, and/or Cd107a.

Analysis of tumor growth, survival, and group differences: Mice were randomly assigned a treatment group and tumor volume determined by caliper measurements. Differences in survival were determined for each group by the Kaplan-Meier method and the overall p-value was calculated by the log-rank test using the survival R package. For mouse studies, an event was defined as death or when tumor burden reached a pre-specified size to minimize morbidity. Using the MASS R package, a mixed effect generalized linear model with lognormal distribution for tumor volume data was used to determine differences in growth curves. The significance of all two-way comparisons was determined by a two-sample two-tailed t-test, or by a one-tailed t-test when appropriate. For non-parametric data, a Wilcoxon or rank sum test was used.

Gene set enrichment analysis: RNA-sequencing data from Res 499 resistant cells and B16-F10 parental cells flow sorted from untreated tumor-bearing mice were used for gene expression analysis. Previously described upregulated ISGs associated with cancer and therapy resistance (Weichselbaum et al., (2008) Proc Natl Acad Sci USA 105, 18490-18495) were confirmed to be enriched in Res 499 compared to B16 by gene set enrichment analysis (GSEA) and denoted the ISG Resistance Signature (ISG.RS). For genes associated with IFNG signaling, the IFNG gene set from the Hallmark gene sets was used (IFNG.GS). GSEA was performed and the normalized enrichment scores and p-values calculated using the fgsea R package. For some genes like OAS1, orthologs were used when converting between mouse and human gene names.

Single-cell RNA-sequencing analysis: Single-cell RNA-sequencing data from melanoma patients were downloaded from the GEO (Tirosh et al., (2016) Science 352, 189-196) and converted to TPM values. Several filtering steps were performed including, eliminating genes with low average expression and genes with greater than 20% zero values. This resulted in 8213 genes that was then imputed using the SAVER R package (Huang et al., (2018) Nat Methods 15, 539-542) followed by log 2 transformation. Dimensionality reduction was performed using tSNE as implemented in the Rtsne R package and resulting clusters were annotated using the provided cell type labels. The expression of each ISG metagene for cells belonging to each cell type was calculated and compared visually and by two sample t-test. For single-cell immune cell data from mouse tumors using the 10× Genomics platform, data were first processed using the Cell Ranger pipeline (10× Genomics). This included demultiplexing BCL files into FASTQ, performing alignment with STAR, UMI counting, and aggregating replicates of the same condition. Cells that had fewer than 500 genes detected, over 10% mitochondrial content, or over 3.5 times the median UMI count were removed. Genes expressed in less than 1% of cells were also removed. After these QC steps, UMI counts were imputed with SAVER. Seurat was then used to normalize data to sequencing depth using a LogNormalize implementation, and mitochondrial contamination and cell cycle effects were regressed out. Clustering was performed using Seurat's graph-based clustering approach and visualized with tSNE. Clusters were classified using a collection of manually curated immune marker genes (FIG. 23). Metagene values for IFNG.GS was determined similarly to the clinical analysis. The average scaled values for Mki67 and Top2a, and the average scaled values for Cxcl9 and Cxcl10 were used to calculate the proliferation and Cxcl9/10 metagene, respectively. For visualization purposes, metagene values less than or greater than 2.5 times the interquartile range were removed. Comparison of expression values between groups was done using a Wilcoxon rank-sum test. GSEA was performed using the fgsea R package. Gene sets for LCMV terminal exhausted T cells, progenitor exhausted T cells, and intratumoral ILC1 populations were curated from previously published reports (Gao et al., (2017) Nat Immunol 18, 1004-1015; Miller et al., (2019) Nat Immunol 20, 326-336).

Analysis of genomic features from clinical melanoma samples: Processed bulk RNA-seq data from two different cohorts of melanoma patients treated with anti-PD1 (Hugo et al., (2016) Cell 165, 35-44; Riaz et al., (2017) Cell 171, 934-949.e15) were downloaded from the GEO. CIBERSORT (Newman et al., (2015) Nat Methods 12, 453-457) was used to infer the relative frequencies of immune cells in the tumor, and for immune cell types with values for both resting and activated states, the variables were combined by subtracting the resting values from the activated values. To calculate metagenes, gene expression data were centered and scaled using the sample mean and standard deviation, respectively. Then, the average expression of the genes in each gene set was calculated for each sample to give the metagene value. For tumor mutational burden, provided values were log 10 transformed.

Multivariate classification, regression, and survival analysis: Random forest (RF) for classification, regression, and survival analysis is a multivariable non-parametric ensemble partitioning tree method that can be used to model the effect of all interactions between genes on a response variable (Breiman (2001) Random forests. Machine Learning; Chen and Ishwaran, (2012) 99, 323-329). The randomForestSRC package version 2.5.1.14 was used with the following parameters: 5000 trees, node size of 2, and default values for mtry. The default splitting rule was used for classification and the log-rank slitting rule was used for survival analysis. The default value for nsplit was used except for models containing both 2-level factor variables and continuous variables. In this case, the nsplit parameter was set to 2 in order to prevent bias against the factor-level variables. Importance scores were calculated using the random ensemble method. For classification problems where the two classes were imbalanced, a random forest quantile-classifier approach was employed. Response was defined as complete or partial response. All predicted values, error rates, and importance scores were based on cross-validation using out-of-bag samples and the average of 500-1000 Monte Carlo replications.

To assess immune cell populations that statistically interact with the ISG.RS, variables for immune cell frequencies were used along with TMB, IFNG.GS, and the ISG.RS in a model for anti-PD1 response. Prior treatment status and cohort were included to ensure the lack of confounding from these variables. Balanced undersampling of the majority class was performed and variable selection and statistical interaction with the ISG.RS was determined using minimal depth and the maximum subtree method (Ishwaran et al., (2010) Journal of the American Statistical Association 105, 205-217). The frequency that each variable was selected and its associated minimal depth value was averaged over 100 iterations.

To complement the RF approach for modeling probability of clinical response to immune checkpoint blockade, we also performed multivariable logistic regression. From this, odds ratios and 95% confidence intervals were determined for each log 10 increase in TMB or 0.5 unit increase in metagene expression values. To complement RF variable selection using minimal depth, we performed lasso regression using the glmnet R package. Both RF and linear regression methods yielded comparable results.

High-dimensional flow cytometry analysis: Fluorescence intensity data were analyzed using the flowCore R package and transformed using the logical method. After excluding debris, dead cells, doublets and CD45$^-$ cells, CD8 T cells and NK/ILC1 cells were gated and separately analyzed. CD8 T cells were identified as TCRB+ and CD8+, while NK/ILC1 cells were identified as TCRB⁻ and NK1.1+. For each population, an aggregate data matrix from random sampling of 1000 events from each sample was used for dimensionality reduction and for clustering analysis. Clusters were identified using Phenograph (Levine et al., (2015) Cell 162, 184-197) as implemented in the cytofkit R package and visualized by tSNE. Using cluster membership as class definitions, a random forest classifier was developed using the same aggregate data matrix. After confirming a low misclassification error rate for each class, this RF classifier was used to assign all cells in all samples to one of the Phenograph-defined clusters. Using the two-dimensional tSNE coordinates, a random forest classifier was also developed and used to assign all cells to the tSNE map. In this way, the distribution and frequencies of immune cells across clusters were estimated for each sample. To analyze which immune clusters are strongly associated with wild type or IFNGR knockout tumors, the frequencies of immune cells within each cluster were used as features in a random forest model, and the resulting importance scores were examined.

Whole exome sequencing and neoantigen prediction: Preprocessing and variant calling were done with the Genome Analysis Toolkit (GATK) version 4.0.2.1 following its Best Practices workflow. In brief, raw paired-end reads were aligned to the reference mouse genome GRCm38 release 68 using the bwa-mem algorithm from BWA version 0.7.17. Duplicates were marked using MarkDuplicates from Picard tools version 2.17.11. Systematic errors in base quality scores were detected and recalibrated using GATK's BaseRecalibrator and ApplyBQSR. Known variants for recalibration were downloaded from the Mouse Genome Project SNP and Indel release version 5. Somatic SNVs and indels were then called with Strelka and MuTect2 using a matched normal germline of either C57BL/6 or BALB/c mice, and only variants shared by both methods were kept. Variants were then filtered with FilterMutectCalls using GATK's preset thresholds that are tuned for diploid somatic analyses. Based on gene expression from RNA-seq data, variants from transcripts that were not detectably expressed were removed. The MHC-I binding affinities of variants were then predicted using NetMHC version 4.0 for H-2-Kb and H-2-Db using peptide lengths from 8 to 11. To examine the genomic contraction of variants in Res 499 compared to parental B16, the variant allele frequencies were analyzed for variants with near-heterozygous frequency (0.2 for a tetraploid genome) in one cell line but a subclonal frequency in the other. Significance between the distribution of allelic frequencies between the two groups was estimated by a KS-test and compared to 1000 random variants. In addition, subclonal populations and their frequencies within the tumor were examined using the Canopy R package (Jiang et al., (2016) Proc Natl Acad Sci USA 113, E5528-E5537. High quality variants that meet all the following criteria were used for the analysis: 1) affects only single nucleotides, 2) resides in autosome exonic regions, 3) exhibits VAF variance greater than 0.01, and 4) has mutation calling QUALs that exceed 50. The number of subclones were selected based on a Bayesian information criterion (BIC) after 100000 rounds of simulation across 20 chains. The configuration with the highest posterior likelihood was utilized to generate a phylogenetic tree and the corresponding frequencies of the subclonal populations were determined.

Variant analysis of clinical lung cancer tumors: Previously published processed data for somatic non-synonymous variants from non-small cell lung cancer patients treated with anti-PD1 and anti-CTLA4 (CheckMate-012 study) or from TCGA was used (Hellmann et al., (2018) Cancer Cell 33, 843-852.e844). Variants of one of 11 genes involved in type I or II IFN pathway signaling (IFNGR1, IFNGR2, IFNAR1, IFNAR2, JAK1, JAK2, TYK2, STAT1, STAT2, IRF9, and B2M) were examined. To exclude likely normal or benign variants, missense variants were annotated with ANNO-VAR. Any missense variant found in all individuals in the ExAC database at a frequency greater than 0.0001 was removed. In order to predict benign from pathogenic missense or nonsense variants, two algorithms for scoring deleterious variants were used that included DANN, a deep learning algorithm, and CADD, a machine learning algorithm. In addition, evolutionary conservation was also assessed using GERP. For each method, an optimal cut point was selected using benign versus pathogenic variants from ClinVar data. ClinVar variants classified as likely benign were considered benign and those classified as likely pathogenic were classified as pathogenic. The optimal cut point based on ROC accuracy from the ClinVar training set were then applied to the lung cancer data. Any variant below the ROC cut points for both DANN and CADD was categorized as benign. This yielded an overall accuracy of 0.80, sensitivity of 0.95, and specificity of 0.54. This criterion was then applied to the TCGA lung cancer data and the lung cancer tumors from CheckMate-012. Indels were evaluated using SIFT. Non-frameshift and indels predicted to be neutral were excluded. Of the remaining IFN pathway variants, any patient with at least one predicted pathogenic missense variant, pathogenic nonsense mutation, or deleterious indel resulting in a frameshift was classified as IFN pathway variant positive.

The progression-free survival (PFS) of patients stratified by IFN pathway variant status was determined by Kaplan-Meier survival. The likelihood of response was determined by a multivariable logistic regression using variant status, log 10 transformed values for TMB, and a previously used % PDL1 staining cut off of greater than or equal to 1%. The p-value for odds ratios was calculated by bootstrapping. In addition, a non-parametric model for response employing multivariable random forest was also used and without the need to transform any of the variables. The out-of-bag error rate and importance scores from this random forest model was then determined. To evaluate the significance of the observed association between IFN pathway variant status with PFS and decreased % PDL1 staining, the variant status of random sets of 11 genes were evaluated and used to stratify patients. Then, the hazard ratio for PFS and the associated p-value, and the % PDL1 staining for variant-positive and negative patients were recorded for 10,000 iterations and compared to the observed values.

The results of the experiments are now described.

Figure 1C:
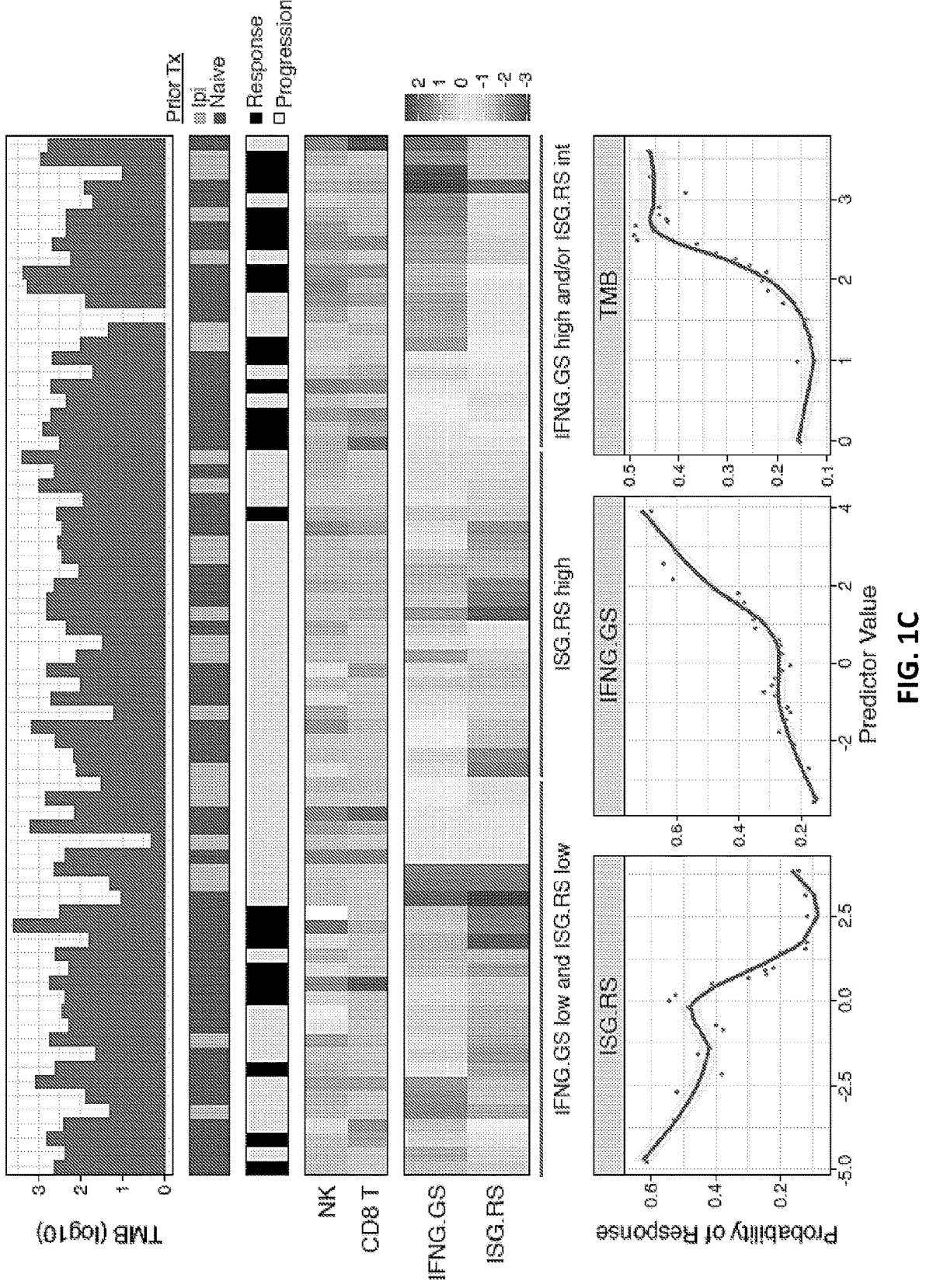
Figures 1D, 1E:
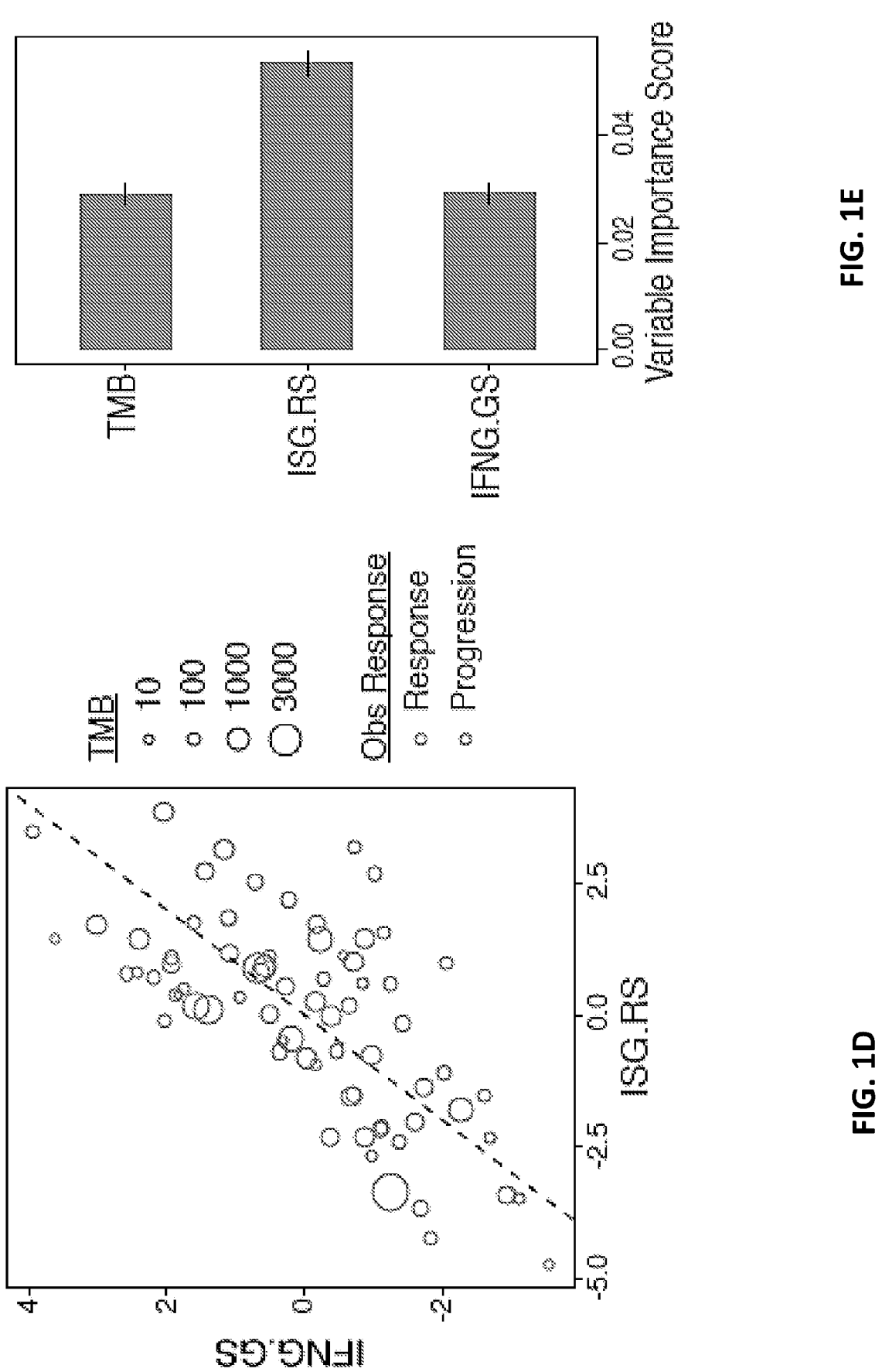
Figure 1F:
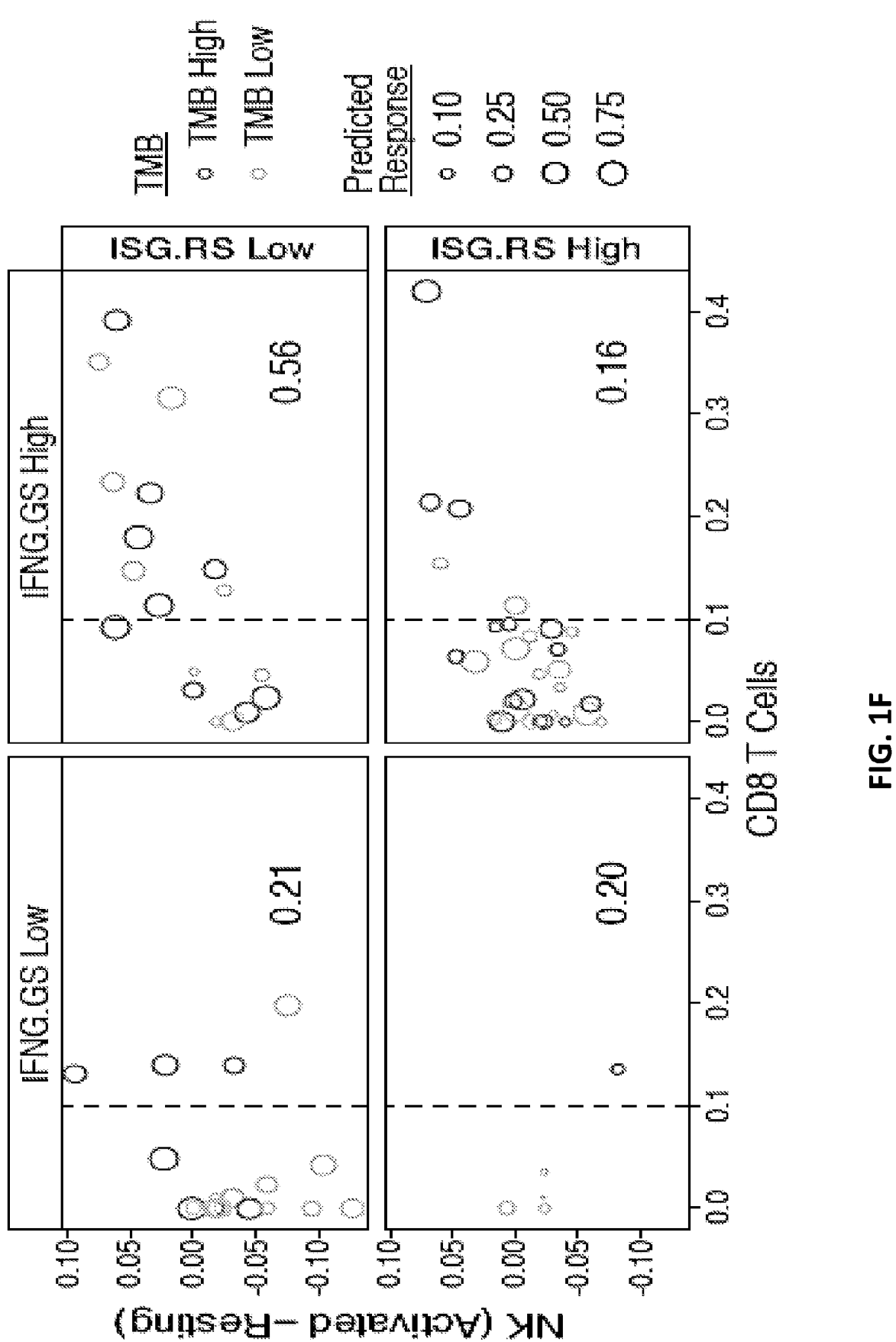

Example 1: ISGs are Differentially Expressed by Cancer and Immune Cells and Predict Either Clinical Response or Resistance to Immune Checkpoint Blockade It was previously reported that a large proportion of common human cancers differentially express a subset of ISGs, and high expression of these ISGs can be associated with resistance to radiation and chemotherapy (Weichselbaum et al., (2008) Proc Natl Acad Sci USA 105, 18490-18495). Interestingly, this ISG resistance signature (ISG.RS) is also associated with resistance to ICB, as demonstrated by elevated expression in ICB-resistant tumors from the Res 499 melanoma cell line (FIG. 1A), which is a mouse cell line derived from B16-F10. However, ISGs are also associated with increased probability of clinical ICB response, especially ISGs typically associated with IFNG signaling. To begin reconciling these seemingly disparate observations, the ISG.RS and genes from the IFNG hallmark gene set (IFNG.GS) were examined by dividing them into two non-overlapping subsets (FIG. 1i). The expression of these distinct ISGs was then examined across different cellular populations in human melanomas using previously published single-cell RNA-seq data (Tirosh et al., (2016) Science 352, 189-196). This revealed that a metagene for the IFNG.GS is predominantly expressed by intratumoral immune cells such as T cells, NK cells, and macrophages (FIGS. 1B and 8A). In contrast, the ISG.RS is predominantly expressed in cancer cells, albeit with variable expression.

Figure 8B:
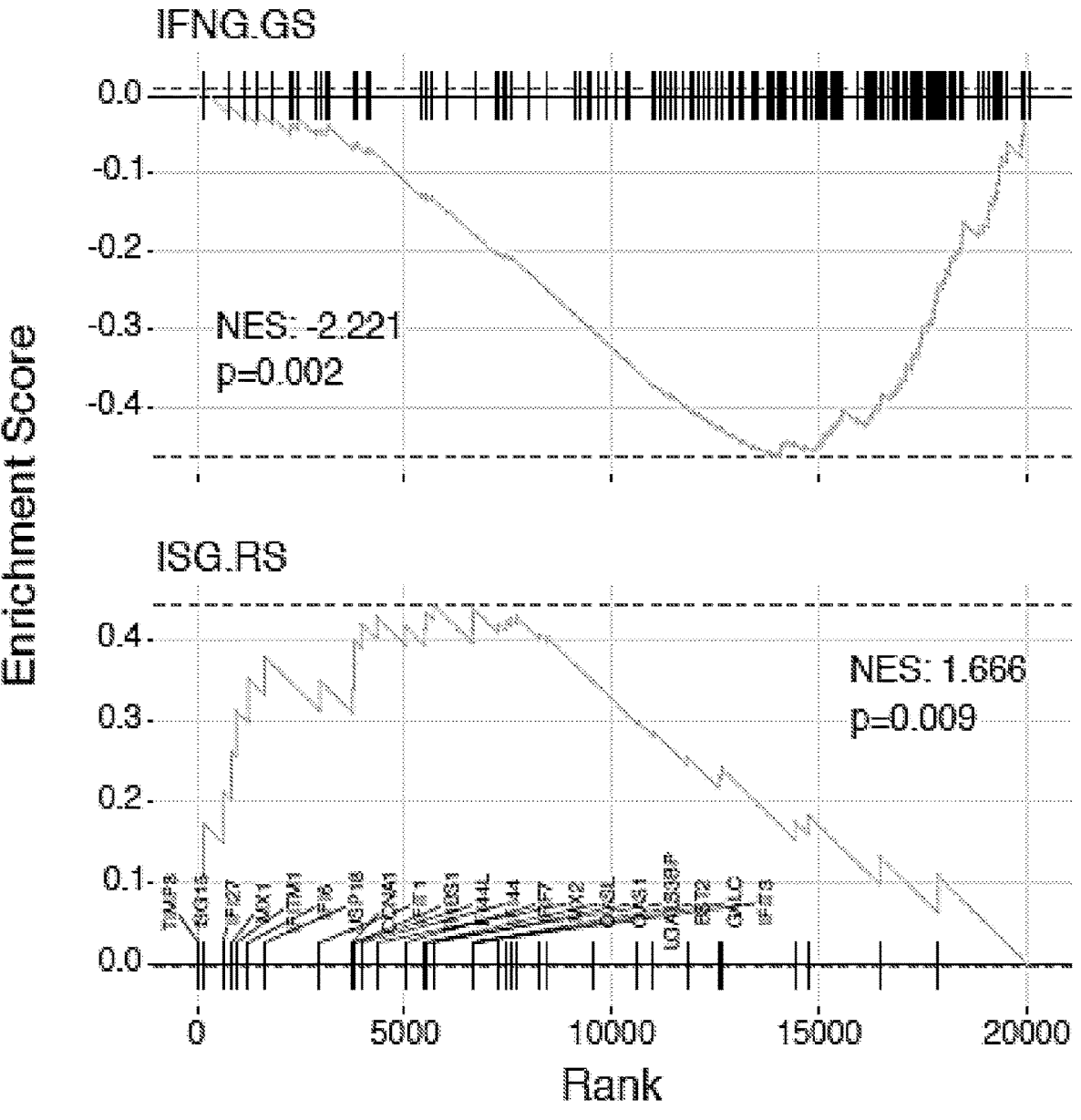

To understand the potential consequences of these expression differences, bulk RNA-seq data combined from two cohorts of melanoma patients treated with anti-PD1 were analyzed (Hugo et al., (2016) Cell 165, 35-44; Riaz et al., (2017) Cell 171, 934-949.e15). The majority of genes in the IFNG.GS are depressed in tumors from non-responders to anti-PD1 (FIG. 8B). However, like ICB-resistant murine Res 499 tumors, most ISG.RS genes are enriched in tumors from non-responders (FIG. 8B). Random forest machine learning was applied to more closely analyze how metagenes for these two sets of ISGs, along with tumor mutational burden (TMB), impact the probability of response (FIG. 1C). Results from out-of-bag samples (samples not used in model training) to provide unbiased estimates reveal that higher levels of TMB and IFNG.GS are associated with clinical response (FIG. 1C, bottom), consistent with previous reports; however, prediction error using these two features is high (43%). When the ISG.RS is added to the model, prediction error falls (36%). The improved performance is attributable to the ISG.RS predicting lower rather than higher likelihood of response to anti-PD1 (FIG. 1C, bottom). Despite predicting the opposite clinical outcome, expression of the ISG.RS positively correlates with IFNG.GS, consistent with IFN controlling both metagenes (FIG. 1D). However, when expression of the ISG.RS exceeds the IFNG.GS, resistance is favored (FIG. 1D; FIG. 1C). In contrast, most responses occur when IFNG.GS is similar to or greater than ISG.RS (FIG. 1D; FIG. 1C). Under this latter condition responses occur in tumors with high and low TMB (circle sizes), consistent with the ISGs contributing to prediction accuracy independently of TMB, as measured by importance scores (FIG. 1E). Thus, while levels of ISGs expectedly track together, response to ICB for both TMB high and low tumors is strongly influenced by the balance between distinct ISGs that are predominantly expressed in either immune cells or cancer cells.

Consistent with the importance of CD8 T cells in response, tumors with high IFNG.GS but low ISG.RS also have the greatest proportion of CD8 T cells (FIG. 1I, top right quadrant) as inferred by CIBERSORT (Newman et al., 2015) (FIG. 8C). The higher frequencies of CD8 T cells are accompanied by increased number of activated NK cells (FIG. 1I, regression line), which also has been associated with clinical ICB response. To understand how these immune and interferon-related variables independently contribute to ICB response, a multivariable logistic regression model was utilized. This revealed that while higher IFNG.GS increases the odds ratio for response, ISG.RS independently decreases the likelihood (FIG. 1E). The significance of both of these variables are independent of tumor mutational burden (TMB) status, which expectedly correlates with response. In contrast, neither the abundance of CD8 T cells nor NK cells are significant in the model. A random forest model, which does not assume linearity and incorporates interaction effects, revealed that ISG.RS exhibits a higher importance score than either IFNG.GS or TMB (FIG. 1K). In total, these data suggest that while expression of IFNG.GS by immune cells is associated with CD8 T cell abundance, accumulation of activated NK cells, and ICB response, all of these effects are opposed by high levels of ISG.RS in cancer cells.

Figure 8D:
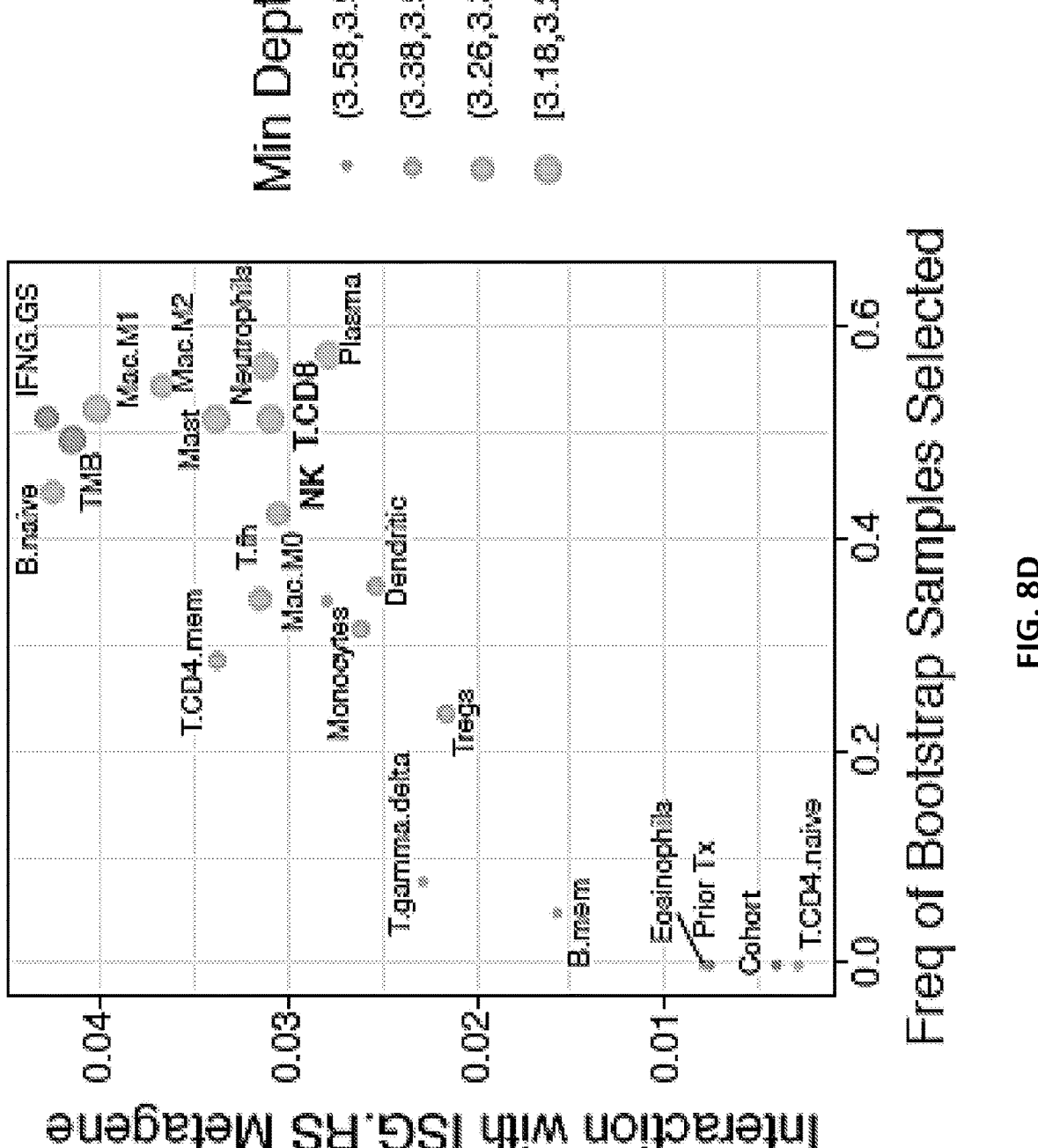

To further understand the significance of distinct ISGs expressed in immune cells versus cancer cells, how the ISG.RS might statistically interact with immune cells to predict response was examined. For this, the frequency of various intratumoral immune populations inferred by CIBERSORT (Newman et al., 2015) were randomly incorporated into the random forest model (FIG. 8C). Then for each variable, both the importance score and the strength of the statistical interaction with the ISG.RS were assessed. CD8 T cells and NK cells are among the immune cell populations that frequently have high importance scores and interact with the ISG.RS (FIG. 8D). Closer analysis reveals that the proportion of activated NK cells correlates with prevalence of CD8 T cells, and both populations are highest when IFN.GS is high but ISG.RS is low (FIG. 1F, upper right). Thus, elevated IFNG-related ISGs in immune cells but depressed ISGs in tumor cells correlates with intratumoral expansion of both CD8 T cells and NK cells.

Figure 1G:
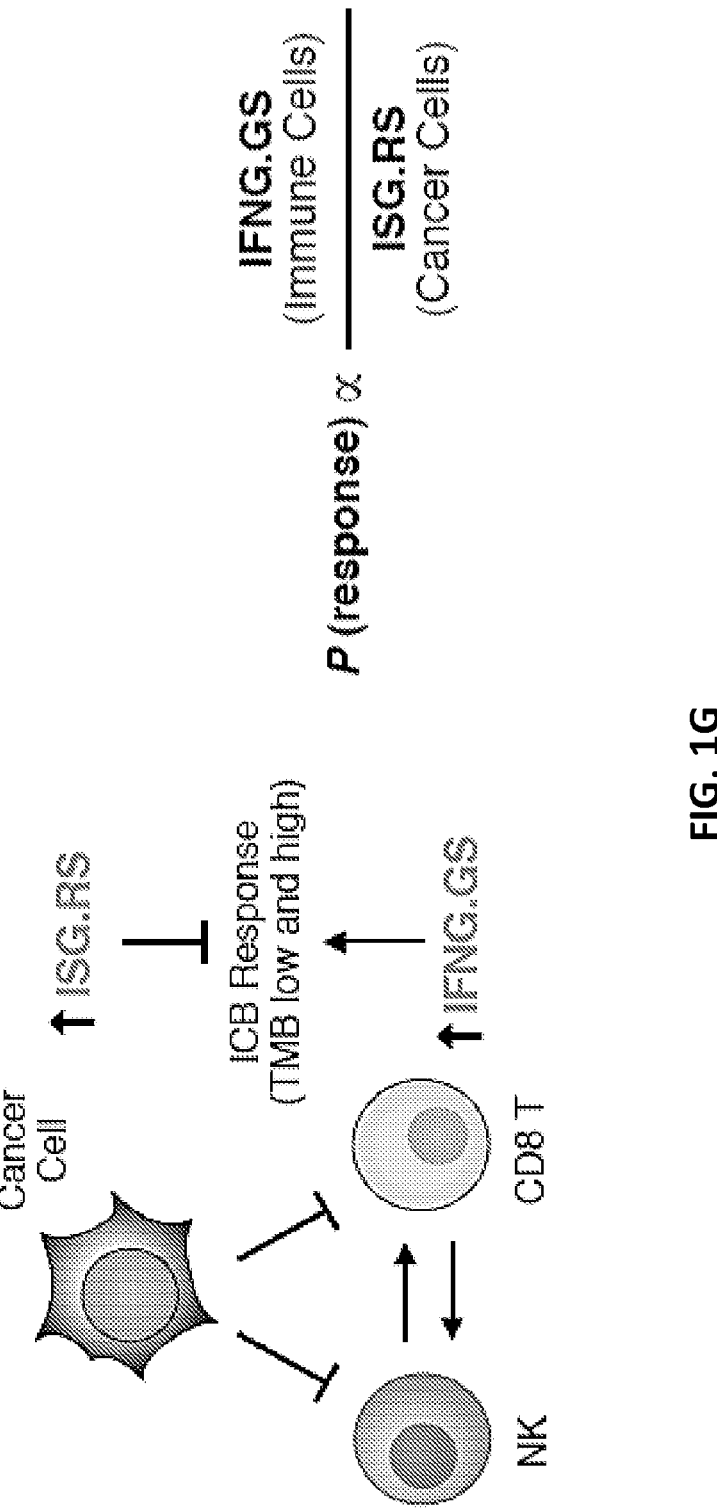
Figure 1H:
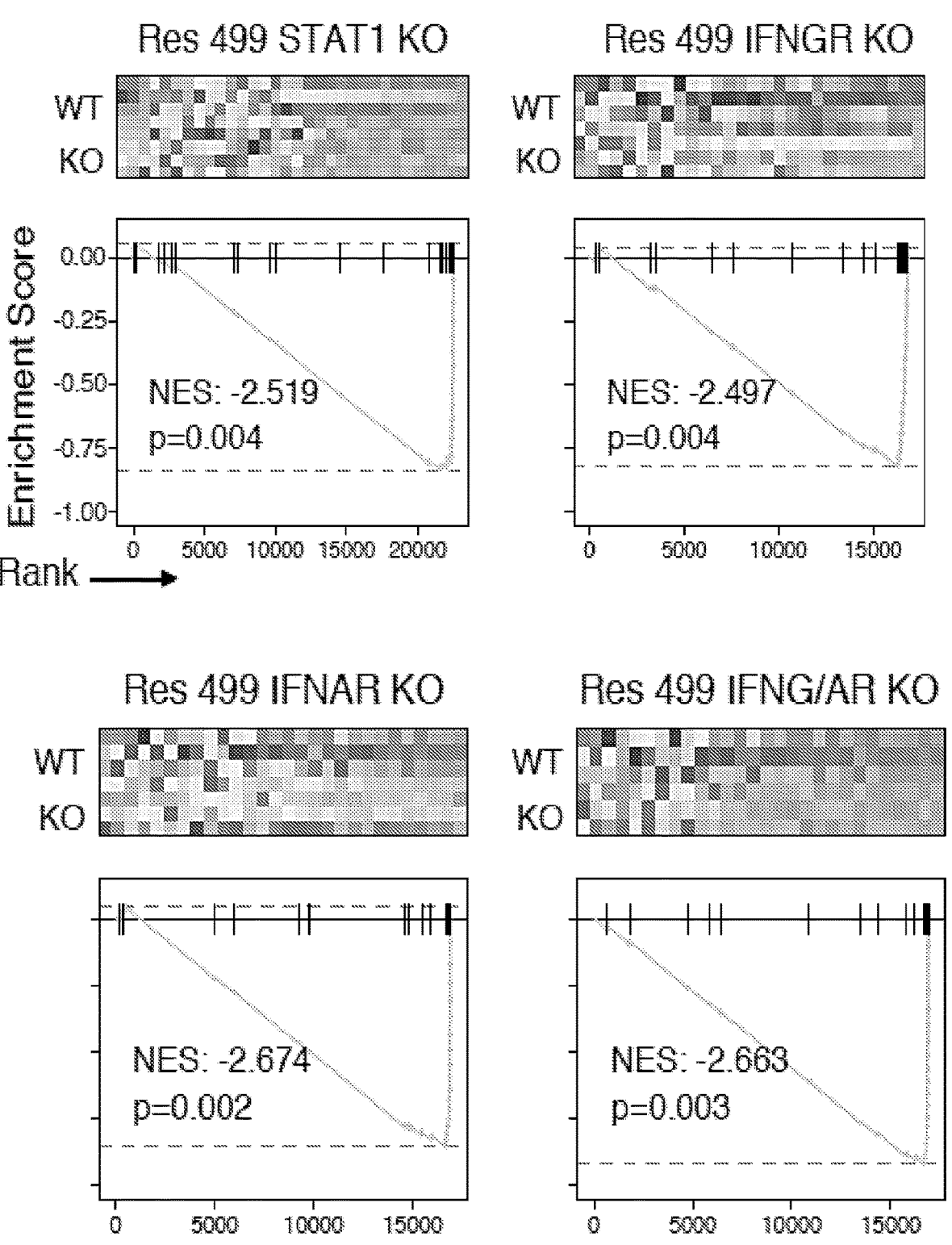
Figures 1I, 1J:
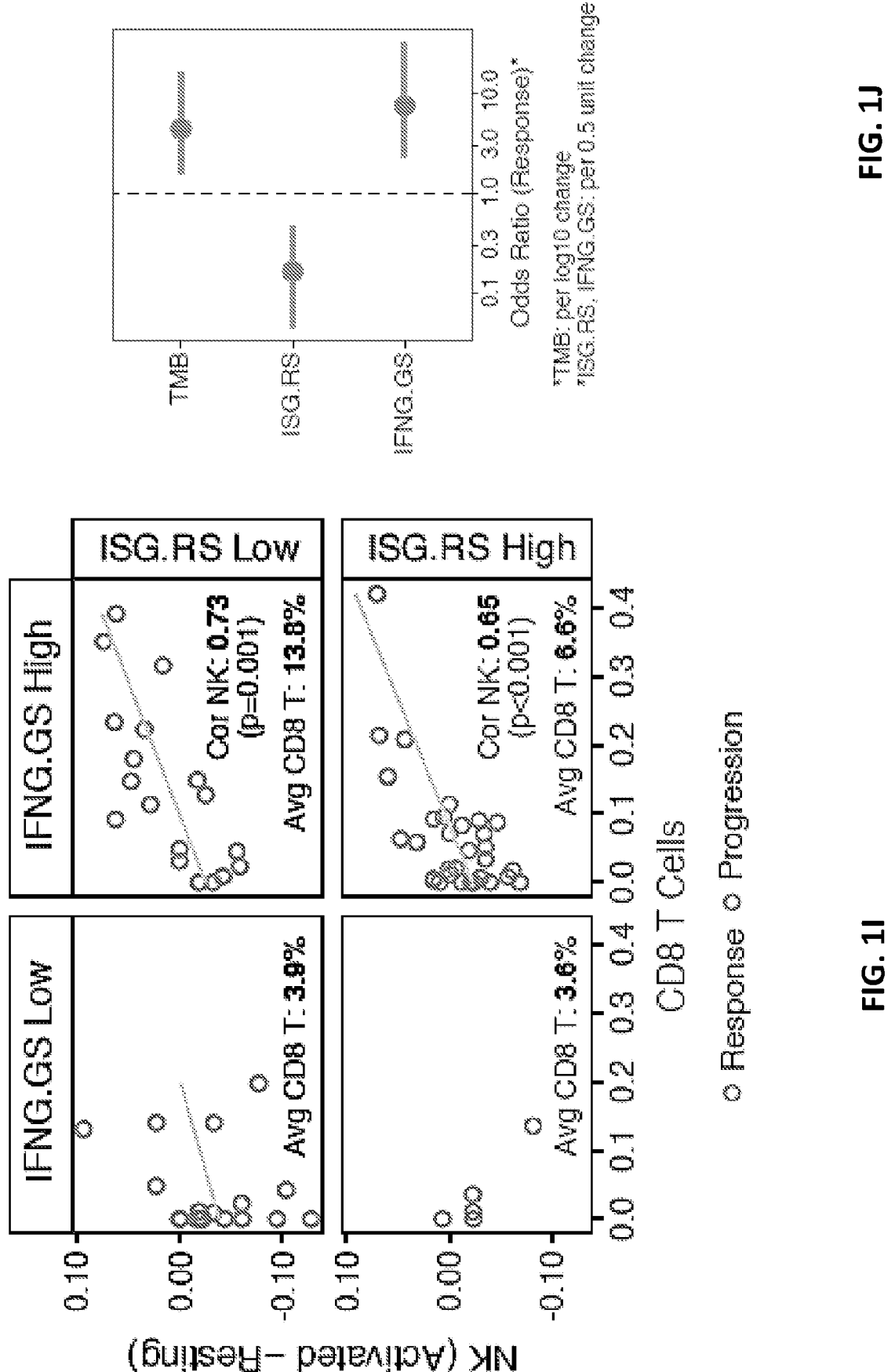
Figure 1K:
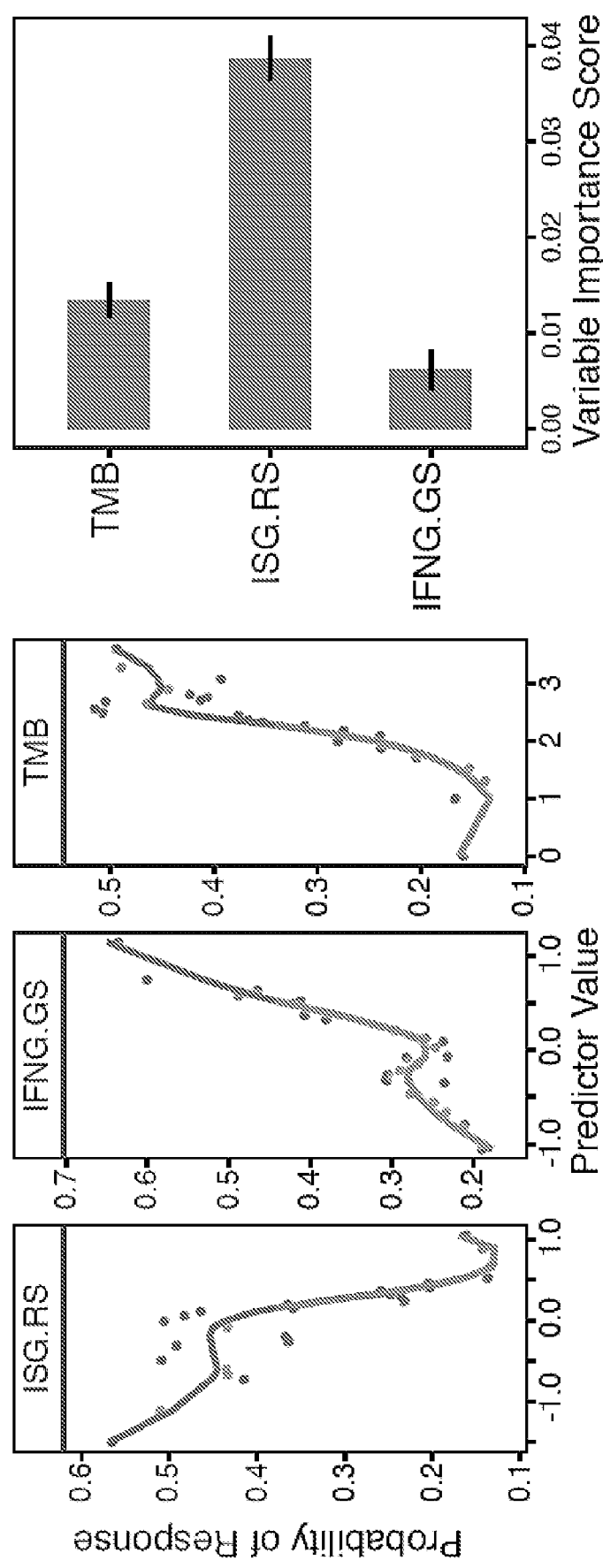
Figure 1L:
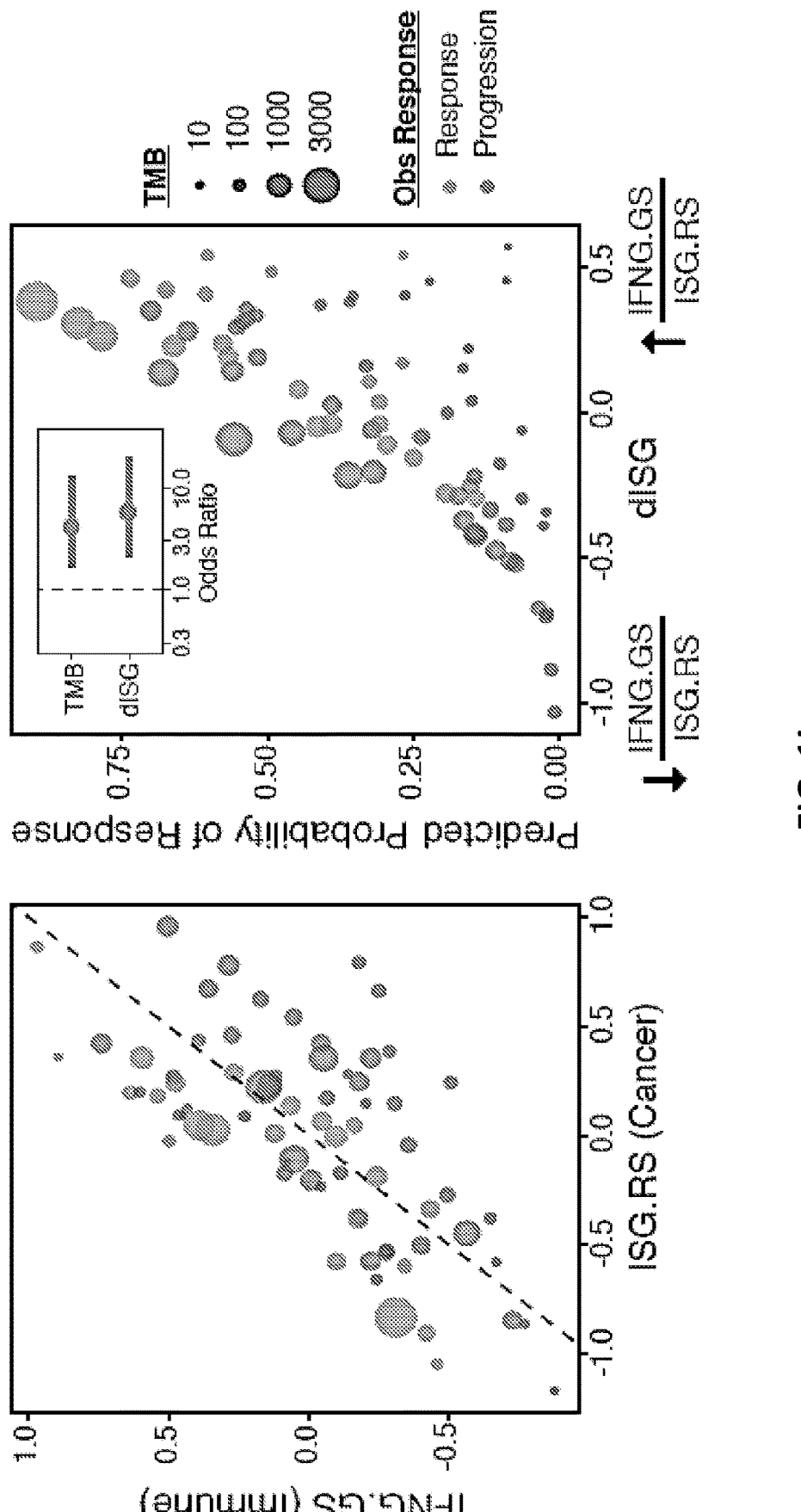
Figure 1M:
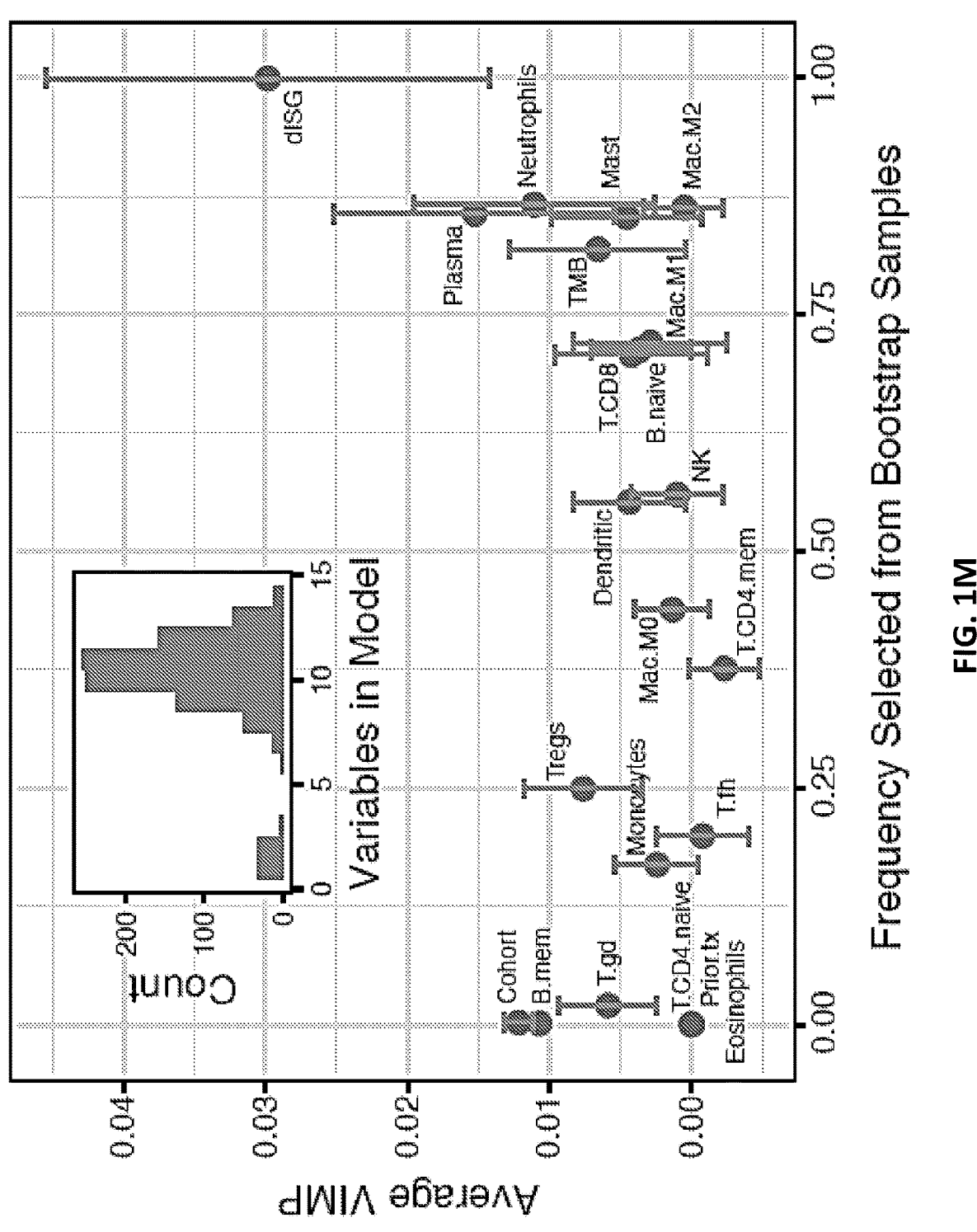

Although the IFNG.GS and ISG.RS predict opposite clinical outcomes, their expression is positively correlated, consistent with IFN controlling both metagenes (FIG. 1L). An explanation for this apparent "paradox" lies in the relative expression of each metagene. When expression of the ISG.RS exceeds the IFNG.GS, resistance is favored (FIG. 1L, left plot). In contrast, most responses occur when IFNG.GS is similar to or greater than ISG.RS (FIG. 1L). Based on these findings, the two metagenes were combined into a ratio of IFNG.GS over ISG.RS (or, the difference of these two metagenes in log transformed space). By logistic regression, this composite variable (dISG) is strongly associated with response and is independent of TMB (FIG. 1L, right plot and inset). Specifically, the probability of response is low when either the ratio or TMB is low but increases when either increase. Furthermore, random forest machine learning and bootstrapping revealed that the ISG ratio has the highest robustness and average variable importance compared to TMB and multiple immune features (FIG. 1M).

In total, the single-cell and bulk RNA-seq analysis suggests distinct ISGs differentially expressed by cancer and immune cells can oppose each other to influence CD8 T cell infiltrate and NK activation, and can be combined into a ratio that predicts ICB response independent of TMB (FIG. 1G). The mechanistic underpinnings inferred by these statistical relationships were then investigated.

Example 2: Opposing Functions of Tumor IFN Signaling Dictate Outcome after ICB

If the probability of ICB response is influenced by the ratio of IFNG-related ISGs expressed by immune cells over inhibitory ISGs expressed by cancer cells, one way to enhance the ratio in favor of response is to prevent IFN signaling in cancer cells. It was first confirmed whether the ISG.RS, which is elevated in ICB-resistant Res 499 tumors, is regulated by tumor IFN signaling and STAT 1. Indeed, CRISPR knockout of either STAT 1, IFNGR, and/or IFNAR significantly diminishes ISG.RS levels (FIG. 1H). However, recent reports indicate that loss of IFN/STAT1 signaling in tumor cells can render cancers less responsive to immunotherapy due to compromised MHC-I and antigen processing, suggesting that the impact from ablating tumor IFN signaling might be context dependent. In light of this, two situations were surmised whereby the benefit of inhibiting IFN-driven resistance could outweigh the negative impact on MHC-I. The first is when constitutive MHC-I is high, minimizing effects that loss of IFN-inducible MHC-I has on CTL-mediating killing. A second situation is when tumors have depleted or poor neoantigens. Here, diminished CTL recognition presumably makes MHC-I status less consequential for T cell-mediating killing, but interference with IFN-driven resistance mechanisms could improve innate immune function.

Figure 2A:
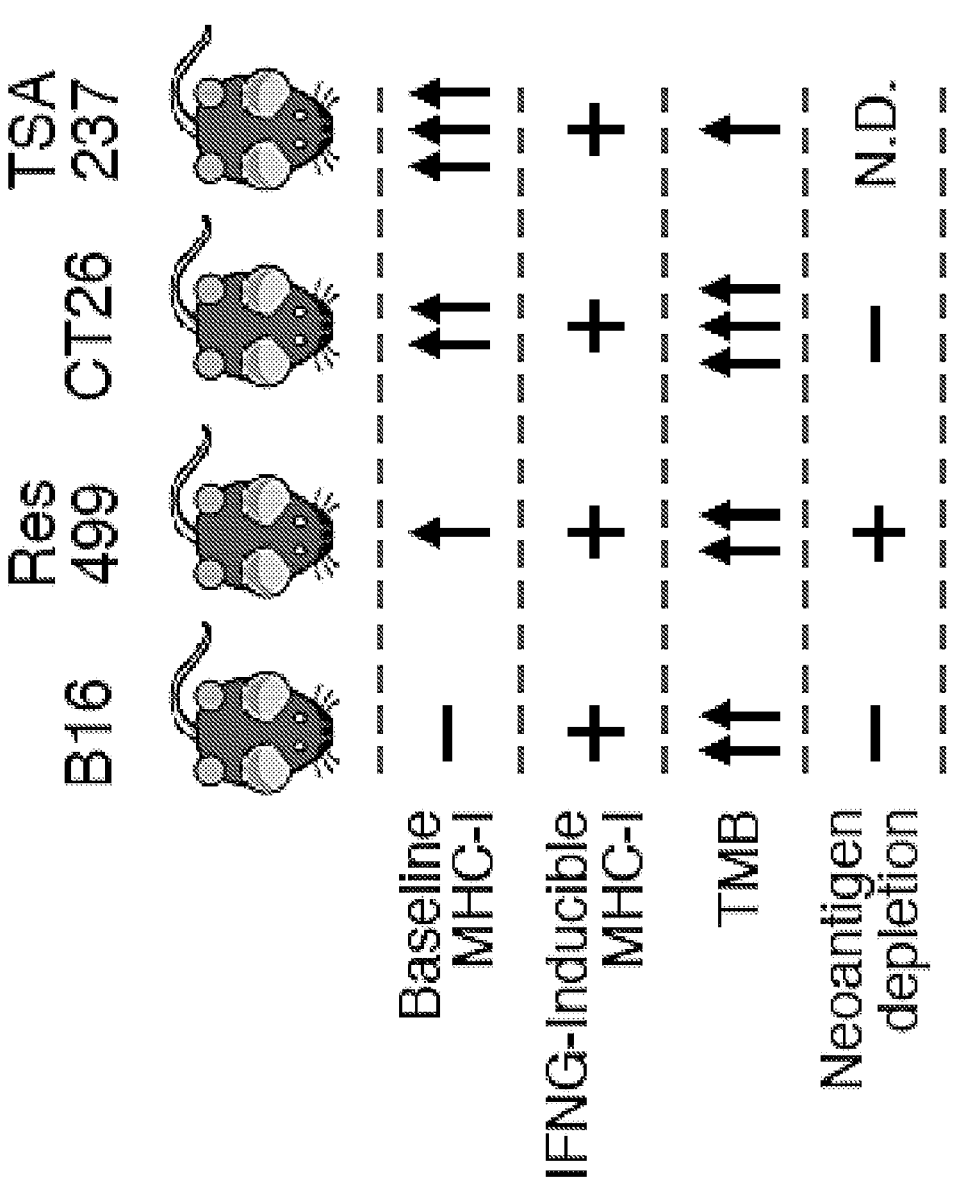
Figure 2B:
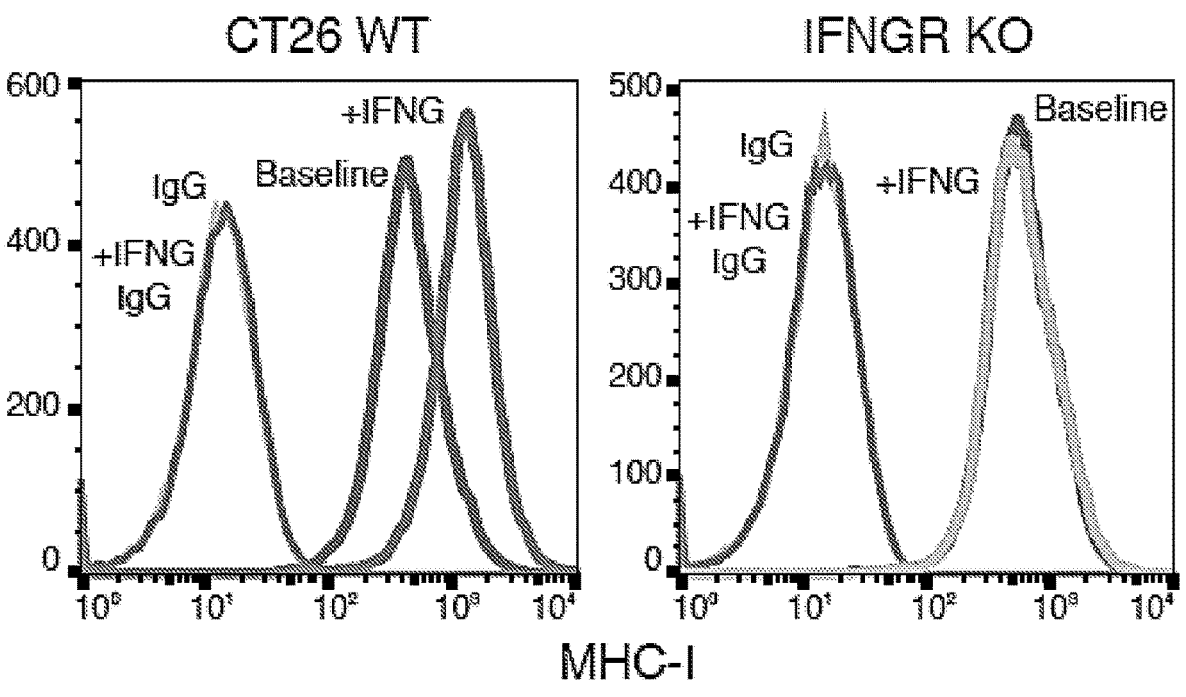
Figure 2C:
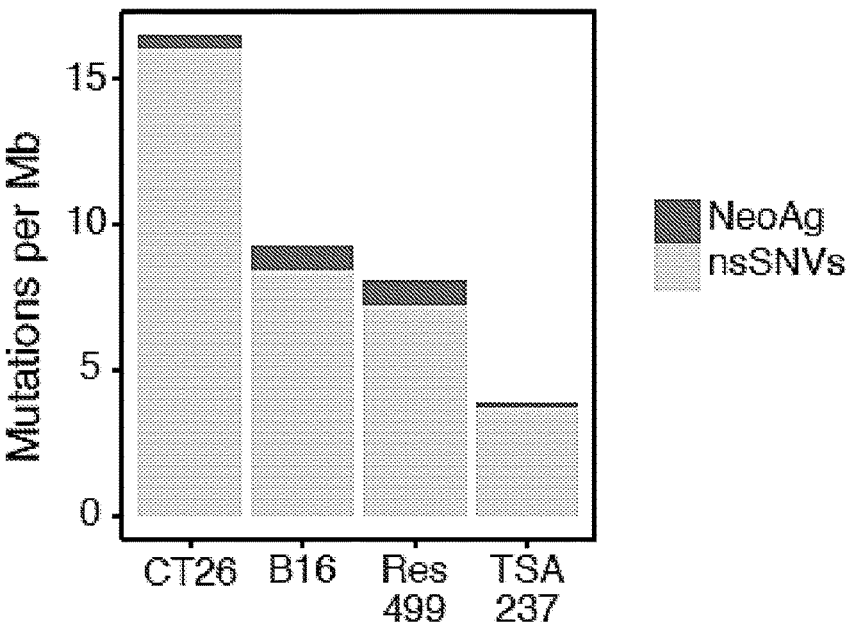
Figures 2D, 2E:
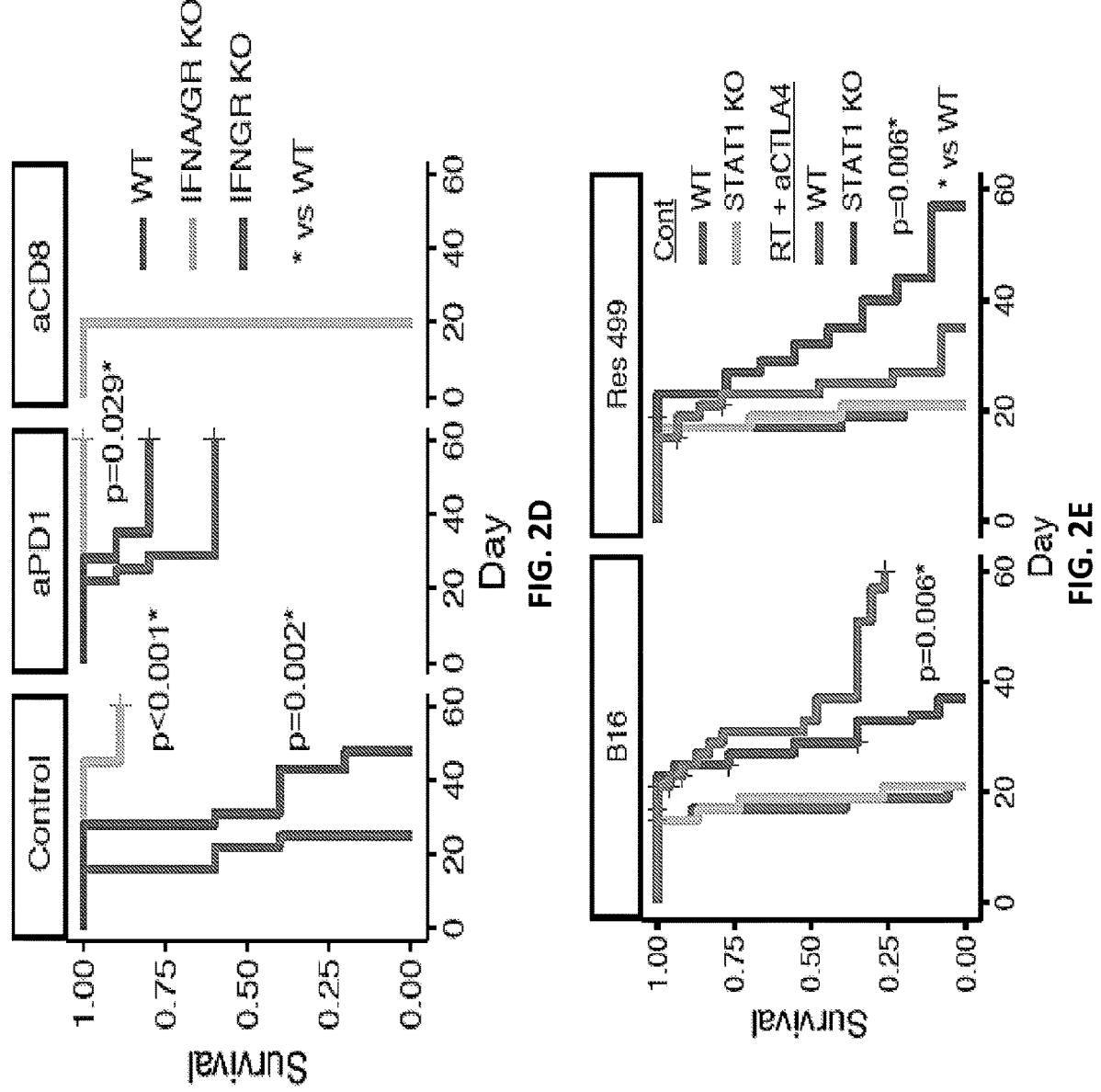
Figures 9A, 9B:
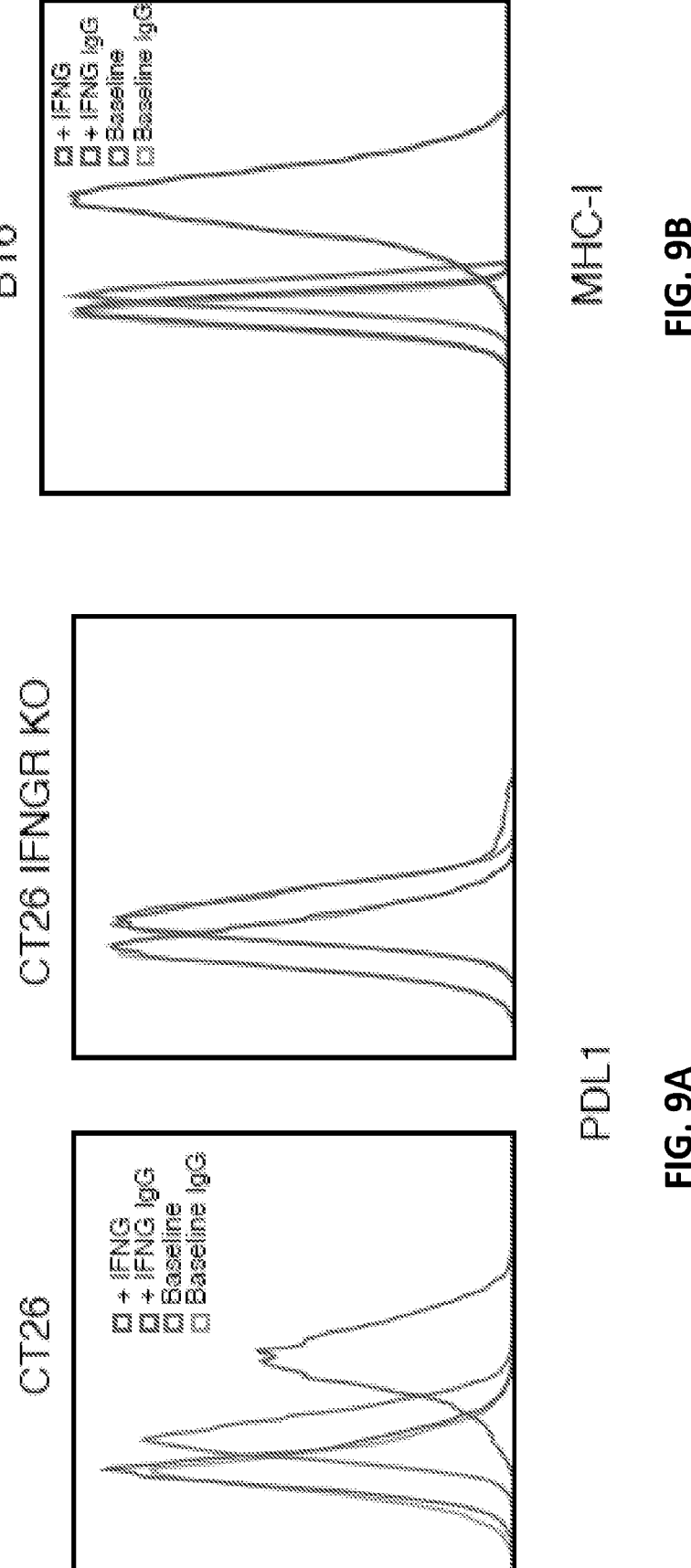
FIGS. 9A-9E illustrates the effect of blocking tumor IFN signaling on MHC-I, immunological memory, and durability of ICB response.
Figures 10A, 10B:
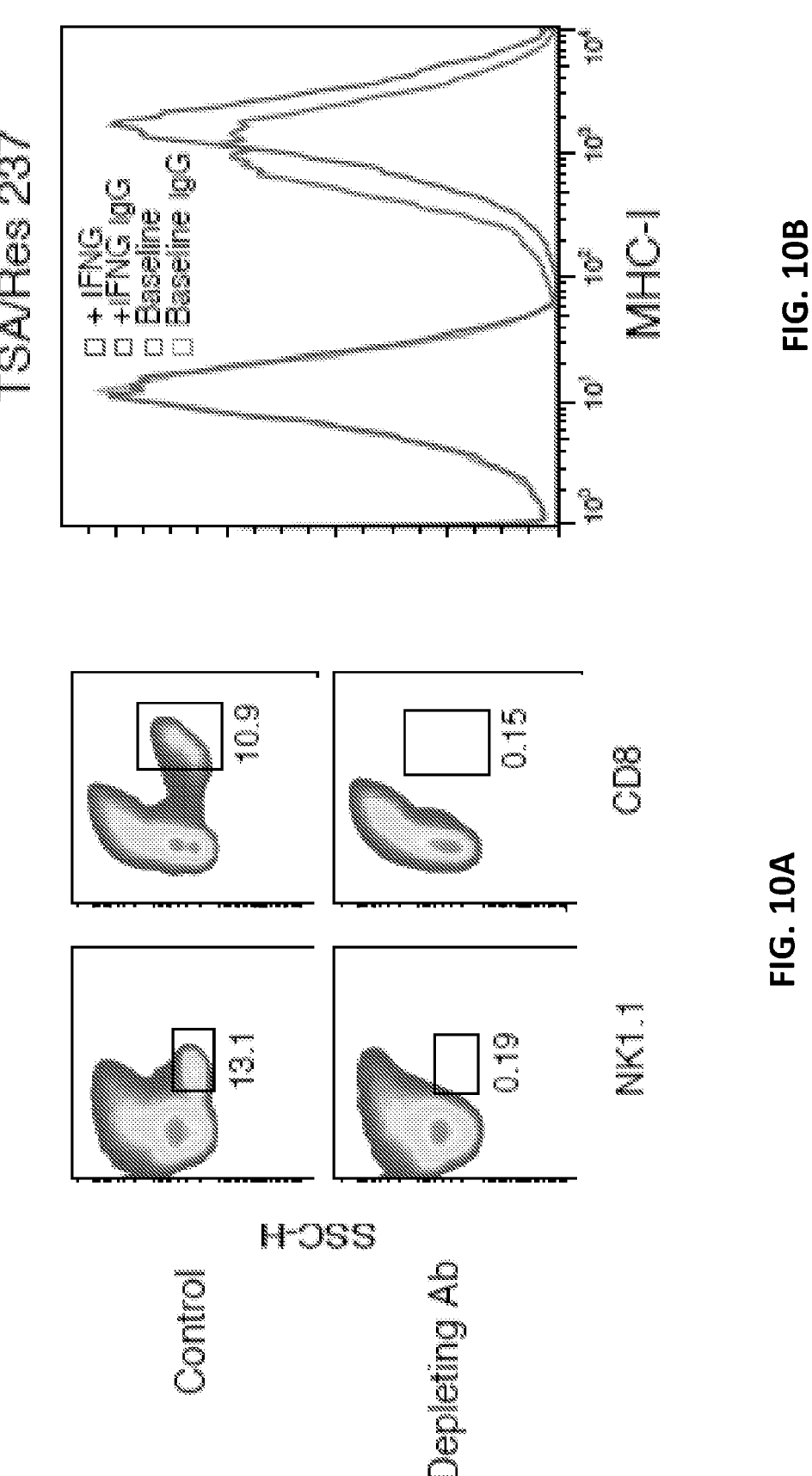
Figure 10E:
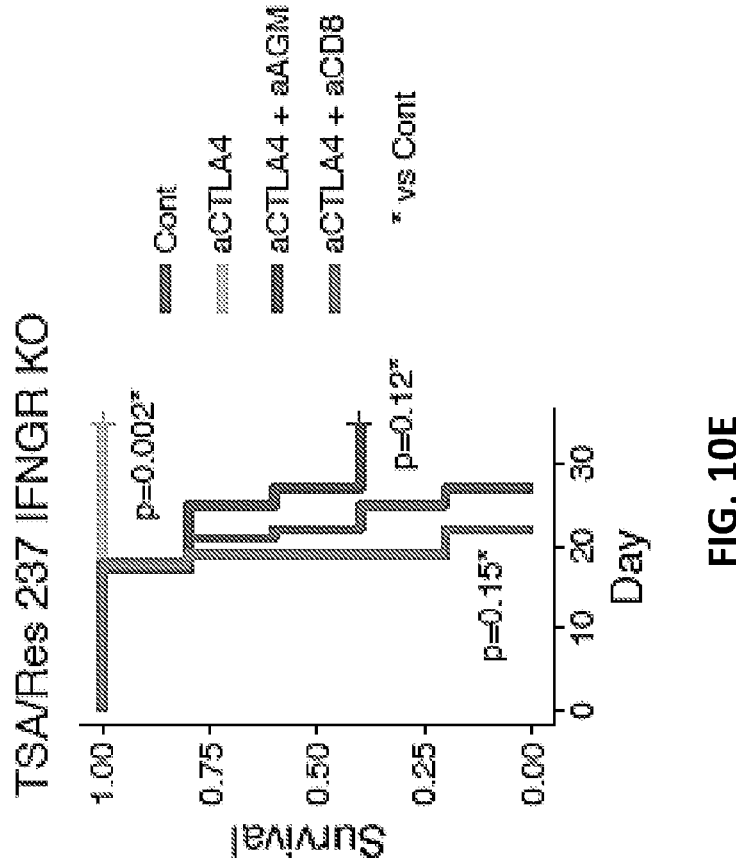

To investigate these ideas, various mouse tumor models differing in MHC-I expression, TMB, and predicted neoantigen status were utilized (FIG. 2A). Of these mouse models, CT26 colorectal cancer has the highest TMB (FIG. 2C) and maintains high MHC-I in the absence of IFNG signaling (FIGS. 2J and 2G). Similarly, TSA-derived Res 237 breast cancer cells also have high IFNG-independent baseline MHC-I but exhibit lower TMB (FIGS. 2C, 2J, and 10B). In contrast, B16 and/or Res 499 melanoma have intermediate TMB, low constitutive MHC-I, and rely on IFNG for high MHC-I expression (FIGS. 2C, 2G and 9B). Since Res 499 originated from an abscopal B16 tumor that relapsed several weeks after radiation (RT) plus anti-CTLA4, it was surmised that Res 499 may additionally have undergone immunoediting prior to relapse. Recent evidence suggests that neoantigens that have clonal or near-clonal representation are predominantly targeted by the immune system, while neoantigens at low clonal fractions can remain immunologically silent. In accord with this notion, there is a significant decrease in the cumulative frequency of predicted high affinity (<100 nM) neoantigens with clonal (near-heterozygous or greater) frequencies in Res 499 compared to B16 (FIG. 2K). In particular, a cluster of predicted neoantigens (cluster 6, FIG. 2L) are present at clonal frequencies in B16 but fall to subclonal or near-zero frequencies in Res 499 tumors (FIG. 2L, lower right quadrant). This cluster of neoantigens is predicted to reside in a subpopulation of cells (subclone 3, FIG. 2M) that is nearly eliminated in Res 499 compared to B16, consistent with immunoediting. In contrast, the subpopulation with the largest reciprocal increase in Res 499 (subclone 4) is characterized by a mutation cluster (cluster 7) with low clonal frequencies (FIG. 2L, lower left quadrant), as expected for resistant subclones. Together, these data define several tumor models that differ in reliance on IFNG for high MHC-I and in predicted neoantigen availability.

Figure 18A:
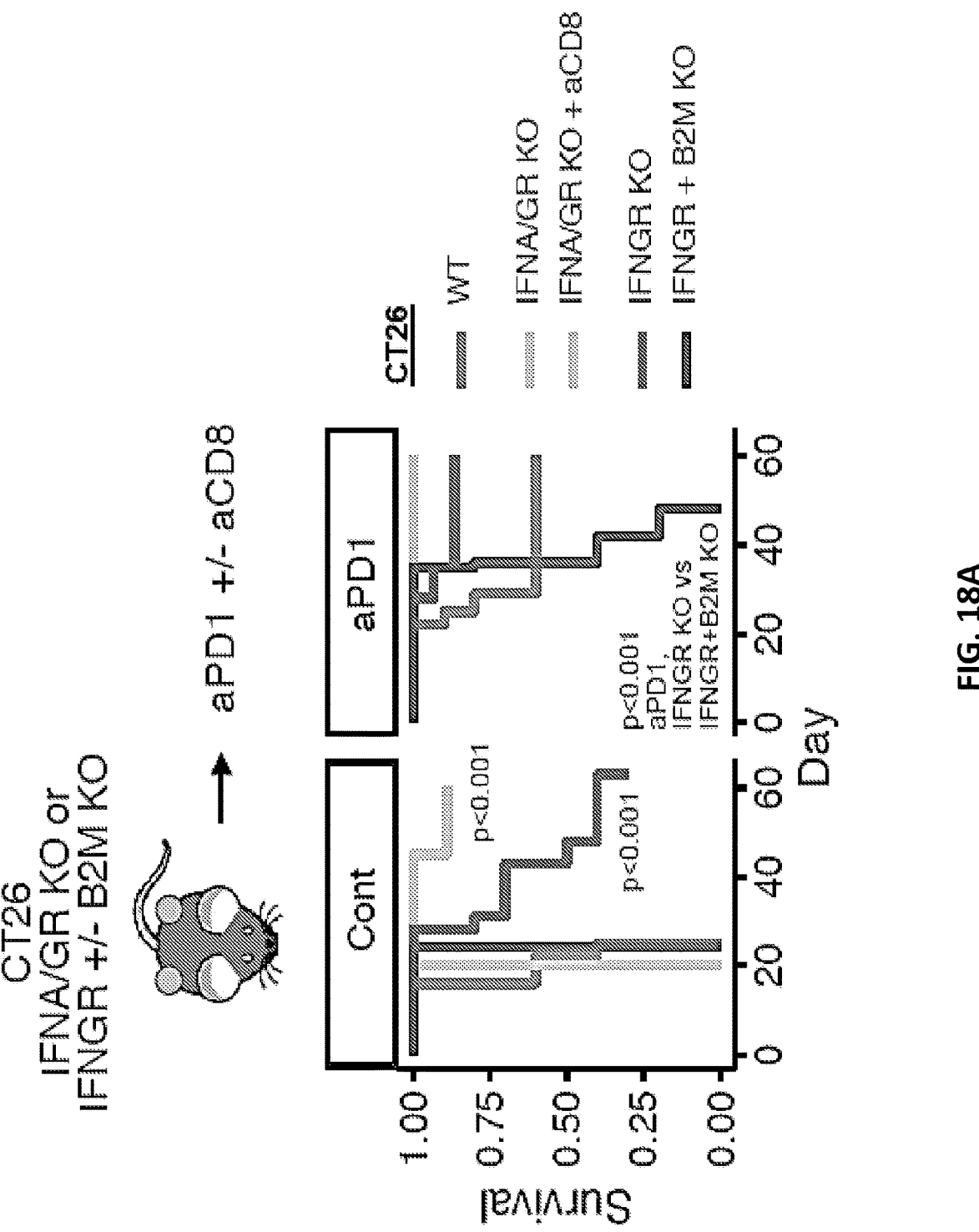
FIGS. 18A-18H illustrate the finding that preventing tumor IFN signaling promotes CD8 T cell-dependent and/or NK/ILC1-dependent ICB response.

Example 3: Blocking Tumor IFN Signaling Broadly Improves ICB Response Through CD8 T and Innate Immune Cells CT26 cells exhibit high constitutive levels of IFN-independent MHC-I (FIG. 2B), high TMB, and multiple predicted high-affinity neoantigens (FIG. 2C), suggesting that deficiency in tumor IFN signaling may only modestly impact T cell recognition. Indeed, knockout of IFNGR or both IFNGR and IFNAR led to progressive improvement in the rate of spontaneous tumor regression in CT26 colorectal tumors (FIGS. 2D and 9A). The CT26 model was used to examine whether tumors with high constitutive MHC-I and TMB demonstrate improved response when ISG.RS is decreased by blocking tumor IFN signaling. Remarkably, when both IFNGR and IFNAR are ablated, mice either show slower growth or spontaneous regression that is CD8 T cell dependent (FIG. 18A), as determined by antibody-mediated depletion of CD8 T cells (FIG. 10A). The addition of anti-PD1 further improves anti-tumor effects and survival. Both spontaneous regression and durable response to anti-PD1 requires B2M and hence MHC-I. All mice with complete response are also resistant to tumor rechallenge (8 out of 8 mice), further indicative of a T cell dominant response. Thus, decreasing ISG.RS by preventing IFN signaling in tumors with high baseline MHC-I does not interfere with CTL-mediating killing and markedly enhances immunogenicity.

Figure 18B:
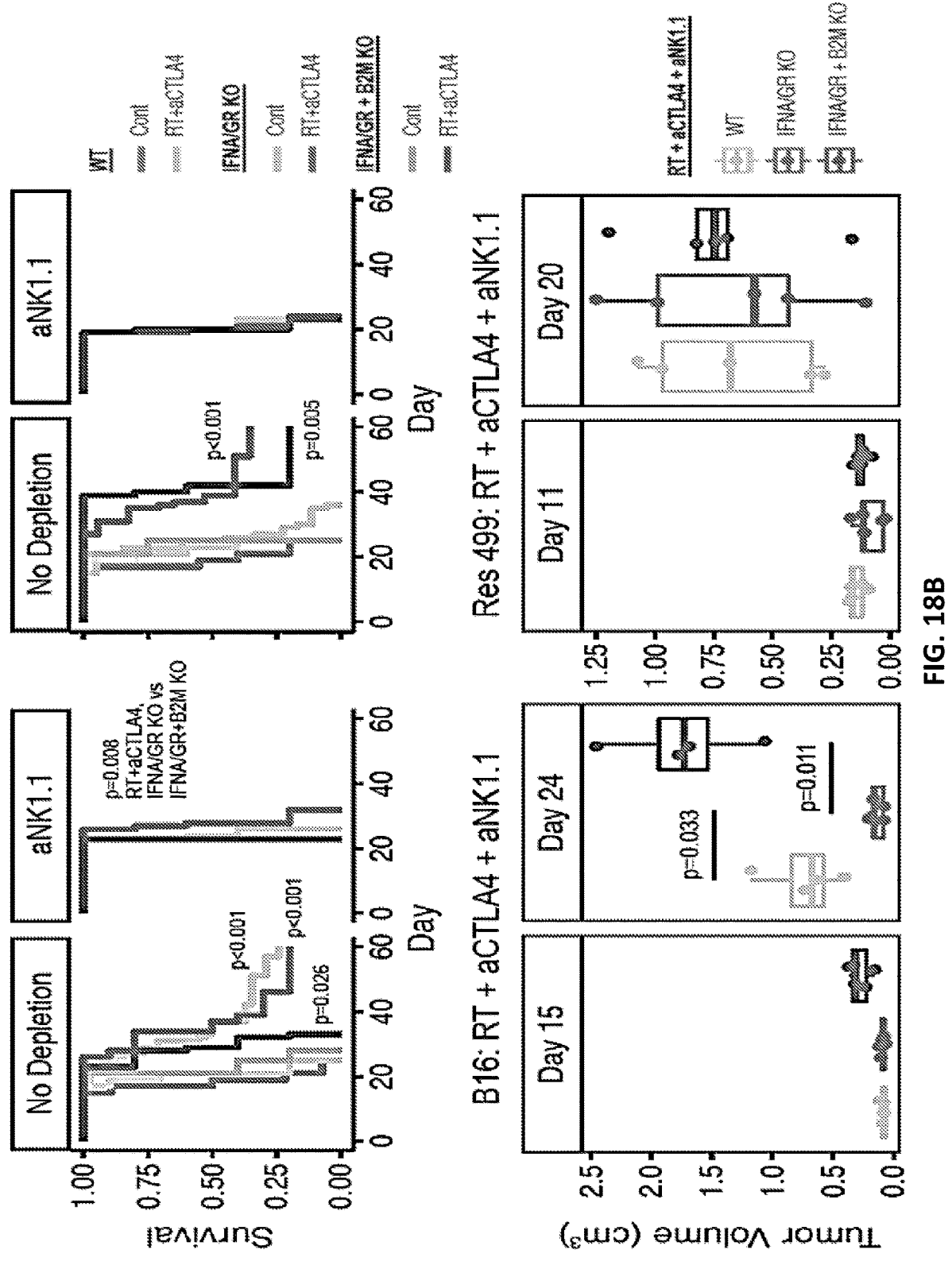

In contrast to CT26, B16 cells have little constitutive MHC-I and are reliant on IFN for adequate expression (FIG. 9B). B16 tumors respond poorly to anti-PD1 but respond to RT+anti-CTLA4, a combination that enhances T cell repertoire diversity and improves response over anti-CTLA4 alone. Here, knockout of tumor IFN signaling results in worse tumor response and survival after anti-CTLA4 and radiation (FIG. 2E), a combination that enhances T cell repertoire diversity and typically results in approximately 30% complete responses. Surprisingly, knockout of IFNGR and IFNAR in B16 tumors does not negatively impact the efficacy of RT+anti-CTLA4 (FIG. 3B, top left plots), suggesting that other immune-mediated killing mechanisms may compensate for low MHC-I and compromised CTL recognition in this context. Indeed, partial response of IFNGR knockout tumors to RT+anti-CTLA4 is maintained even after B2M is ablated (FIG. 18B, top left plots). However, when B2M knockout is accompanied by depletion of NK1.1+ cells (FIG. 10A), which are typically conventional NK cells and ILC1s, response is completely eliminated (FIG. 18B, left top and bottom plots, grey vs red). In contrast to B16, Res 499 tumors are resistant to RT+anti-CTLA4 and have relative depletion of predicted neoantigens (FIGS. 2K and 2M). Despite this, knockout of IFNGR and IFNAR restores Res 499 response to levels at least as high as parental B16 tumors (FIG. 18B, right plots). Consistent with loss of neoantigens and reliance on innate immune killing, co-ablation of B2M has no discernible effect while depletion of NK1.1+ cells alone abrogates the benefit from IFNGR+IFNAR knockout (FIG. 18B, right top and bottom plots).

Figure 2F:
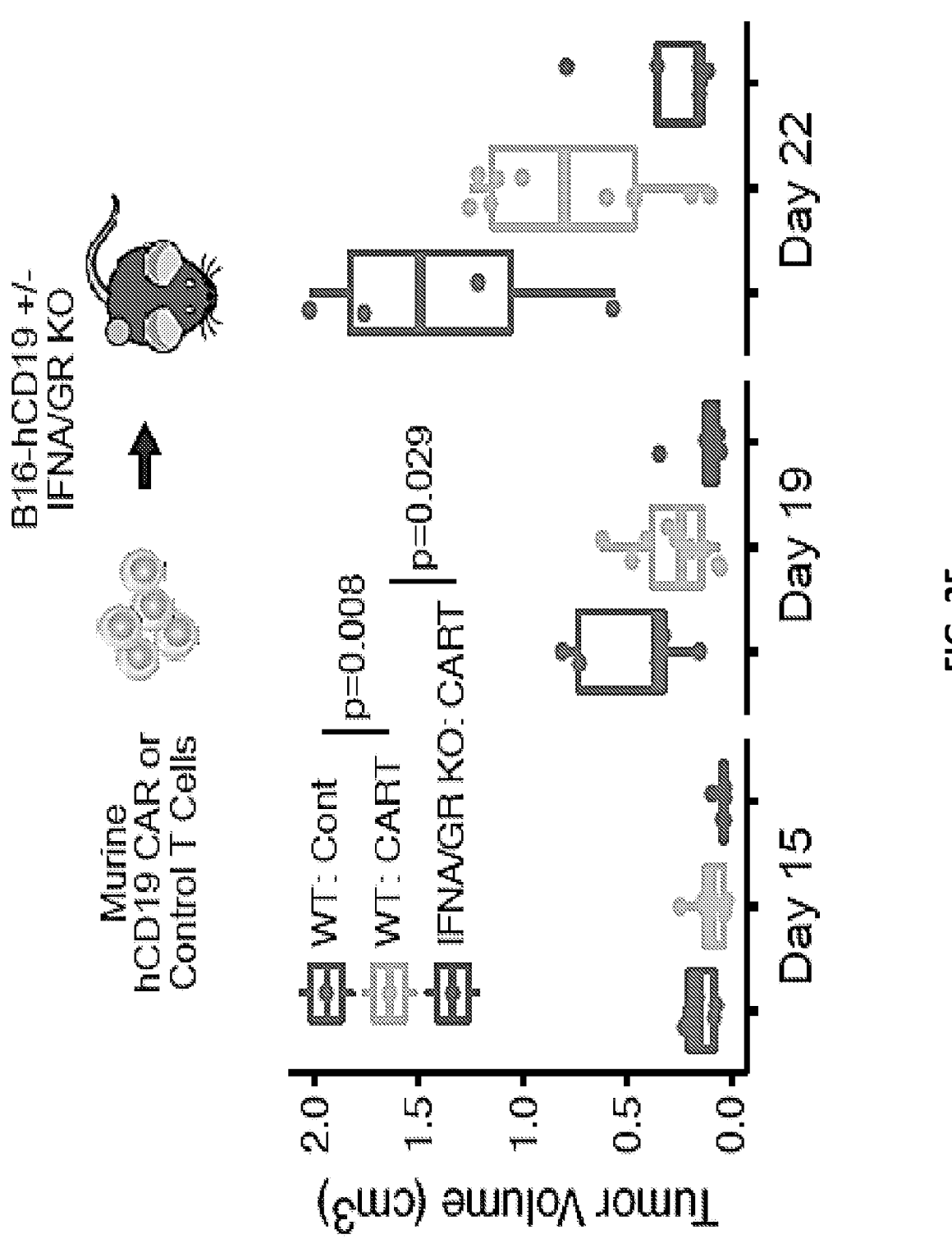
Figure 18C:
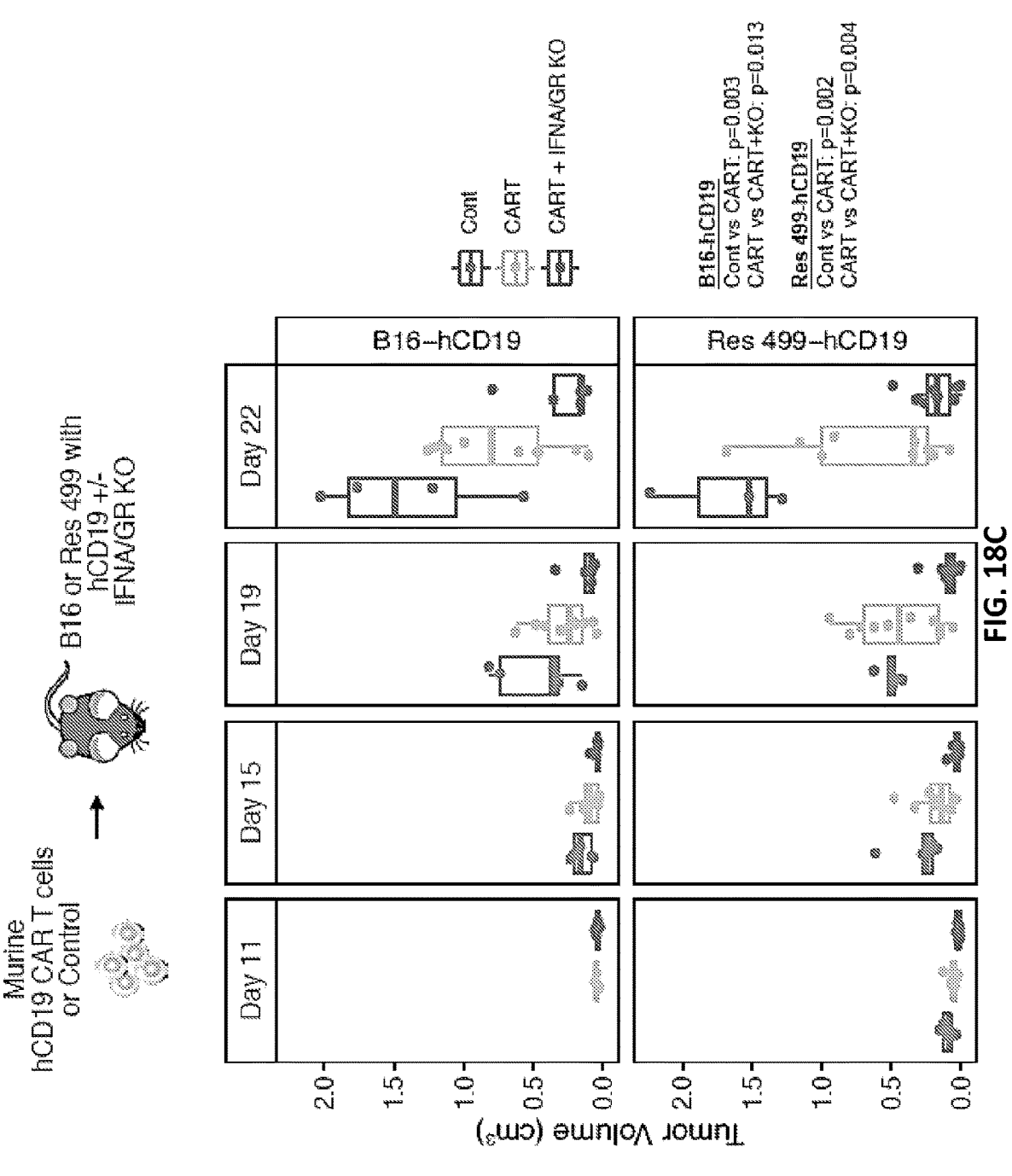

However, if the requirement for MHC-I is bypassed by using a murine CAR T cell against ectopically expressed human CD19 (FIG. 9C), blocking tumor IFN signaling similarly improves response of both B16 and Res 499 tumors (FIGS. 2F and 18C). In the absence of CAR T cells, IFNGR+IFNAR knockout tumors grow similarly to control (FIG. 18). Thus, blocking tumor IFN signaling can impact both CD8 T cell and NK/ILC effector function.

These data suggest that blocking tumor IFN signaling can improve T cell-mediated killing when antigen recognition is not limited by inhibiting IFN function, as in the case of CT26 tumors and use of CAR T cell therapy. In tumors with low MHC-I, preventing tumor IFN signaling may compromise CTL-mediated recognition but anti-tumor effects of NK/ILC1s can compensate to maintain response, as in the case of B16 tumors. In tumors such as Res 499 that are highly resistant and otherwise poorly recognized by T cells, the dispensability of MHC-I allows for restored response through NK/ILC-mediated killing.

Thus, these results suggest that tumors dependent on IFN for adequate MHC-I and antigen presentation are rendered poorly responsive with loss of IFN signaling, while tumors with high baseline MHC-I and high TMB can exhibit enhanced immunogenicity when tumor IFN signaling is ablated.

Figure 2H:
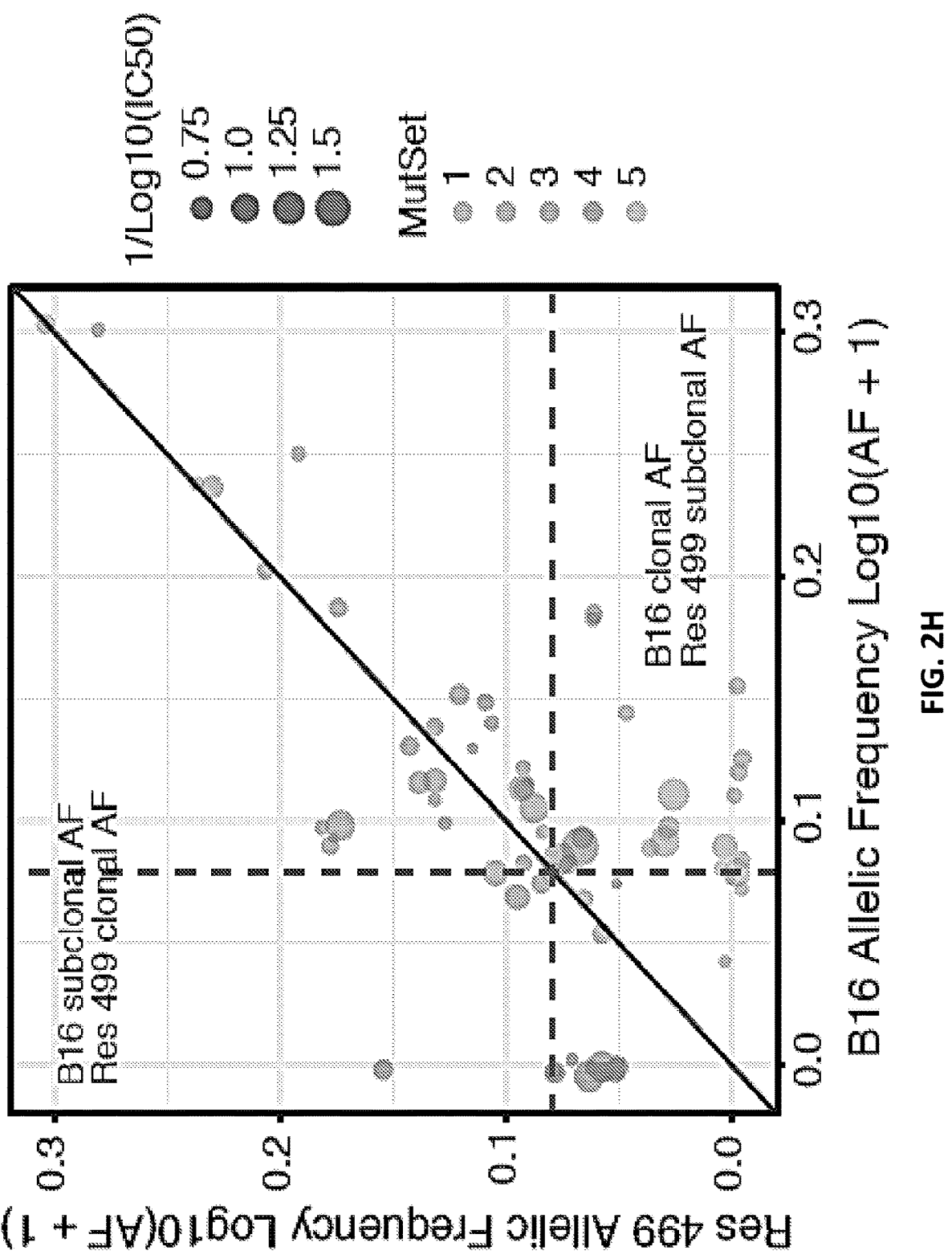
Figures 2I, 2J:
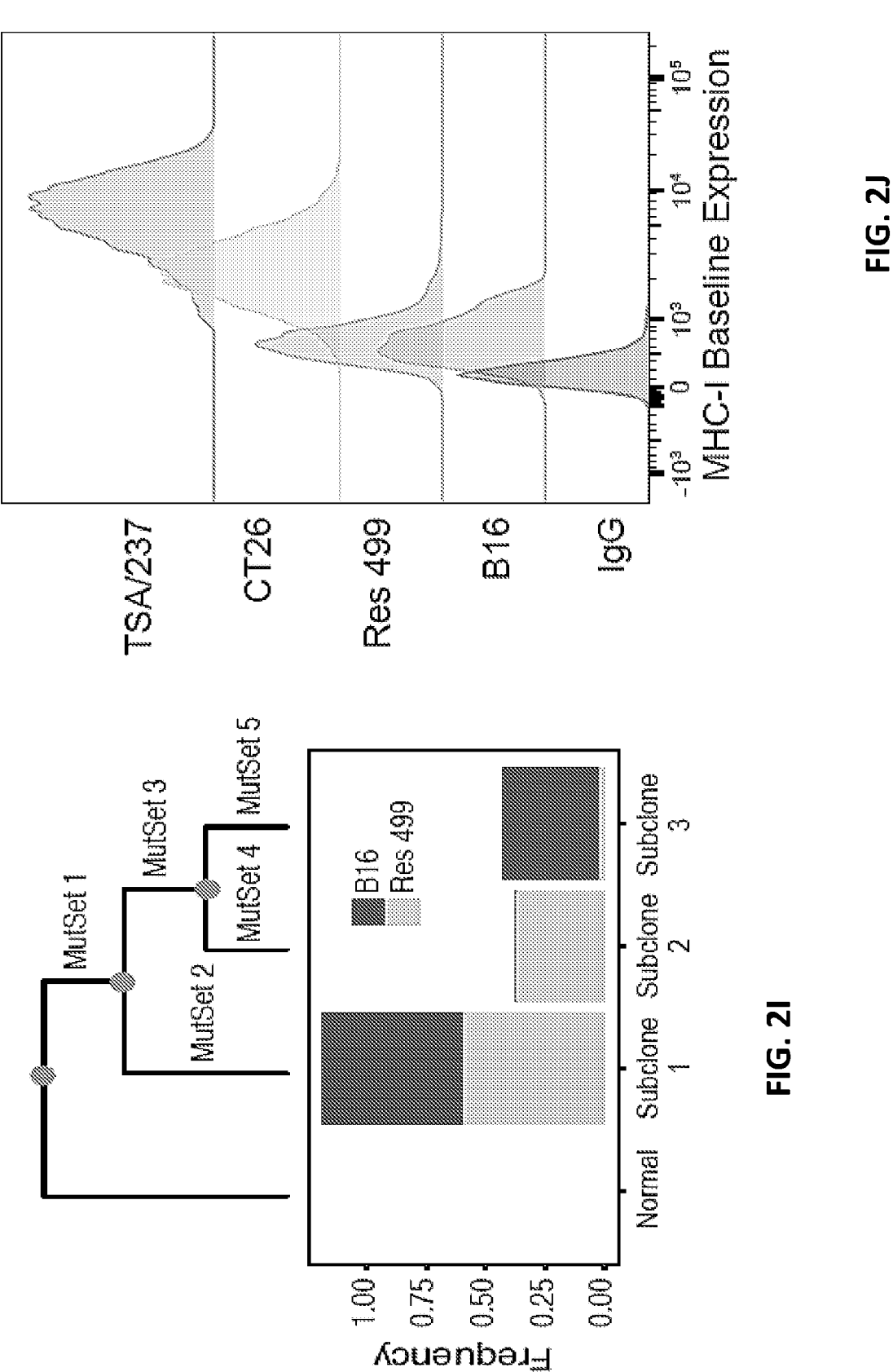
Figure 2K:
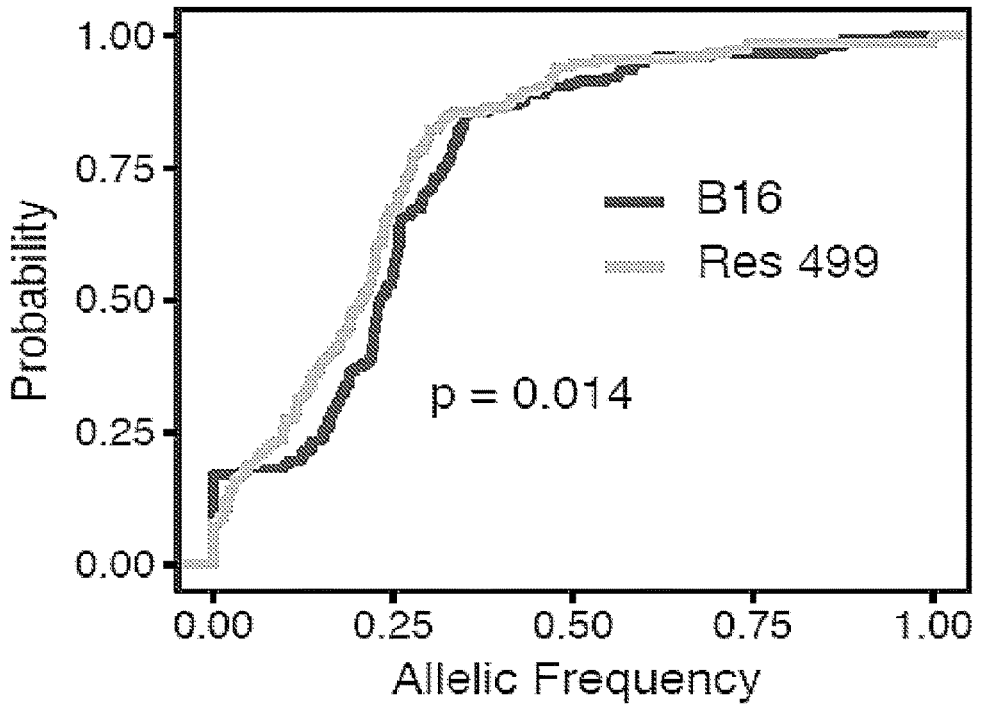
Figure 2L:
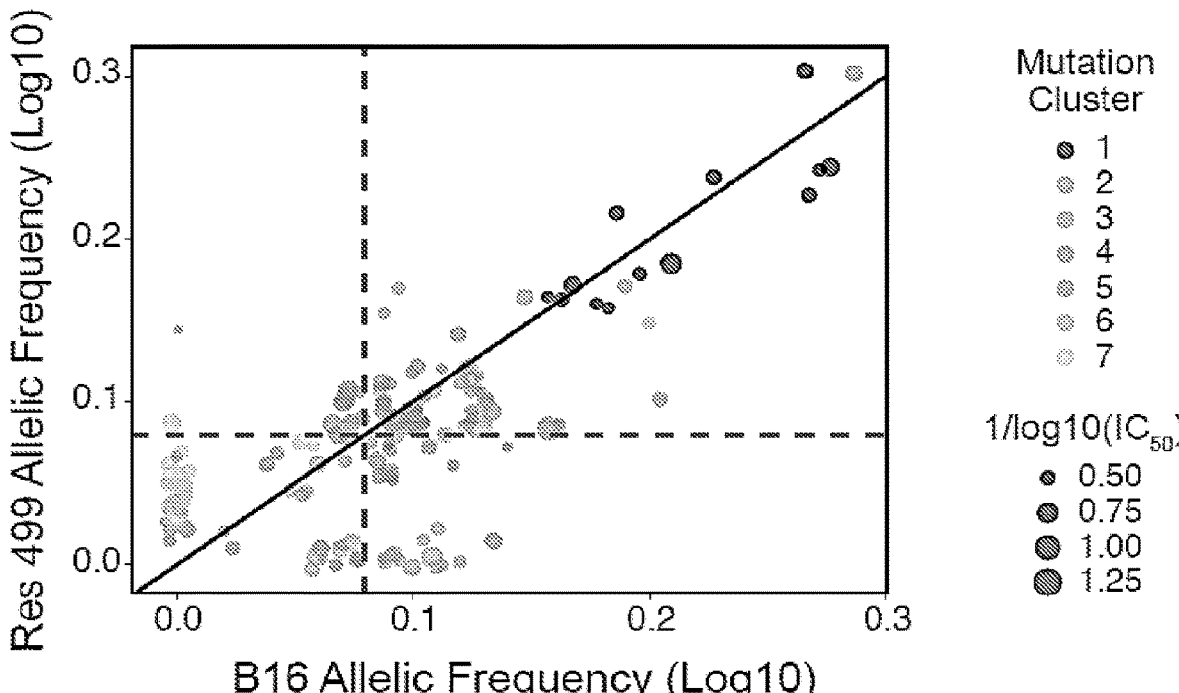
Figure 2M:
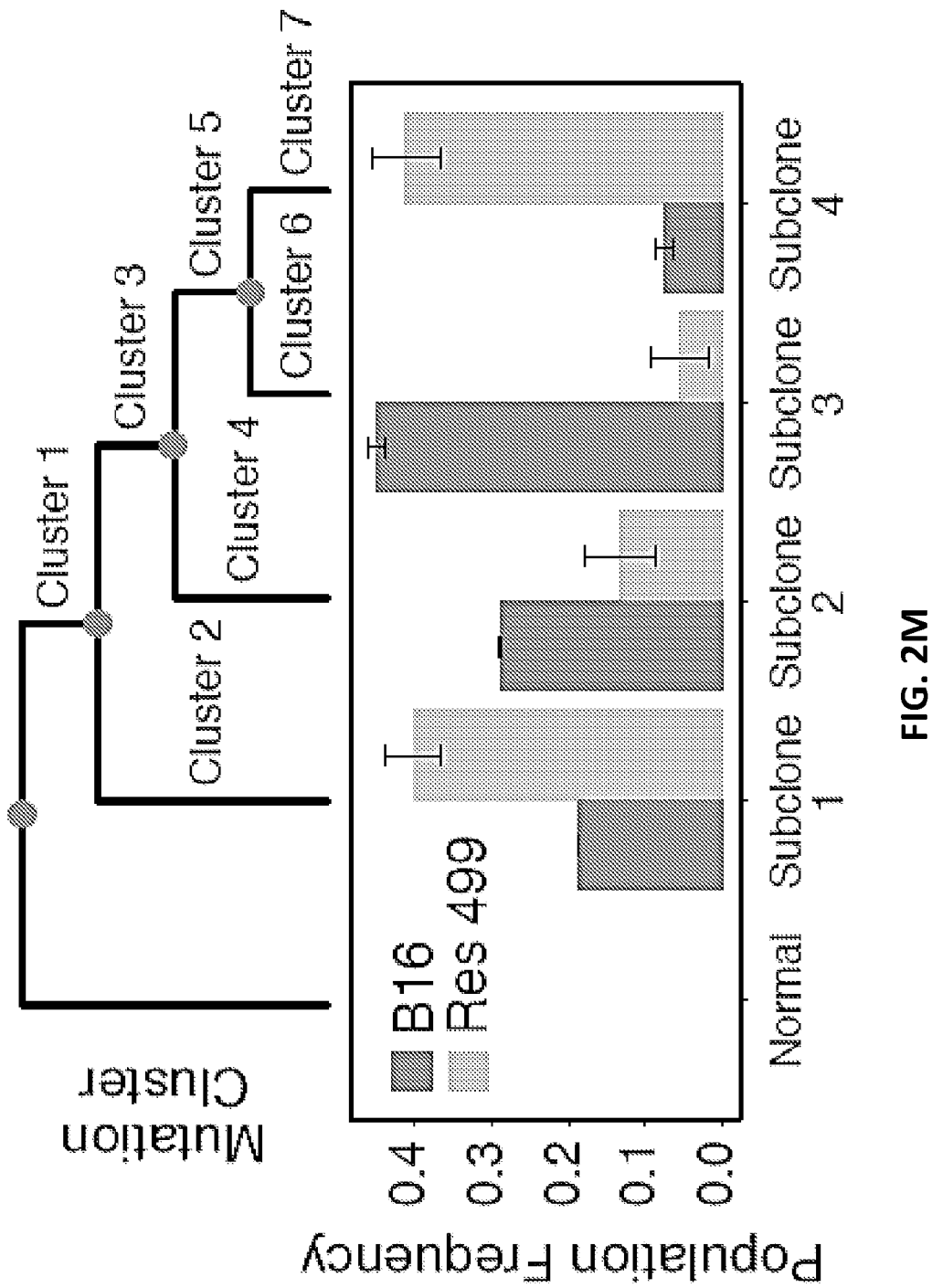
Figures 9C, 9D, 9E:
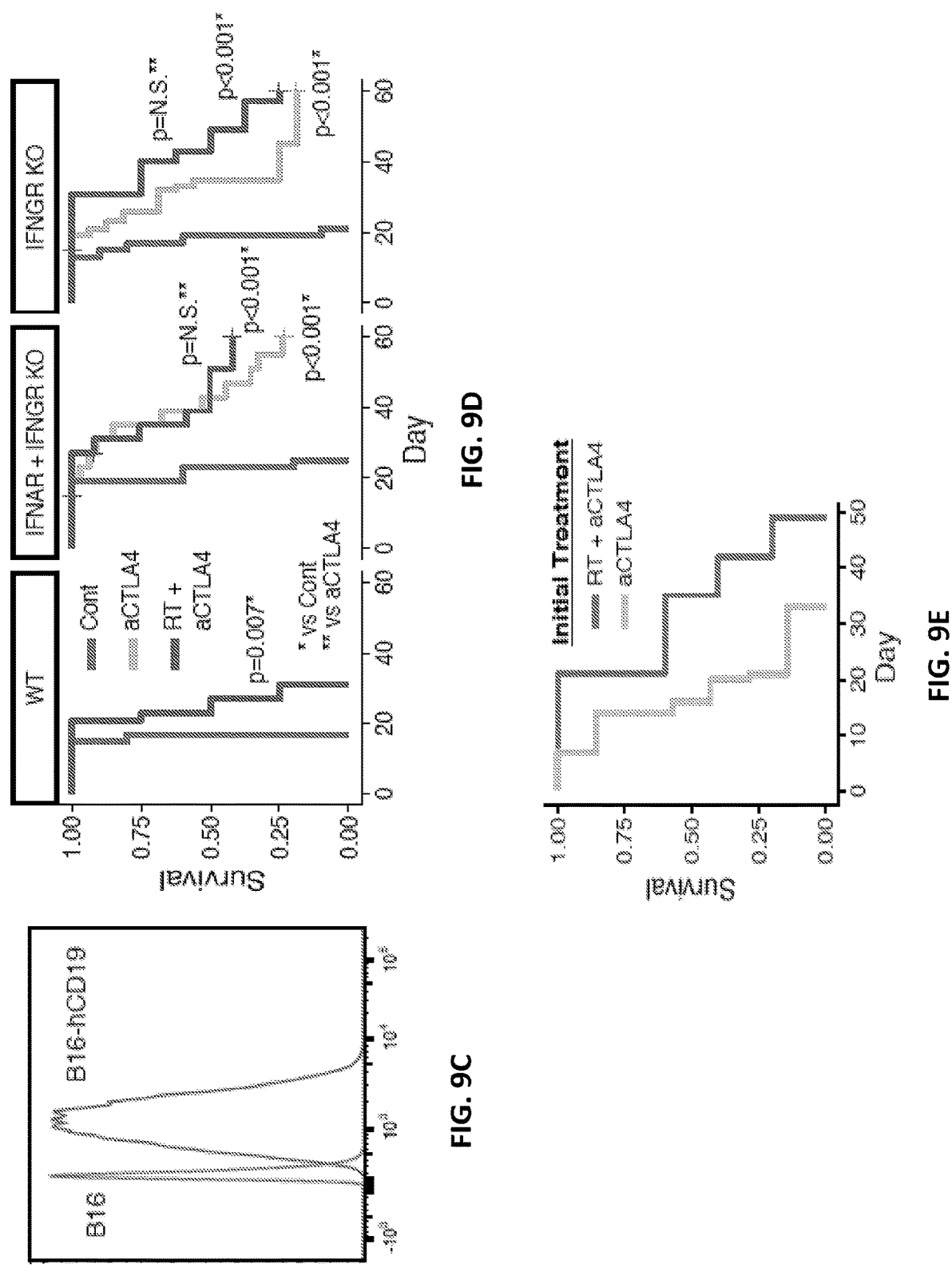

To examine how tumors with poor neoantigens respond to ICB after knockout of tumor IFN signaling, Res 499 melanoma cells were examined, which were isolated from a B16 tumor that relapsed three weeks following treatment with radiation and anti-CTLA4. Compared to B16, Res 499 has higher IFN-independent baseline MHC-I (FIG. 2G) but similar TMB (FIG. 2C). However, as expected for a relapsed tumor, Res 499 shows evidence for genomic contraction of numerous predicted high affinity (<100 nM) neoantigens (FIG. 2H). Specifically, a collection of neoantigens, denoted MutSet 5, have clonal (near-heterozygous or greater) allelic frequencies in B16 but have sub-clonal frequencies in Res 499 (FIG. 2H, lower right quadrant). The MutSet 5 neoantigens are predicted to reside in a subpopulation of cells (Subclone 3) that is nearly eliminated in Res 499 compared to B16 (FIG. 2I), consistent with ICB-mediated immunoediting and depletion of neoantigens prior to relapse. However, despite the depletion of neoantigens, loss of tumor IFN signaling in Res 499 tumors through knockout of STAT1, IFNAR, and/or IFNGR restores response to anti-CTLA4 with or without radiation (FIGS. 2E and 9D). These results suggest compromised MHC-I after loss of tumor IFN signaling is less consequential for tumors with depleted neoantigens, allowing blockade of IFN-driven resistance mechanisms to improve anti-tumor response.

In total, these findings suggest that inhibiting IFN signaling in tumors with adequate neoantigens but reliant upon IFN for sufficient MHC-I expression (e.g., B16) can interfere with anti-tumor immune responses. For tumors with 1) strong neoantigens and high constitutive MHC-I (e.g., CT26) or 2) poor or depleted neoantigens (e.g., Res 499), the benefit of blocking IFN-driven resistance outweighs the detrimental impact on inducible MHC-I levels—in the former condition, CD8 T cell-dependent immunity is markedly enhanced, while in the latter condition, the dispensability of MHC-I presumably enables non-T cell-mediated killing mechanisms.

Figure 3A:
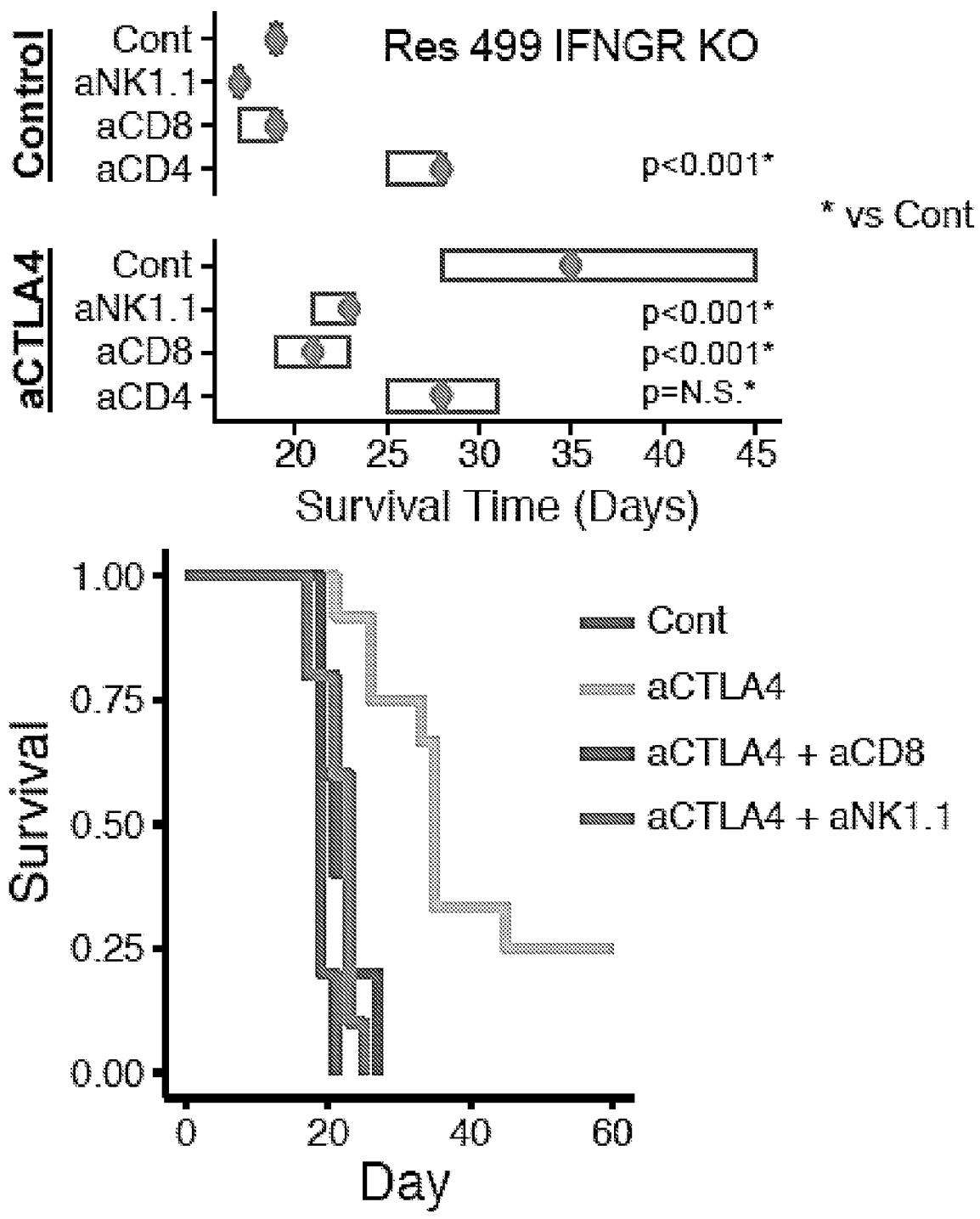
FIGS. 3A-3G illustrate the finding that blockade of tumor IFNG signaling promotes CD8 T cell-dependent NK/ILC maturation and tumor killing that is independent of Perforin and MHC-I.
Figure 3B:
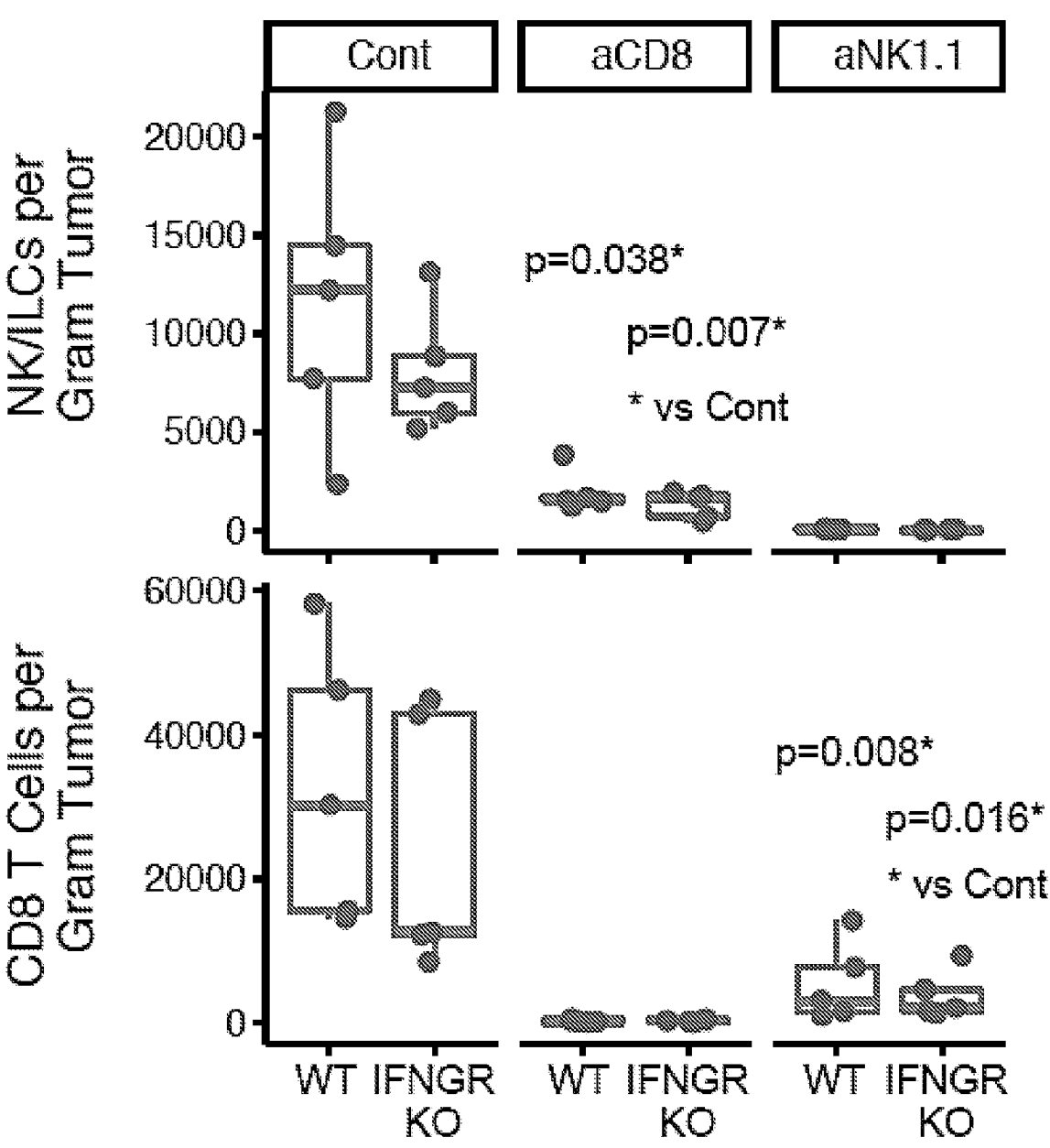

Example 4: Inhibition of Tumor IFNG Signaling Enables CD8 T Cells to Support NK/ILC-Mediated Killing of Neoantigen-Depleted and MHC-I-Deficient Tumors Without adequate neoantigens, restored ICB response from blocking tumor IFN signaling in Res 499 cells is unlikely due to direct T cell killing. To better understand the mechanism and to avoid conflating effects of type I and II IFN, the next set of experiments focused on how IFNG orchestrates resistance in tumors with neoantigen depletion. The addition of radiation, which enhances the diversity of the T cell repertoire, did not improve response of Res 499 IFNGR knockout tumors compared to anti-CTLA4 alone (FIG. 9D). Moreover, no durable immunological memory occurred upon rechallenging mice that cleared IFNGR-deficient tumors after initial treatment with anti-CTLA4 with or without radiation (FIG. 9E). This is in contrast to mice with CT26 tumors whereby a complete response generates resistance to tumor rechallenge (8 out of 8 mice). To determine what immune cells may explain restored ICB responses but lack of durable memory after IFNGR knockout of neoantigen poor Res 499 tumors, various immune populations were depleted (FIGS. 3A and 10A). This revealed that improved ICB response requires NK1.1+ innate immune cells, which are typically conventional NK cells, ILC1s, and possibly a subset of ILC3s. However, CD8 T cells are also needed for response. A similar requirement for both immune cell types was also observed after IFNGR knockout in a TSA breast cancer model that exhibits relatively low TMB and a paucity of predicted strong neoantigens (FIGS. 2C and 10B-10E). Indeed, depletion experiments demonstrate that an interaction between NK/ILCs and CD8 T cells is evident. The abundance of NK1.1+NK/ILCs in Res 499 tumors is dramatically curtailed when CD8 T cells are depleted, while the frequency of intratumoral CD8 T cells reciprocally falls when NK/ILCs are depleted (FIG. 3B).

Figure 3C:
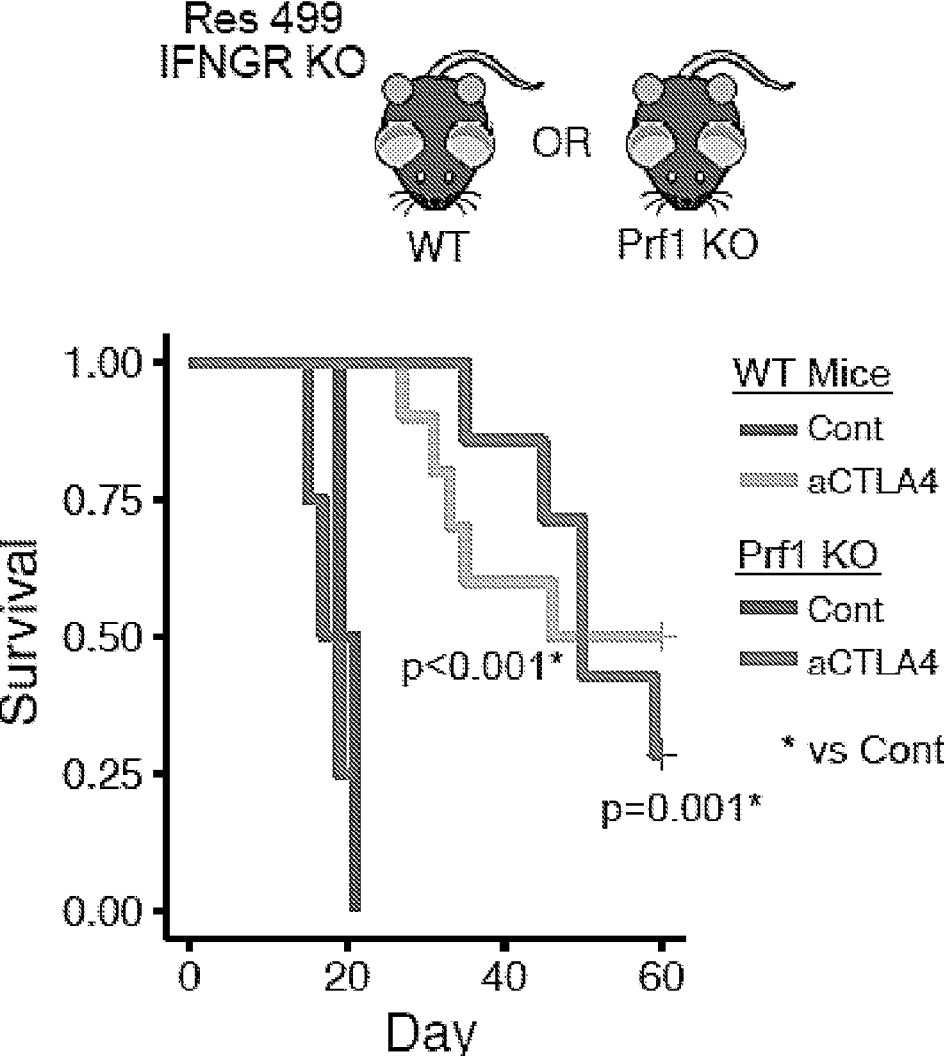
Figure 3D:
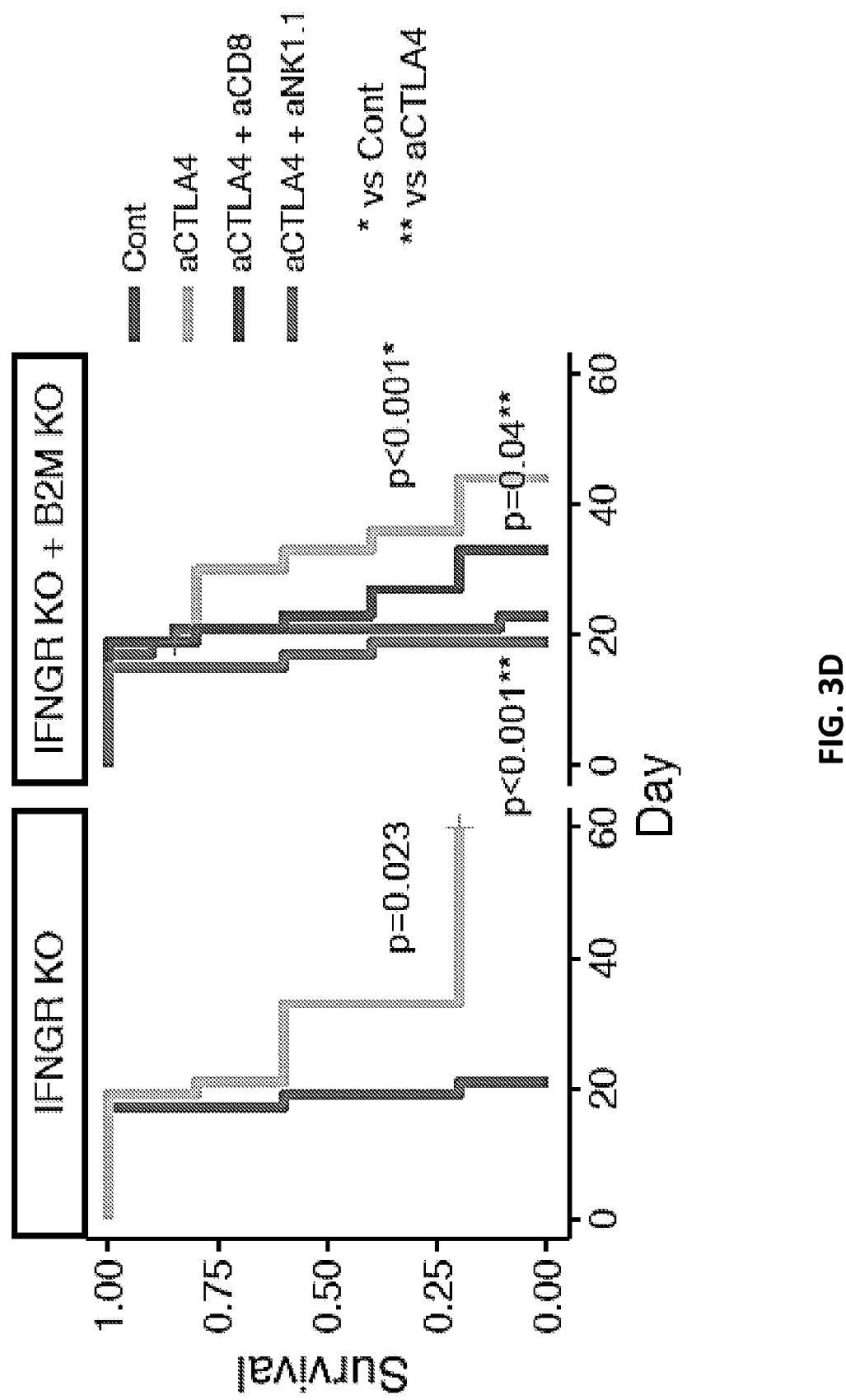
Figure 3E:
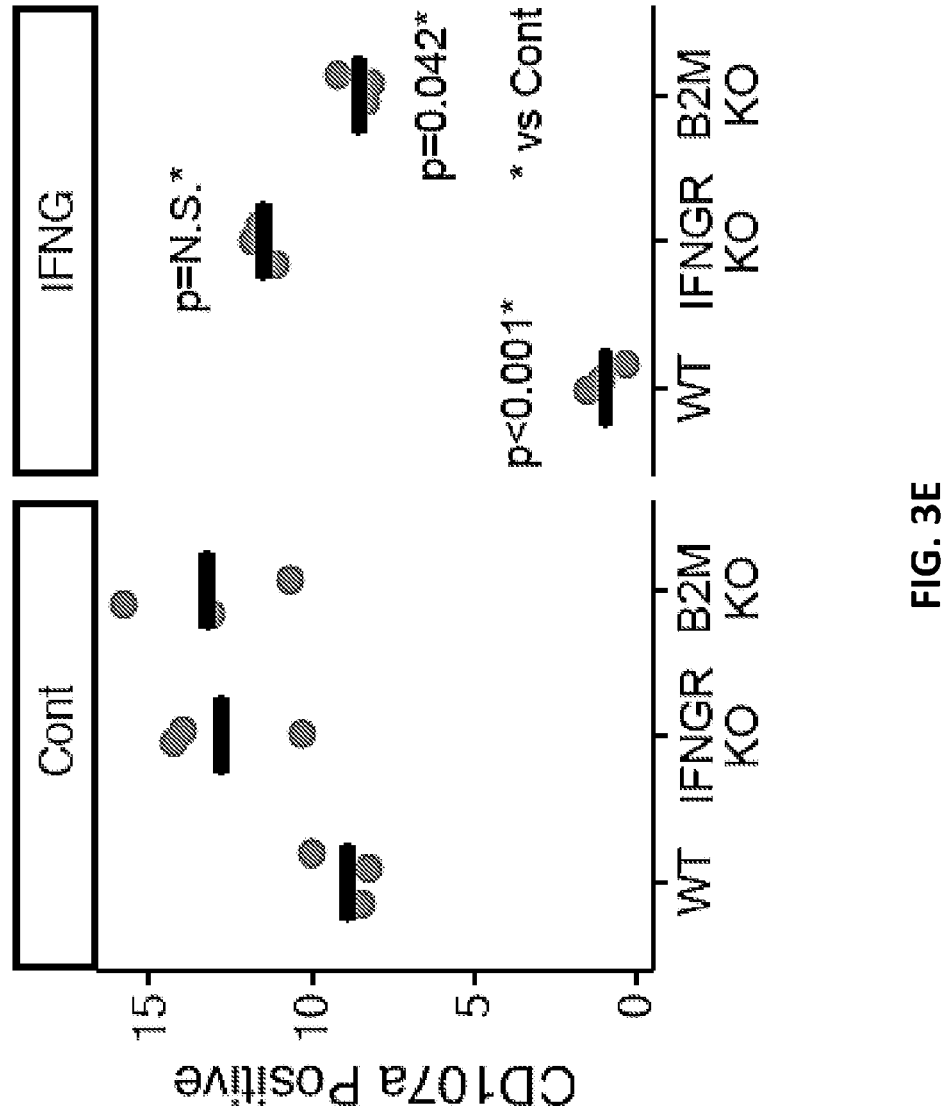
Figure 3F:
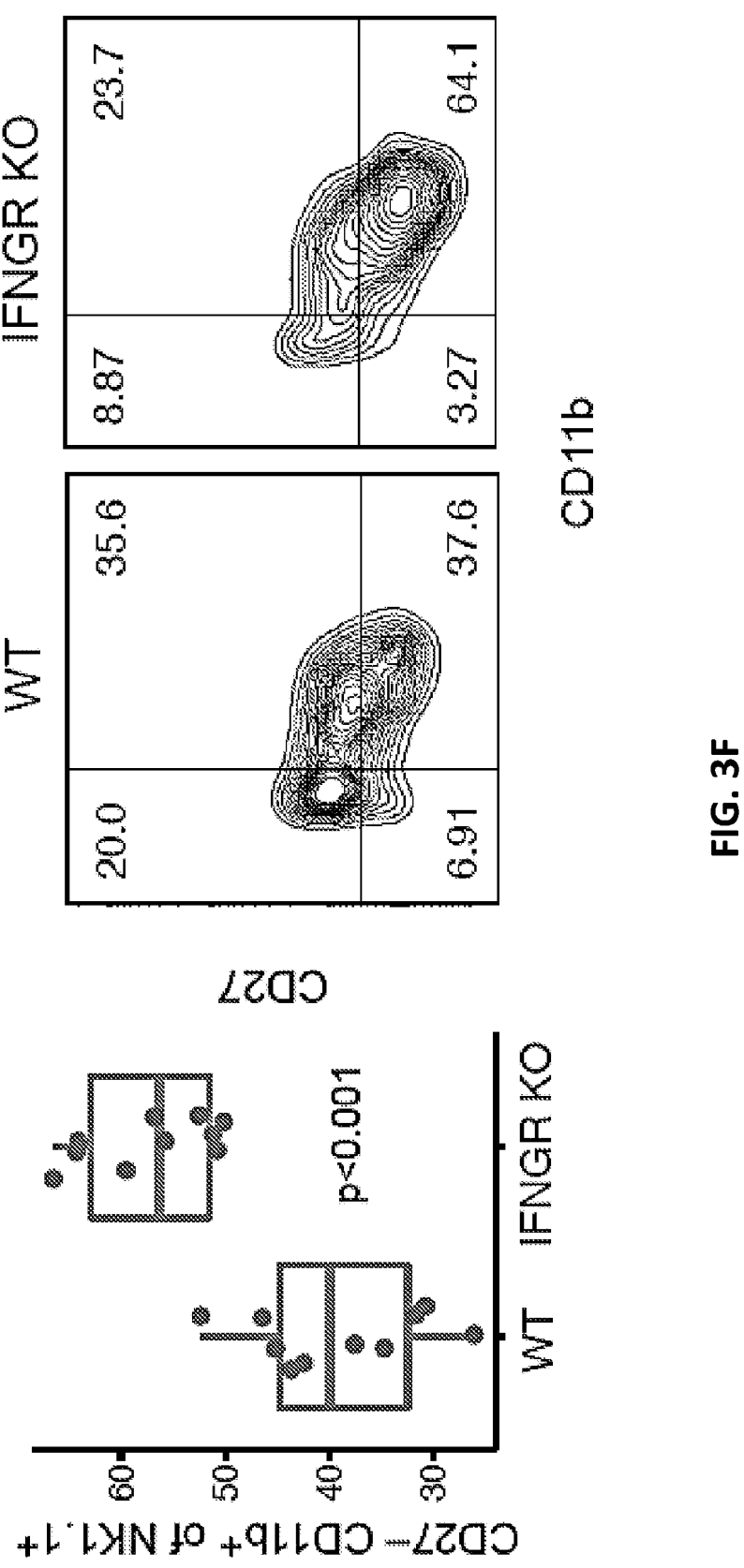
Figure 3G:
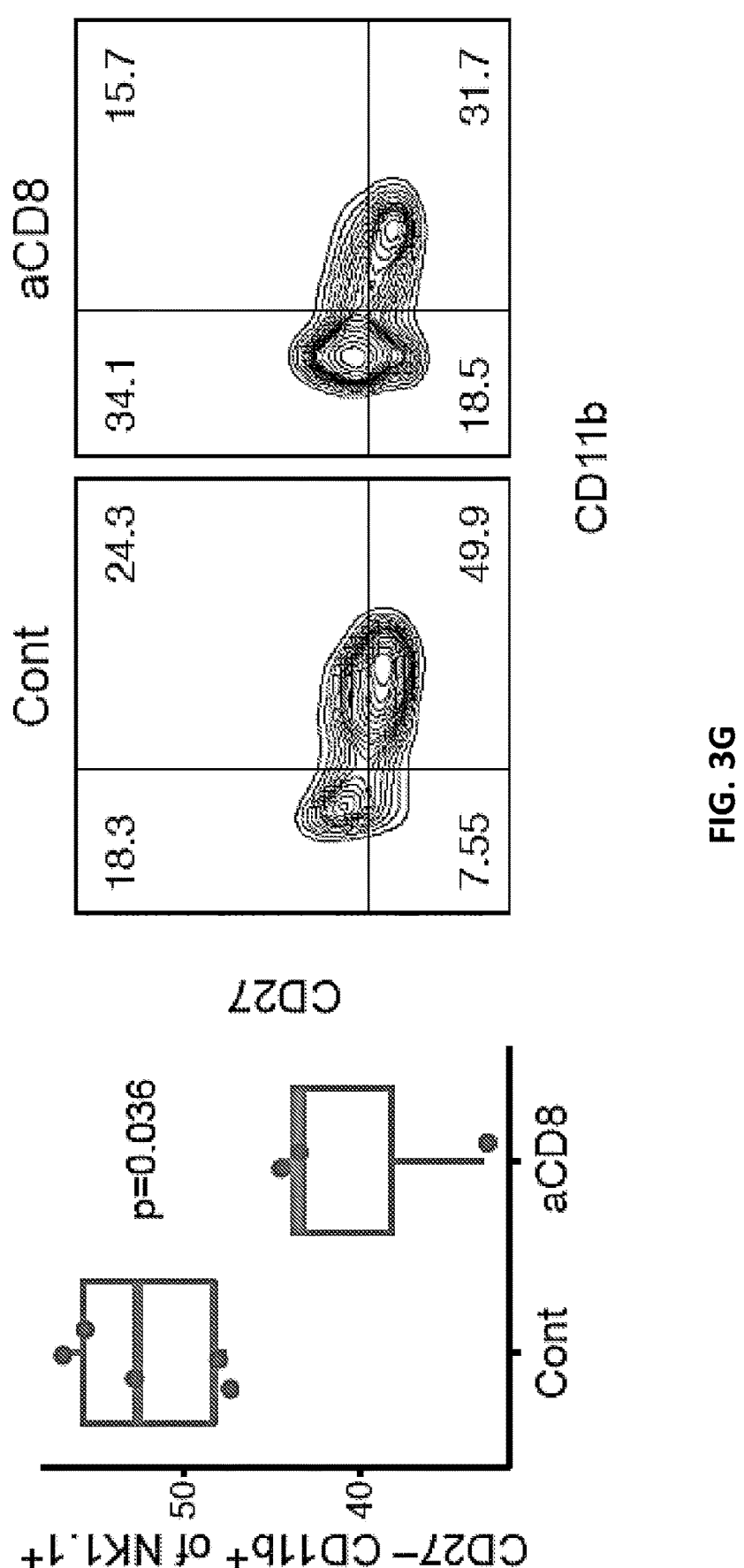

Since NK1.1+NK/ILCs and CD8 T cells influence each other and both are needed for response after IFNGR knockout, it was examined which immune population is directly responsible for tumor killing and which has a supportive role. Restored ICB response of neoantigen poor Res 499 tumors after IFNGR knockout neither requires perforin (FIG. 3C) nor B2M (FIG. 3D and FIG. 10F) yet response in the absence of B2M remains dependent on both NK/ILCs and CD8 T cells (FIG. 3D). The dispensability of perforin and B2M suggest that CD8 T cells do not directly kill tumors after IFNGR ablation but may support NK/ILC-mediated cytotoxicity. To assess whether tumor IFNG signaling directly impacts NK/ILC-mediating killing, poly I:C stimulated splenic NK cells were co-cultured with Res 499 cells in vitro. This results in NK-mediated cytotoxicity as measured by CD107a, which is used as a marker for NK effector function irrespective of the mode of cytotoxicity. Consistent with tumor IFNG signaling impeding NK/ILC killing, IFNG treatment of wild type but not IFNGR knockout Res 499 cells prior to co-culture was sufficient to increase resistance even in the absence of B2M (FIG. 3E). Conversely, in mice bearing Res 499 tumors, loss of tumor IFNGR increases the proportion of intratumoral CD27⁻ CD11b+NK/ILCs (FIG. 3F), a mature NK population that has acquired full cytotoxic function. Interestingly, when CD8 T cells are depleted, the frequency of mature CD27⁻ CD11 b+NK/ILCs decreases (FIG. 3G), indicating that CD8 T cells are needed to support NK/ILC-mediated killing. Together, these results suggest that the killing of neoantigen depleted tumors after IFNGR knockout is predominantly mediated by NK/ILCs, while CD8 T cells have an essential indirect role to enhance intratumoral NK/ILC abundance and maturation, allowing these innate immune cells to kill neoantigen poor tumors.

Figure 4A:
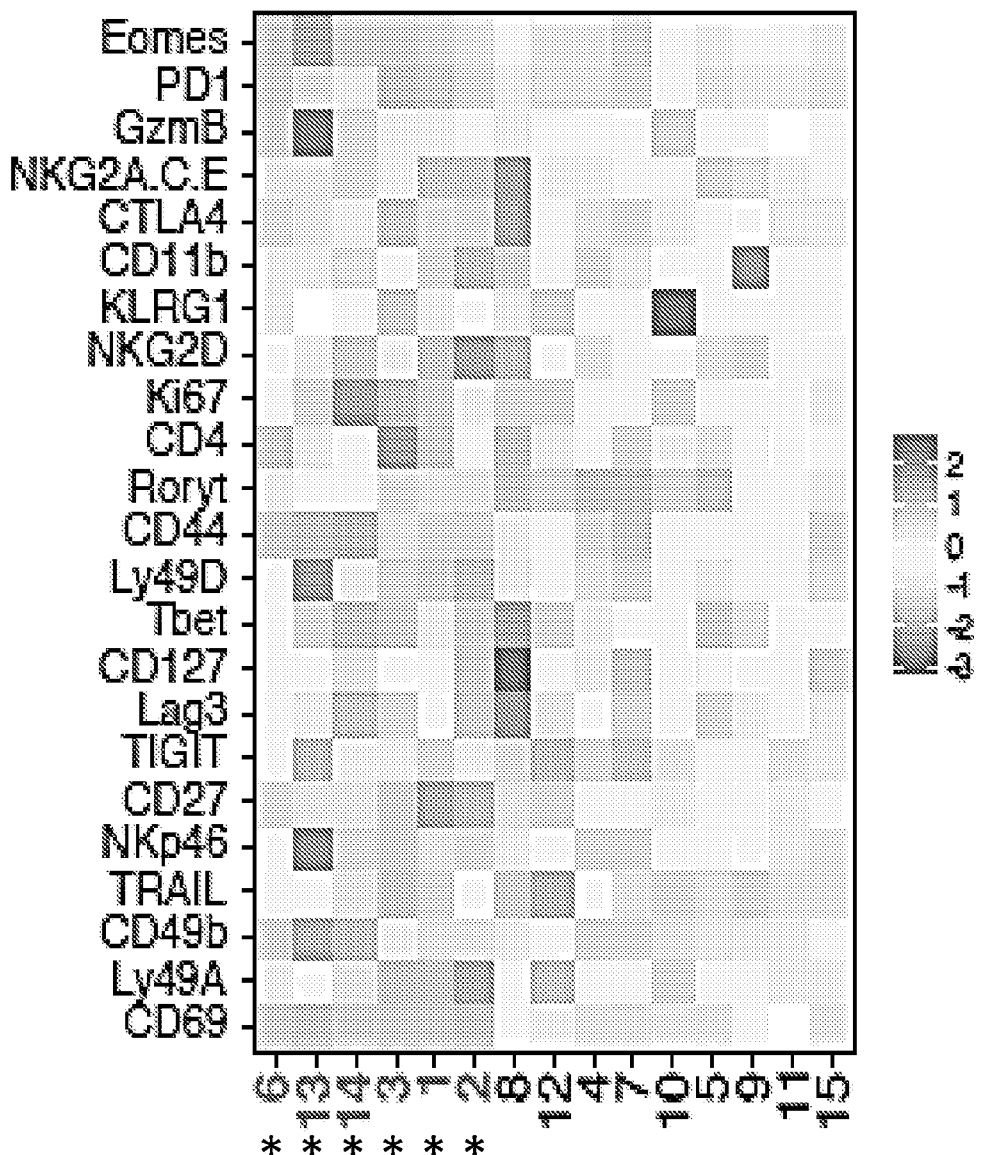
FIGS. 4A-4F illustrate improved $T_{ex}$ function and NK/ILC maturation after blockade of tumor IFNG signaling is associated with a PD1+ TRAIL+ILC1-like subset. CD45+ immune cells in Res 499 tumors with or without IFNGR knockout were profiled by 28-color flow cytometry. Dimensionality reduction and cluster identification were separately performed on (FIG. 4A) TCRB+ CD8+ T cells and (FIG. 4B) TCRB⁻ NK1.1+NK/ILCs. Heatmaps show the scaled MFI for each of the indicated markers for the identified clusters. For the CD8 T cells, clusters enriched for PD1+ Eomes+$T_{ex}$ are denoted with an *. For the NK/ILCs, clusters denoted with an * indicate CD11b$^{int/high}$ innate immune cells. NK/ILC clusters that are most strongly associated with IFNGR knockout tumors are shown in the bar plot.
Figure 4B:
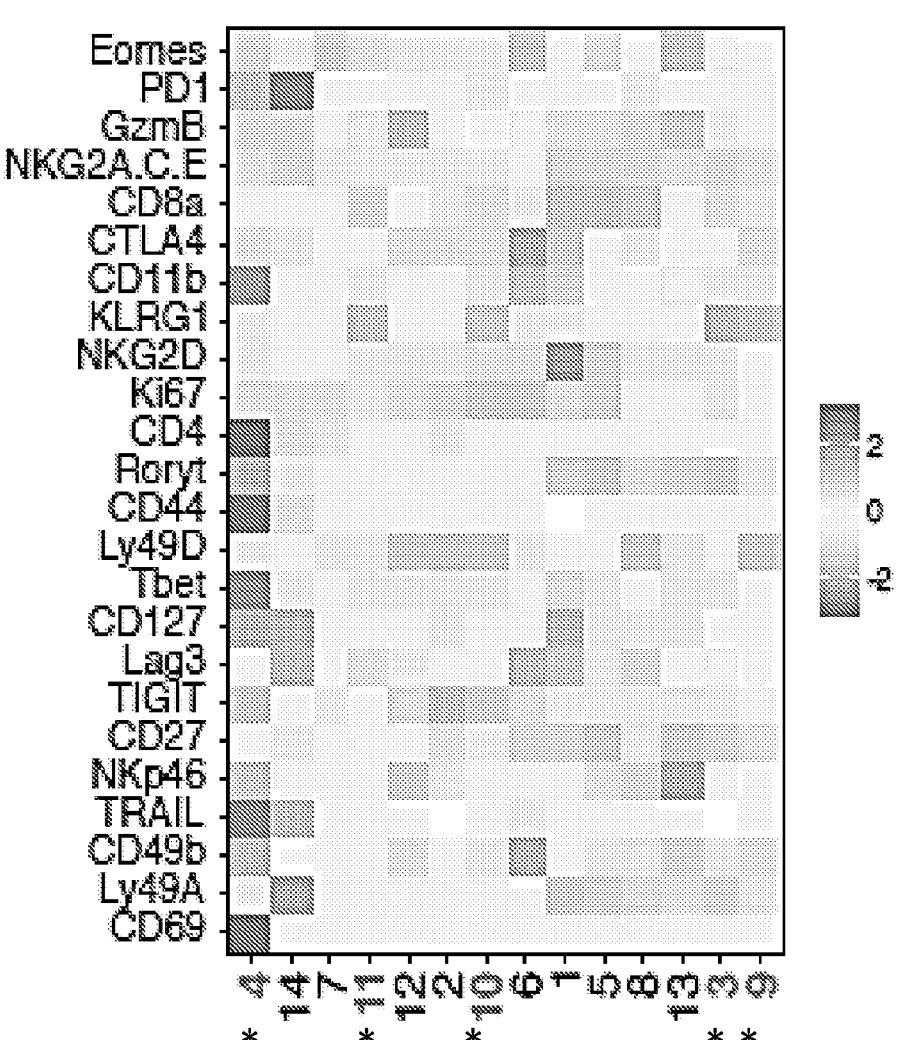
Figure 11A:
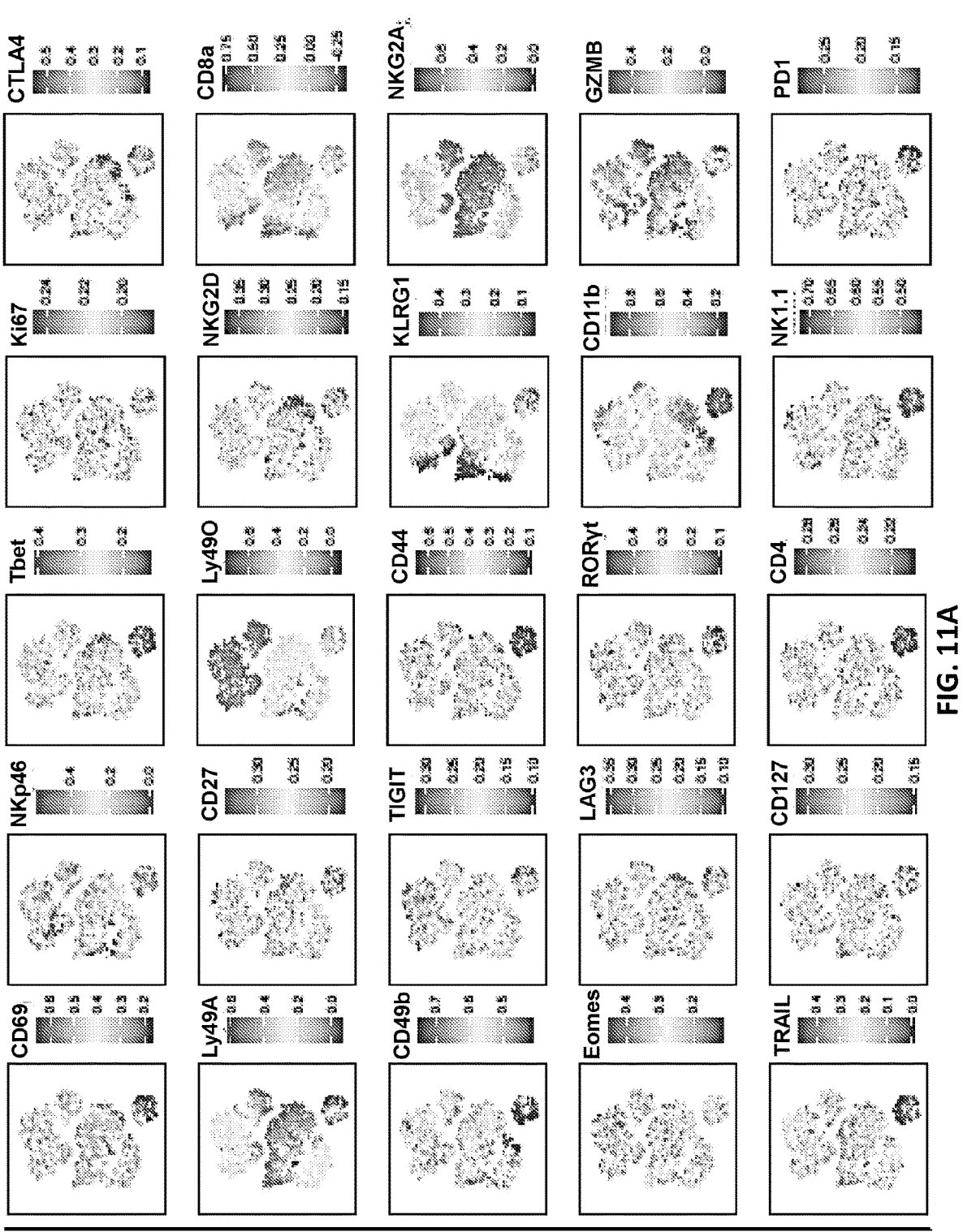
FIGS. 11A-11B illustrate improved $T_{ex}$ function and NK/ILC maturation after blockade of tumor IFNG signaling. tSNE plots show the expression of the indicated markers on (FIG. 11A) NK/ILCs or (FIG. 11B) CD8 T cells. Colors represent expression values and are scaled to the range for each marker.
Figure 11B:
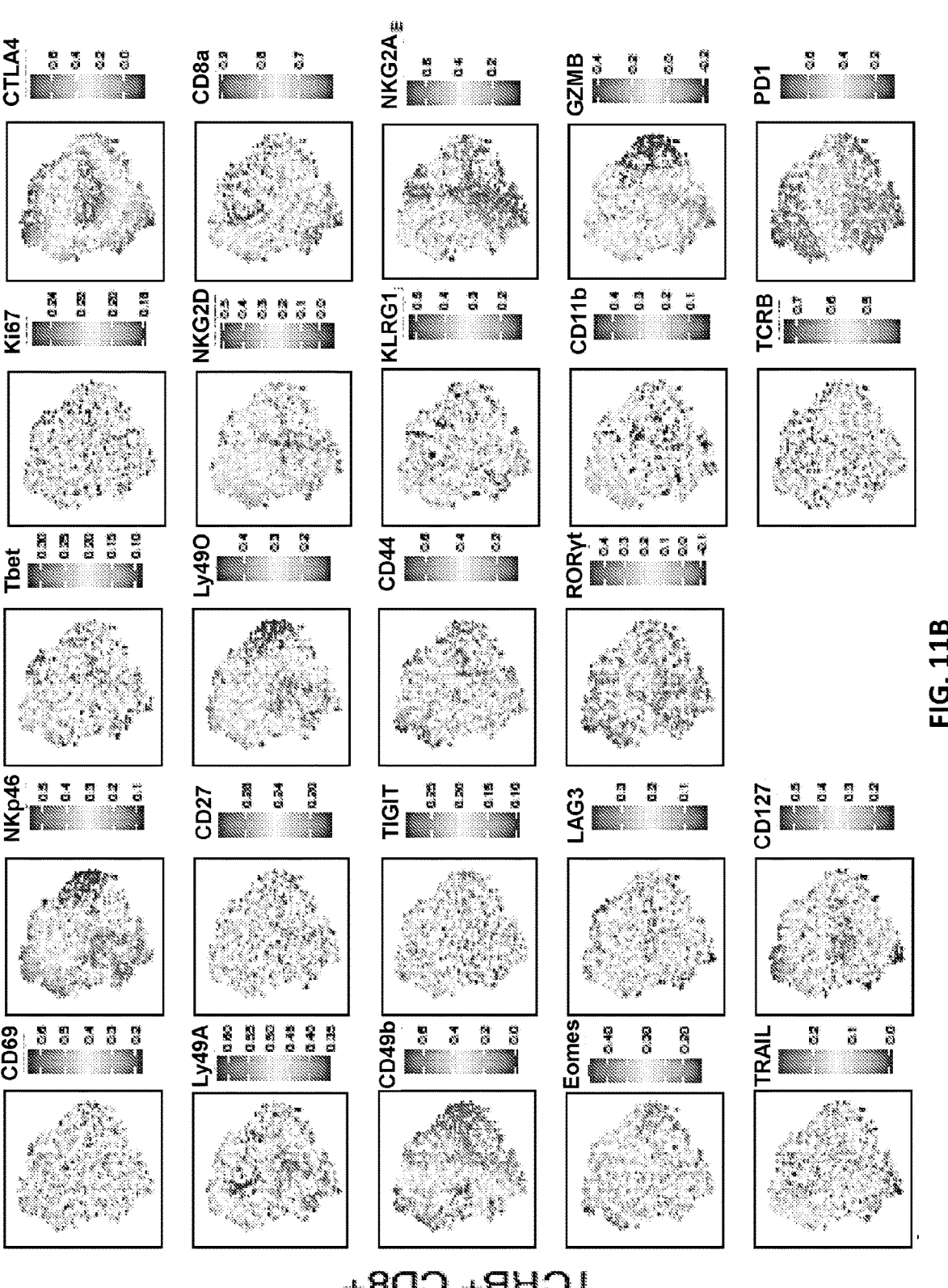

Example 5: Blocking Tumor IFNG Signaling Improves CD8 T$_{ex}$ Function and NK/ILC Maturation that Includes a PD1+ TRAIL+ILC1-Like Subset To better understand how blocking tumor IFNG signaling impacts intratumoral CD8 T cells to support NK/ILCs, 28-color flow cytometry was used to characterize each immune cell type in Res 499 tumors (FIG. 11A-B). Examination of intratumoral PD1+CD8 T cells (FIG. 4A), which was previously demonstrated to be influenced when both tumor IFNAR and IFNGR are blocked, revealed a major population expressing high levels of the exhaustion-related transcription factor Eomes. These PD1+Eomes+ T cells have variable expression of other inhibitory receptors such as CTLA4 and are either low for GzmB and Ki67 (clusters 1, 2, 3), which is consistent with T cell exhaustion, or high for these activation markers (clusters 6, 13, 14). Examination of NK1.1+ TCRB⁻ intratumoral immune cells (FIG. 4B) confirmed that most of these NK/ILCs can be separated into immature CD11b$^{low}$CD27$^{high}$ clusters with low expression of Ki67 and GzmB (clusters 1, 5, 8) or more mature CD11b$^{int/high}$ cD$_{27}$$^{low/high}$ clusters (clusters 3, 4, 9, 10, 11). Indeed, analysis of the changes in NK/ILC cluster frequencies that occur as a result of IFNGR knockout reveal that the most predictive changes are a decrease in the immature CD11b$^{low}$ clusters and a corresponding increase in mature CD11b$^{int/high}$ clusters (FIG. 4B, right). Among the mature CD11b$^{int/high}$ clusters exists a PD1+ TRAIL+population (cluster 4) that also has additional features that resemble ILC1 s such as high expression of Tbet and CD127 but low levels of Eomes and KLRG1 (FIGS. 4B and 11A). Despite these features, under inflammatory conditions it is not always possible to distinguish between ILC1s from NK cells (typically low for CD127 and Tbet) or from ILC1s that transdifferentiated from either ILC2s (typically high for GATA3 rather than Tbet) or ILC3s (typically RORgt high). Indeed, the PD1+ TRAIL+ cluster exhibits notable heterogeneity in markers such as Tbet, CD127, and RORgt (FIG. 11A).

Figure 4D:
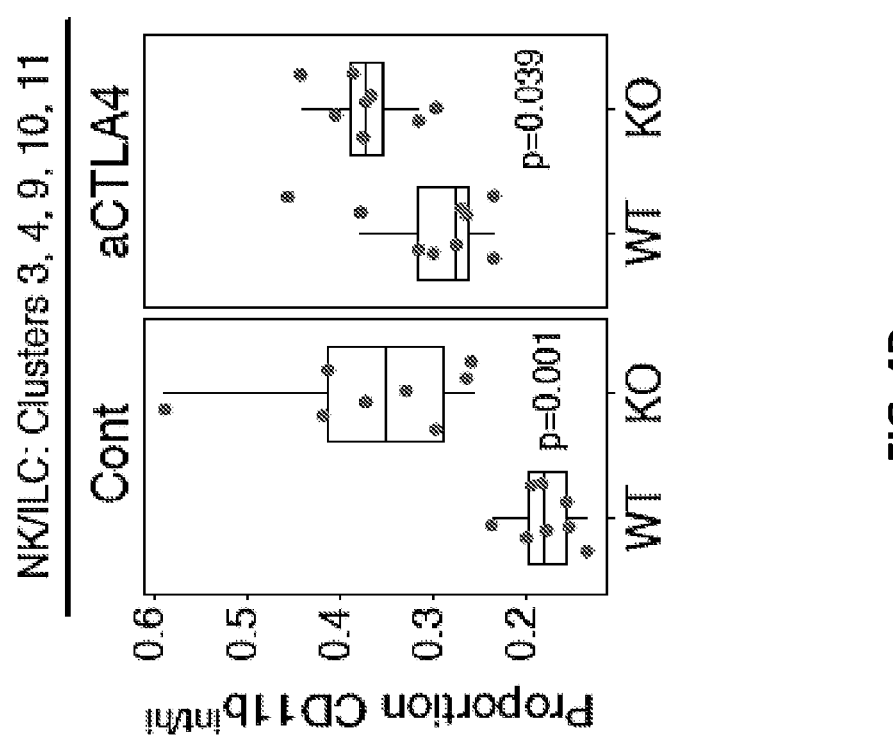
Figure 4C:
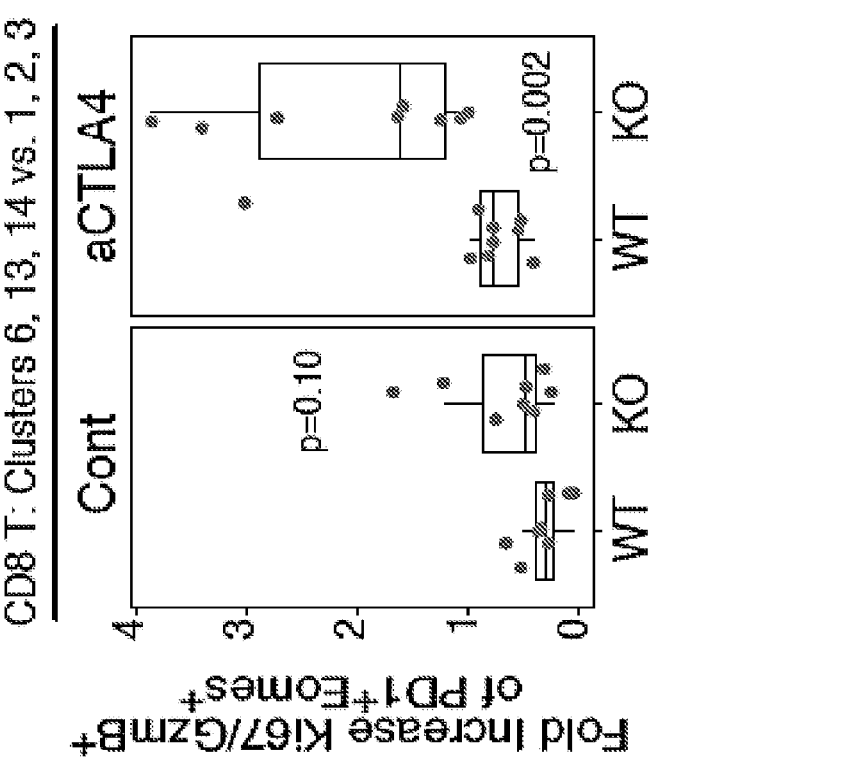
Figure 4E:
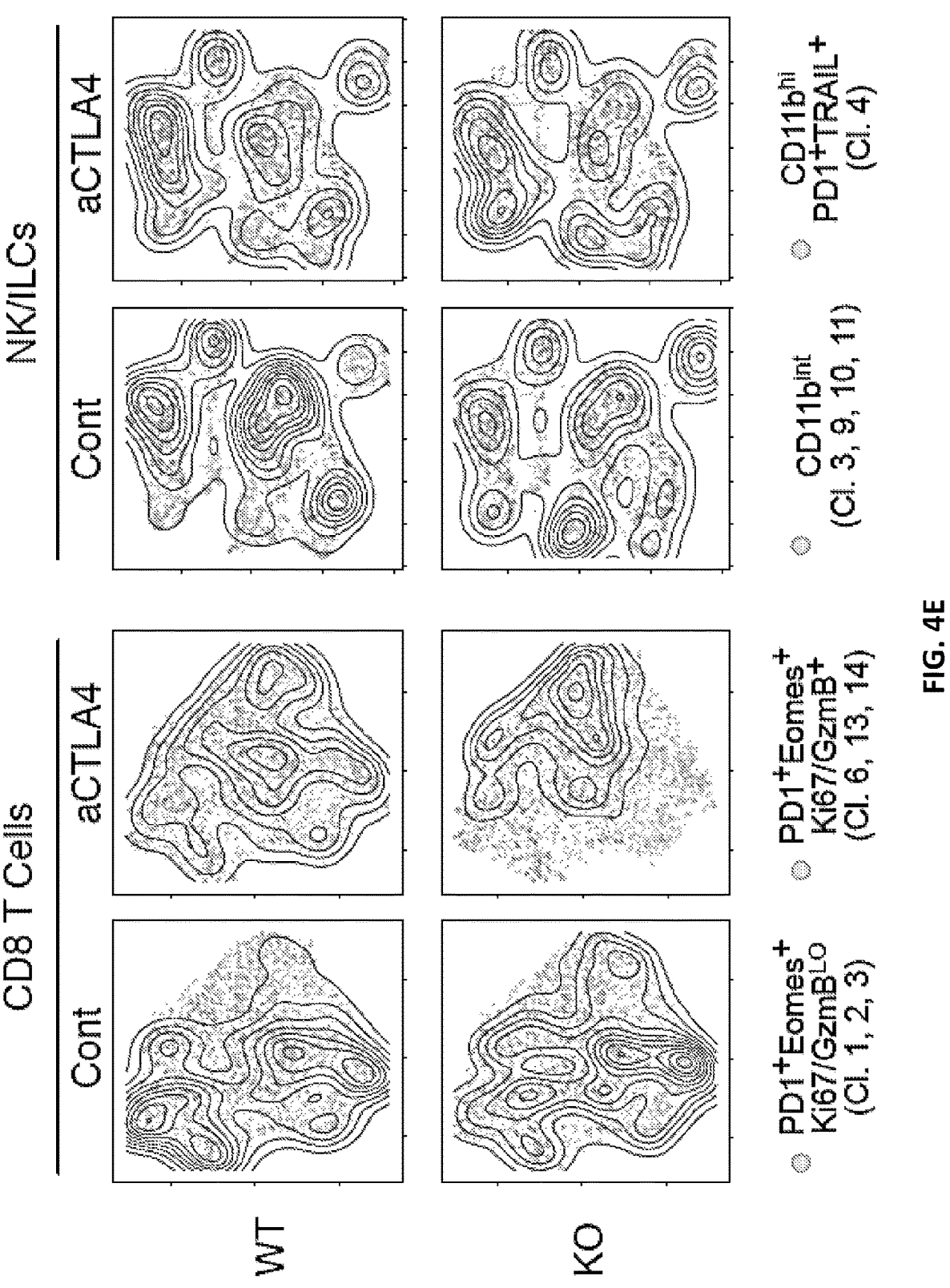
Figure 4F:
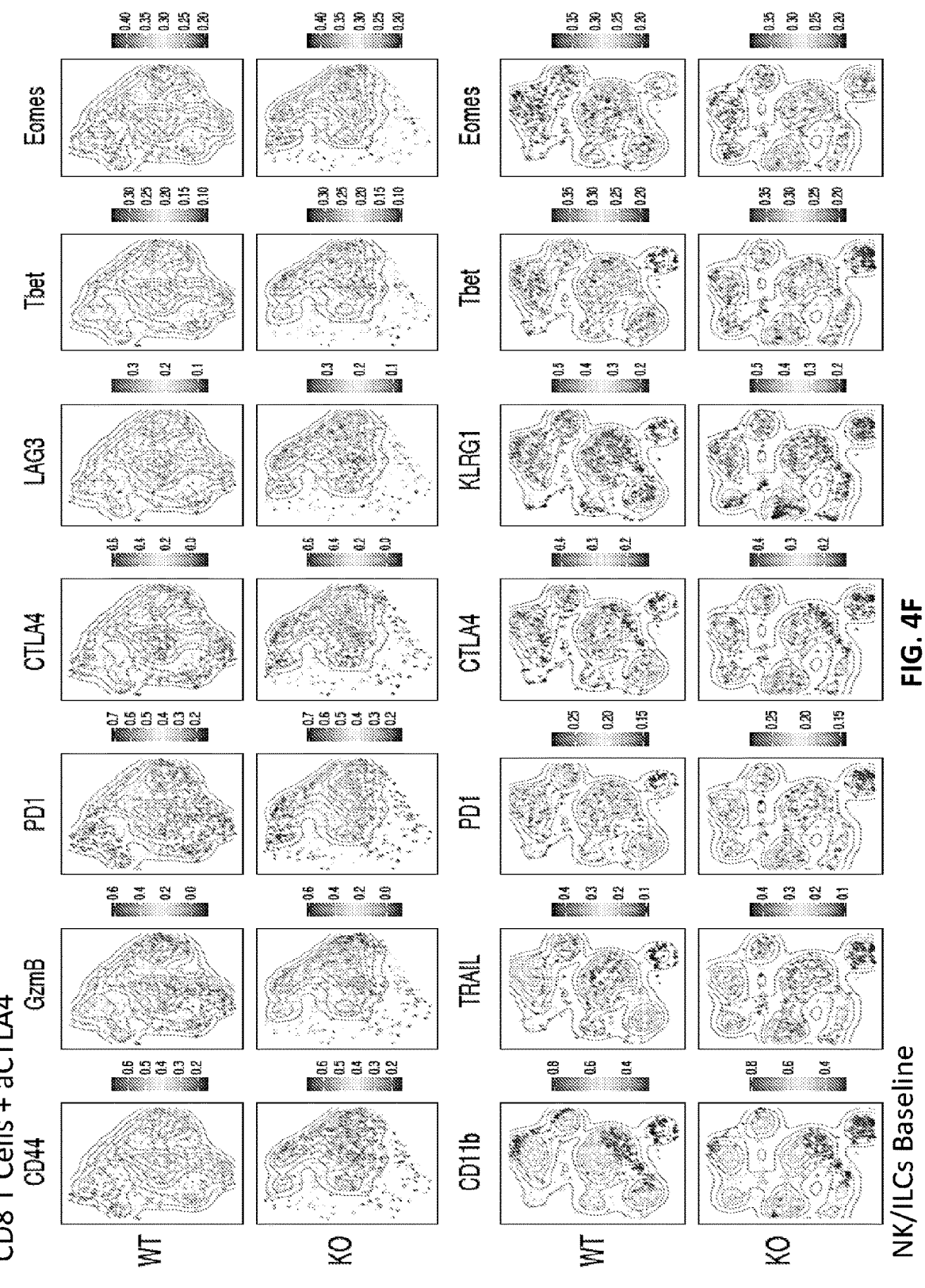

For the intratumoral PD1+Eomes+CD8 T$_{ex}$, knockout of IFNGR in Res 499 tumors modestly increases the proportion that show enhanced activation (or reinvigoration), as measured by Ki67 and/or GzmB (FIG. 4C). However, this population expressing activation markers is significantly augmented by treatment with anti-CTLA4. Overlaying the distribution of CD8 T cells from control and IFNGR knockout tumors onto a tSNE map representing all CD8 T cell clusters (FIG. 4E) reveals that the majority of intratumoral CD8 T cells shifts after anti-CTLA4 to become more activated PD1+Eomes+T$_{ex}$ (cluster 6, 13, 14). For the NK/ILCs, knockout of IFNGR alone is sufficient to induce a substantial shift toward the more mature CD11b$^{int/high}$ clusters that include the PD1+ TRAIL+NK/ILCs (FIGS. 4D and 4E). This shift resulting from IFNGR knockout was comparable to treating wild type tumors with anti-CTLA4. Overlaying the expression of various markers onto the tSNE map for either CD8 T cells treated with anti-CTLA4 or NK/ILCs at baseline further details these aforementioned shifts resulting from tumor IFNGR deficiency (FIG. 4F). Thus, these data suggest that disruption of tumor IFNG signaling improves effector function in T$_{ex}$, particularly after ICB, and enhances the maturation of NK/ILCs that include a PD1+TRAIL+ ILC1-like subset.

Figures 5A, 5B:
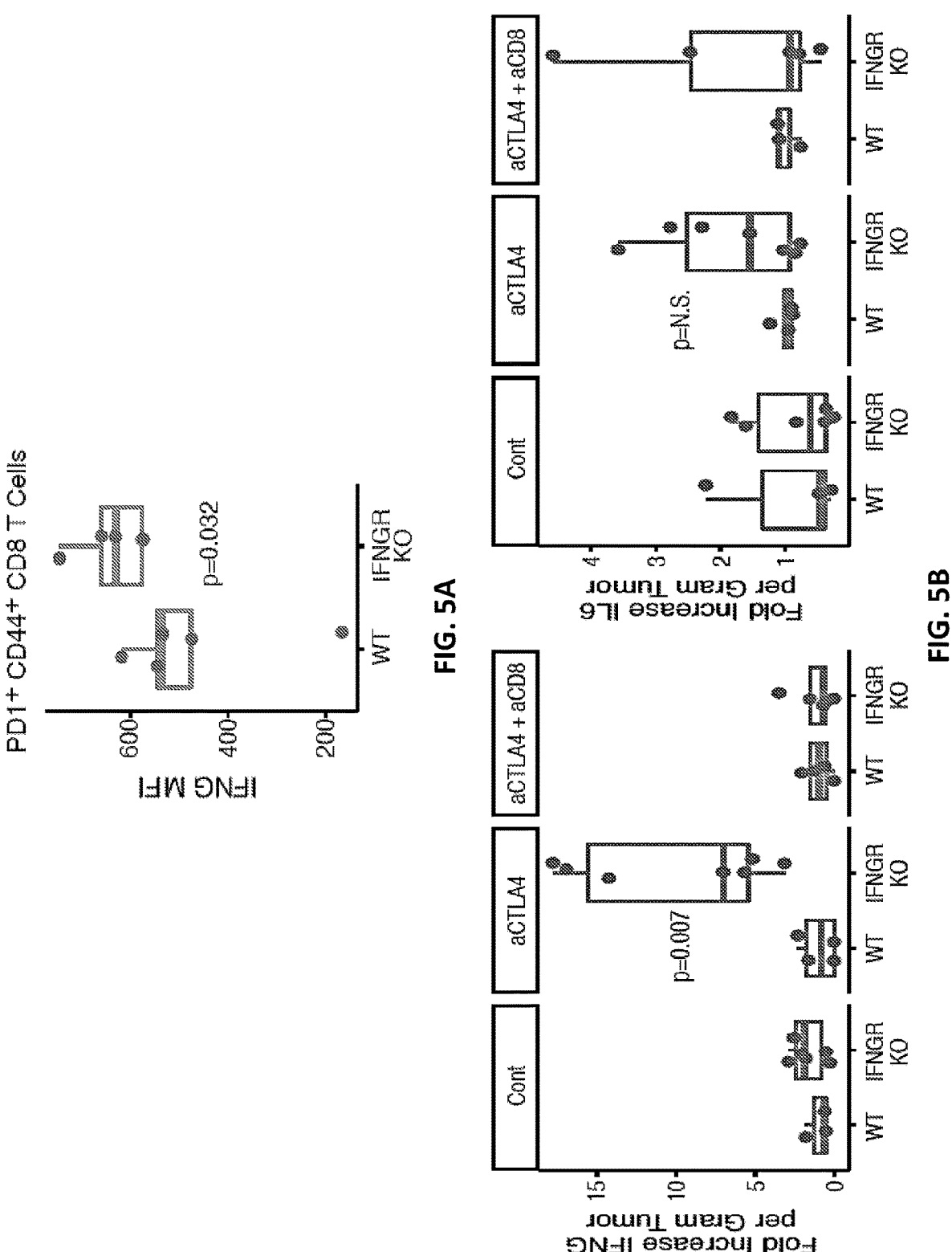
FIGS. 5A-5H illustrate the finding that increased IFNG produced by $T_{ex}$ after blockade of tumor IFNG signaling orchestrates NK/ILC-mediated killing of neoantigen depleted tumors.
Figure 5C:
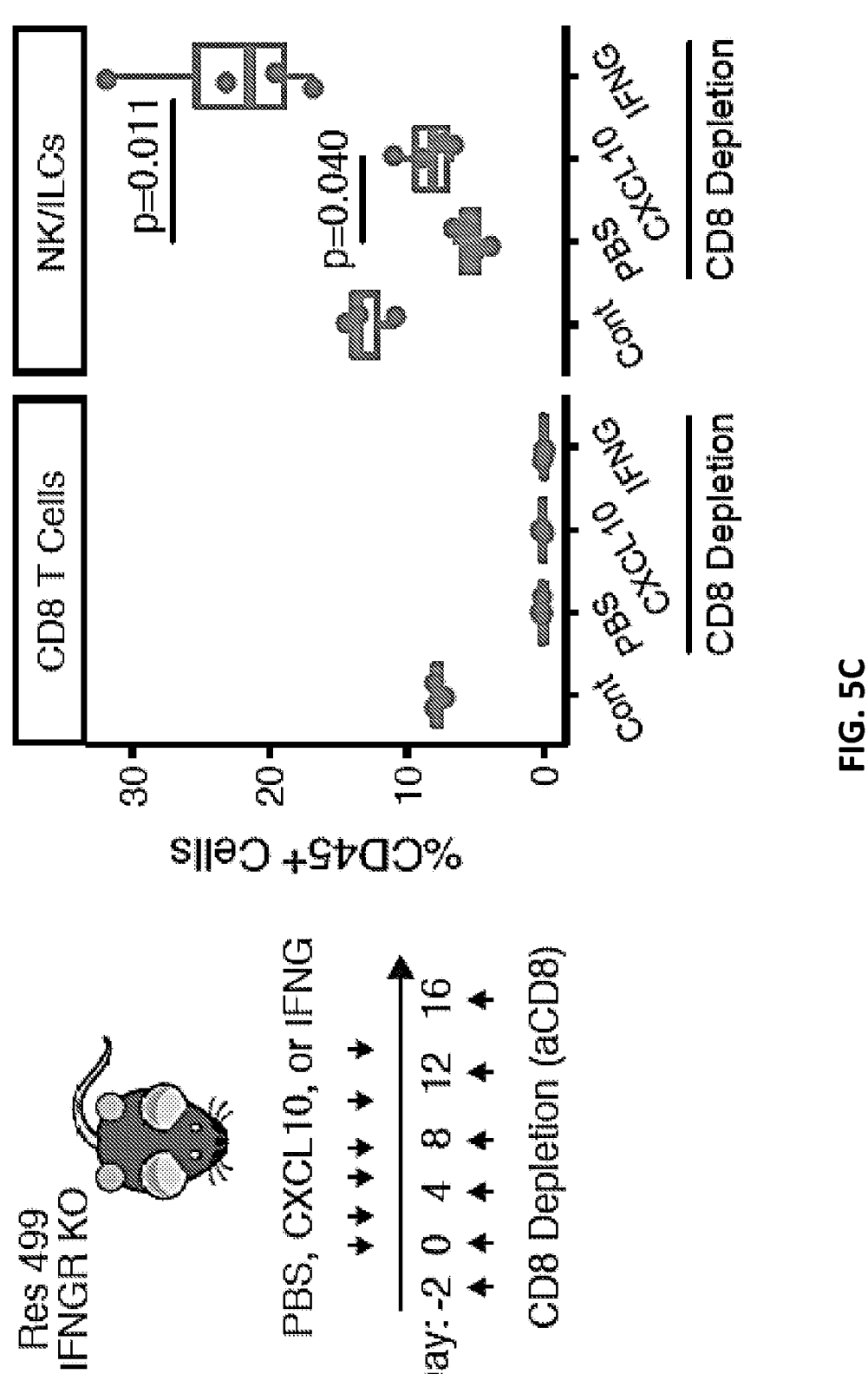
Figures 5D, 5E:
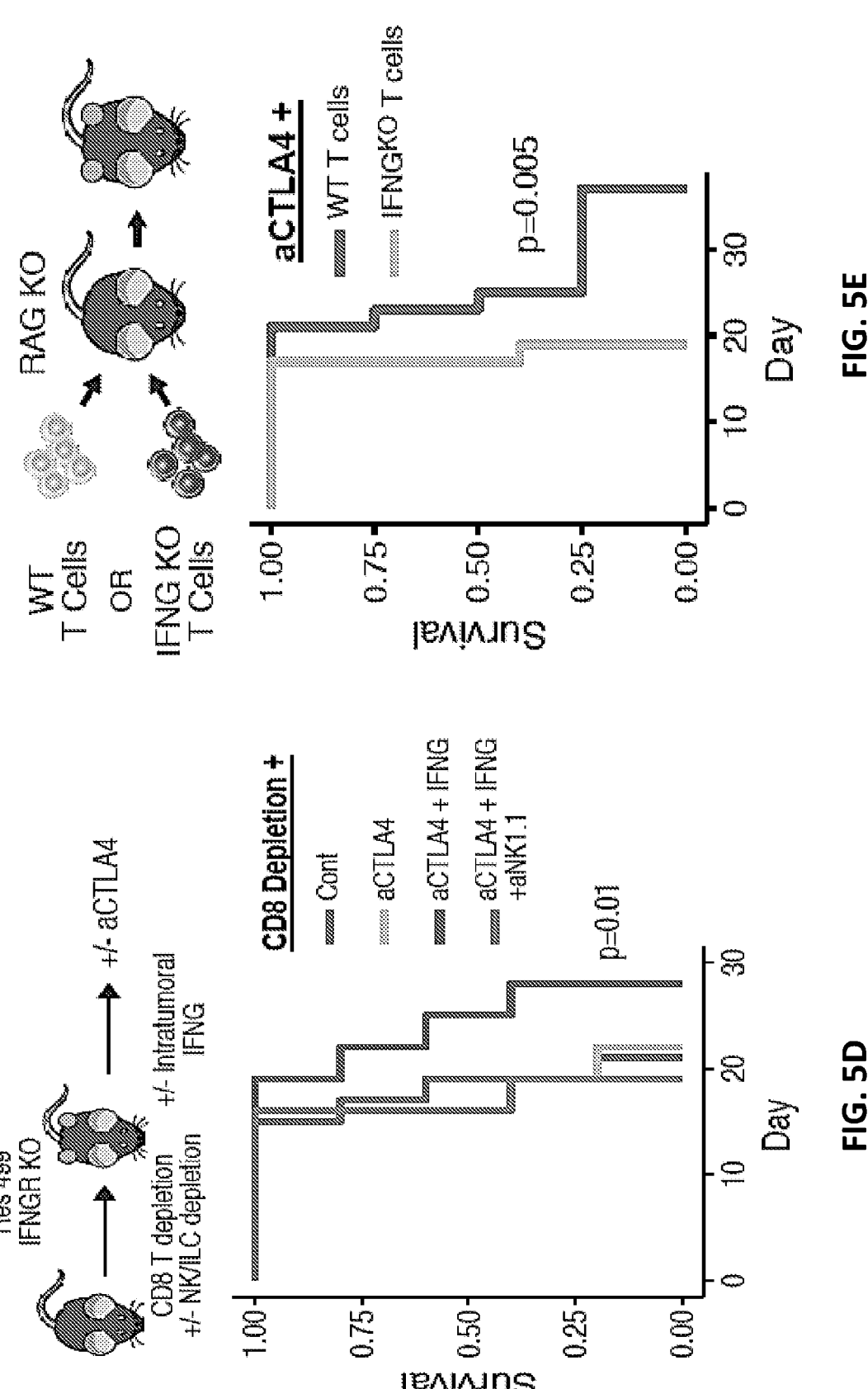
Figures 12A, 12B:
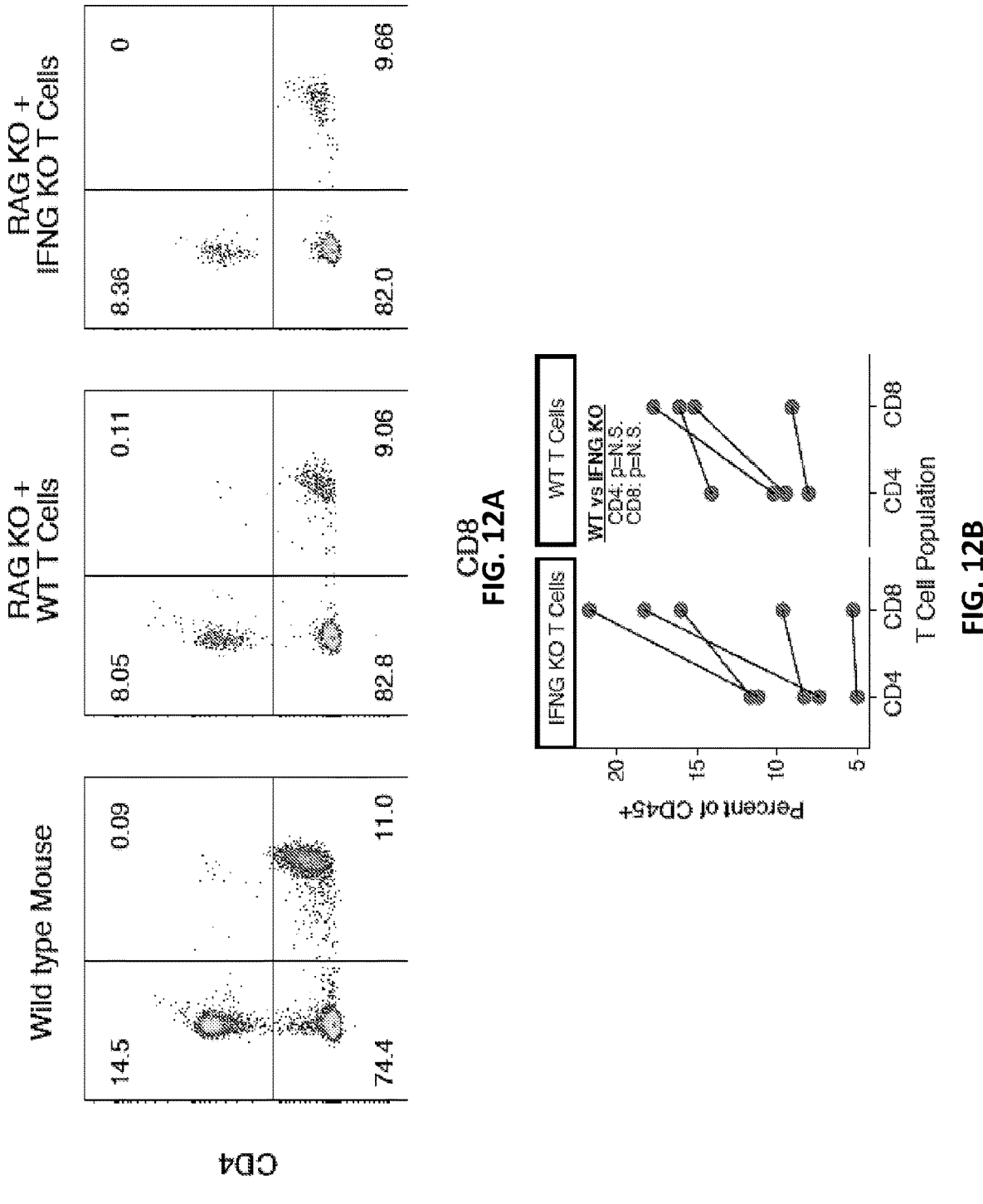
FIGS. 12A-12B illustrate adoptive transfer of wild type and IFNG knockout T cells.

Example 6: IFNG Produced by T$_{ex}$ is Augmented after Blockade of Tumor IFNG Signaling and Promotes NK/ILC-Dependent Tumor Killing How ablating tumor IFNG signaling and treatment with anti-CTLA4 allows CD8 T$_{ex}$ to support NK/ILC function was investigated. It was considered that even if improved T$_{ex}$ function resulting from treating IFNGR-deficient tumors with ICB does not lead to direct tumor cell killing, the enhanced cytokine production by T$_{ex}$ nonetheless may have immunostimulatory properties that could impact NK/ILCs. Of the many cytokines that could serve this role, IFNG itself was first considered, given that high IFNG.GS in T and NK cells along with low ISG.RS in cancer cells is associated with T and NK cell abundance and with clinical ICB response (FIGS. 1B-C and 1F). Indeed, intracellular expression of IFNG in PD1+CD8 TILs increases after IFNGR knockout of Res 499 tumors (FIG. 5A). In parallel with the large increase in reinvigorated T$_{ex}$ (FIG. 4C, cluster 6, 13, 14), levels of intratumoral IFNG correspondingly increase in a CD8 T cell-dependent manner, particularly after mice are treated with anti-CTLA4 (FIG. 5B). In contrast, numerous other cytokines such as IL-6 are either poorly expressed or not significantly affected by either the status of tumor IFNG signaling or anti-CTLA4 (FIG. 5B). IFNG can increase production of multiple CXCR3 ligands like CXCL10 in order to facilitate NK cell recruitment. Accordingly, direct intratumoral injection of IFNG or CXCL10 can rescue or partially rescue, respectively, the decrease in NK/ILC frequency that accompanies CD8 T cell depletion (FIG. 5C). Ectopic IFNG also restores the anti-tumor response that is lost after depleting CD8 T cells, a rescue effect that is dependent on NK/ILCs (FIG. 5D). To corroborate that IFNG produced by CD8 T cells is required for restored ICB response after ablating tumor IFNGR, transferred CD8 T cells were adoptively from wild type or IFNG knockout mice into RAG-deficient hosts and then implanted them with Res 499 IFNGR knockout tumors (FIGS. 5E and 12A-12B). This revealed that IFNG production by CD8 T cells is required for anti-CTLA4 response.

Figure 5F:
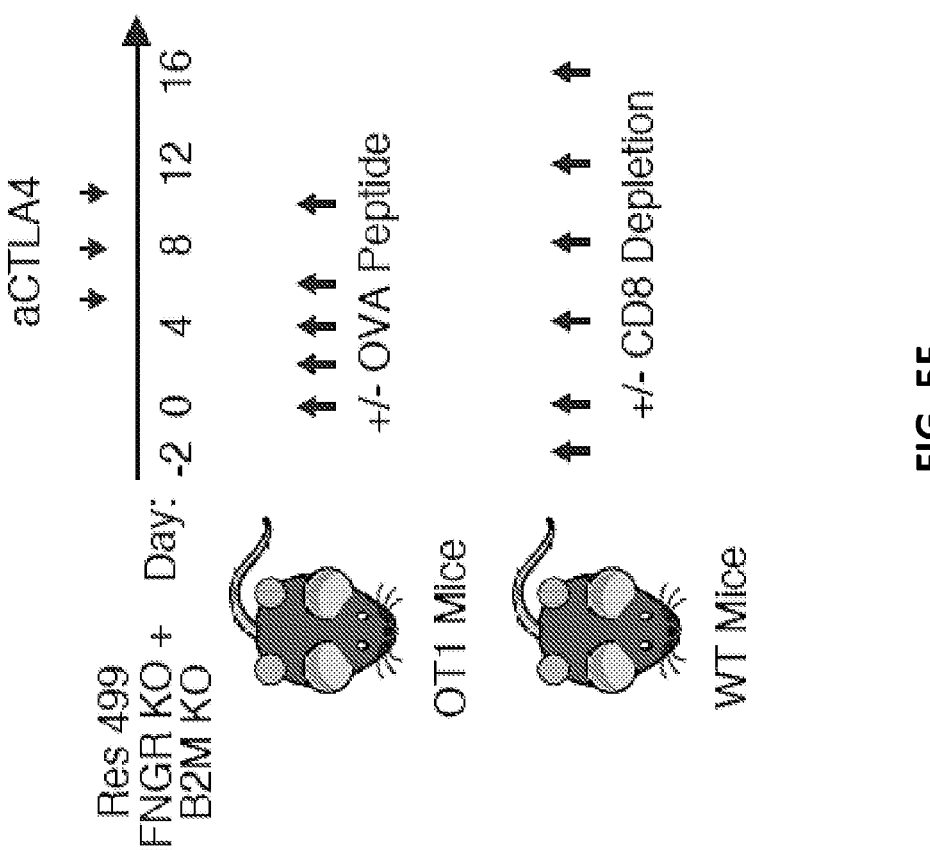
Figure 5G:
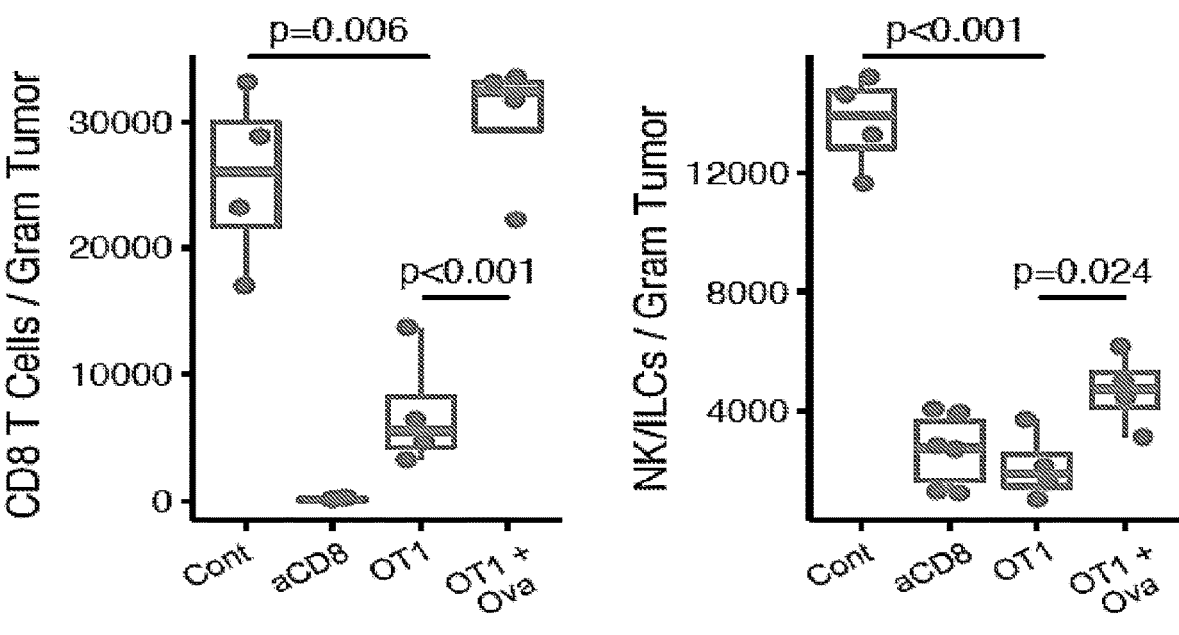
Figure 5H:
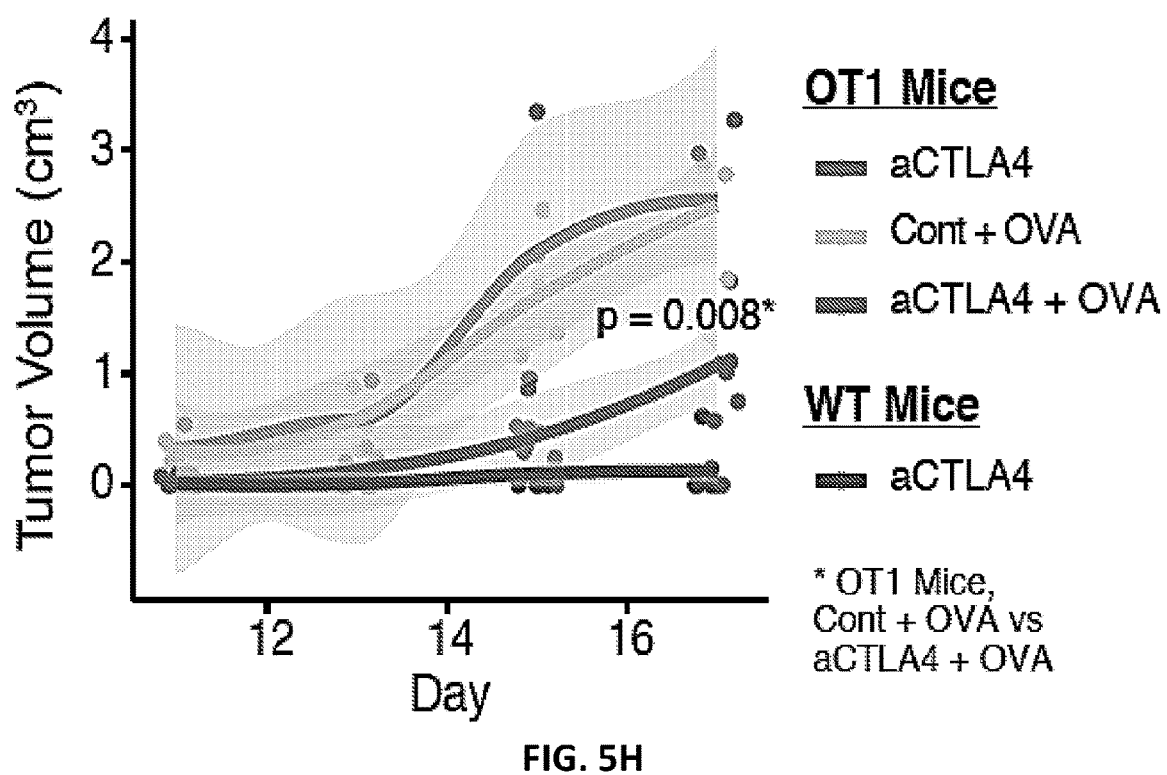

Despite the requirement for IFNG produced by reactivated CD8 T$_{ex}$, the dispensability of tumor B2M and the depletion of neoantigens observed in Res 499 tumors suggests that presentation of strong neoantigens by tumor cells is not necessary for enabling T$_{ex}$ to support NK/ILC function after tumor IFNGR knockout. To corroborate this, Res 499 tumors deficient in both IFNGR and B2M were implanted in either wild type mice or OT-1 mice expressing a transgenic T cell receptor to an OVA peptide antigen, which is not expressed by Res 499 tumors (FIG. 5F). The accumulation of both intratumoral CD8 T cells and NK/ILCs was markedly reduced in OT-1 mice compared to wild type mice (FIG. 5G). However, intratumoral injection of the OVA antigen specific for OT-1 T cells rescued the compromised CD8 T cell frequency and partially restored NK/ILC levels as well. The ability of tumor IFNGR knockout to restore ICB response was also lost in OT-1 mice but partially rescued by intratumoral injection of OVA antigen, despite the absence of B2M on tumor cells (FIG. 5H). Thus, NK/ILC-dependent ICB response after tumor IFNGR knockout need not depend on neoantigen presentation by tumor cells. Rather, cross-primed and/or bystander T cells can suffice.

Altogether, our findings suggest that elevated IFNG produced by reactivated T$_{ex}$ and/or cross-primed or bystander T cells facilitate NK/ILC recruitment, accumulation, and/or maturation when tumor IFN-driven resistance is inhibited. The intratumoral NK/ILCs can then subsequently attack neoantigen depleted tumors. Collectively, these results are consistent with our modeling of anti-PD1 response in melanoma patients—namely, low ISGs in tumor cells and high IFNG-related ISGs in T and NK cells are associated with 1) intratumoral accumulation of both CD8 T cells and NK cells, and 2) ICB response in TMB high and low tumors.

Figures 6A, 6B:
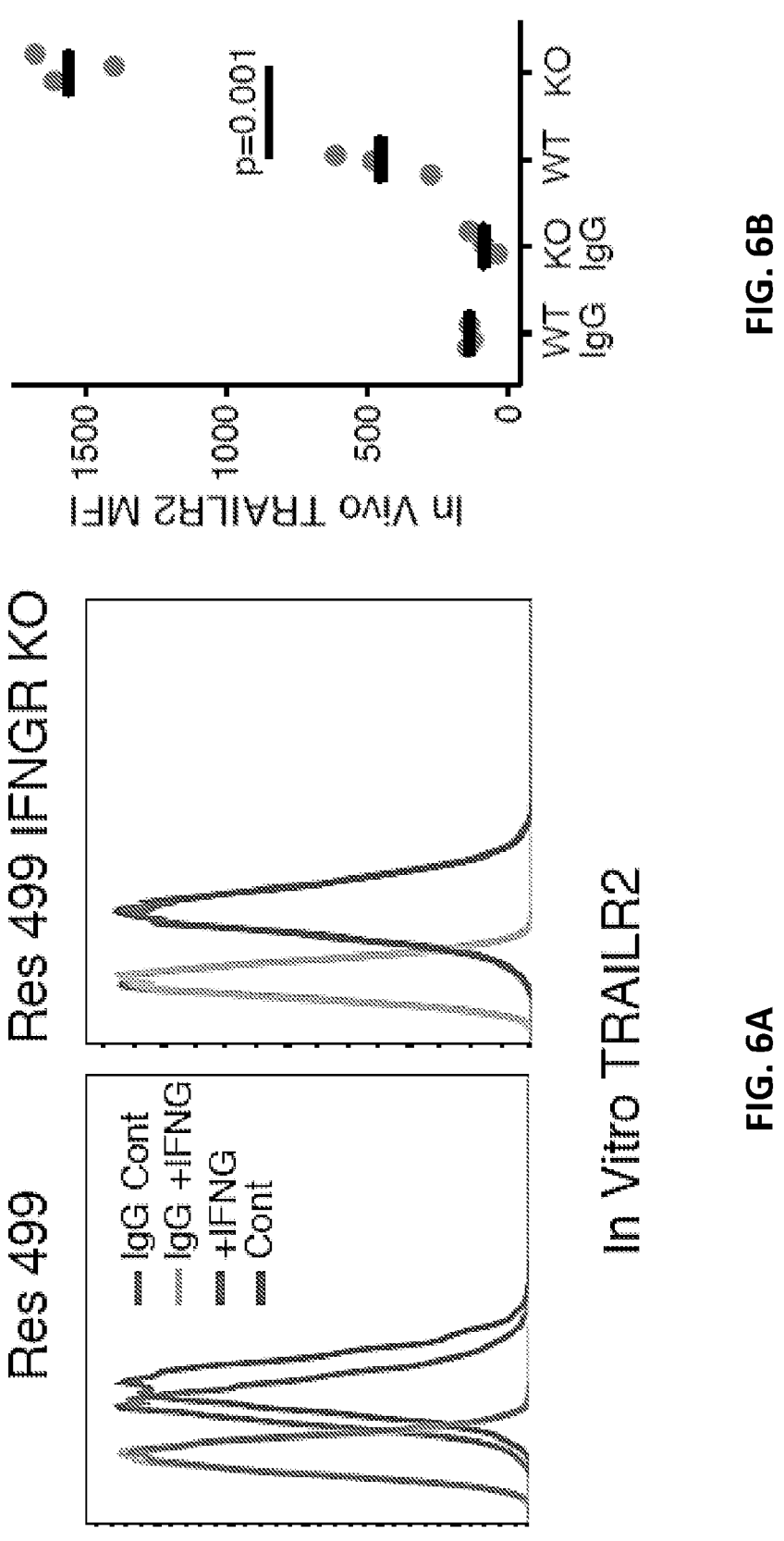
FIGS. 6A-6I illustrate the finding that blockade of tumor IFNG signaling prevents feedback inhibition through TRAIL receptor and PDL1 and enables NK/ILC-mediated killing of neoantigen depleted tumors. TRAIL receptor (TRAILR2) expression (FIG. 6A) in vitro after IFNG treatment of Res 499 cells or (FIG. 6B) in vivo from Res 499 tumors with or without IFNGR knockout.
Figures 6C, 6D:
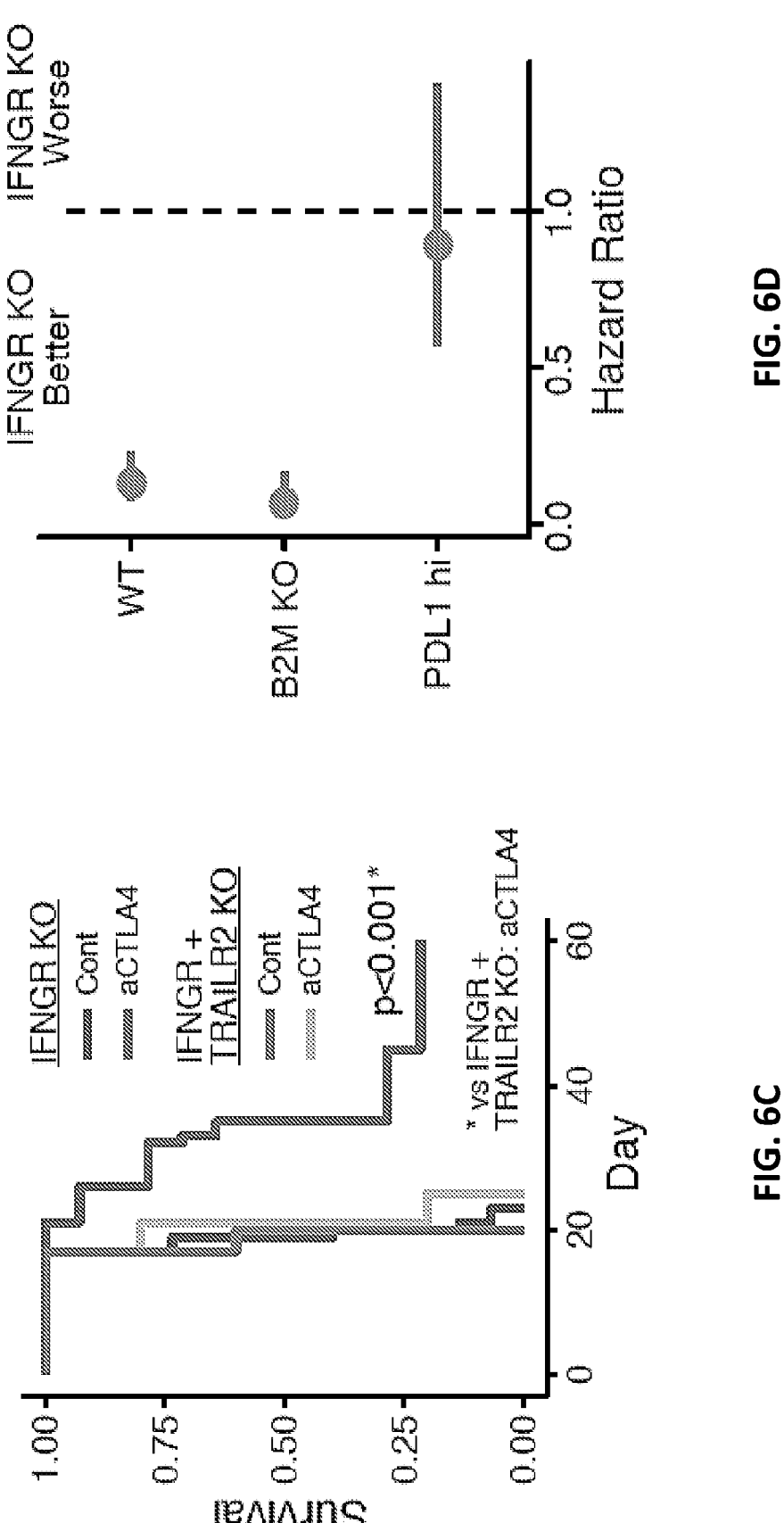
Figure 6E:
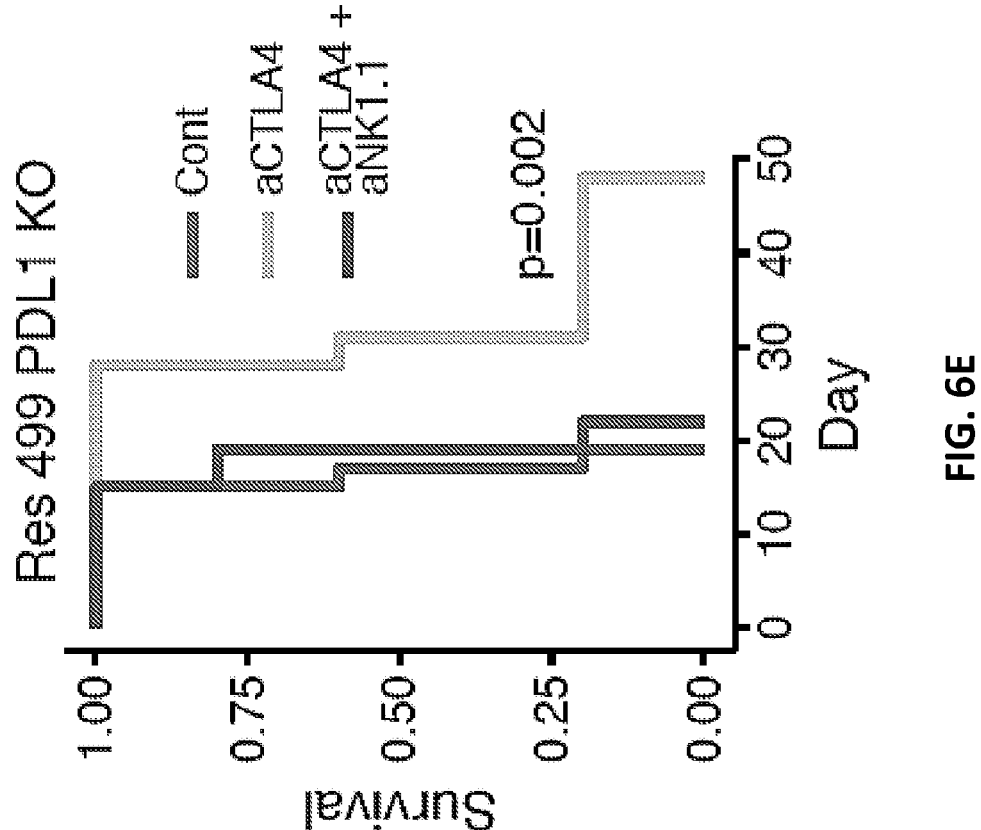
Figure 6F:
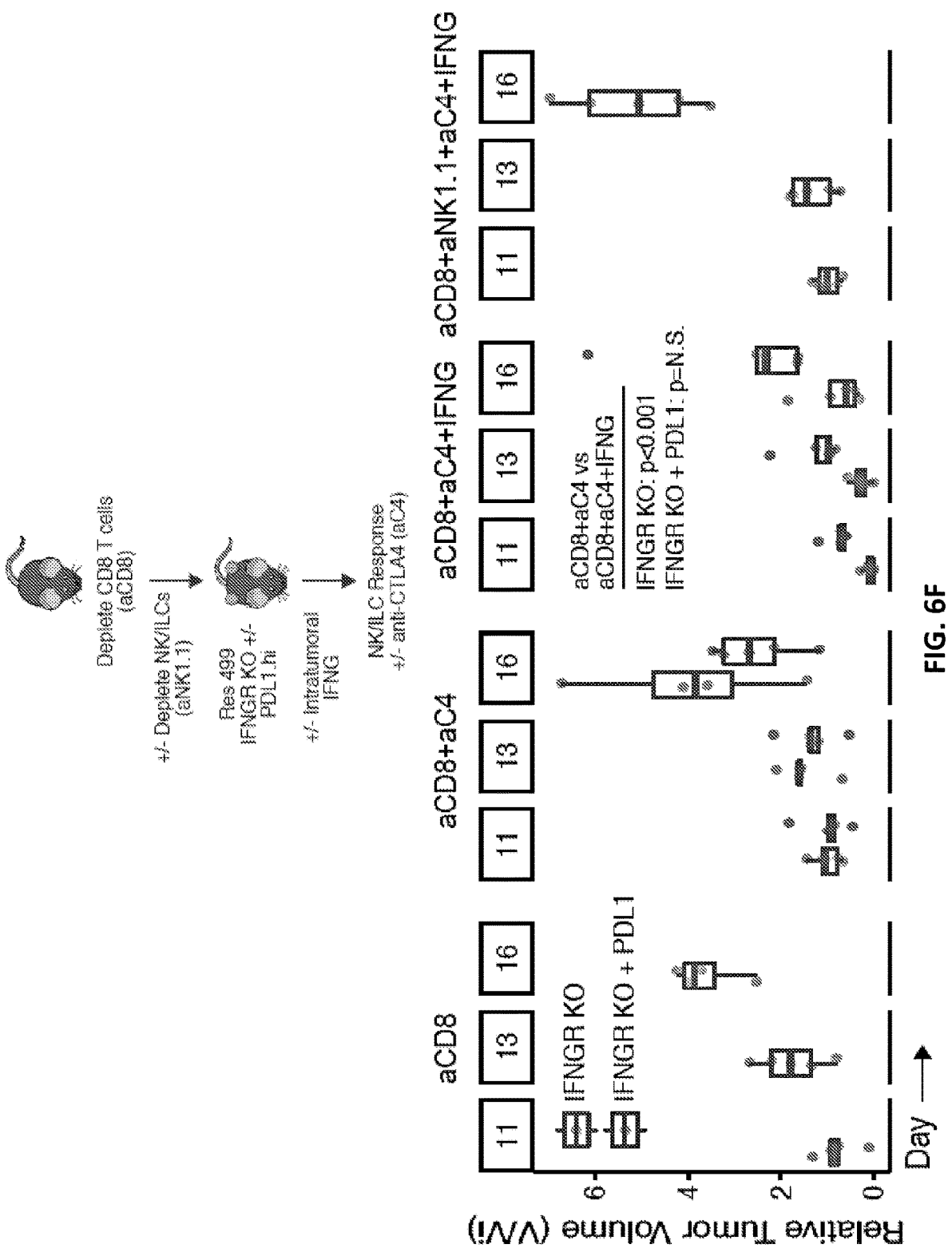
Figure 13A:
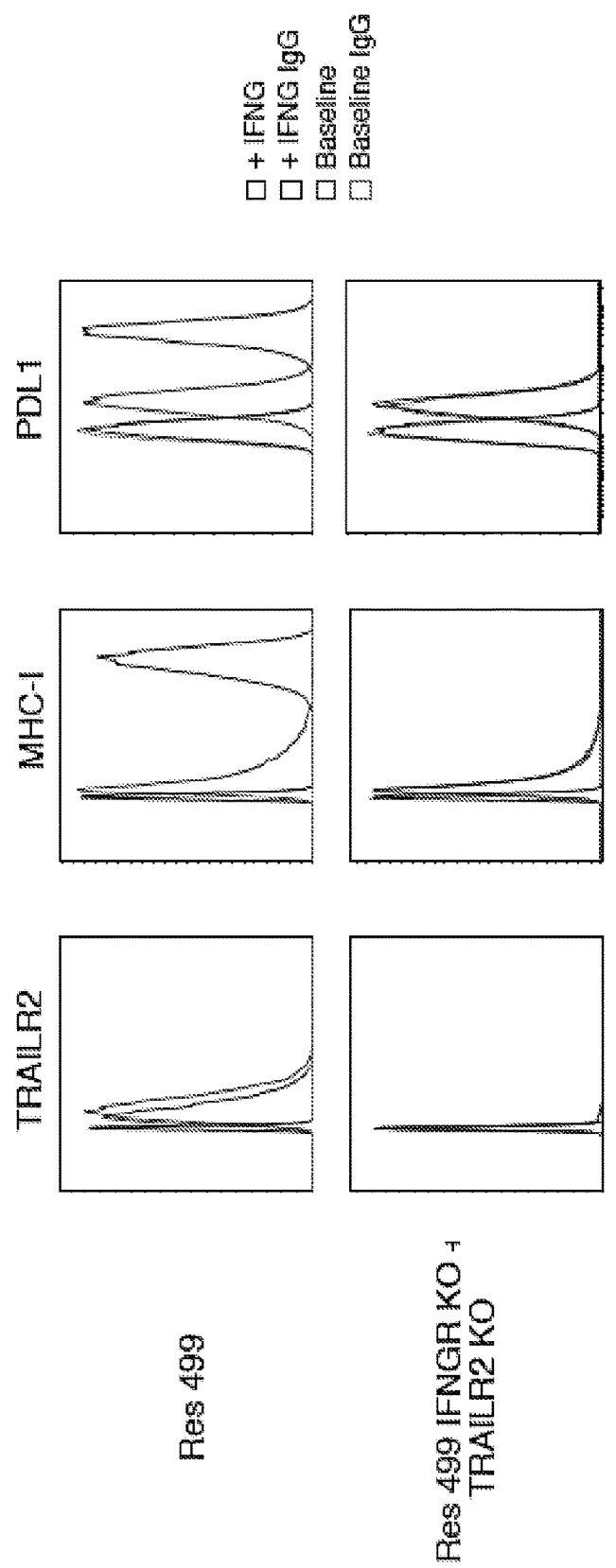
FIGS. 13A-13D illustrate regulation of NK/ILC function through the TRAIL pathway, PD1/PDL1, and Tregs.
Figures 13B, 13C:
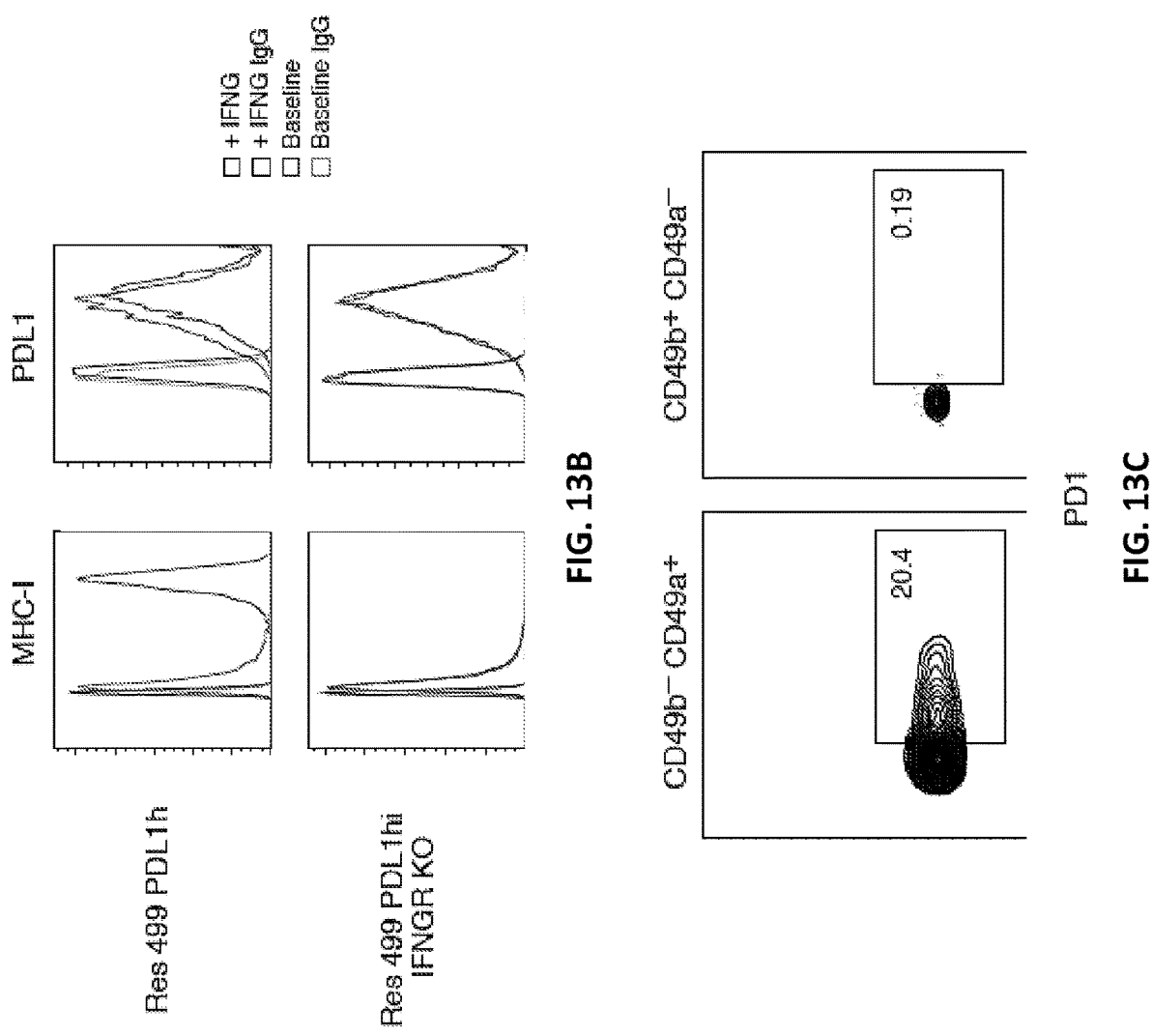

Example 7: Interfering with Tumor IFNG Signaling Prevents Feedback Inhibition Through TRAIL Receptor and PDL1 to Enable NK/ILC-Mediated Killing Although ablating tumor IFNGR signaling promotes intratumoral NK/ILC function indirectly through IFNG generated by T$_{ex}$, it was surmised that knockout of tumor IFNGR may also have direct effects on NK/ILCs, in particular the PD1+ TRAIL+NK/ILC population. Indeed, Res 499 tumors not only express PDL1 but also the TRAIL receptor (TRAILR2) (FIG. 6A). Stimulation of Res 499 cells with IFNG enhances PDL1 levels while decreasing TRAILR2 in vitro and in vivo, an effect that is abrogated by IFNGR knockout (FIG. 6A-B). Deletion of TRAILR2 in IFNGR-deficient Res 499 tumors (FIG. 13A) reveals that tumor killing after anti-CTLA4 is largely dependent on TRAIL/TRAILR2 interaction (FIG. 6C). To investigate the role of PDL1, PDL1 was ectopically expressed in PDL1 knockout Res 499 tumors to make PDL1 levels independent of IFNG signaling (FIG. 13B). In contrast to wild type or B2M-deficient Res 499 tumors, the ability of IFNGR deletion to improve anti-CTLA4 response is lost when PDL1 levels are fixed (FIG. 6D). Conversely, improved ICB response resulting from PDL1 deletion requires NK/ILCs (FIG. 6E). To examine if tumor PDL1 can inhibit NK/ILCs, CD8 T cells were depleted but NK/ILC function was restored in IFNGR-deficient Res 499 tumors by intratumoral administration of IFNG (FIG. 6F). Consistent with tumor PDL1 inhibiting NK/ILC killing, fixing PDL1 expression despite IFNGR knockout prevented NK/ILC-dependent ICB response. To corroborate that PD1/PDL1 can directly inhibit NK/ILC killing, CD49a+PD1+liver NK cells (FIG. 13C) were cultured with IFNGR-deficient Res 499 cells with and without ectopic PDL1. This confirmed that restoring PDL1 can at least partially restore resistance to PD1+NK/ILCs (FIG. 6G), while no effect was observed using PD1⁻ CD49b+ counterparts. In total, these results suggest that IFNG signaling in tumor cells drives feedback inhibition through both PDL1 and TRAIL pathways to directly and indirectly regulate NK/ILC function.

Figure 6G:
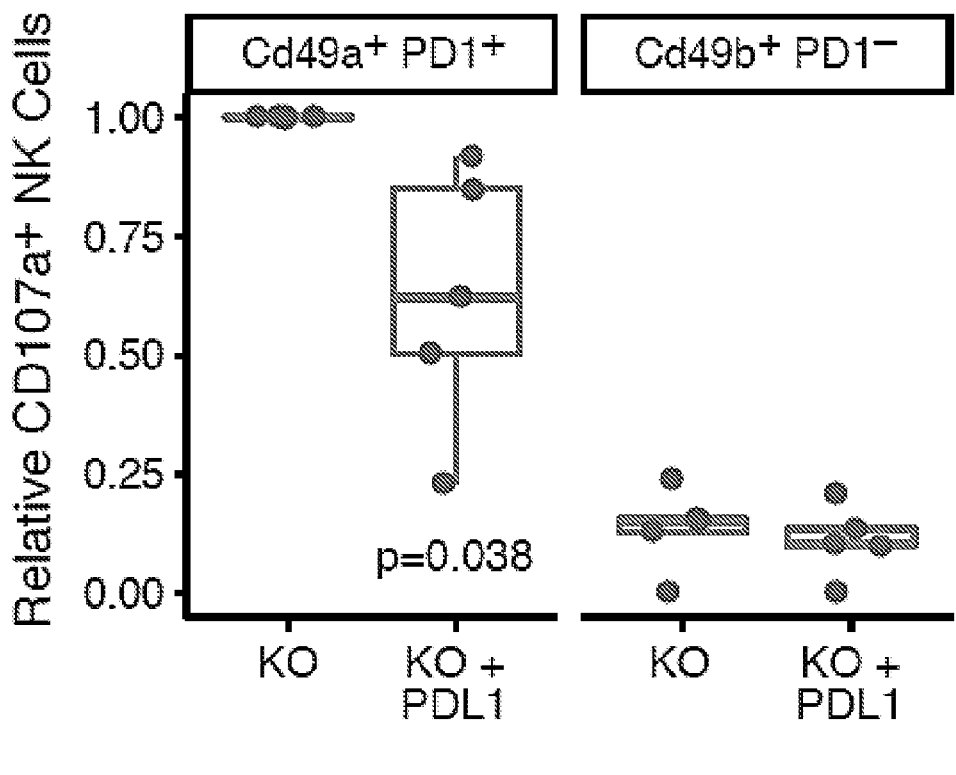
Figure 6H:
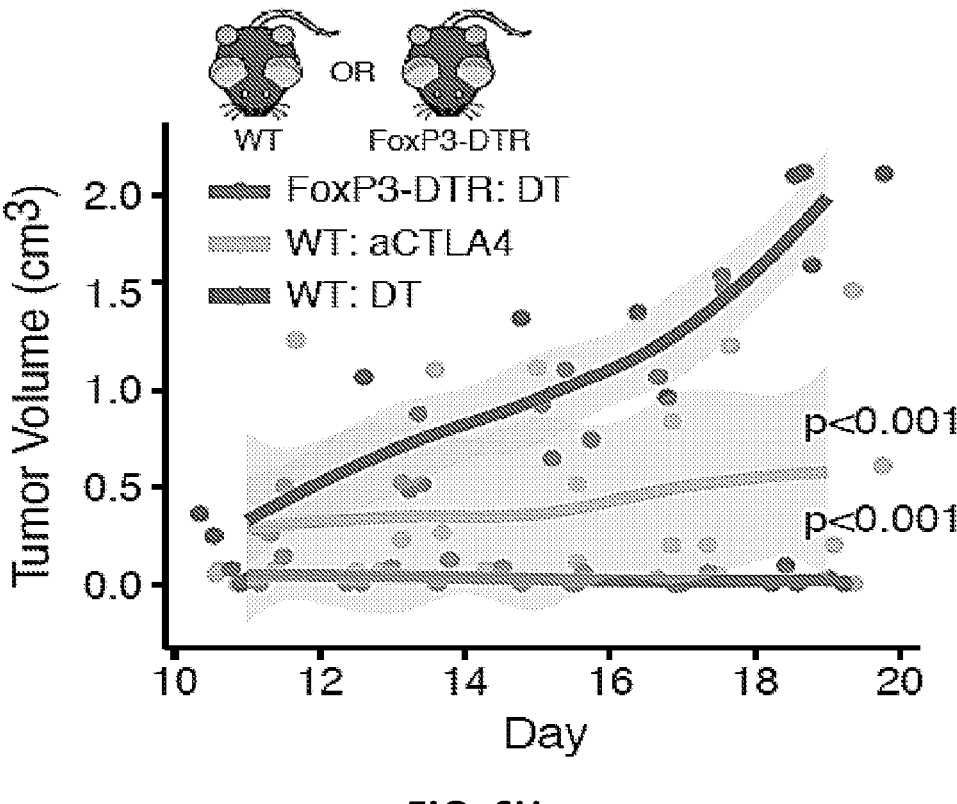
Figure 6I:
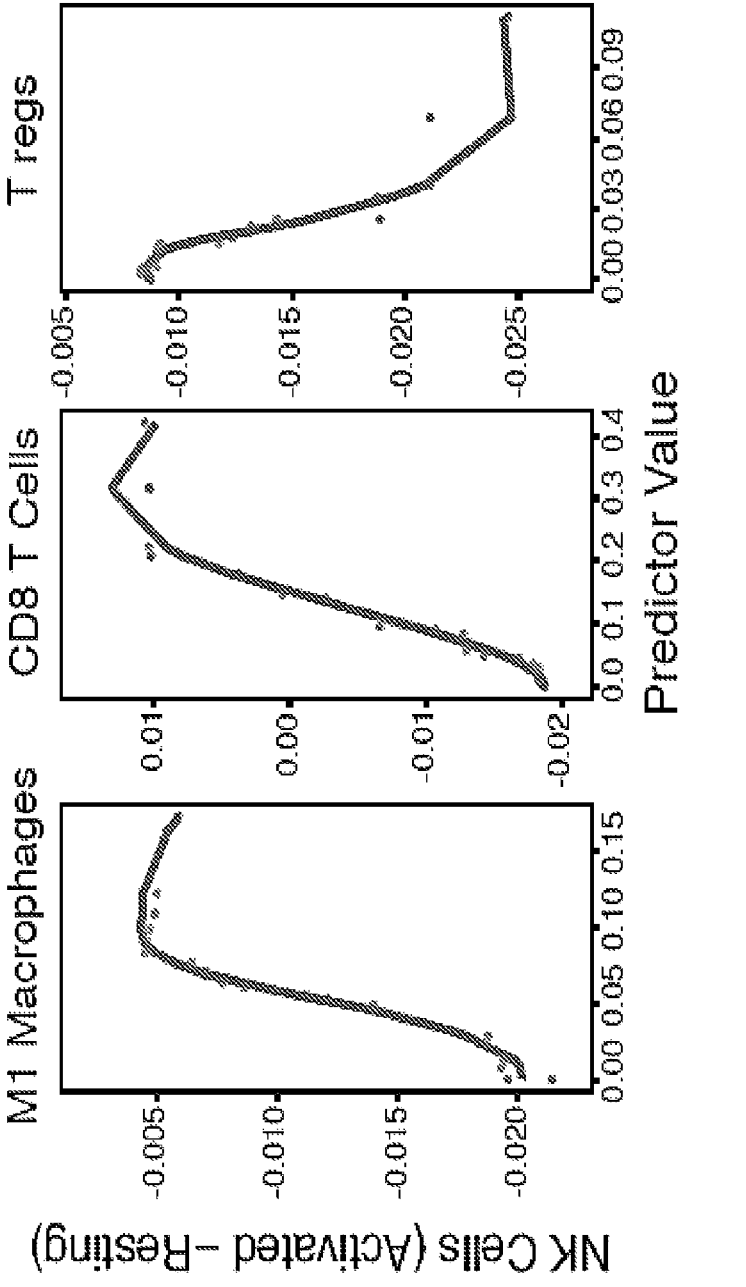
Figure 13D:
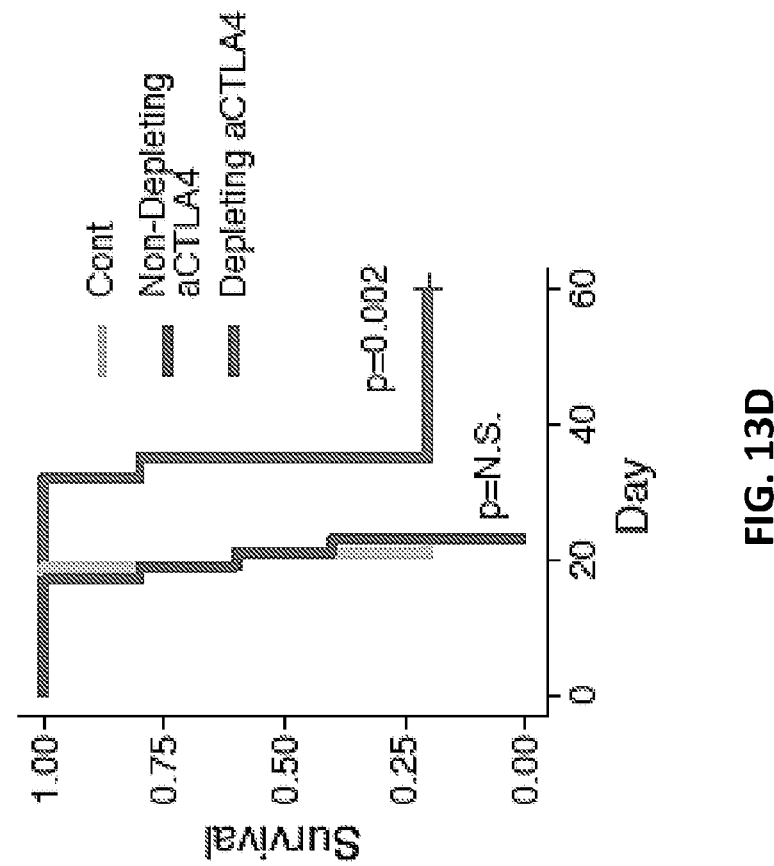

Example 8: T Regulatory Cells Inhibit ICB Response after Ablating Tumor IFNG Signaling Although disrupting tumor IFNG signaling interferes with the inhibitory function of PD1/PDL1 on adaptive and innate immune cells, anti-CTLA4 is still required for tumor regression of Res 499. Moreover, initial studies revealed that depletion of CD4 T cells unexpectedly increased survival in mice with IFNGR-deficient Res 499 tumors even in the absence of therapy (FIG. 3A). In mouse models, and possibly in humans, antagonistic CTLA4 antibodies not only block CTLA4 function but can also deplete CD4+ T regulatory cells (Tregs). To investigate the importance of Tregs, an antibody against CTLA4 was used that does not concurrently deplete T regs. In contrast to the Treg-depleting 9H10 antibody, this clone fails to elicit a response against Res 499 IFNGR knockout tumors (FIG. 13D). Conversely, depleting Tregs by stimulation of the diptheria toxin receptor under control of FoxP3 recapitulates the effects of 9H10 by potently preventing tumor growth of IFNGR-deficient Res 499 tumors (FIG. 6H). To corroborate the potential role of Tregs in inhibiting NK/ILCs, we investigated which immune cell populations inferred by CIBERSORT predicts the frequency of activated NK cells in tumors from melanoma patients treated with anti-PD1. Accounting for all immune populations predicted by CIBERSORT results in a model that explains 39% of the variance. The top three immune populations filtered by variable importance score and effect size include Tregs, CD8 T cells, and M1 macrophages (FIG. 6I). Thus, mechanisms that antagonize cooperation between CD8 T cells and NK/ILCs can occur through both tumor cell intrinsic IFNG effectors such as PDL1 and immune populations such as T regs. Additionally, these findings imply that blockade of both CTLA4 and PD1 may promote innate immune function better than monotherapy approaches.

Example 9: Tumor Mutations in IFN Pathway Genes Predict Clinical Response to Dual Blockade of PD1 and CTLA4

Figure 7A:
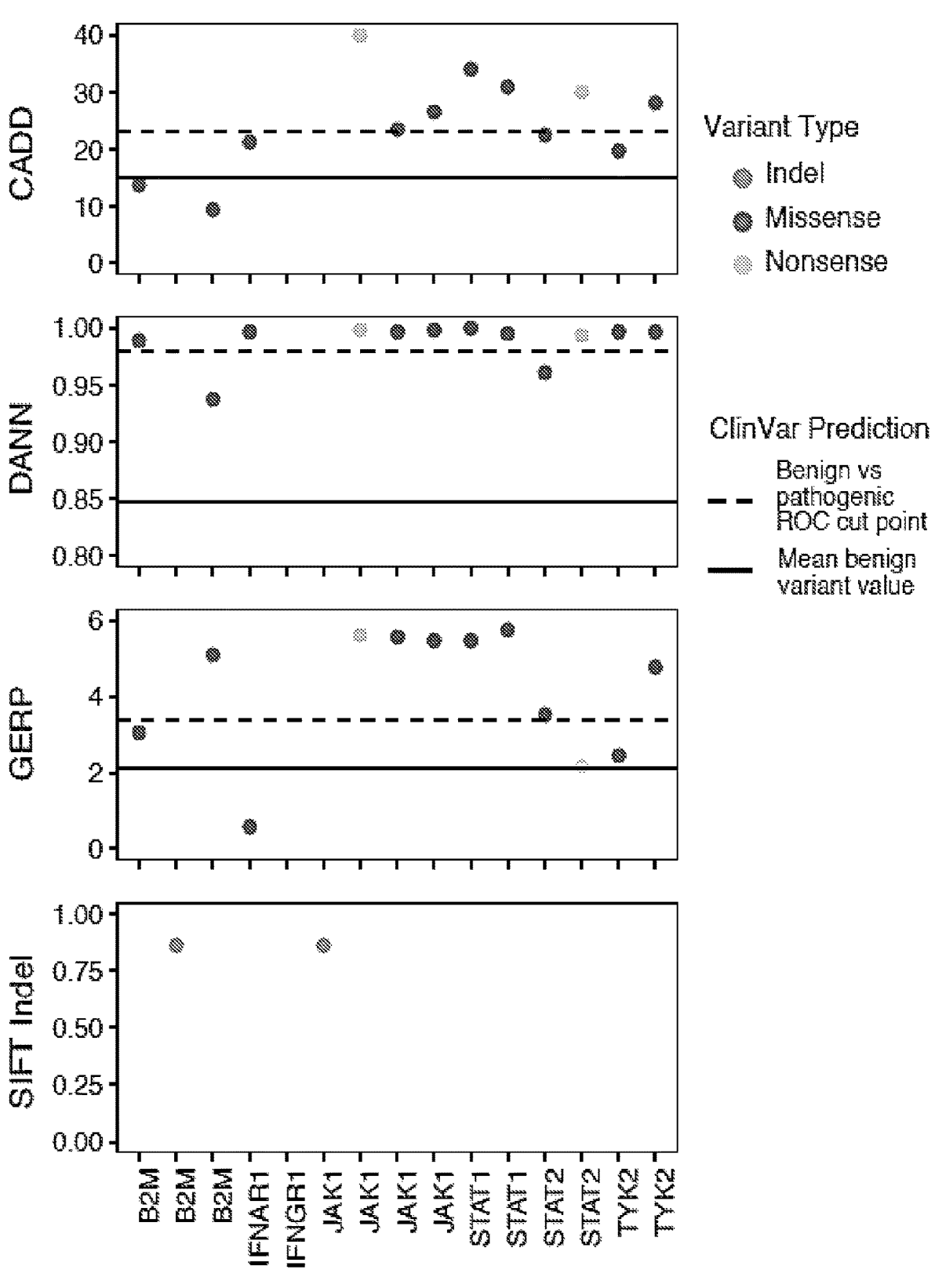
Figures 7B, 7C:
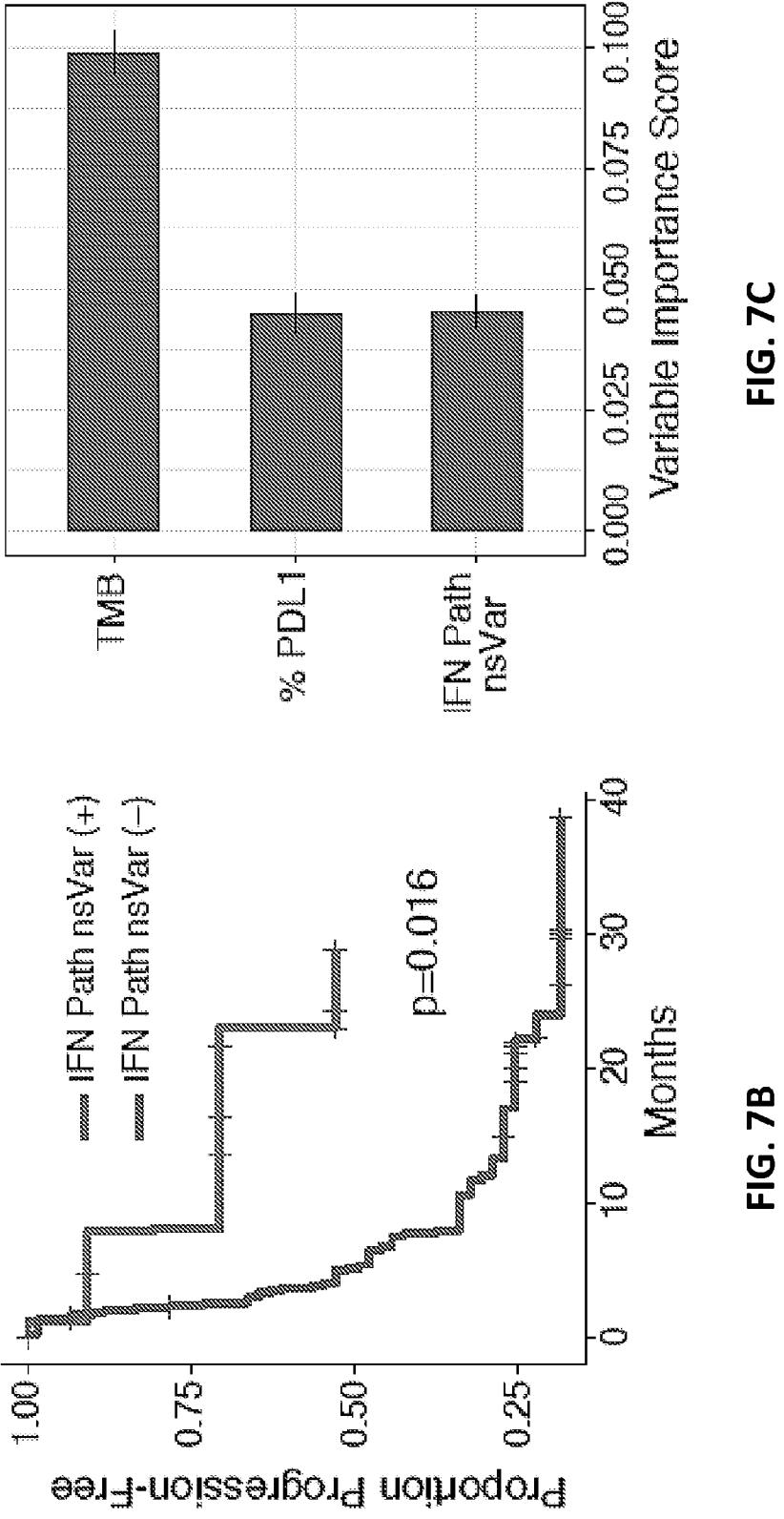
Figure 7E:
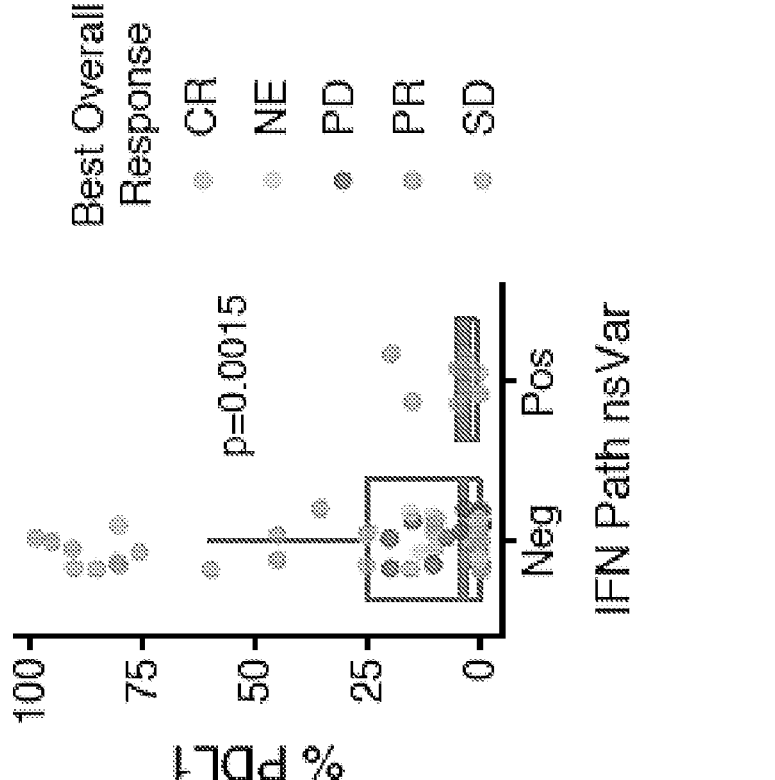
Figure 7F:
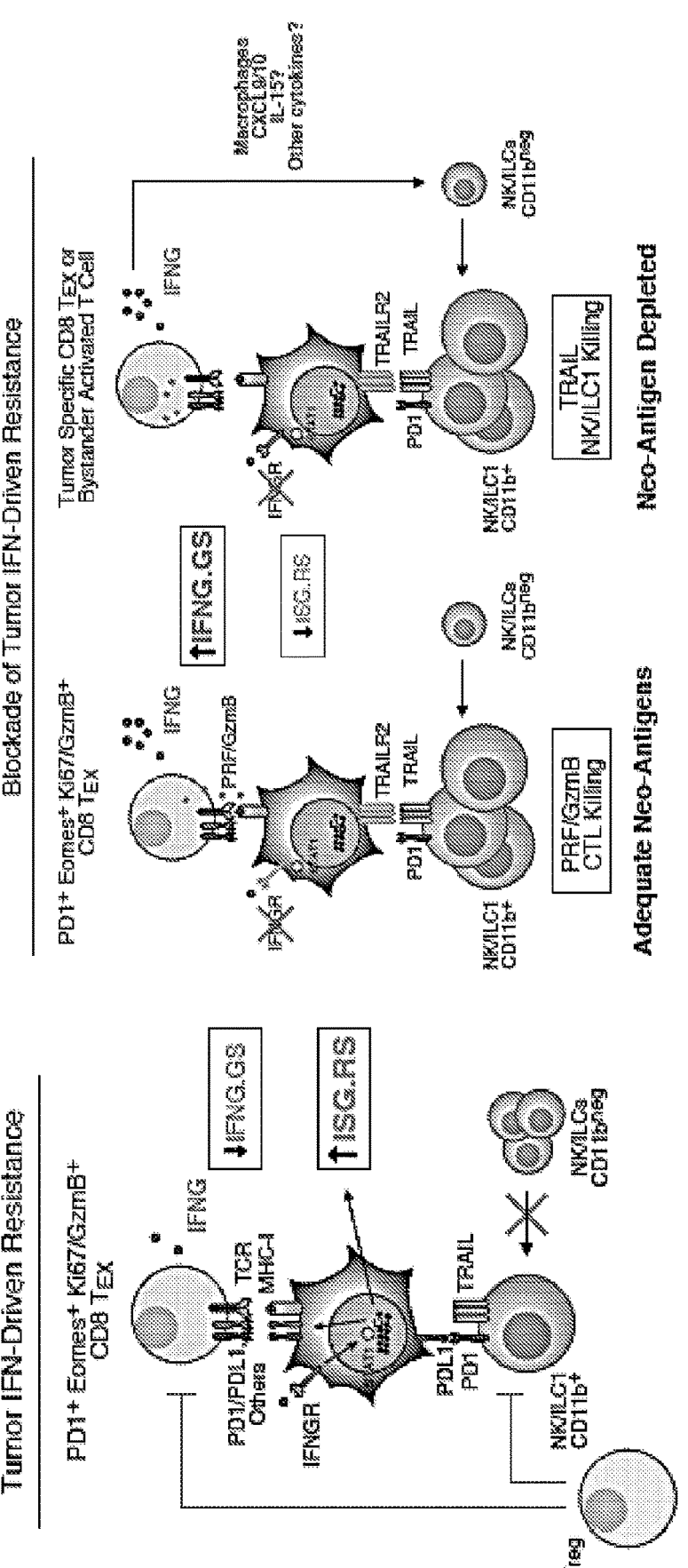
Figures 7G, 7H:
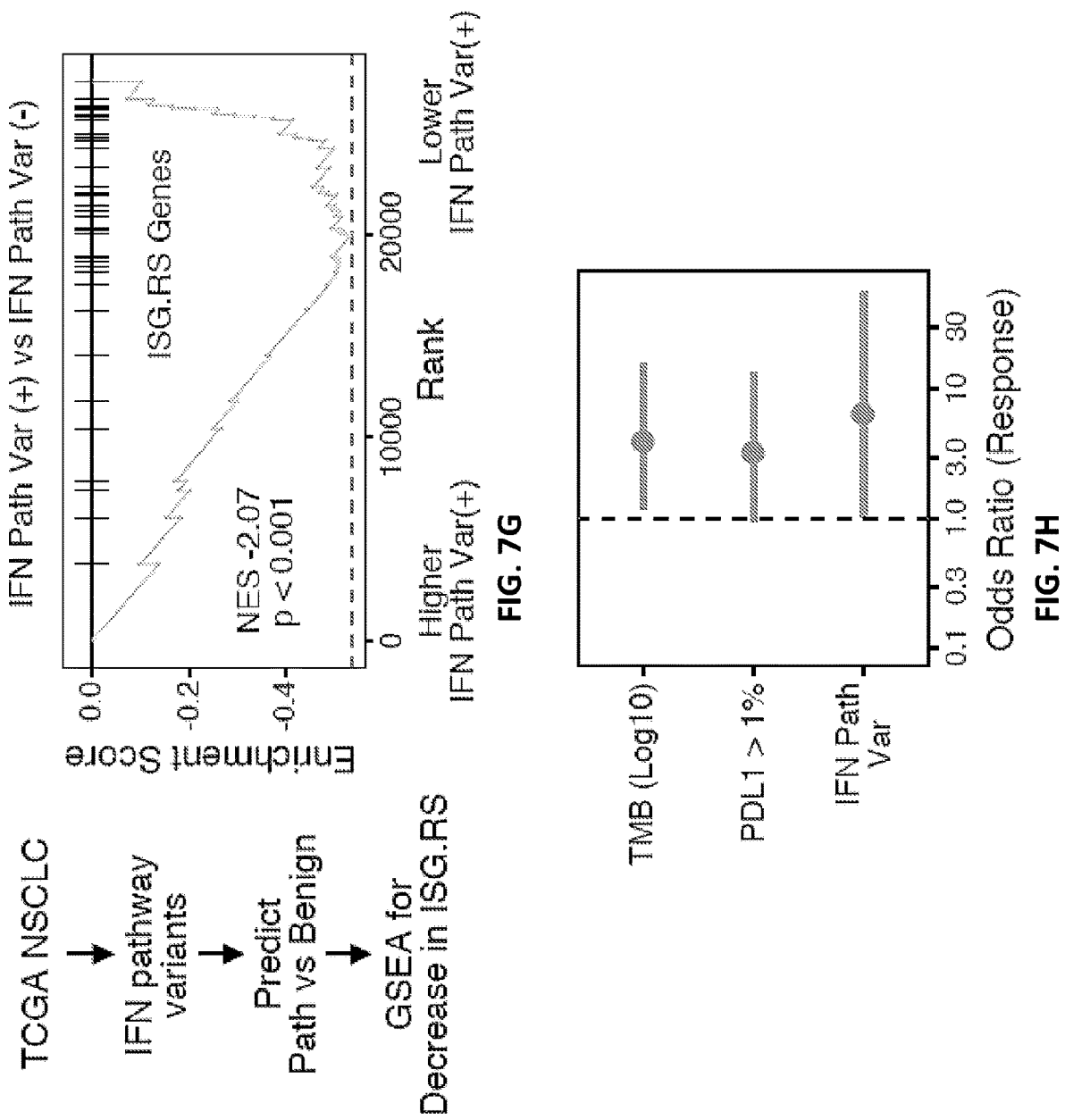
Figure 14A:
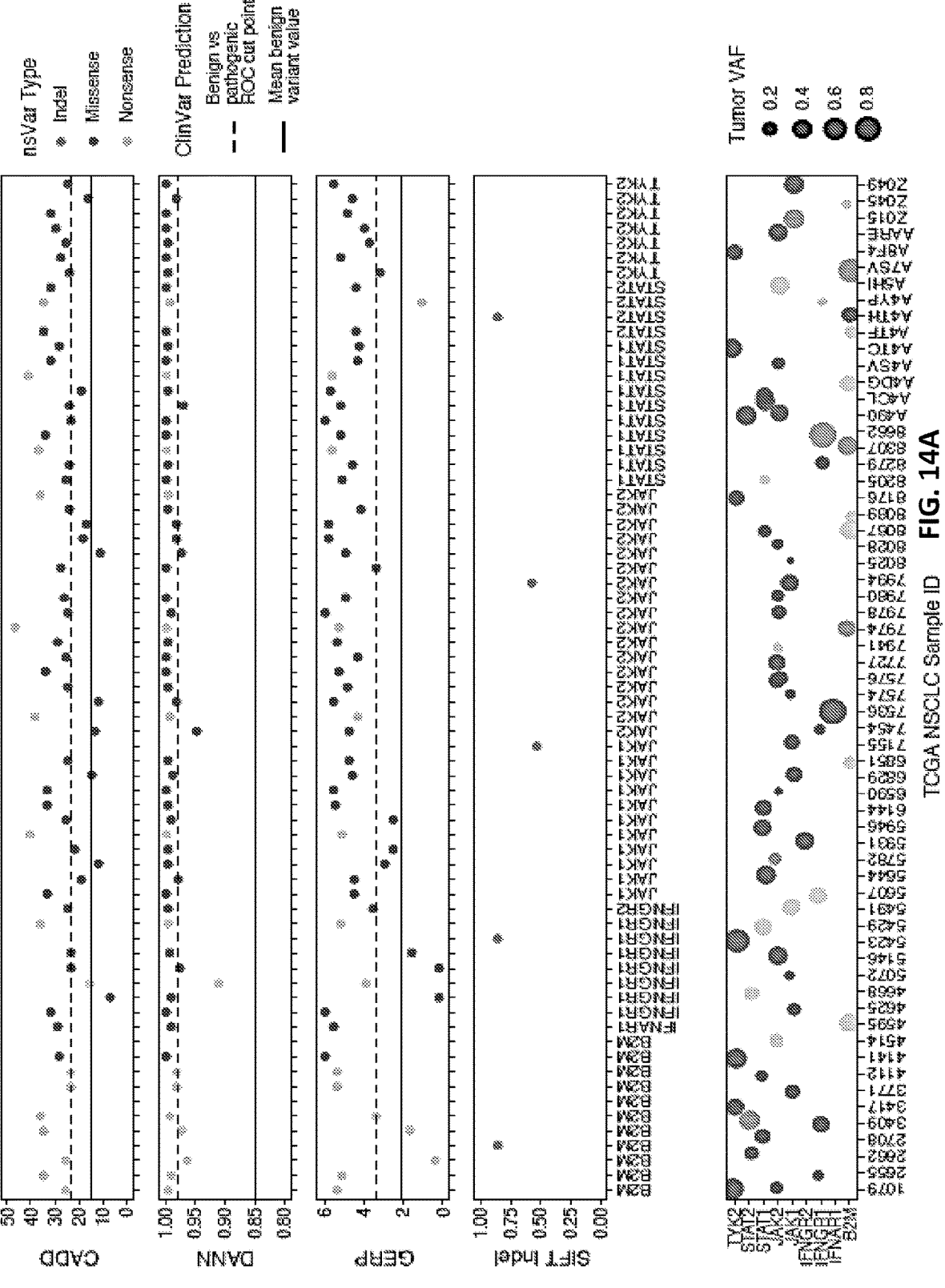
FIGS. 14A-14I illustrate the finding that tumor mutations in IFN pathway genes predict decreased ISG.RS and increased survival of lung cancer patients treated with anti-CTLA4 and anti-PD1.
Figure 14B:
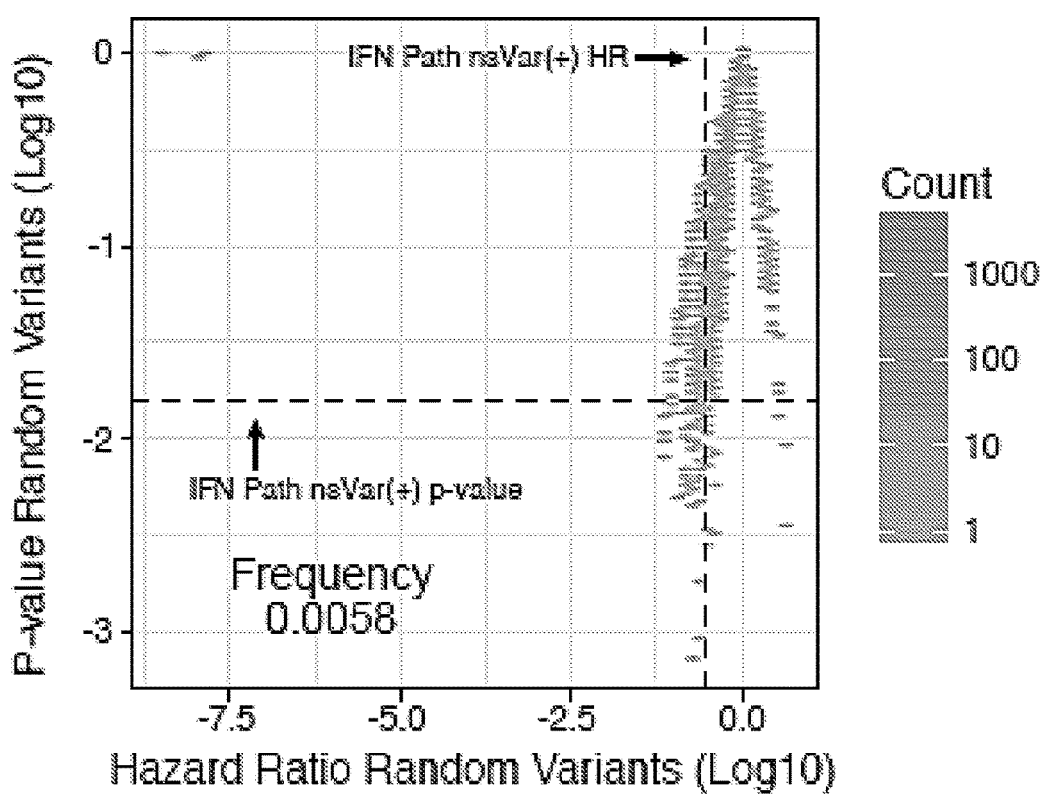
Figure 14C:
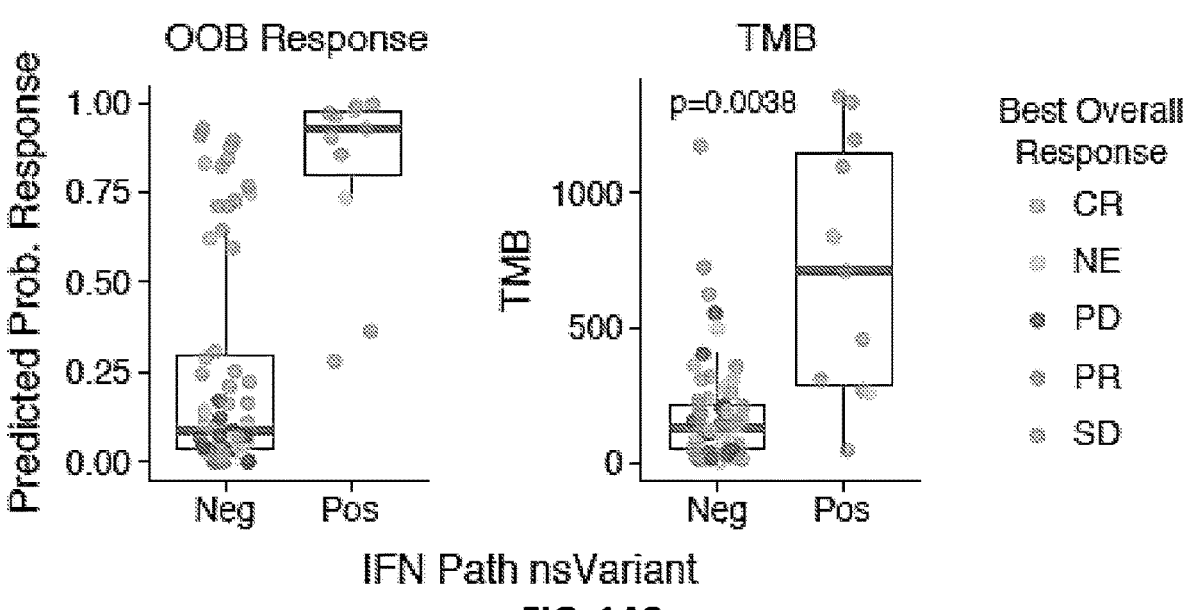
Figures 14D, 14E:
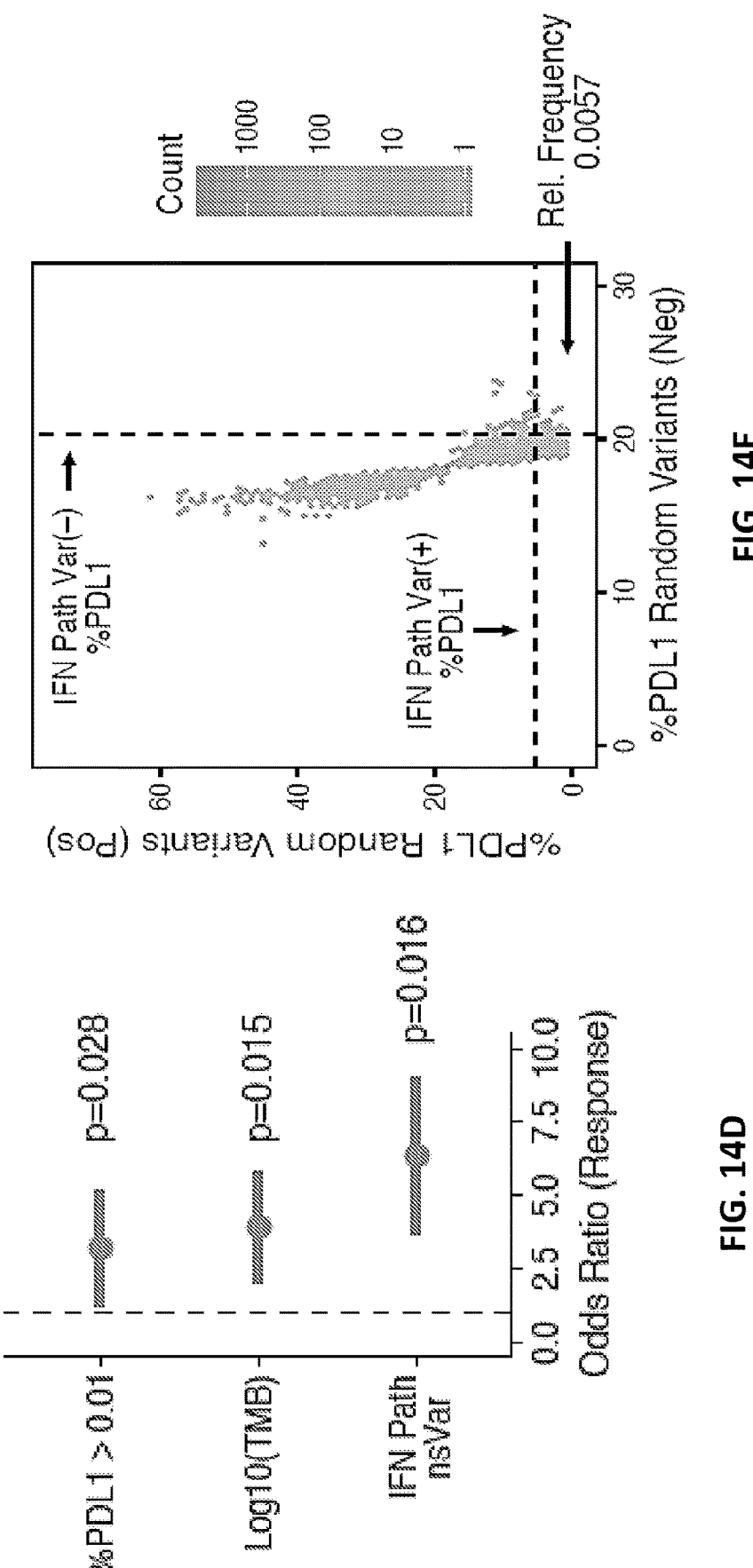
Figure 14F:
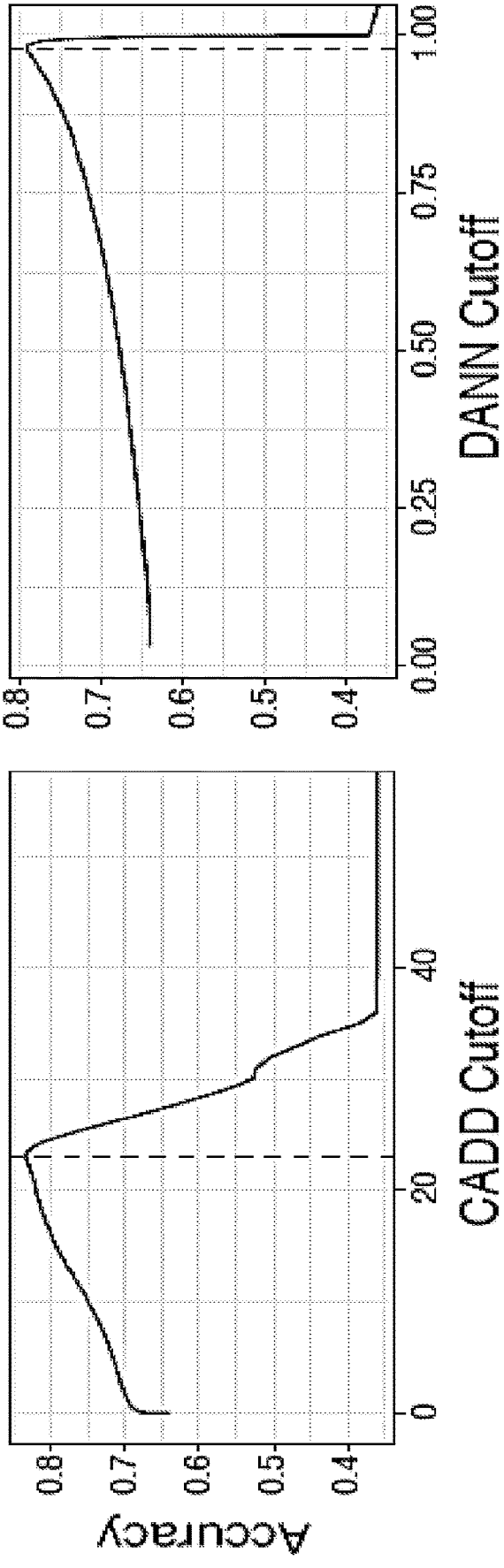
Figure 14G:
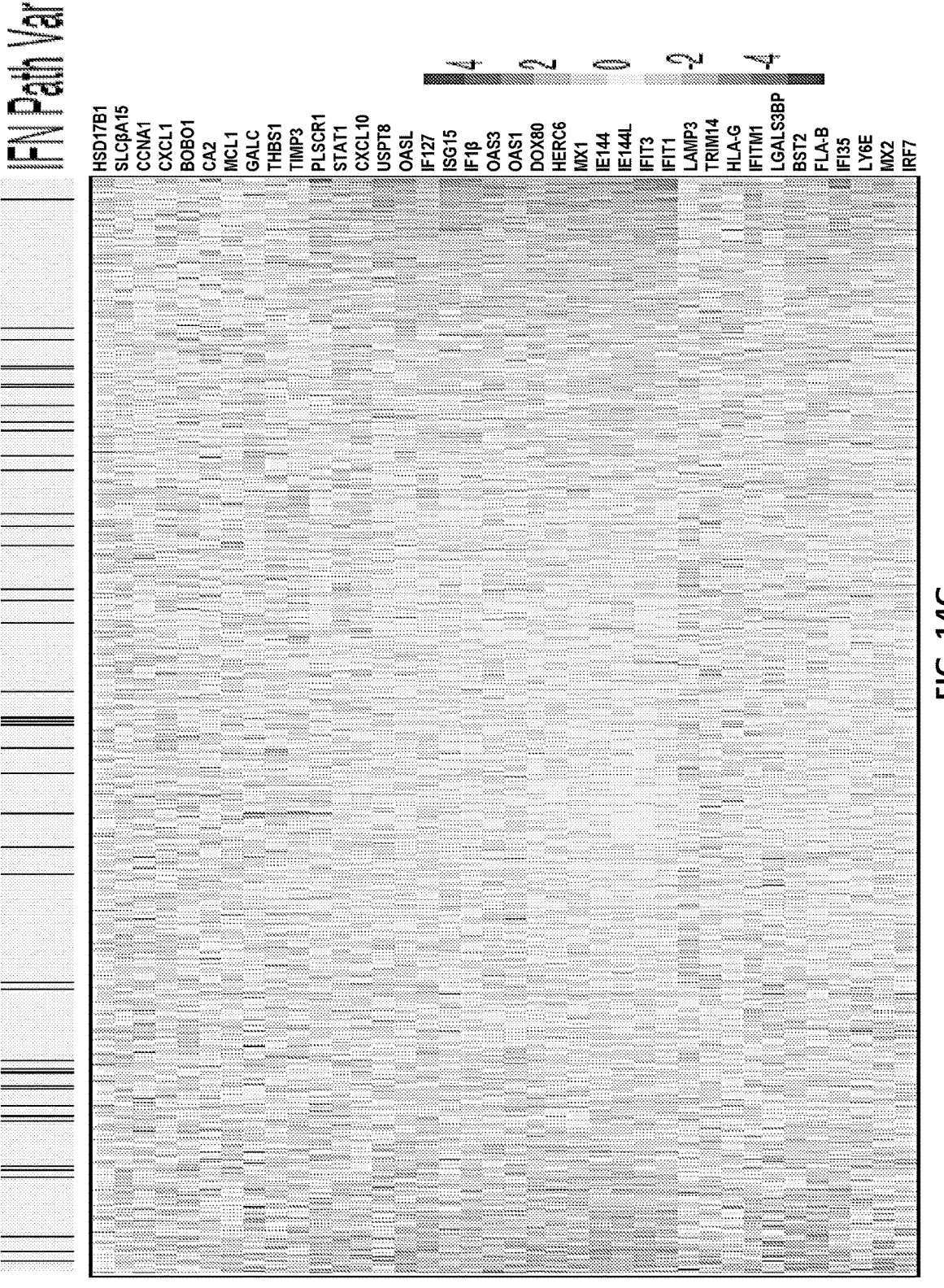
Figure 14H:
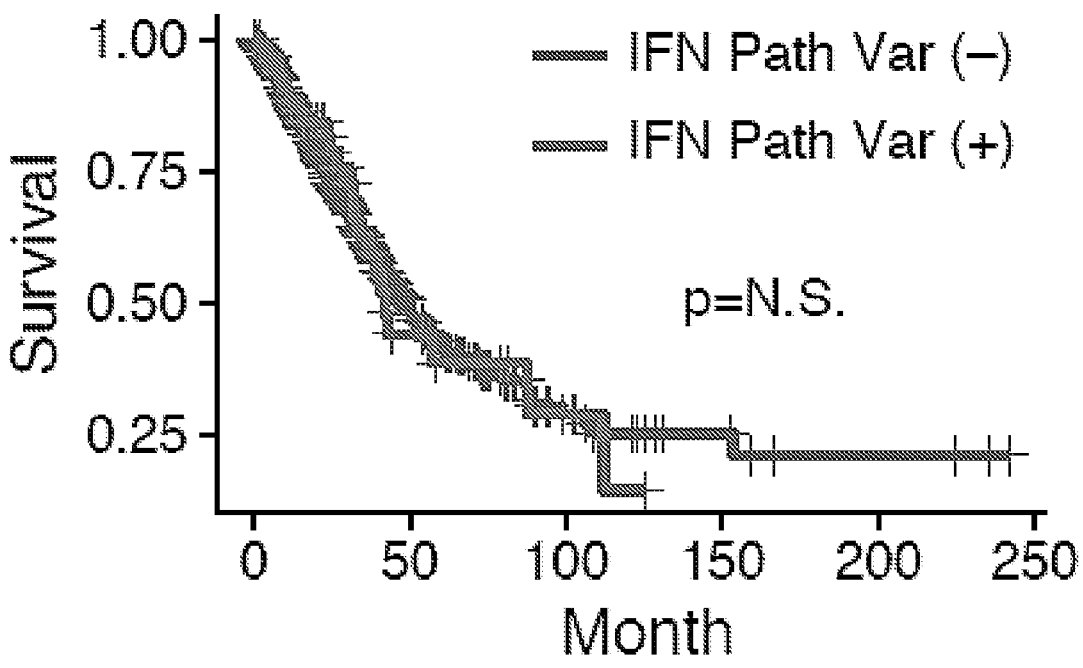
Figure 14I:
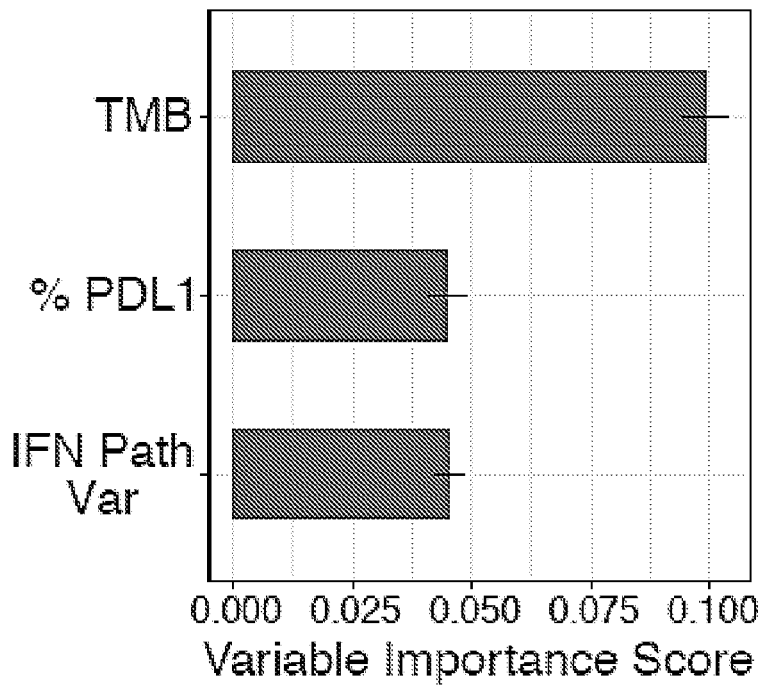
Figure 15:
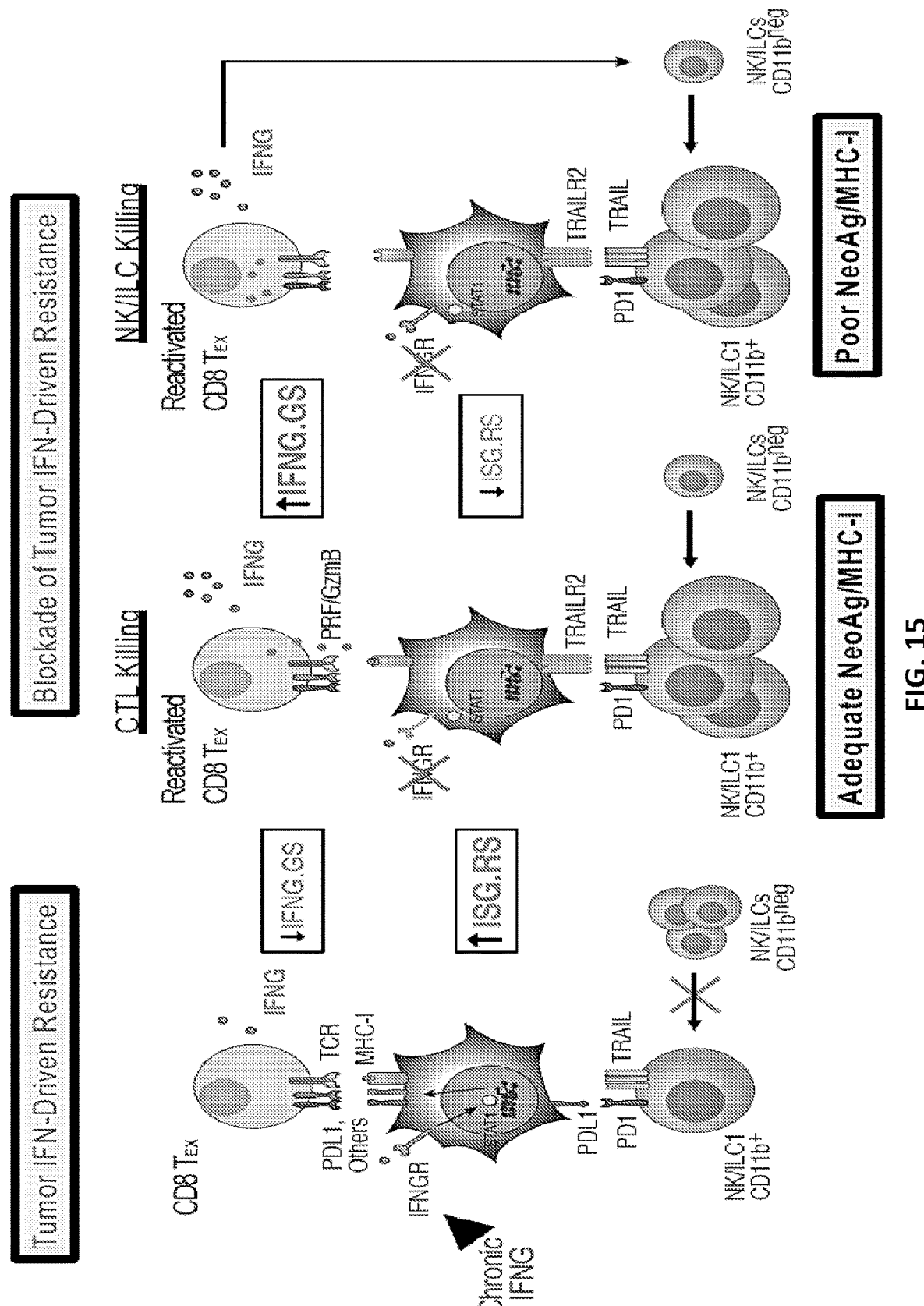
FIG. 15 illustrates the finding that opposing roles of IFN in cancer and immune cells dictate response in NeoAg Hi and Lo tumors.
Figure 16:
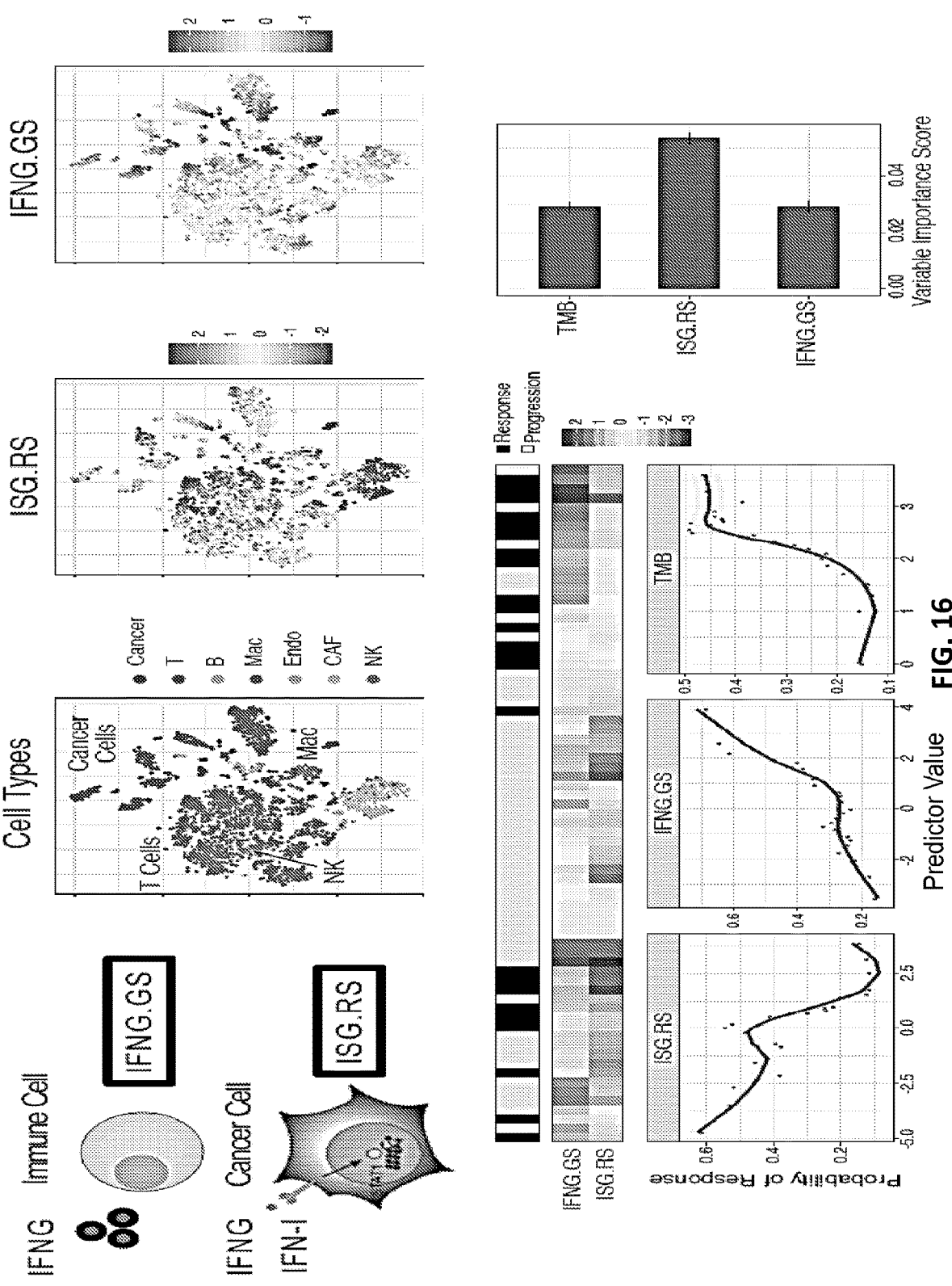
FIG. 16 illustrates the finding that low ISGs in cancer cells and high ISGs in immune cells favors anti-PD1 response in melanoma.

These findings suggest that mutations predicted to reduce tumor IFN signaling might associate with decreased ISG.RS and improved clinical response to ICB. To investigate this, the analysis of recently described exome-sequencing data from non-small cell lung cancer (NSCLC) patients from either TCGA or a clinical trial using anti-PD1 plus anti-CTLA4 (Hellmann et al., 2018, *Cancer Cell* 33, 843-852.e844) was extended. After excluding common non-disease single-nucleotide variants (SNVs), predicted pathogenic missense and nonsense mutations were identified using two algorithms, CADD and DANN, that were trained on a catalog of benign and pathogenic variants from the ClinVar database (FIG. 7G). Indels were also evaluated as damaging or neutral using SIFT. This revealed that 14.7% of patients had tumors harboring at least one predicted pathogenic missense/nonsense mutation or damaging frameshift indel in a core set of 11 type I and II IFN pathway genes (FIG. 7A). This frequency is comparable to the 8.7% incidence of predicted pathogenic variants found in NSCLC patients from TCGA (FIG. 14A). In the TCGA, there is an 8.6% incidence of patient tumors with at least one predicted pathogenic variant in a core set of 11 type I and II IFN pathway genes (14A-14B). These tumors exhibit a decrease in ISG.RS genes, consistent with an enrichment for IFN pathway variants with defective signaling (FIGS. 7G and 14F). In the patients treated with anti-PD1 plus anti-CTLA4, 14.7% of patients have patients with at least one IFN pathway variant and these patients have improved progression-free survival (PFS) after dual ICB (FIGS. 7A-7B). In contrast, only 0.58% of random gene sets of similar size yielded PFS differences that are as significant (FIG. 14B) and IFN pathway variants do not associate with survival in TCGA patients (FIG. 14C), arguing that variant status is not a general prognostic marker. Although the presence of IFN pathway variants is associated with higher TMB (FIG. 14C), multivariable random forest (FIG. 7C) and logistic regression (FIG. 14D) revealed that variant status improves prediction of ICB response independently of TMB and PDL1 expression (FIGS. 7H and 14I). All evaluable patients with an IFN pathway variant had a complete response (CR), partial response (PR), or stable disease (SD), and an average probability of response (CR or PR) of 92.9% versus 8.7% for variant negative patients based on multivariable modeling (FIGS. 7D and 14C). Both models yield predicted probabilities of response (CR or PR) that correlate well to actual observed responses (FIG. 7I, top panel; FIG. 14I, right plot). Notably, despite a higher likelihood of response, tumors with an IFN pathway variant also exhibited a lower average % PDL1 staining of 5.4% versus 20.3% (FIG. 7D-7E), consistent with the variants having a negative impact on tumor IFN signaling that interferes with tumor-specific PDL1 expression. In contrast, stratification by variant status of random gene sets rarely yields a difference in % PDL1 this large (frequency $5.7 \times 10^{-3}$) (FIG. 14E). Notably, one patient had a tumor with multiple alleles of B2M with a frameshift indel or predicted pathogenic missense mutations who nonetheless had a PR to ICB (FIG. 7D, patient 40). This is consistent with a previous report describing a NSCLC patient responding to anti-PD1 despite deleterious B2M mutations and loss of B2M expression confirmed by immunohistochemistry. Thus, genetic alterations of the IFN pathway in human NSCLC are associated with decreased ISG.RS, decreased tumor PDL1, and improved ICB response independent of TMB status.

Example 10: Discussion

The present study describes how IFN signaling between immune cells and cancer cells orchestrates opposing functions to both impact and predict ICB response. In immune cells, IFNG signaling supports anti-tumor responses, while in cancer cells IFNG augments MHC-I expression. Opposing these immune stimulatory effects, IFNG signaling in tumor cells drives feedback inhibition by increasing multiple inhibitory pathways that include PDL1, while decreasing levels of cytotoxic effectors like TRAILR2. As a consequence, these inhibitory pathways on cancer cells not only promote T cell exhaustion but also interfere with maturation of NK/ILCs and protect against their cytotoxic effects. Thus, in tumors that are less reliant on IFN for MHC-I expression and antigen presentation, blocking tumor IFN-driven resistance can improve ICB response (FIG. 7F). For tumors with adequate neoantigens and high constitutive MHC-I, the improved function of $T_{ex}$ enables CTL-mediated anti-tumor responses. This condition is associated with immunological memory and can even result in profound spontaneous regression in the absence of ICB. For tumors with depleted neoantigens and otherwise likely resistant to ICB, ablating tumor IFN signaling also improves $T_{ex}$ function. In this situation, loss of IFN-inducible MHC-I is less consequential for CTL function. Improved ICB response results from enhanced IFNG production by T cells that promotes intratumoral NK/ILC accumulation and maturation. The simultaneous decrease in tumor PDL1 and increase in TRAILR2 that occurs after blocking tumor IFNG signaling likely allows a PD1+ TRAIL+NK/ILC1-like subset to restore ICB response, an effect that is facilitated by inhibition of Tregs. Altogether, these results illustrate how IFNG operates between adaptive immune cells, innate immune cells, and cancer cells to coordinate immune stimulatory and inhibitory effects. When the inhibitory effects directed by tumor cells are targeted, this can unleash a feed-forward mechanism coordinated by adaptive and innate cells with the potential to improve ICB response even in tumors with neoantigen or MHC-I deficiency.

Biomarkers and multivariate models that can accurately predict clinical ICB response is an important step in effectively translating immunotherapies. TMB and IFNG-related genes such as PDL1 are undoubtedly important predictive features. High TMB and expression of IFNG-related genes both can positively associate with ICB response, while genomic or copy number alterations within B2M and IFN pathway genes can portend resistance and relapse. However, it is also clear that these features are imperfect predictors and refinement is needed. For example, patients with high PDL1 or IFNG-related genes frequently fail to respond, while patients with low TMB tumors or mutations in B2M or the IFN pathway may nonetheless benefit from ICB. Reasons for such incongruent observations include the failure of gene signatures to capture the inhibitory functions of IFN signaling, somatic IFN pathway variants that unknowingly interfere with these inhibitory functions, or the possibility that these inhibitory functions impact not only adaptive immunity but innate-immune killing as well. Herein it was found that incorporating the ISG.RS or IFN pathway variants into models that include TMB and IFNG-related genes improves the ability to predict clinical ICB response. Indeed, the biology uncovered by the experimental models herein reflects this improvement and the statistical associations that accompany it. Thus, although using ISGs from experimental models to predict clinical response requires further optimization, and the functional properties of tumor variants in IFN pathway genes requires experimental investigation, these results highlight the importance of biomarkers that capture opposing functions of IFN signaling.

In addition to corroborating known immunostimulatory effects of IFNG, additional properties of IFNG signaling between innate and adaptive immune cells that can promote ICB response were describe. This work suggests that even if CD8 T cells are not able to effectively mediate cytolytic anti-tumor killing due to poor neoantigens or defective antigen presentation, improving the ability of $T_{ex}$ to generate IFNG is important for the accumulation of intratumoral NK/ILCs that can mediate tumor killing. Such a function of CD8 T cells and $T_{ex}$ to support NK/ILCs through IFNG are reminiscent of NKT cells. In fact, our studies suggest that CD8 T cells required to generate IFNG need not be tumor-specific, as revealed by the ability of cross-primed and/or bystander T cells to sustain NK/ILC accumulation and NK/ILC-dependent tumor killing. These findings may provide insight into a potential utility of bystander T cells to common viruses and other non-tumor antigens that are abundant in human tumors. These stimulatory effects of IFNG on NK/ILCs may be indirect. IFNG from CD8 T cells may act on macrophages to drive NK/ILC expansion through cytokines such as IL-15, enhance NK/ILC recruitment through CXCR3 ligands, or promote transdifferentiation of ILCs into ILC1s through cytokines like IL-12. Consistent with this notion, macrophages from melanoma patients express the IFNG.GS (FIGS. 1B and 8A) and positively correlate with the frequency of activated intratumoral NK cells (FIG. 6I). In mice, IFNG and the IFNG-regulated CXCR3 ligand CXCL10 influences intratumoral NK/ILC accumulation and/or phenotype. Altogether, our findings suggest that IFNG can be harnessed by immunotherapy approaches to link tumor-specific $T_{ex}$, bystander CD8 T cells, and various types of innate immune cells against tumors differing in neoantigen status.

In contrast to IFNG signaling in immune cells, IFNG signaling in tumor cells orchestrates resistance to ICB. It was previously demonstrated that this tumor-driven feedback inhibition is initiated and maintained by chronic IFN signaling. This results in high levels of PDL1 and multiple other inhibitory receptor ligands (e.g., TNFRSF14, LGAL9, CD86, etc.) that promotes the accumulation of $T_{ex}$ with markers of severe exhaustion. Besides the resulting $T_{ex}$ having poor cytolytic function, these data suggest that a consequence of diminished IFNG generated by severe exhaustion is the accumulation of immature $CD11b^{-/low}$ NK/ILCs, which themselves have decreased production of cytokines such as IFNG, low cytotoxic function, and is associated with human tumors with a poor prognosis. However, tumor IFNG can also directly interfere with NK/ILC function. One mechanism involves the same IFNG-regulated inhibitory receptor ligands that promote $T_{ex}$. The present study focused on PDL1 but did not rule-out a role for the other ligands on tumor cells that are controlled by IFNG. A second mechanism involves IFNG decreasing expression of TRAILR2 on tumor cells. For tumors with poor or depleted neo-antigens, our findings suggest the need to first block PD1 on $T_{ex}$ to support NK/ILC maturation, and then to block PD1 on a NK/ILC1-like subset to enable TRAIL-mediated killing. Whether targeting other IFN-regulated pathways or inhibitory receptor ligands on tumor cells or other cell types can further improve NK/ILC function will be important to investigate.

How NK/ILC recruitment and maturation specifically relates to the PD1+ TRAIL+CD11b$^{high}$ NK/ILC subset is currently unclear. Recent reports demonstrate that distinct ILC1-like cells expressing TRAIL have roles in cancer immunosurveillance or in cancer immunosuppression. For the latter, an ILC1-like population that expresses multiple inhibitory receptors such as PD1, CTLA4, and LAG3, is less able to control tumor growth compared to conventional NK cells. In fact, evidence suggests that TGF-beta can promote immune suppression by driving the conversion of conventional NK cells into these ILC1-like counterparts. Although comparison between ILC populations between studies is a challenge, these TGF-beta-regulated ILC1-like cells may share features with the PD1+ TRAIL+CD11b$^{high}$ NK/ILCs in our study. If so, there may be a precursor-product relationship between maturing CD11b$^{int}$ NK/ILCs and CD11b$^{high}$ PD1+ TRAIL+NK/ILC1s. Alternatively, these two populations might belong to separate lineages that are both dependent on a common cytokine like IL-15, or the ILC1-like cells may arise from the transdifferentiation of ILC2s and ILC3s under the influence of inflammatory cytokines. Regardless, by simultaneously increasing tumor TRAILR2 and decreasing expression of PDL1 and multiple other inhibitory ligands, ablating tumor IFNG signaling may help to reactivate otherwise poorly cytotoxic ILC1-like cells. These findings also suggest that additionally interfering with Tregs is important to initiate killing by these NK/ILCs, illustrating the diversity of the immunosuppressive mechanisms that need to be targeted. Thus, a growing understanding of how NK/ILC function can be restored may enable approaches that leverage innate immune killing of neoantigen poor tumors or tumors that have lost MHC-I expression. Observations that tumors with B2M deficiency can nonetheless respond to ICB highlight the potential of such strategies.

This study focused on how IFNG signaling between tumor cells, T cells, and innate immune cells orchestrate cooperative and opposing effects on anti-tumor immune responses. Besides IFNGR, inhibiting STAT1, IFNAR, or IFNGR and IFNAR in tumor cells also diminishes the expression of resistance-associated ISGs and in some cases result in greater anti-tumor responses than IFNGR knockout alone. Thus, how IFN-I contributes to IFN-driven resistance and differs from IFNG requires additional investigation, as does the roles of individual ISGs in ICB resistance. Such questions are particularly relevant given that mutations in human tumors potentially affecting either or both type I and II IFN pathways are observed.

Example 11: Steps to Make the Evaluator

1) Creating a single feature from the expression values of 36 ISG.RS genes: Start with 36 genes that are a subset of the 49 IRDS genes from Weichselbaum et al, (Weichselbaum et al., (2008) Proc Natl Acad Sci USA 105, 18490-18495). These 36 genes are the ones that are upregulated (knowing to use the subset of 36 genes from the 49 is not obvious). The values of these 36 genes are scaled and a "SAM statistic" is calculated, which is a modified t-statistic. Using this statistic in view of all the possible statistic methods that are available is not obvious. Then, the average value of all SAM statistics >0 is taken to create a single score for each patient. This score is what is used for the ISG.RS.

2) Creating a single feature from the expression values for the 187 IFNG.GS genes: Start with 187 IFNG-related genes. Then, omit 24 genes of the 187 that overlap with the 36 ISG.RS genes to minimize overlapping signal. Then, a SAM statistic is calculated for these 163 IFNG.GS genes and a single score determine for the IFNG.GS using the same method as step #1.

3) Creating a multivariable classifier for predicting probability of response: The ISG.RS, IFNG.GS, and tumor mutational burden (TMB) are used to model clinical response using random forest machine learning and an algorithm called "imbalanced forest". This yields the results shown herein. Importantly, omitting TMB only modestly influences prediction accuracy.

Figure 10F:
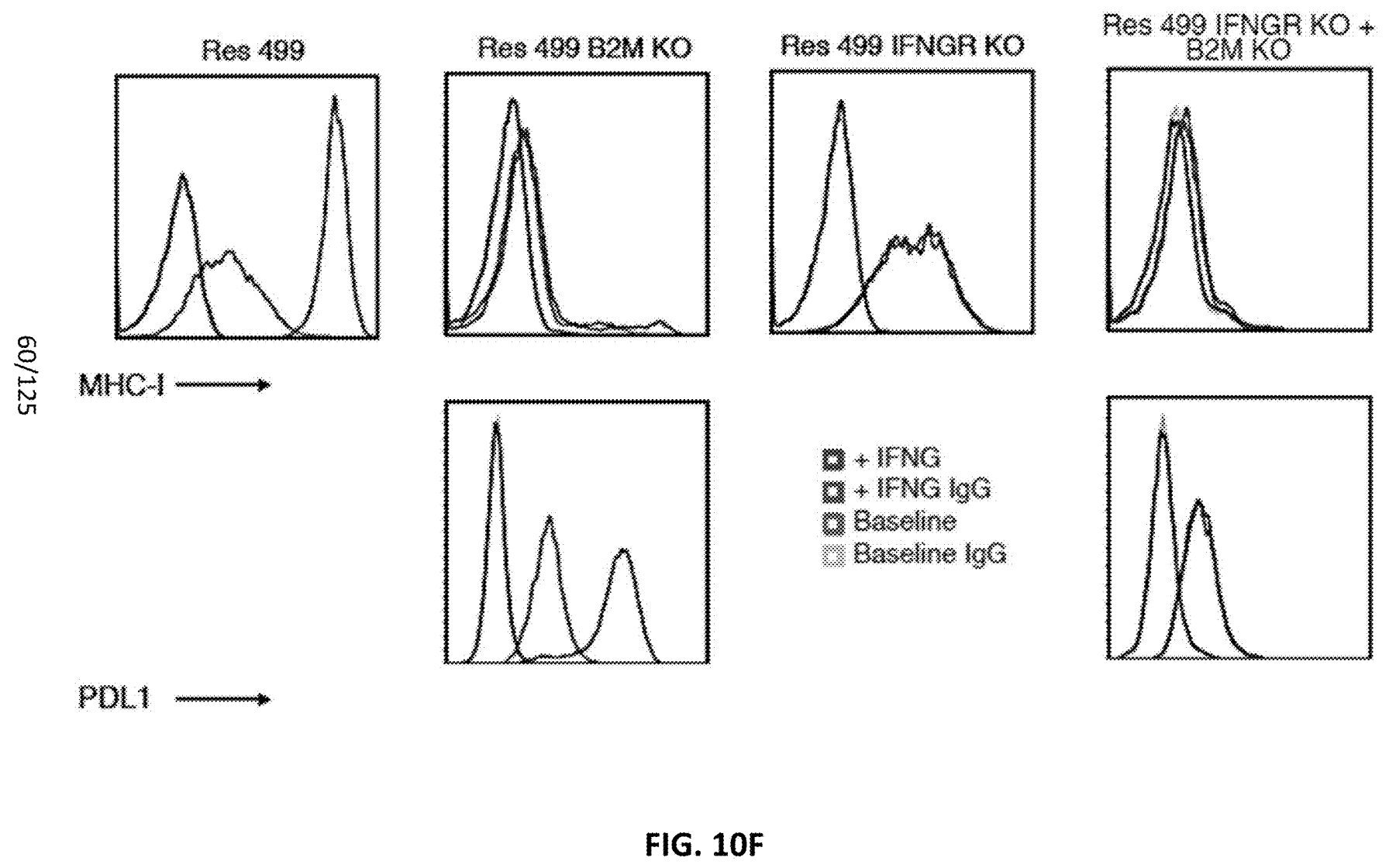
Figure 18D:
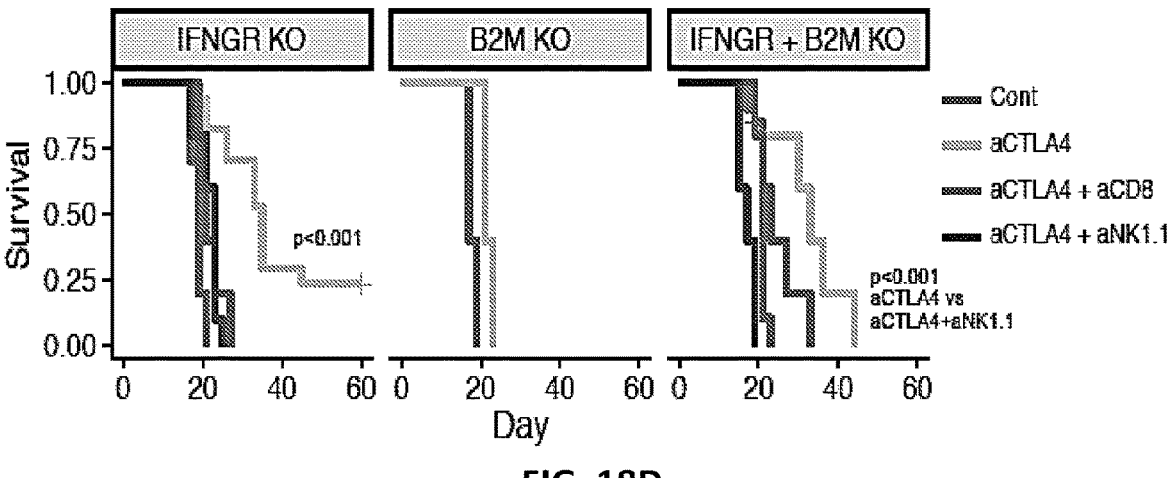
Figure 18E:
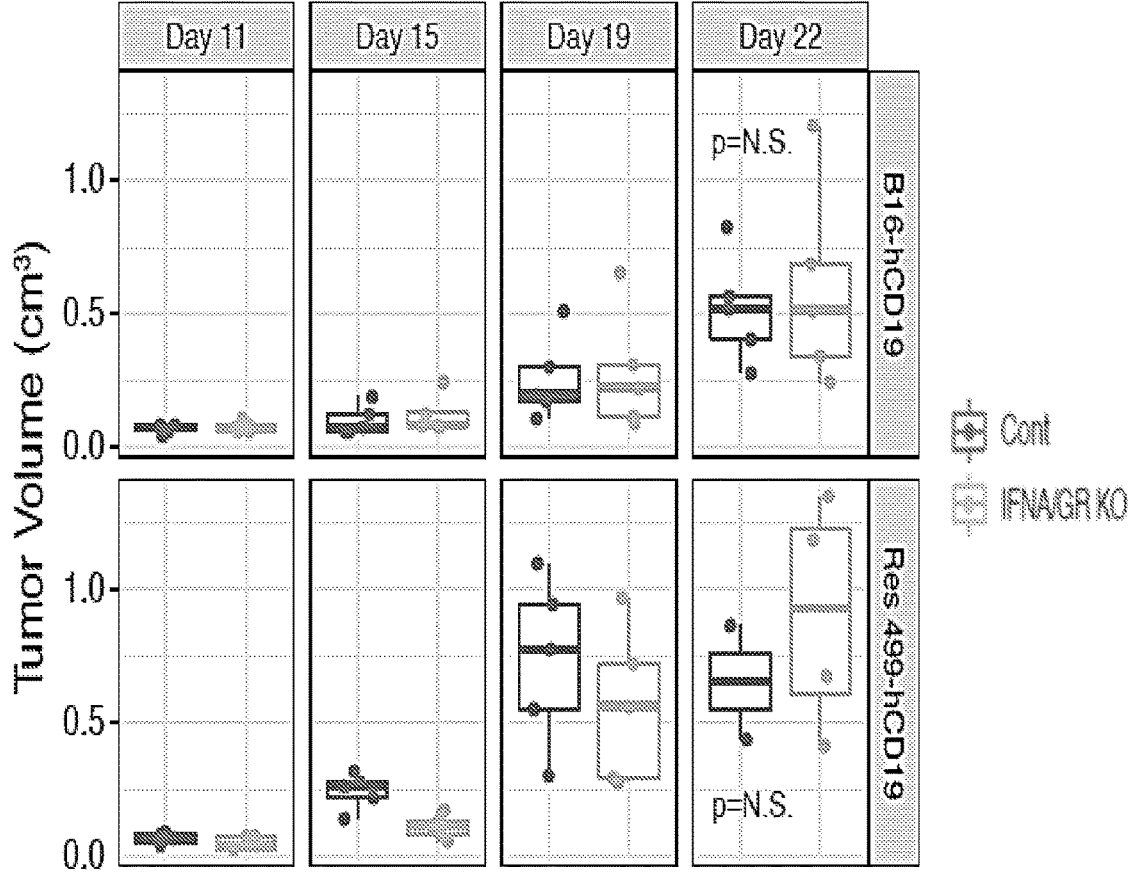
Figures 18F, 18G:
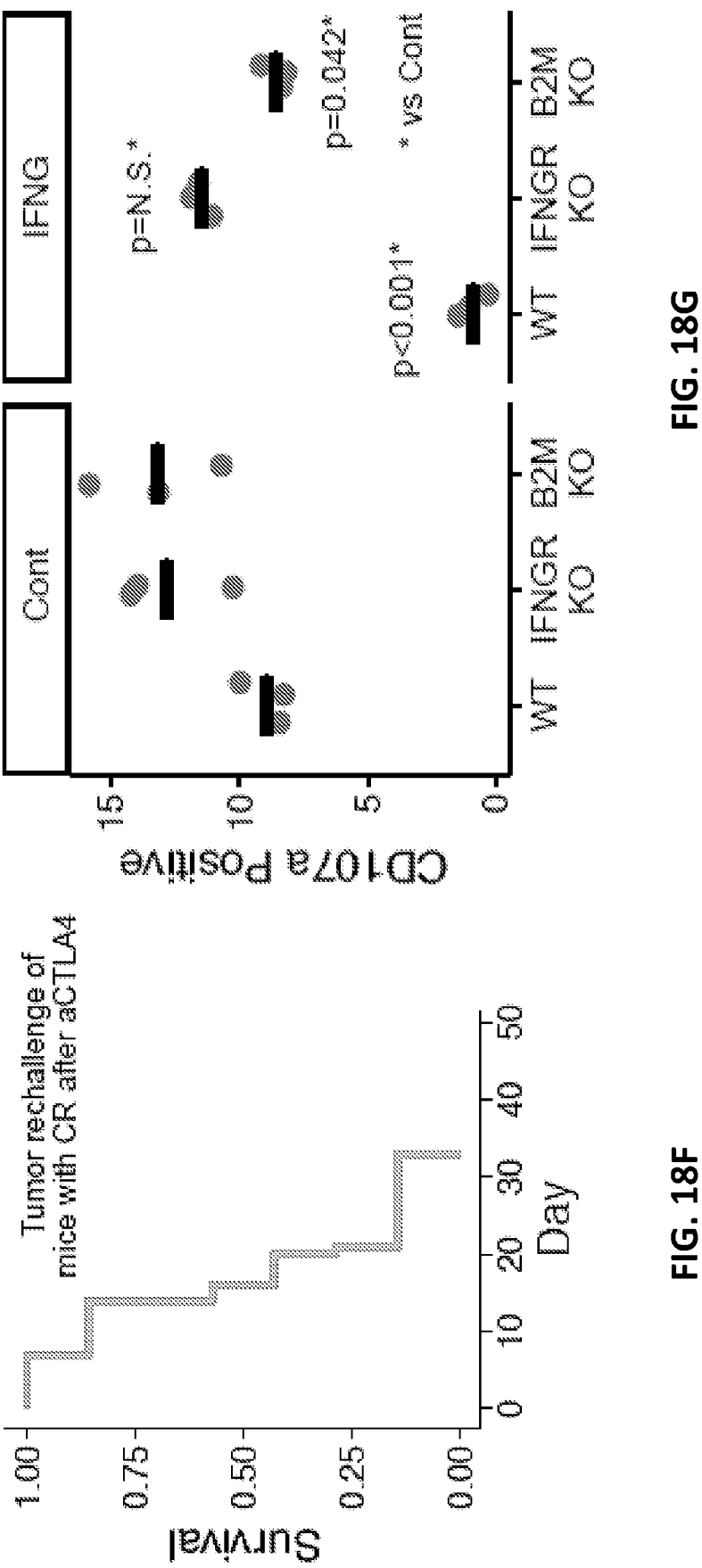

Example 12: Inhibition of Tumor IFNG Signaling Enables CD8 T Cells to Support NK/ILC-Mediated Killing To understand how blocking tumor IFN signaling restores ICB response in resistant or relapsed tumors and to avoid conflating effects of type I and II IFN, the mechanism by which IFNGR knockout restores response in the Res 499 model was investigated. Anti-CTLA4 monotherapy was opted to use given that addition of RT does not significantly improve response over anti-CTLA4 alone (FIG. 18D vs. 18B). As expected for NK/ILC-mediating killing, IFNGR knockout improved response to anti-CTLA4 in the absence of B2M (FIGS. 18D and 10F). This required NK1.1+ innate immune cells (FIGS. 18D and 10F), was perforin-independent (FIG. 3C), and did not generate durable immunity against tumor rechallenge of mice with complete response (FIG. 18F). To test if NK/ILC-mediated cytotoxicity may be responsible for response after IFNGR knockout, poly I:C stimulated splenic NK cells were co-cultured with Res 499 cells in vitro (FIG. 18G). This resulted in NK-mediated cytotoxicity as measured by CD107a, which was used as a general marker for NK effector function. IFNG treatment of wild type but not IFNGR knockout Res 499 cells prior to co-culture was sufficient to increase resistance even in the absence of B2M, consistent with tumor IFNG signaling impeding NK/ILC killing. Thus, like with inhibition of both type I and II IFN signaling, blocking tumor IFNG signaling restored ICB response by enhancing NK/ILC-mediated effector function.

Figure 18H:
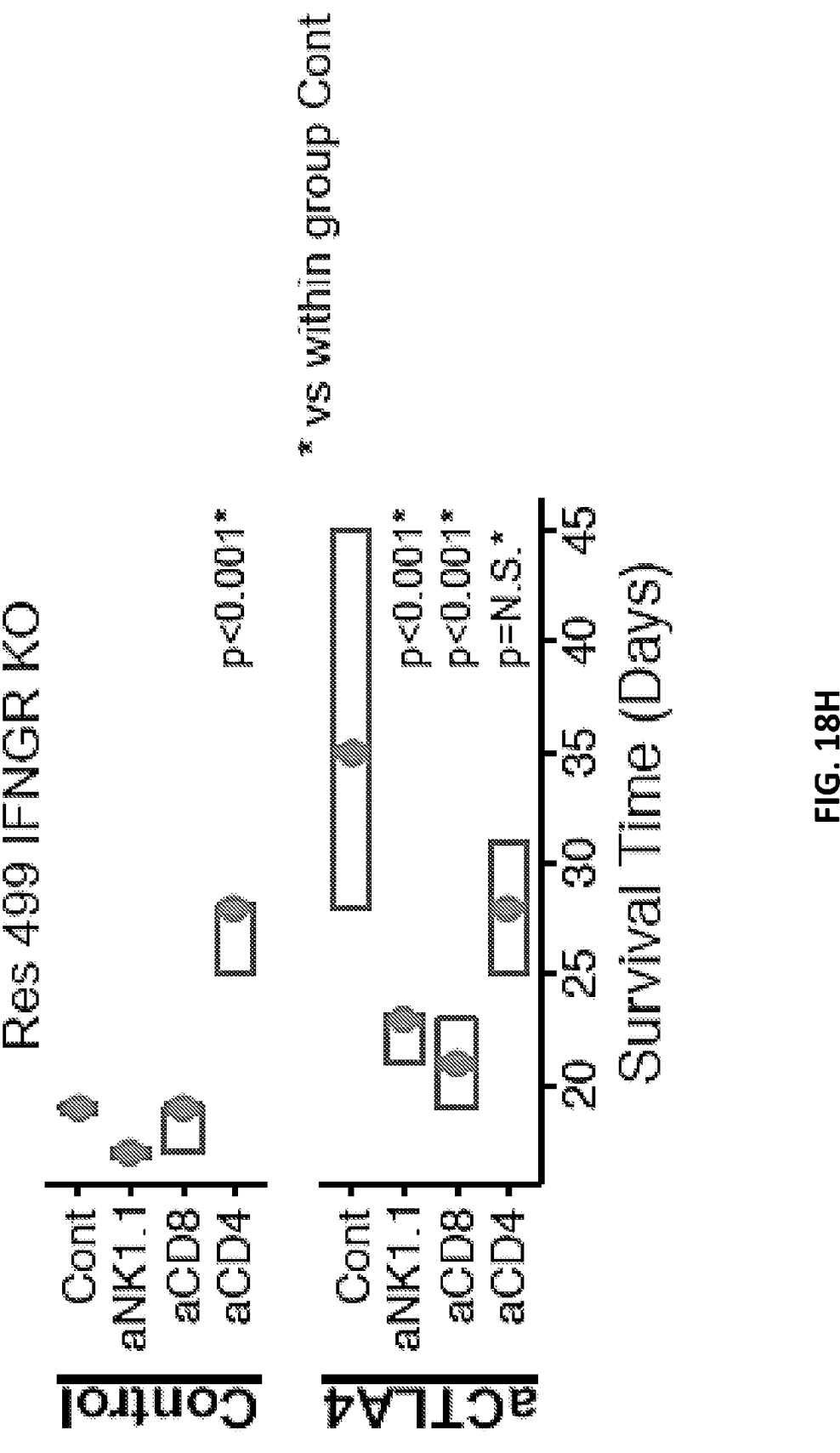

Surprisingly, although depletion of NK1.1+ cells abrogated ICB response of IFNGR knockout Res 499 tumors, depletion of CD8 T cells, but not CD4 T cells, also inhibited response (FIGS. 18D and 18H). A similar requirement for both CD8 T cells and NK/ILC1s was also observed after IFNGR knockout in the resistant TSA/237 breast cancer model that exhibited relatively low TMB and a paucity of predicted strong neoantigens (FIGS. 2C and 10H). These observations suggested that although CD8 T cells do not directly kill IFNGR knockout Res 499 tumors, they may have a supportive role.

Figure 19B:
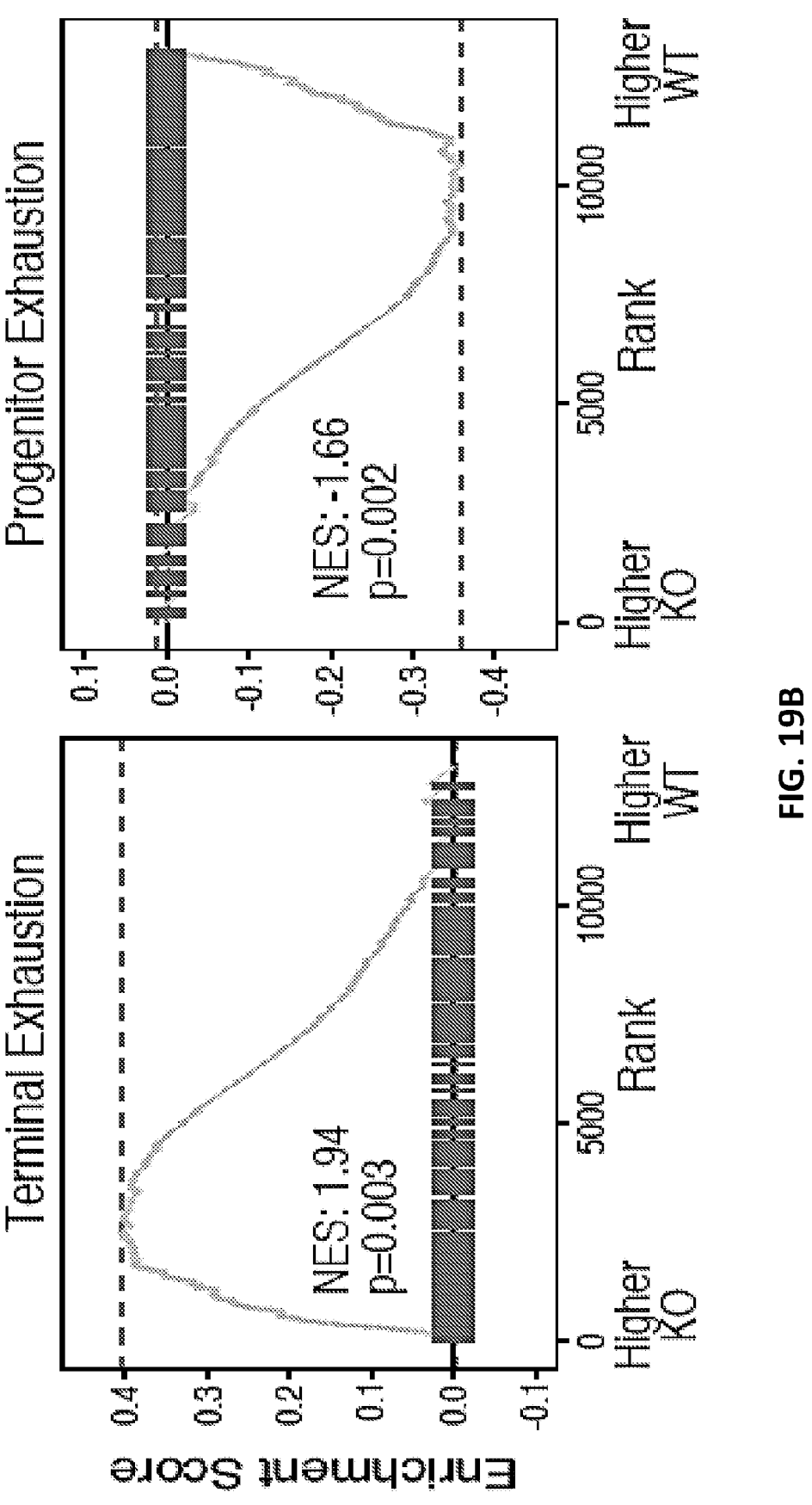
Figure 19C:
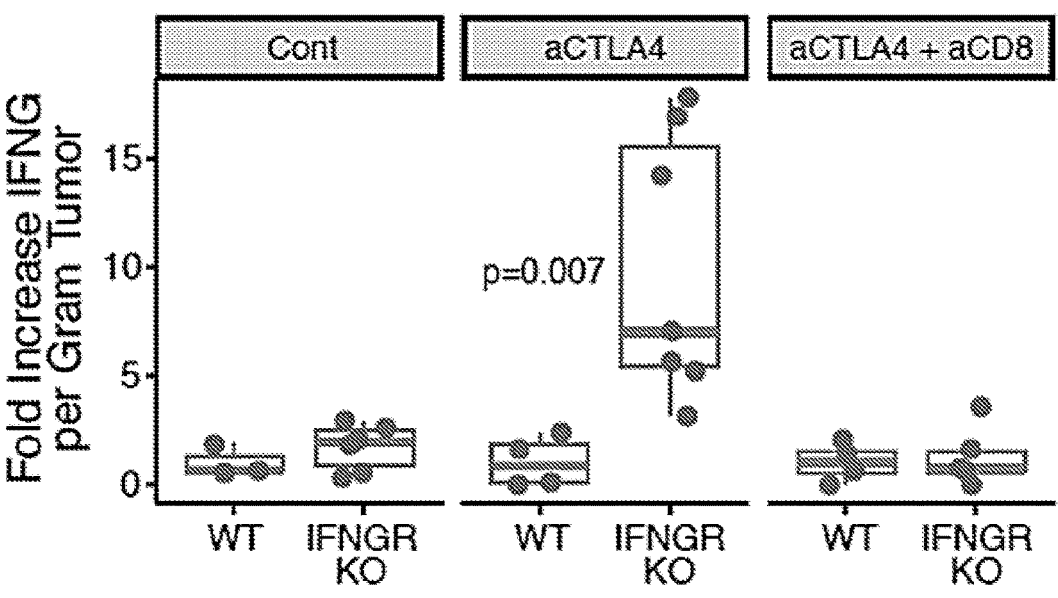
Figure 19D:
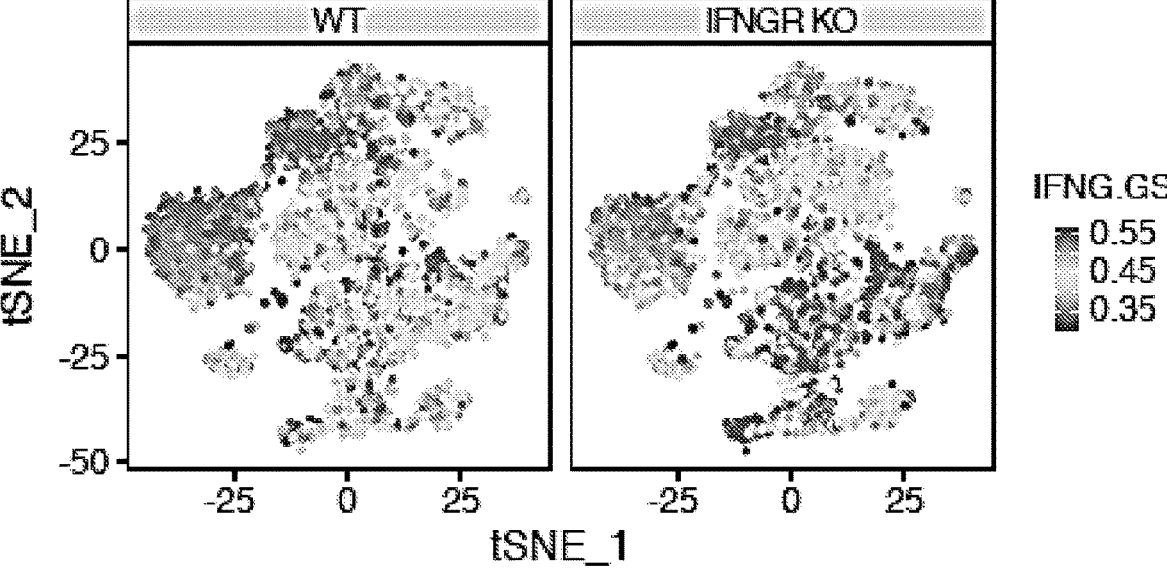

Example 13: Preventing Tumor IFNG Signaling Enhances Immune Cell IFNG Signaling, CD8 T$_{ex}$ Function, and Maturation of NK/ILC1 Cells To examine how CD8 T cells might support NK/ILC1s, single-cell RNA-sequencing (scRNA-seq) and 28-color flow cytometry were employed. Analysis of intratumoral CD45+ immune cells by scRNA-seq revealed that a dominant effect of tumor IFNGR knockout was an increase in the proportion of CD8 T cells (FIG. 19A). Intratumoral CD8 T cells are typically exhausted and reside in either a progenitor exhausted or terminally exhausted population. Although terminally exhausted PD1+CD8 T cells have limited long-term proliferative potential, they can carry out various effector functions such as cytotoxicity and IFNG production. Gene set enrichment analysis (GSEA) using transcriptional signatures of these exhausted subsets (defined using the LCMV infection model) revealed that the expanded CD8 T cells resulting from IFNGR knockout showed a marked increase in terminal exhaustion genes (e.g., Pdcdl, Eomes, Cd38) and a decrease in progenitor exhaustion genes (e.g., Tcf7) (FIGS. 19B and 20A). Accordingly, there was a per cell increase in the amount of IFNG protein produced by PD1$^+$ CD8 T cells (FIG. 20B), and after anti-CTLA4 there was a large increase in IFNG per gram of tumor (FIG. 19C), which was not observed with cytokines such as IL-6 (FIG. 20C). Depletion of CD8 T cells largely abrogated this intratumoral increase in IFNG, highlighting the importance of exhausted CD8 T cells in generating this cytokine. Accompanying the increase in IFNG was a marked increase in the IFNG.GS primarily from myeloid/DC populations (FIG. 19D). Among various IFNG.GS genes, that increase included Cxcl9 and Cxcl10 (FIG. 19E), which are chemokines implicated in NK cell recruitment, activation, or maturation. Thus, disrupting tumor IFNG signaling not only decreased the ISG.RS in cancer cells but also increased production of IFNG by terminally exhausted CD8 T cells. As an apparent consequence, myeloid/DC populations increased expression of IFNG.GS that include chemokines important in innate immune function.

Figures 19E, 19F:
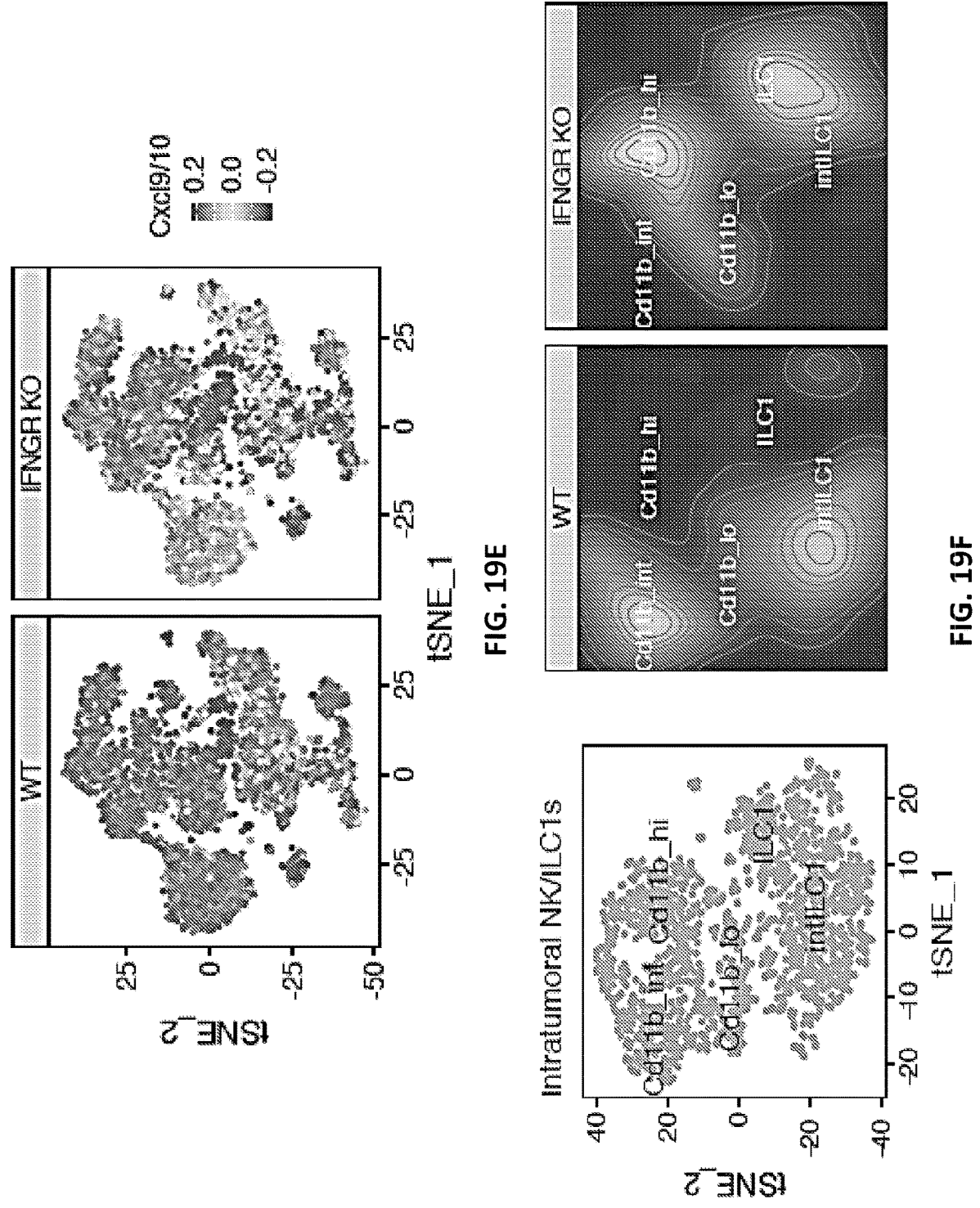
Figures 19G, 19H:
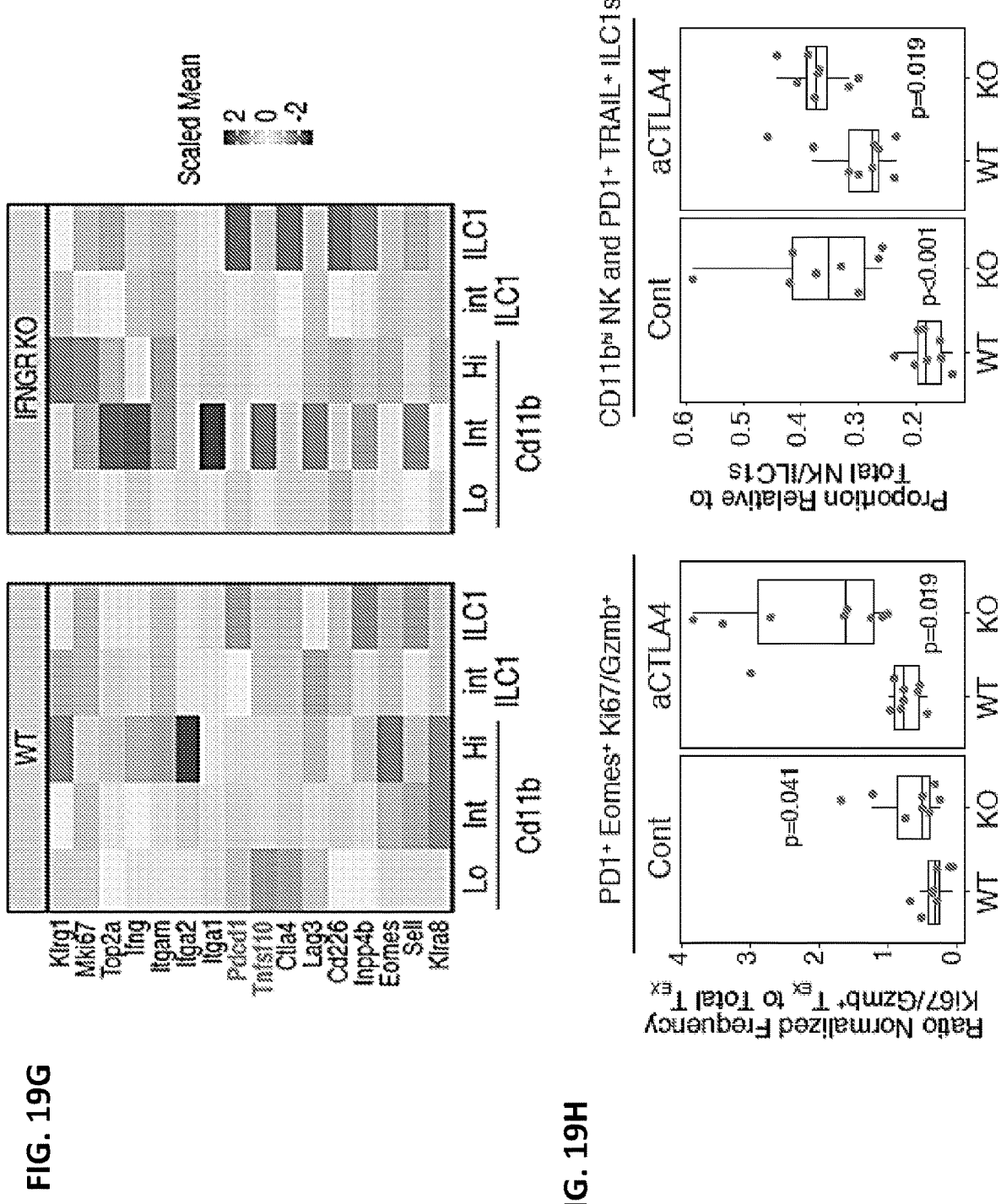
Figure 19I:
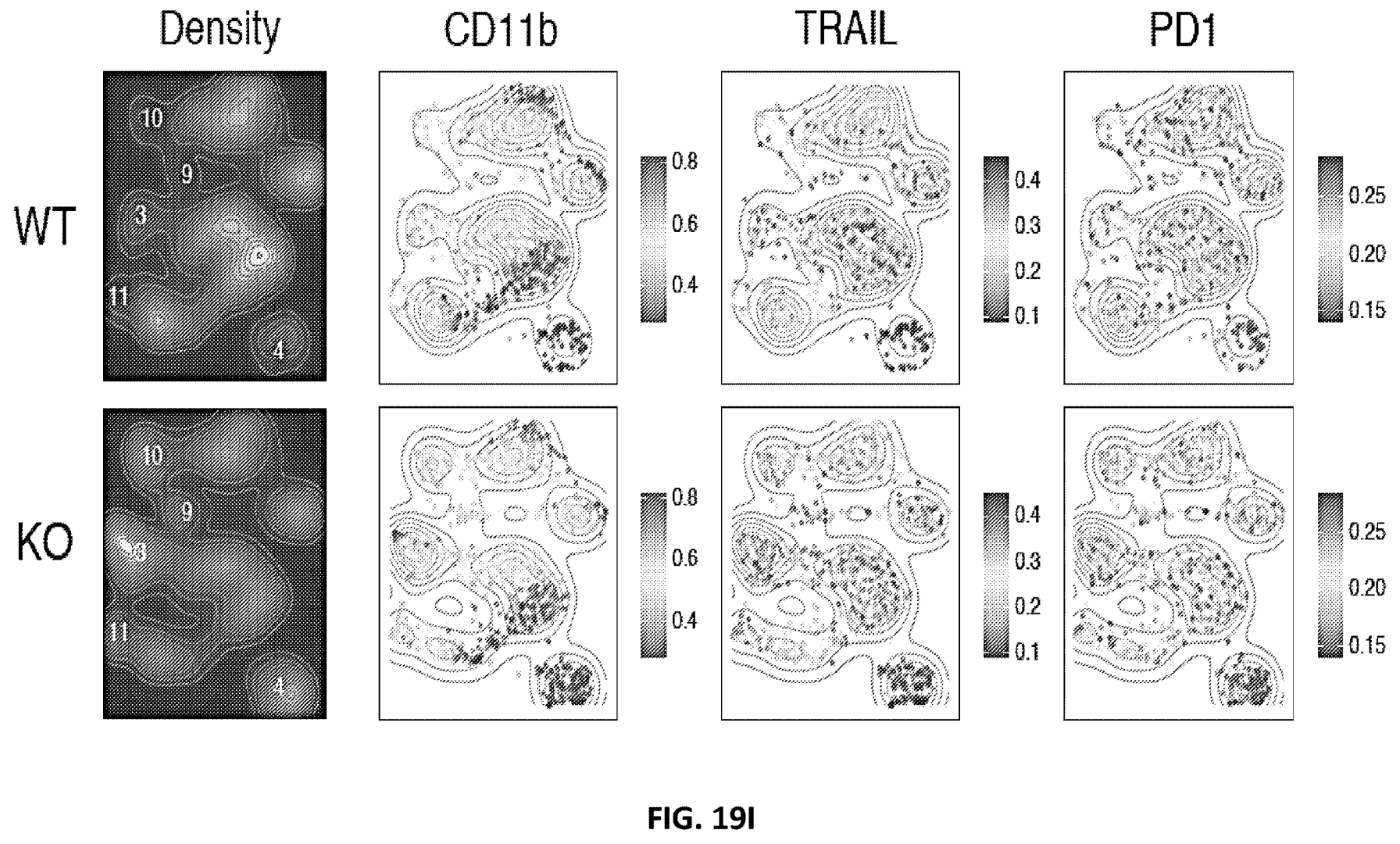
Figures 20A, 20B:
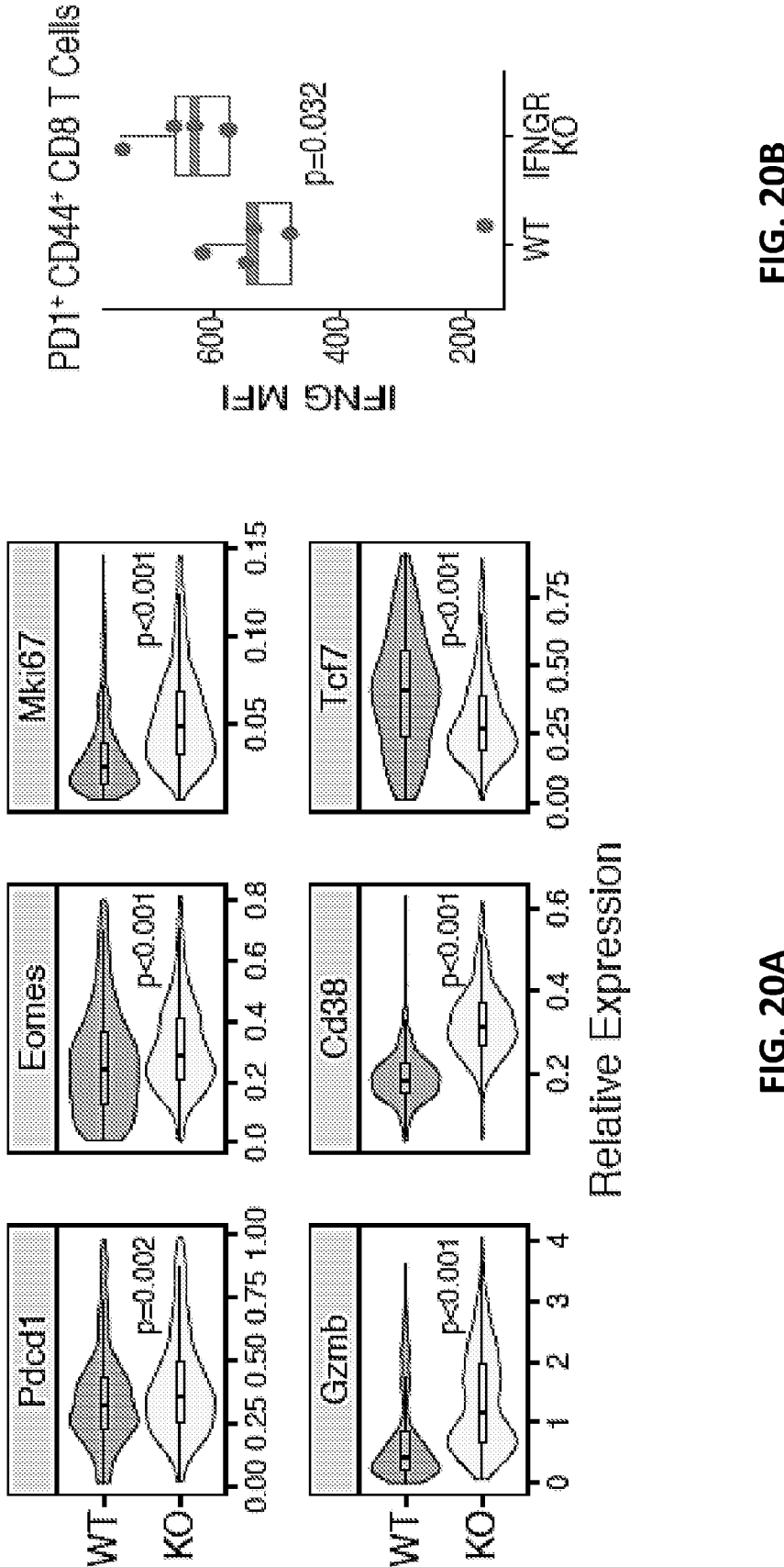
FIGS. 20A-20G illustrate improved T$_{ex}$ function and NK/ILC1 maturation after blocking tumor IFNG signaling.
Figure 20C:
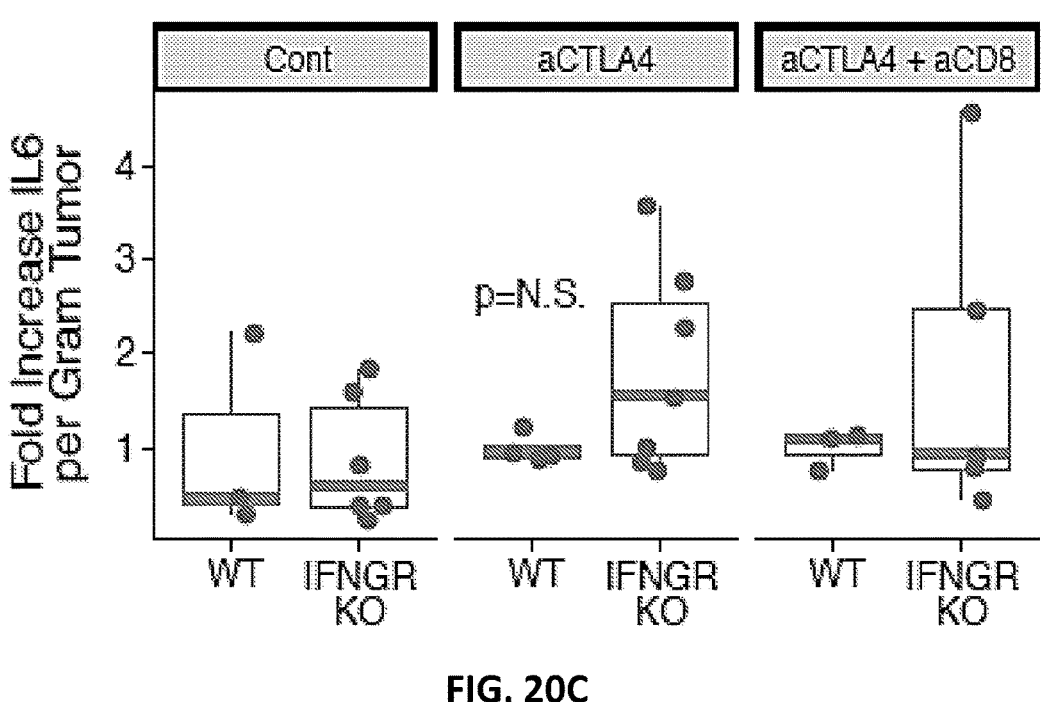
Figure 20D:
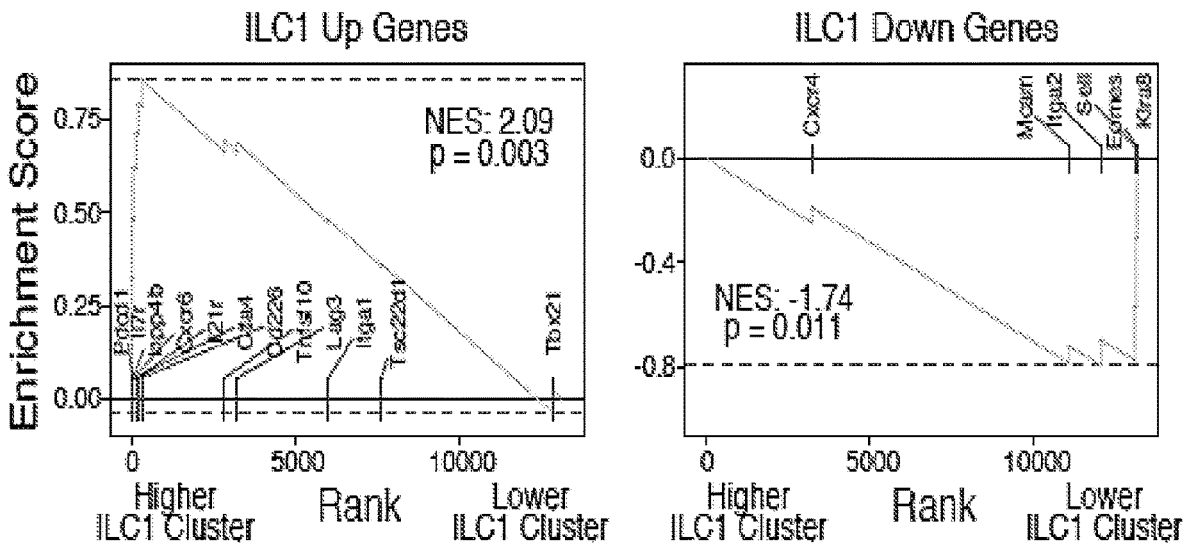
Figure 20E:
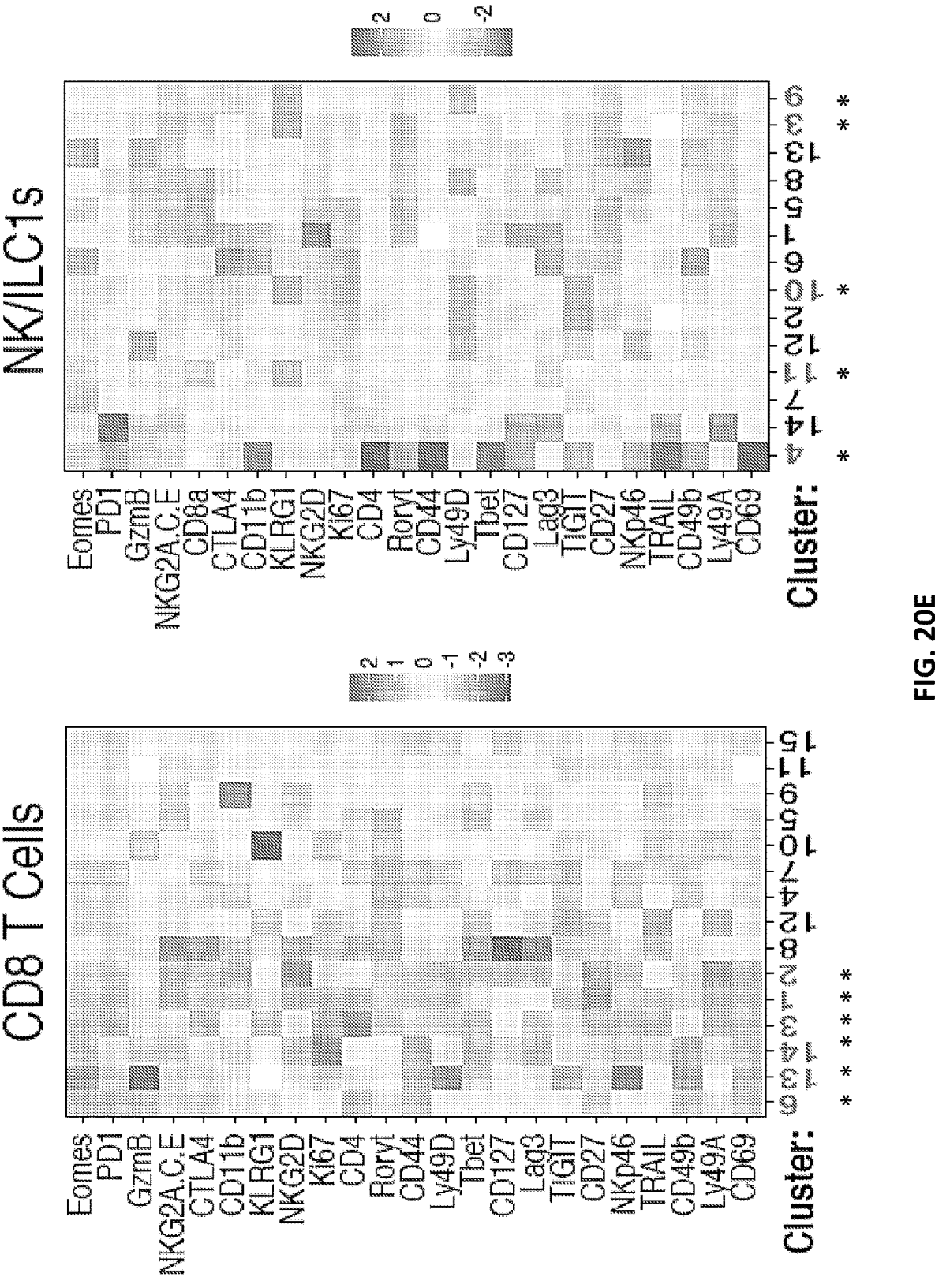
Figure 20F:
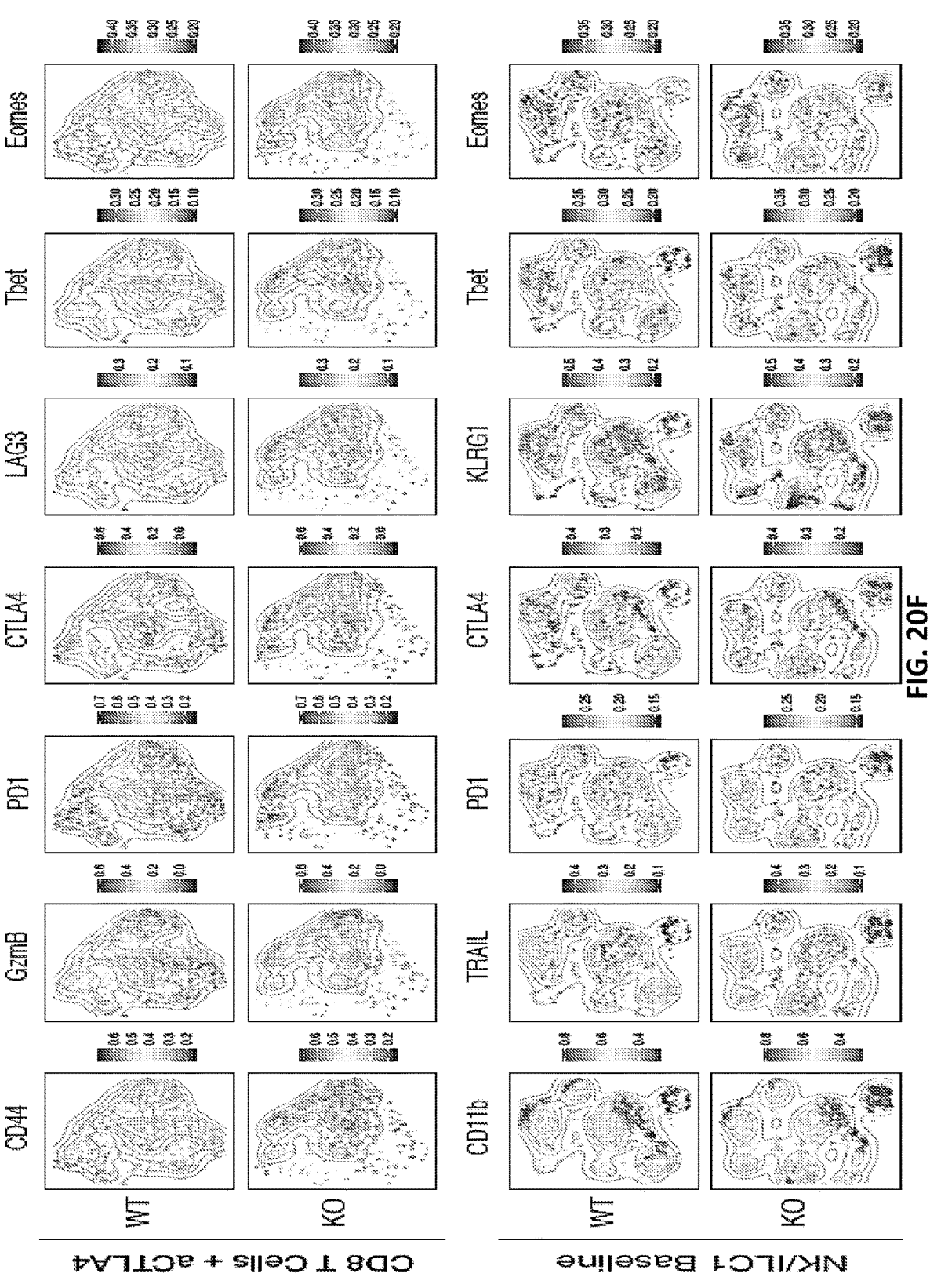
Figure 20G:
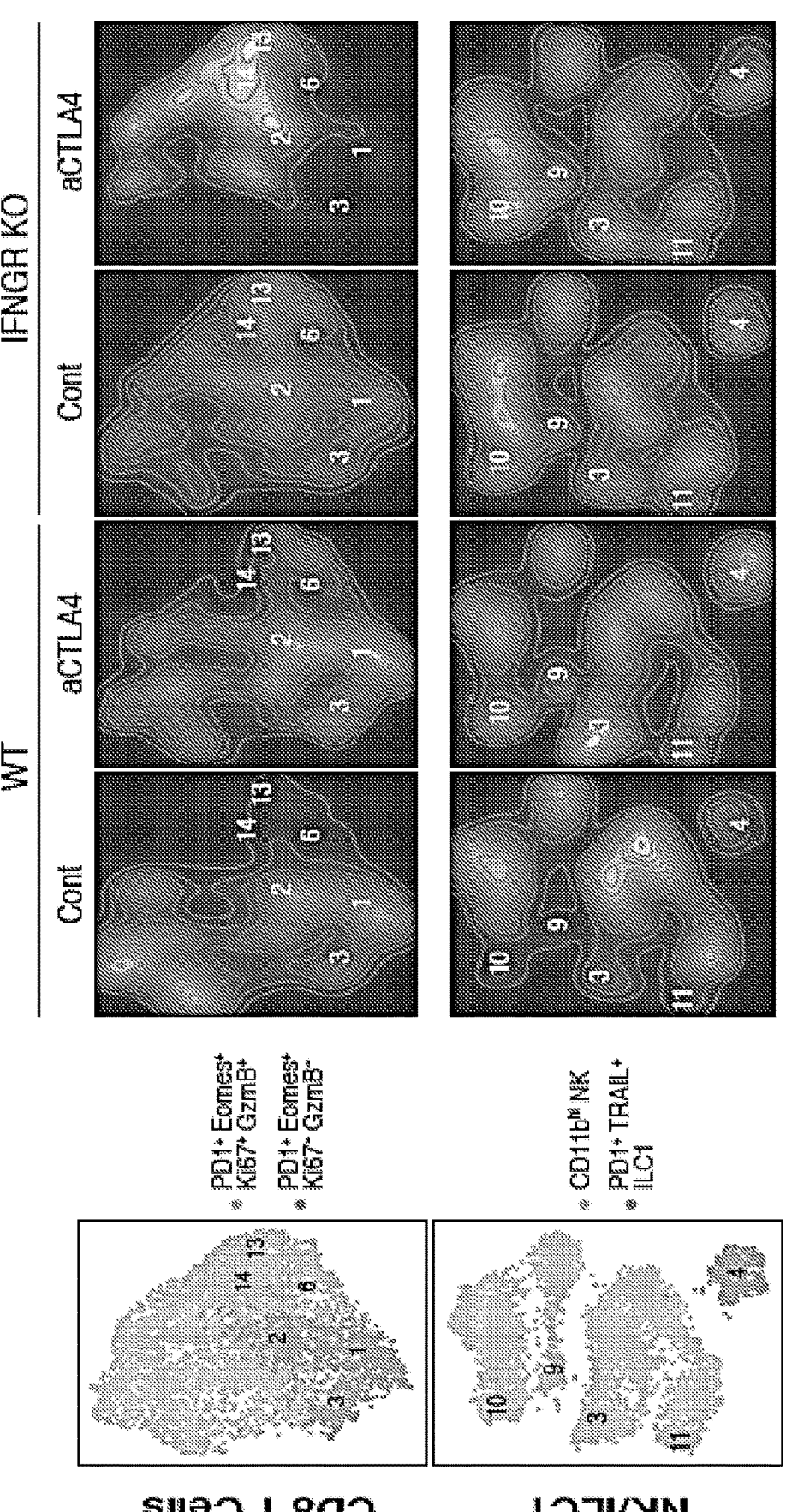

In order to investigate how preventing IFNG signaling in tumor cells impacts NK/ILC1 status, NK/ILC1 populations identified by scRNA-seq were re-clustered (FIG. 19F-19G). This revealed NK populations differing in maturity and effector function, including an immature CD11b$^{low}$ population, an intermediate CD11b$^{int}$ population, and a mature CD11b$^{high}$ cluster that typically possesses the greatest effector function. Moreover, recently described ILC1 and intermediate ILC1 (intILC1) populations were also identified (FIG. 20D). Knockout of tumor IFNGR resulted in a large shift in the NK populations toward the mature CD11b$^{high}$ cluster and an additional shift toward the ILC1 cluster (FIG. 19F, density plots). These ILC1s exhibited relatively high levels of Pd1 (Pdcdl) and Trail (Tfnsf10) (FIG. 19G), consistent with previously reported properties for this population. Using 28-color flow cytometry (FIG. 20E-20F), it was confirmed that tumor IFNGR knockout leads to an increase in the proportion of NK/ILC1s that are CD11b$^{high}$ NK cells or PDI$^+$ TRAIL$^+$ ILC1s (FIGS. 19H-19I and 20G). Flow cytometry also confirmed that this was accompanied by an increase in the proportion of terminally exhausted CD8 T cells, particularly after anti-CTLA4, as indicated by an increase in PD1$^+$ Eomes$^+$ CD8 T cells that expressed multiple inhibitory receptors and relatively high levels of Ki67 and GzmB (FIGS. 19H and 20G).

Together, these results indicated that preventing tumor IFNG signaling expanded CD8 T$_{ex}$ toward terminal exhaustion and increased production of IFNG. In this way, disrupting tumor IFNGR not only decreased ISG.RS in cancer cells but conversely increased IFNG.GS expression by immune cells. This enhanced IFNG signaling in immune cells might then drive maturation and function of NK/ILC1 subsets, including a PD1$^+$ TRAIL$^+$ ILC1 population that potentially contributes to ICB response.

Example 14: Preventing Tumor IFNG Signaling Enables IFNG from CD8 T$_{ex}$ to Drive NK/ILC1 Function while Removing Inhibitory Feedback from PD1/PDL1 and TRAIL/TRAILR2

Given the single-cell findings, it was investigated whether IFNG produced by CD8 T$_{ex}$ is involved in NK/ILC1-mediated killing and whether the PD1/PDL1 and TRAIL/TRAILR pathways, which are implicated due to their presence on intratumoral ILC1s, can contribute to response after IFNGR knockout. To test the role of IFNG produced by CD8

T cells, CD8 T cells from wild type or IFNG knockout mice were adoptively transferred into RAG-deficient hosts and then the mice were implanted with Res 499 IFNGR knockout tumors (FIGS. 5E and 21A). This revealed that IFNG production by CD8 T cells is required for anti-CTLA4 response. Conversely, when CD8 T cells were depleted, there was a decrease in the proportion of mature CD11b$^+$ NK/ILC1s (FIG. 21B) as well as total NK/ILC1s (FIG. 5C). However, direct intratumoral injection of IFNG or CXCL10 could rescue or partially rescue the loss in NK/ILC1 cells (FIG. 5C). NK/ILC1-dependent ICB response (FIG. 5C, boxplots) and survival (FIG. 21C) that was also compromised after depleting CD8 T cells was similarly rescued by injection of IFNG. Thus, these results suggested NK/ILC1-dependent response resulting from blocking tumor IFNG signaling relies on IFNG produced by CD8 T$_{ex}$ and on downstream chemokines such as CXCL10.

Figures 21E, 21F, 21G, 21H:
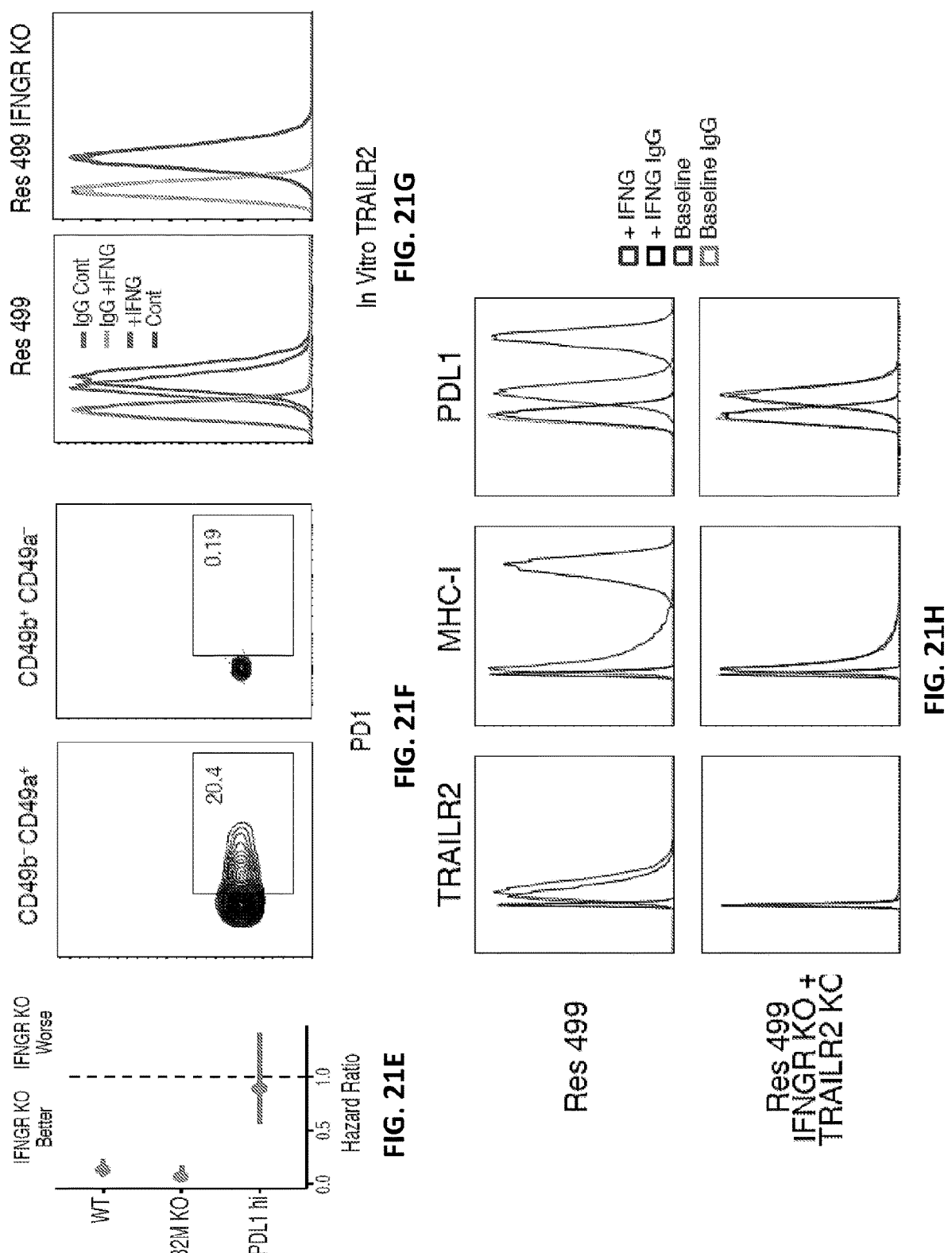

Although IFNG has a critical role in promoting NK/ILC1 function, it also induces high levels of PDL1 on tumors. Given that PD1 is expressed on ILC1 cells, this suggests that the PD1/PDL1 axis may normally function as an IFNG-directed feedback inhibition mechanism to antagonize innate immune function, similar to its role in regulating T cell responses. If so, removal of this feedback inhibition by IFNGR knockout may contribute to the improved response resulting from blocking tumor IFNG signaling. To examine this, PDL1 was ectopically expressed in PDL1 knockout Res 499 tumors to make PDL1 levels independent of IFNG signaling (FIG. 21D). In contrast to wild type or B2M-deficient Res 499 tumors, the ability of IFNGR deletion to improve anti-CTLA4 response was lost when PDL1 levels were fixed (FIG. 21E). To remove effects of PD1 from CD8 T cells, CD8 T cells were depleted but NK/ILC1 function was restored in IFNGR-deficient Res 499 tumors by intratumoral administration of IFNG (FIG. 6F). Consistent with tumor PDL1 inhibiting NK/ILC1 killing, fixing high PDL1 expression despite IFNGR knockout blunted NK/ILC1-dependent ICB response. Conversely, improved anti-CTLA4 response resulting from PDL1 deletion required NK/ILC1s (FIG. 6E). The notion that PD1/PDL1 can directly inhibit NK/ILC1 killing was also corroborated using CD49a$^+$ PD1$^+$ liver NK cells cultured with IFNGR-deficient Res 499 cells with and without ectopic PDL1 (FIGS. 6G and 21F). In total, these results suggested that tumor IFNG signaling normally drives feedback inhibition through tumor PDL1 to regulate NK/ILC1 function. Thus, ablating tumor IFNGR not only increases immune cell IFNG signaling but also enhances innate immune killing by interfering with the PD1/PDL1 inhibitory axis.

Figures 21I, 22A:
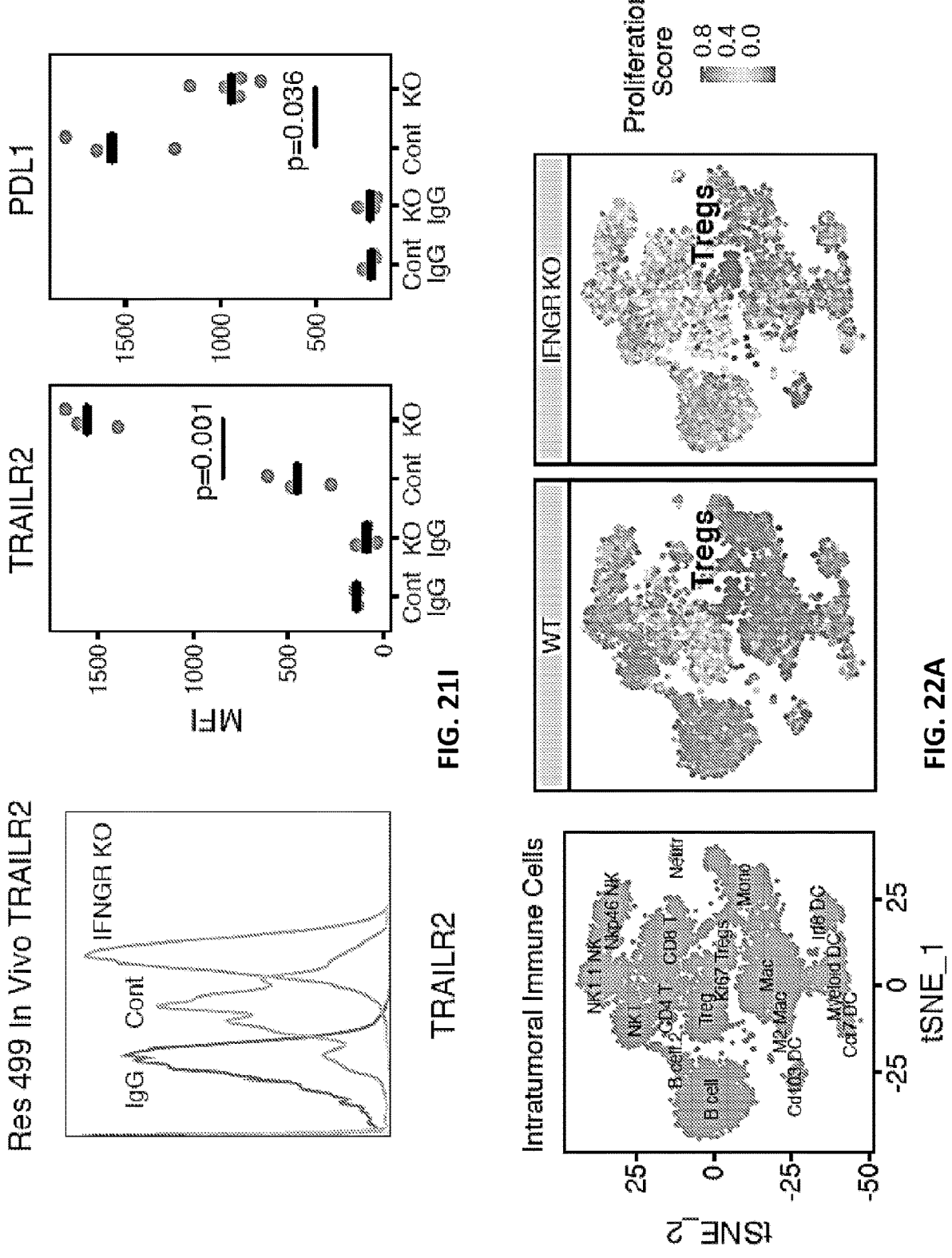

Besides PD1, intratumoral ILC1 cells also expresses TRAIL. Since response from tumor IFNGR knockout was independent of host perforin (FIG. 3C), this suggested that tumor killing may utilize the TRAIL/TRAILR pathway. Indeed, Res 499 tumors not only express PDL1 but also the TRAIL receptor (TRAILR2). Unlike PDL1, TRAILR2 decreased in direct response to IFNG in vitro (FIG. 21G). Accordingly, knockout of tumor IFNGR significantly increased TRAILR2 in vivo, while PDL1 decreased (FIG. 5F). Deletion of TRAILR2 in IFNGR-deficient Res 499 tumors (FIG. 21H) reveals that tumor killing after anti-CTLA4 is largely dependent on TRAIL/TRAILR2 interaction (FIG. 21I). These data suggested that IFNG controls an inhibitory feedback mechanism for NK/ILC1s not only by increasing tumor PDL1 but also by decreasing TRAILR2.

Thus, preventing tumor IFNG signaling enables TRAIL- and NK/ILC1-dependent killing.

Example 15: Adaptive Immune Cell Requirements for Innate Immune Killing after Blocking Tumor IFNG Signaling Despite the finding that response after IFNGR knockout of Res 499 tumors requires IFNG produced by CD8 T cells, the dispensability of tumor MHC-I argues that antigen presentation by tumor cells is not necessary for CD8 $T_{ex}$ to support NK/ILC1 function. To corroborate this, Res 499 tumors deficient in both IFNGR and B2M were implanted in either wild type mice or OT-1 mice expressing a transgenic T cell receptor to OVA antigen, which is not expressed by Res 499 tumors (FIG. 5F). The accumulation of both intratumoral CD8 T cells and NK/ILC1s was reduced and ICB response was lost in OT-1 mice compared to wild type mice (FIG. 5G). However, intratumoral injection of OVA peptide rescued the compromised CD8 T cell frequency and partially restored NK/ILC1 levels. Moreover, despite the absence of tumor MHC-I, response to anti-CTLA4 was also partially rescued (FIG. 5H). Thus, the ability of IFNGR knockout to enhance NK/ILC1-dependent ICB response need not depend on antigen presentation by tumor cells themselves. Rather, cross-primed and/or activated bystander T cells can suffice.

Figures 22B, 22C, 22D:
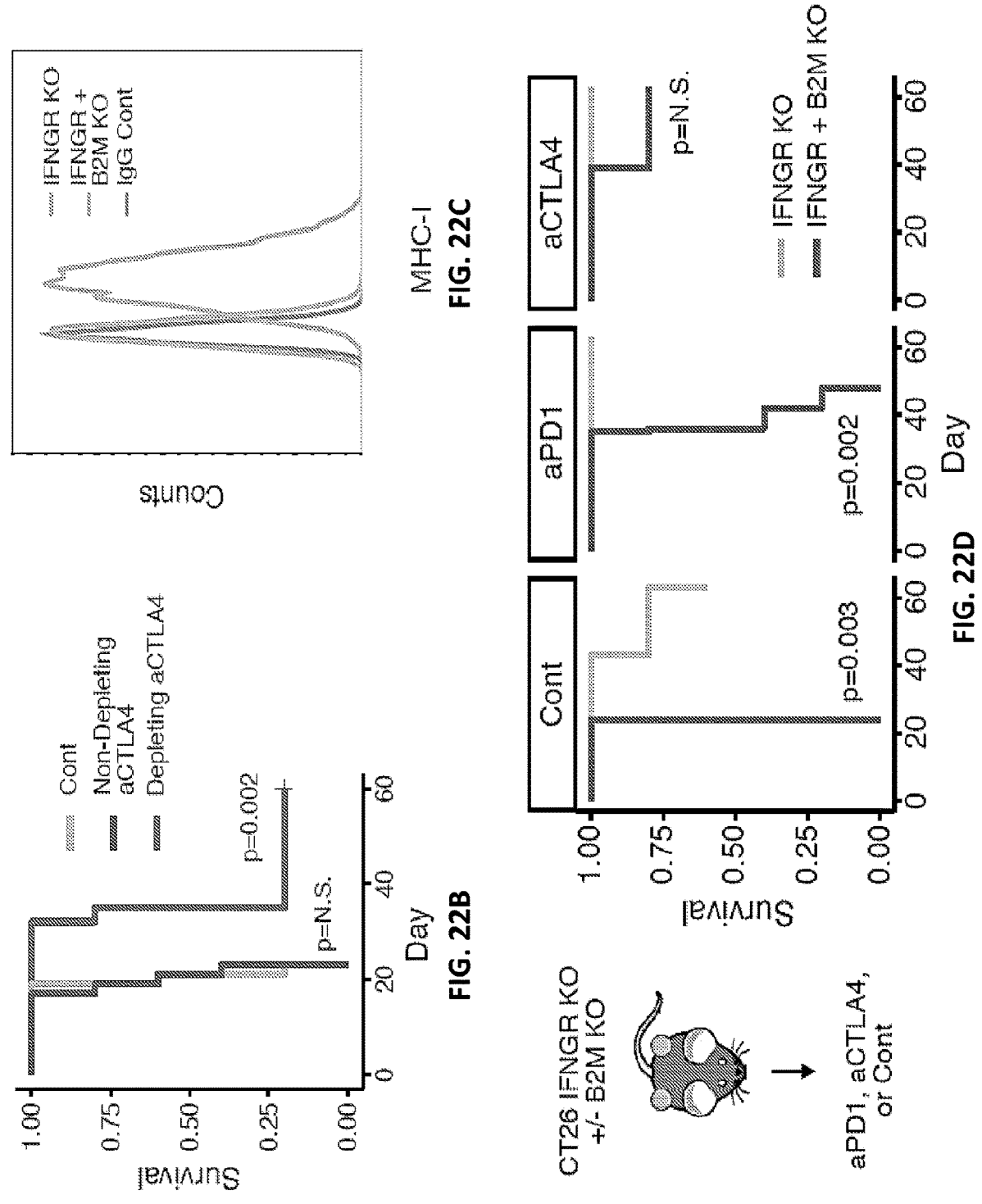

Although disrupting tumor IFNG signaling interferes with the inhibitory effects of PD1/PDL1 between tumor cells and both adaptive and innate immune cells, anti-CTLA4 appears to provide a non-redundant function to PD1/PDL1 inhibition. In mouse models, and possibly in humans, antagonistic CTLA4 antibodies not only block CTLA4 but can also deplete CD4+ T regulatory cells ($T_{reg}$s). Indeed, $T_{reg}$s are among the most proliferative immune cells in Res 499 tumors and this does not appear altered by tumor IFNGR knockout (FIG. 22A). To investigate the importance of inhibiting $T_{reg}$s, the 4F10 antibody against CTLA4, which does not concurrently deplete $T_{reg}$s, was used. In contrast to the Treg-depleting 9H10 antibody, 4F10 failed to elicit a response against Res 499 IFNGR knockout tumors (FIG. 22B). Conversely, depleting $T_{reg}$s by stimulation of the diptheria toxin receptor under control of Foxp3 recapitulated the effects of 9H10 on IFNGR-deficient Res 499 tumors (FIG. 6H). The non-redundant effect of a $T_{reg}$-depleting antibody with tumor IFNGR knockout was also highlighted in the CT26 tumor model. Here, although IFNGR knockout resulted in complete responses to anti-PD1, all mice relapse when B2M was ablated (FIGS. 22B and 22C). However, the 9H10 anti-CTLA4 antibody resulted in complete response despite B2M loss, consistent with the anti-CTLA4 but not anti-PD1 antibody allowing for more optimal NK/ILC1-mediated killing. Corroborating the potential role of $T_{reg}$s in suppressing innate immune cell activity, abundance of activated NK cells inversely associates with $T_{reg}$ abundance in melanoma patients (FIG. 6I). Thus, interfering with the suppressive effects of $T_{reg}$s may be required to fully unleash both adaptive and innate immune killing resulting from blocking tumor IFNG signaling. These findings imply that dual therapy with anti-PD1 plus anti-CTLA4 antibodies that inhibit $T_{reg}$s may promote innate immune function better than monotherapy approaches.

Example 16: Tumor Mutations in IFN Pathway Genes Predict Clinical Response to Dual Blockade of PD1 and CTLA4

Figure 7I:
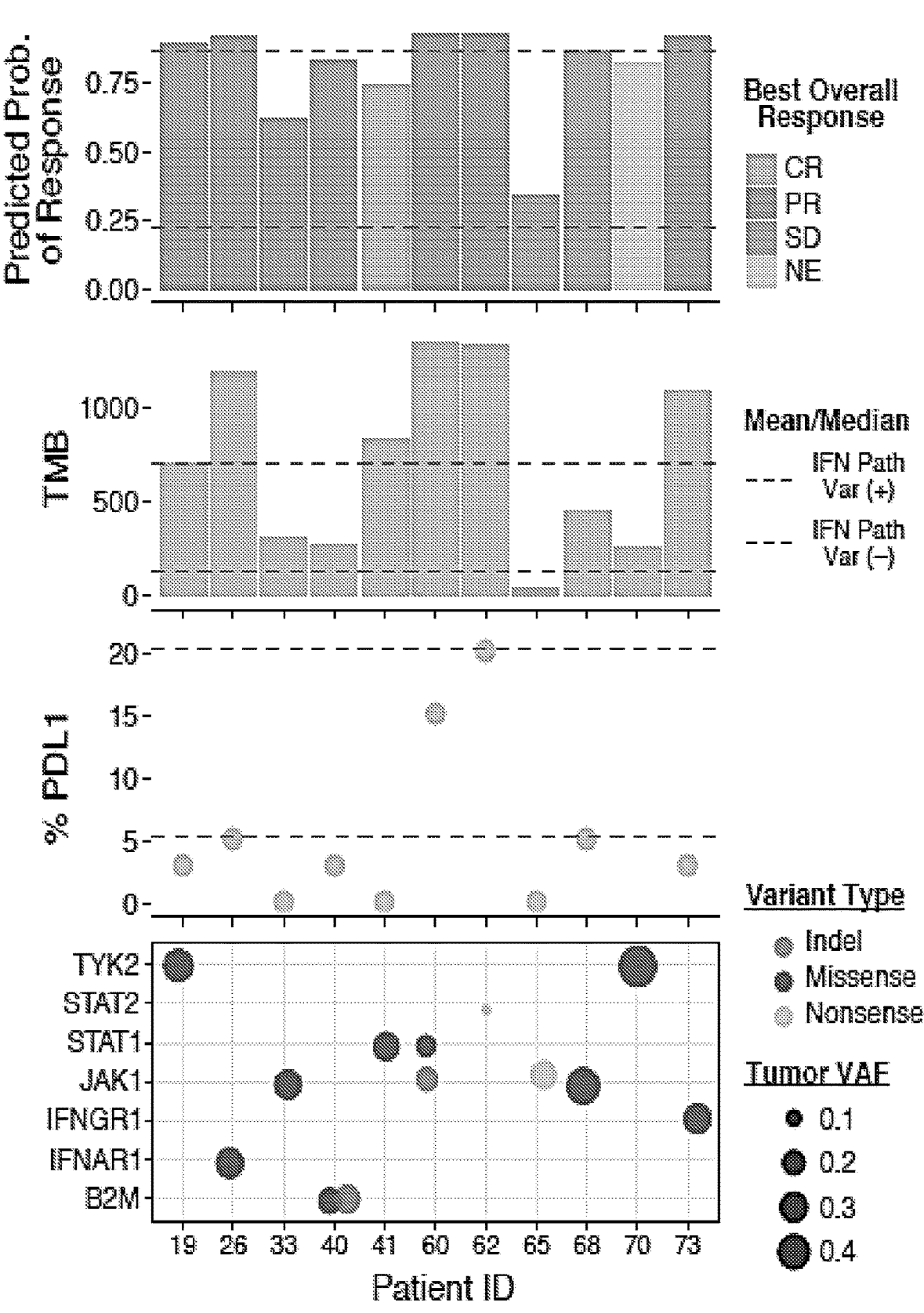

Findings presented herein suggest that mutations predicted to reduce tumor IFN signaling might associate with decreased ISG.RS and improved clinical response to ICB. To investigate this, the analysis of recently described exome-sequencing data of non-small cell lung cancer (NSCLC) patients from either TCGA or a clinical trial using anti-PD1 plus anti-CTLA4 (Hellmann et al., 2018, *Cancer Cell* 33, 843-852.e844) was extended. After excluding common non-disease single-nucleotide variants, pathogenic missense and nonsense mutations were predicted using two algorithms, CADD and DANN, that were trained on a catalog of benign and pathogenic variants from the ClinVar database (FIG. 14F). Indels were also evaluated as damaging or neutral using SIFT. In the TCGA, there is an 8.6% incidence of patient tumors with at least one predicted pathogenic variant in a core set of 11 type I and II IFN pathway genes (FIG. 14A). These tumors exhibit a decrease in ISG.RS genes, consistent with an enrichment for IFN pathway variants with defective signaling (FIGS. 7G and 14G). In the patients treated with anti-PD1 plus anti-CTLA4, 14.7% of patients have at least one IFN pathway variant and these patients have improved progression-free survival (PFS) with dual ICB (FIG. 7A-7B). In contrast, only 0.58% of random gene sets of similar size yield PFS differences that are as significant (FIG. 14B), and IFN pathway variants do not associate with survival in TCGA patients (FIG. 14H), arguing that variant status is not a general prognostic marker. Although the presence of IFN pathway variants is associated with higher TMB (FIG. 14C), multivariable logistic regression and random forest reveal that variant status predicts ICB response independently of TMB and PDL1 expression (FIGS. 7H and 14I). Both models yield predicted probabilities of response (CR or PR) that correlate well to actual observed responses (FIG. 7I, top panel; FIG. 14I, right plot). Notably, despite a higher likelihood of response, variant-positive tumors exhibit lower percent tumor PDL1 expression (5.4% versus 20.3%; FIG. 7E), consistent with variants having a negative impact on tumor IFN signaling. In contrast, stratification by variant status of random genes rarely yields a difference in % PDL1 this large (frequency 5.7× $10^{-3}$) (FIG. 14E). Notably, one patient had a tumor with multiple alleles of B2M with a frameshift indel or predicted pathogenic missense mutations who nonetheless had a PR to ICB (FIG. 7I, patient 40). This is consistent with previous reports describing a NSCLC patient responding to anti-PD1 despite deleterious B2M mutations and loss of B2M expression confirmed by immunohistochemistry. Thus, genetic alterations of the IFN pathway in human NSCLC are associated with decreased ISG.RS, decreased tumor PDL1, and improved ICB response independent of TMB status.

Figures 25A, 25B, 25C:
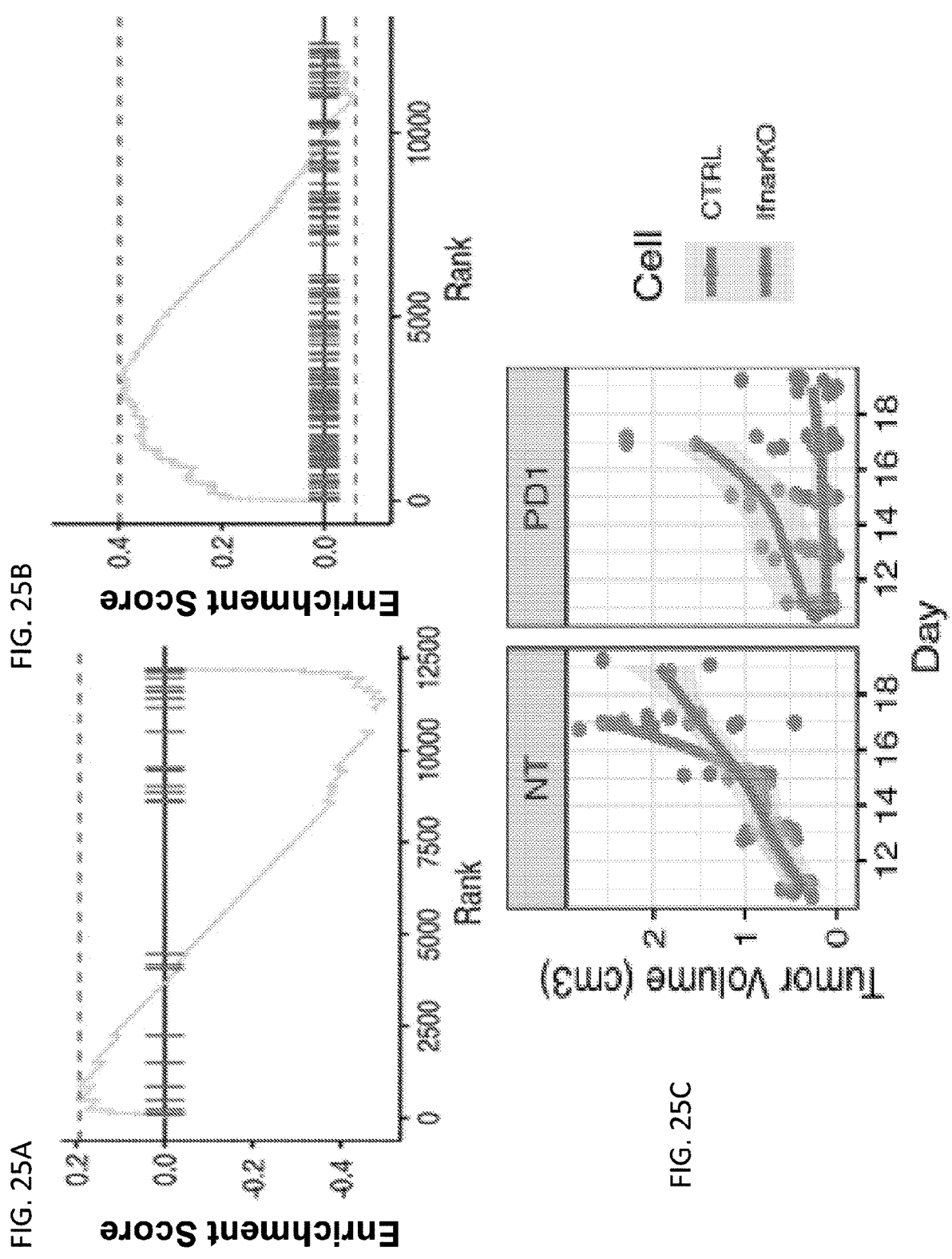
FIGS. 25A-25P illustrate disruption of interferon-$\alpha/\beta$ receptor (Ifnar) signaling alters the ISG.RS to IFNG.GS ratio in the tumor microenvironment and sensitizes ICB resistant cell lines to mono-therapy.
FIG. 25B shows gene set analysis of sorted Ifnar knockout vs Res499 control against IFN.GS genes.
FIGS. 25C-25D illustrate tumor growth of Res499 control and Ifnar knockout cell lines (FIG. 25C) and survival of mice (FIG. 25D) (n=5-10) treated with or without aPD1.
Figures 25D, 25E:
FIG. 25E shows a UMAP projection of CD45+ single cells grouped by clusters.
Figures 25F, 25G:
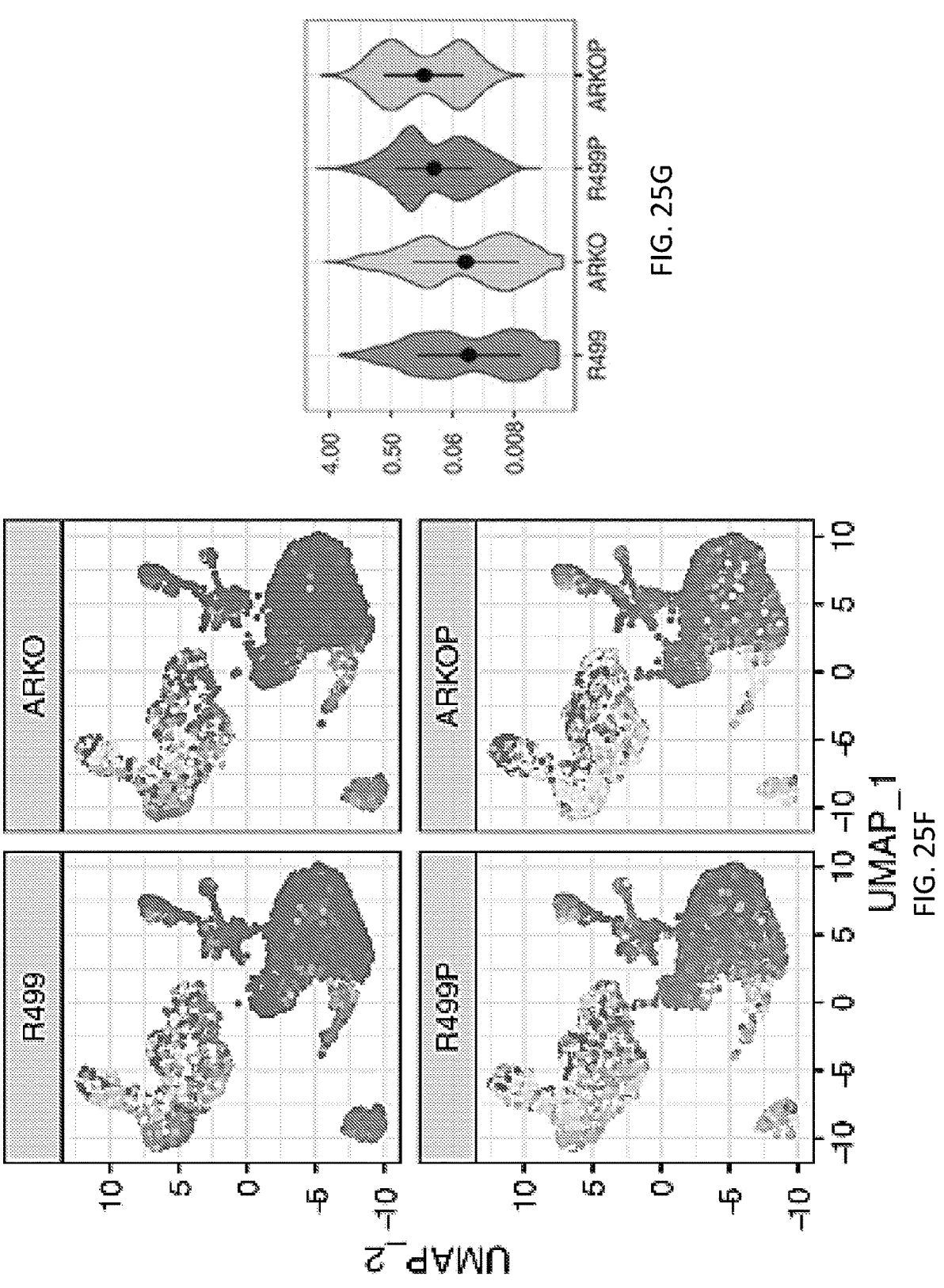
FIG. 25F illustrates Ifnγ expression in sorted CD45+ single cells from Res499 control and Ifnar knockout tumors treated with or without aPD1.
FIG. 25G shows averaged Ifnγ expression from FIG. 25F.
Figures 25H, 25I:
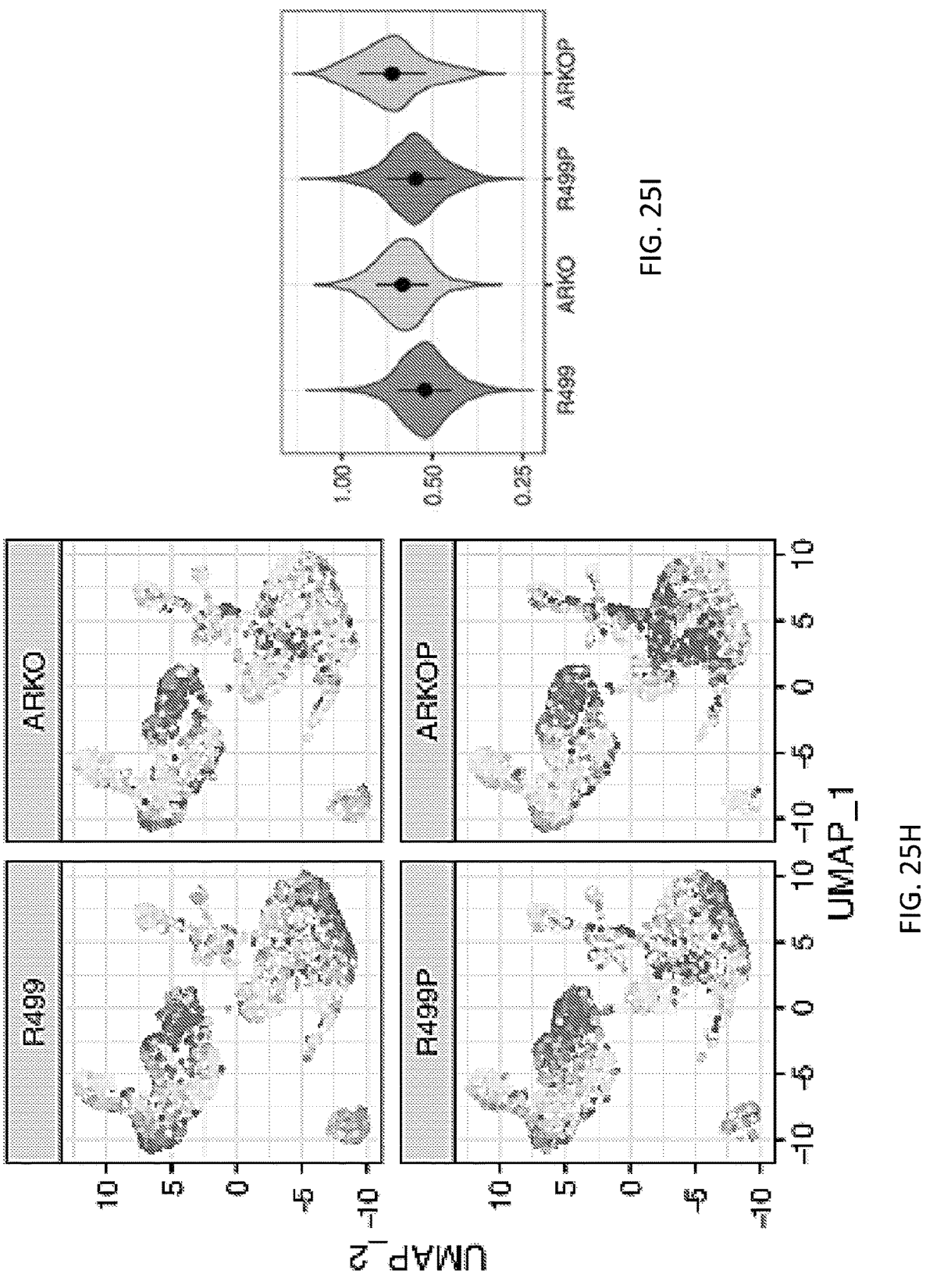
FIG. 25H shows expression of averaged Ifnγ stimulated genes from Hallmark IFN gamma response in sorted CD45+ single cells from Res499 control and Ifnar knockout tumors treated with or without aPD1.
FIG. 25I shows averaged expression of Ifnγ stimulated genes from FIG. 25H.
Figures 25J, 25K:
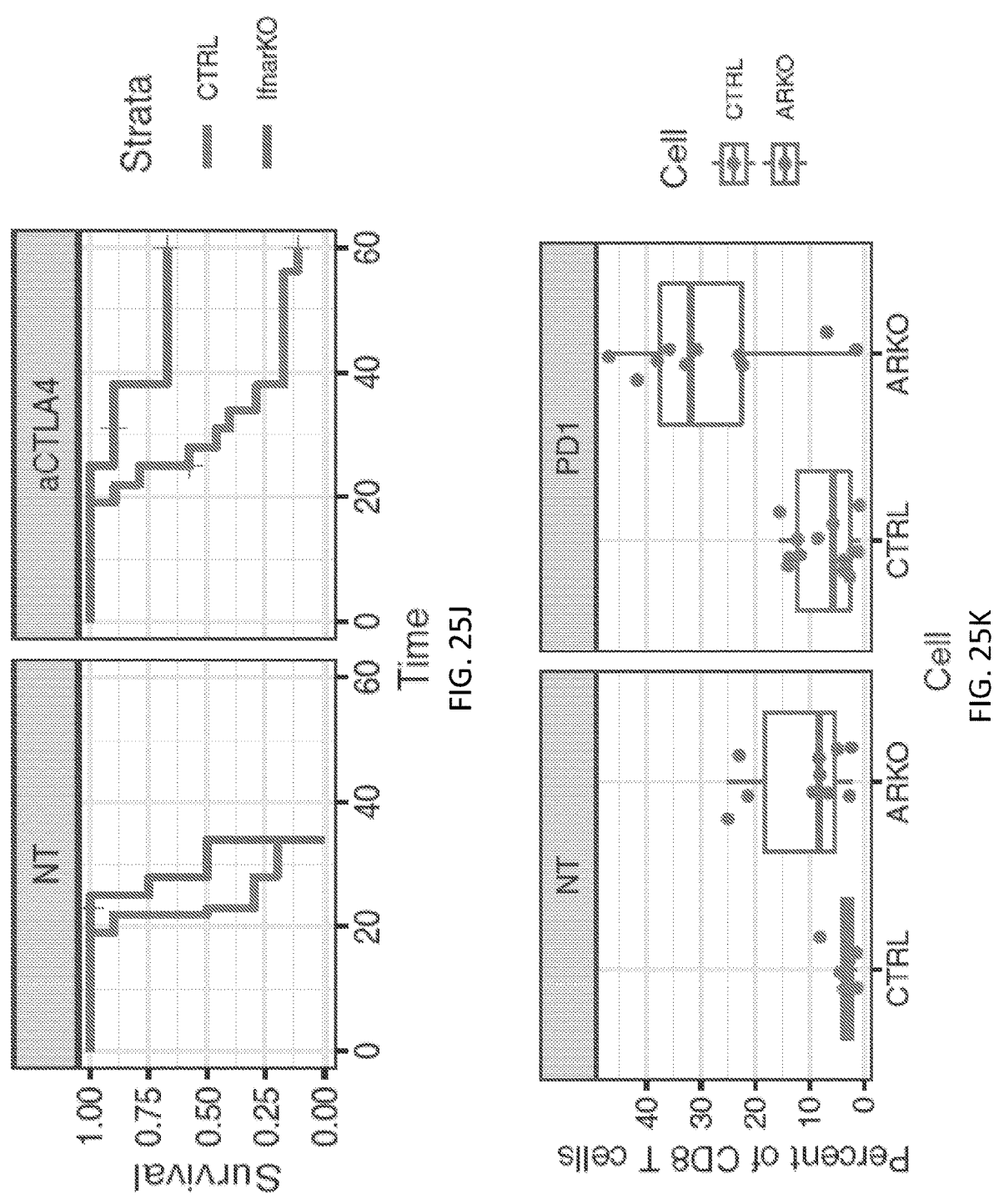
FIG. 25J illustrates survival of mice (n=5-20) injected with Res237 control and Ifnar knockout cell lines treated with or without aCTLA-4.
FIG. 25K shows the percentage of IFNγ+CD8 T cells in Res499 control and Ifnar knockout tumors treated with or without aPD1.
Figures 25L, 25M:
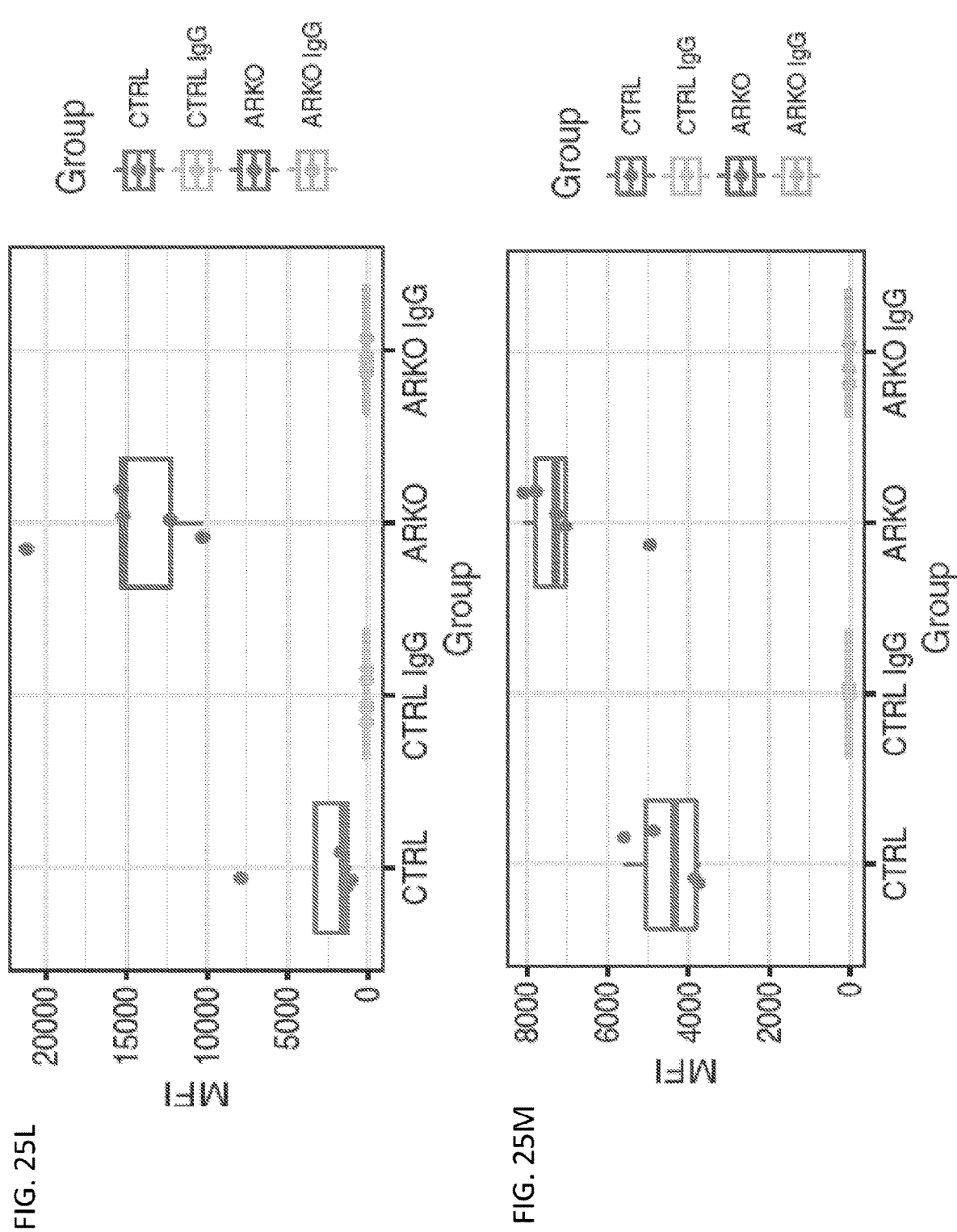
FIGS. 25L-25M show mean fluorescence intensity of surface MHC class I or IgG isotype in Res499 control and Ifnar knockout tumors (FIG. 25L) and Res237 control and Ifnar knockout tumors (FIG. 25M).
Figures 25N, 25O:
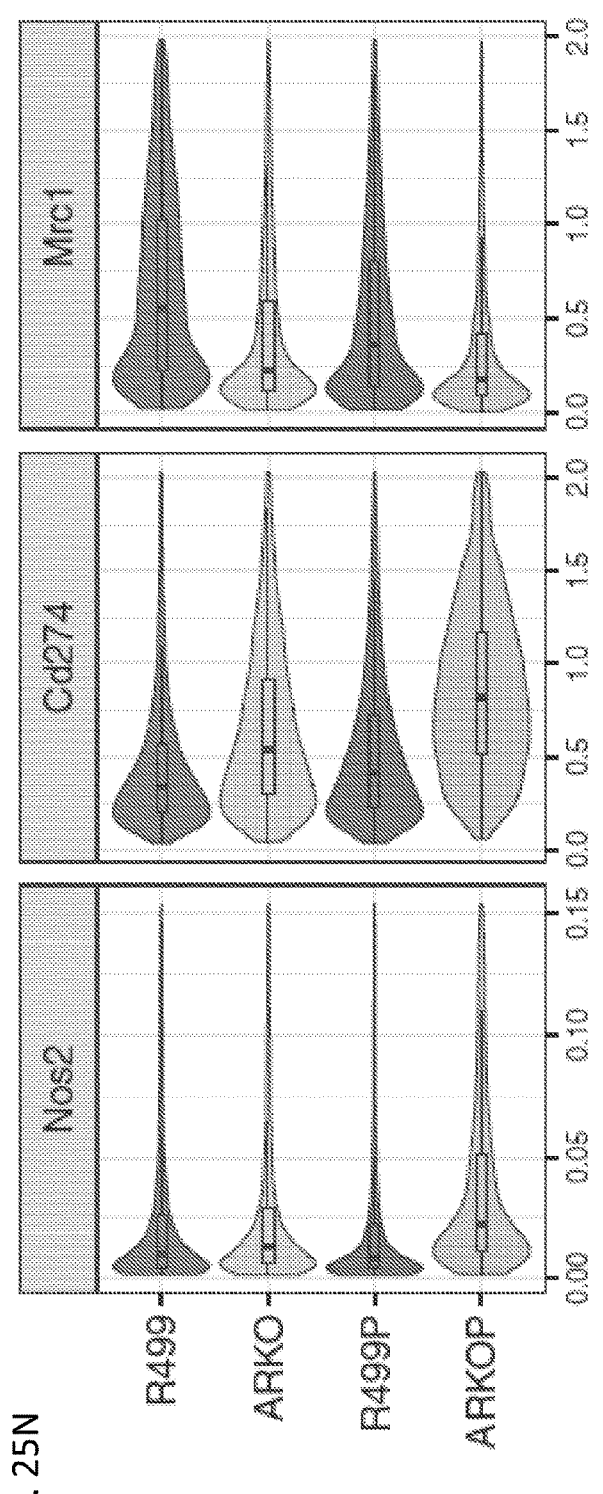
FIG. 25N illustrates expression of Nos2 (iNos), Cd274 (Pd-l1) and Mrc1 (Cd206) in macrophages subsetted on CD45+ single cells by condition.
FIG. 25O is a heatmap displaying normalized expression of select markers in macrophage subsets.
Figure 25P:
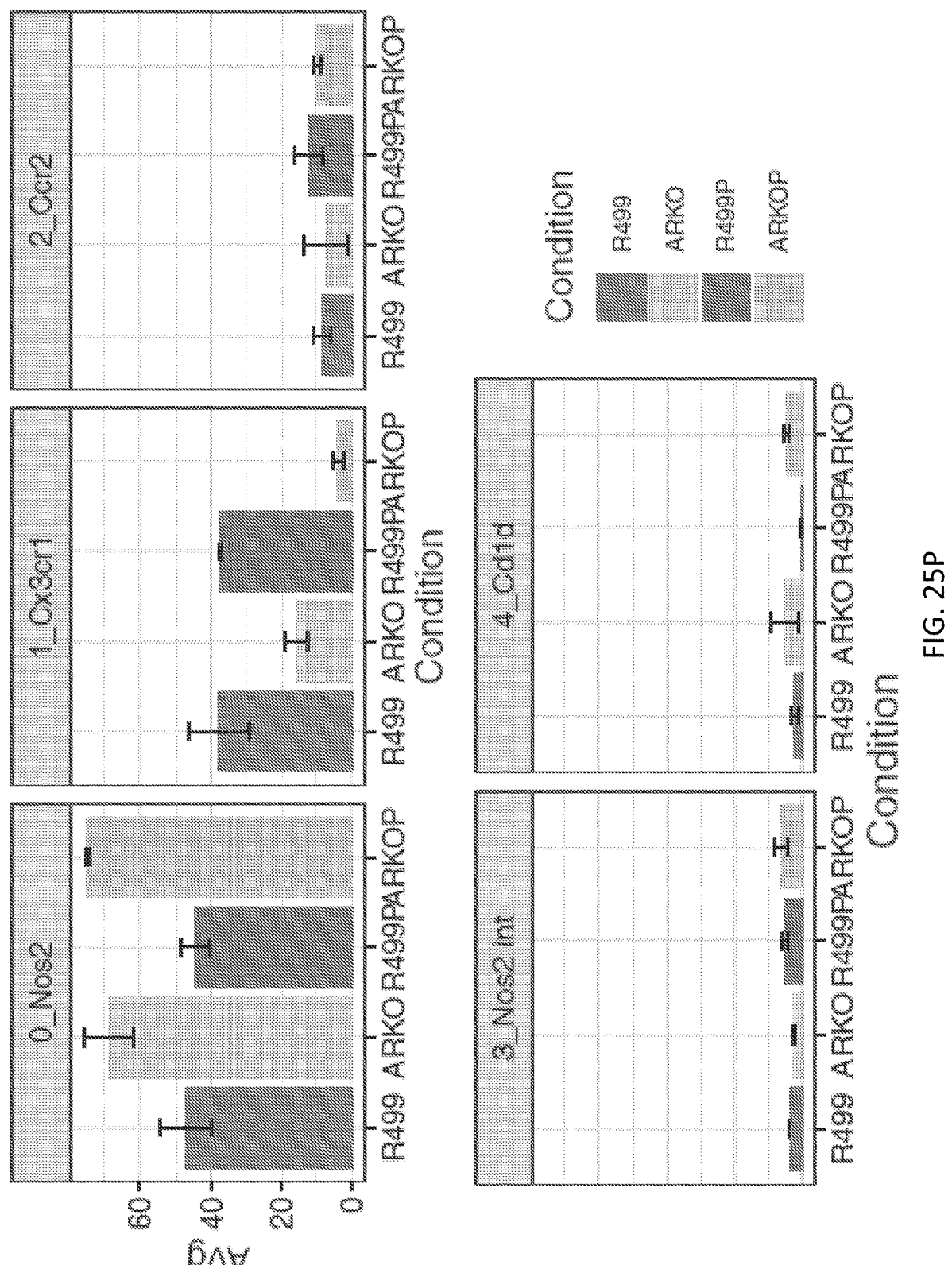

Example 17: Disruption of Ifnar Signaling Alters the ISG.RS to IFNG.GS Ratio in the Tumor Microenvironment and Sensitizes ICB Resistant Cell Lines to Mono-Therapy FIG. 25A shows GSEA of sorted Res499 Ifnar knockout vs Res499 Ifngr knockout tumor cells using ISG.RS genes. FIG. 25B shows gene set analysis of sorted Ifnar knockout vs Res499 control against IFN.GS genes. FIGS. 25C-25D illustrate tumor growth of Res499 control and Ifnar knockout cell lines (FIG. 25C) and survival of mice (FIG. 25D) (n=5-10) treated with or without aPD1. FIG. 25E shows a UMAP projection of CD45+ single cells grouped by clusters. FIG. 25F illustrates Ifnγ expression in sorted CD45+ single cells from Res499 control and Ifnar knockout tumors treated with or without aPD1. FIG. 25G shows averaged Ifnγ expression from FIG. 25F. FIG. 25H shows expression of averaged Ifnγ stimulated genes from Hallmark IFN gamma response in sorted CD45+ single cells from Res499 control and Ifnar knockout tumors treated with or without aPD1. FIG. 25I shows averaged expression of Ifnγ stimulated genes from FIG. 25H. FIG. 25J illustrates survival of mice (n=5-20) injected with Res237 control and Ifnar knockout cell lines treated with or without aCTLA-4. FIG. 25K shows the percentage of IFNγ+ CD8 T cells in Res499 control and Ifnar knockout tumors treated with or without aPD1. FIGS. 25L-25M show mean fluorescence intensity of surface MHC class I or IgG isotype in Res499 control and Ifnar knockout tumors (FIG. 25L) and Res237 control and Ifnar knockout tumors (FIG. 25M). FIG. 25N illustrates expression of Nos2 (iNos), Cd274 (Pd-l1) and Mrc1 (Cd206) in macrophages subsetted on CD45+ single cells by condition. FIG. 25O is a heatmap displaying normalized expression of select markers in macrophage subsets. FIG. 25P shows averaged percentage of cells in macrophage subsets by condition.

Figures 26A, 26B:
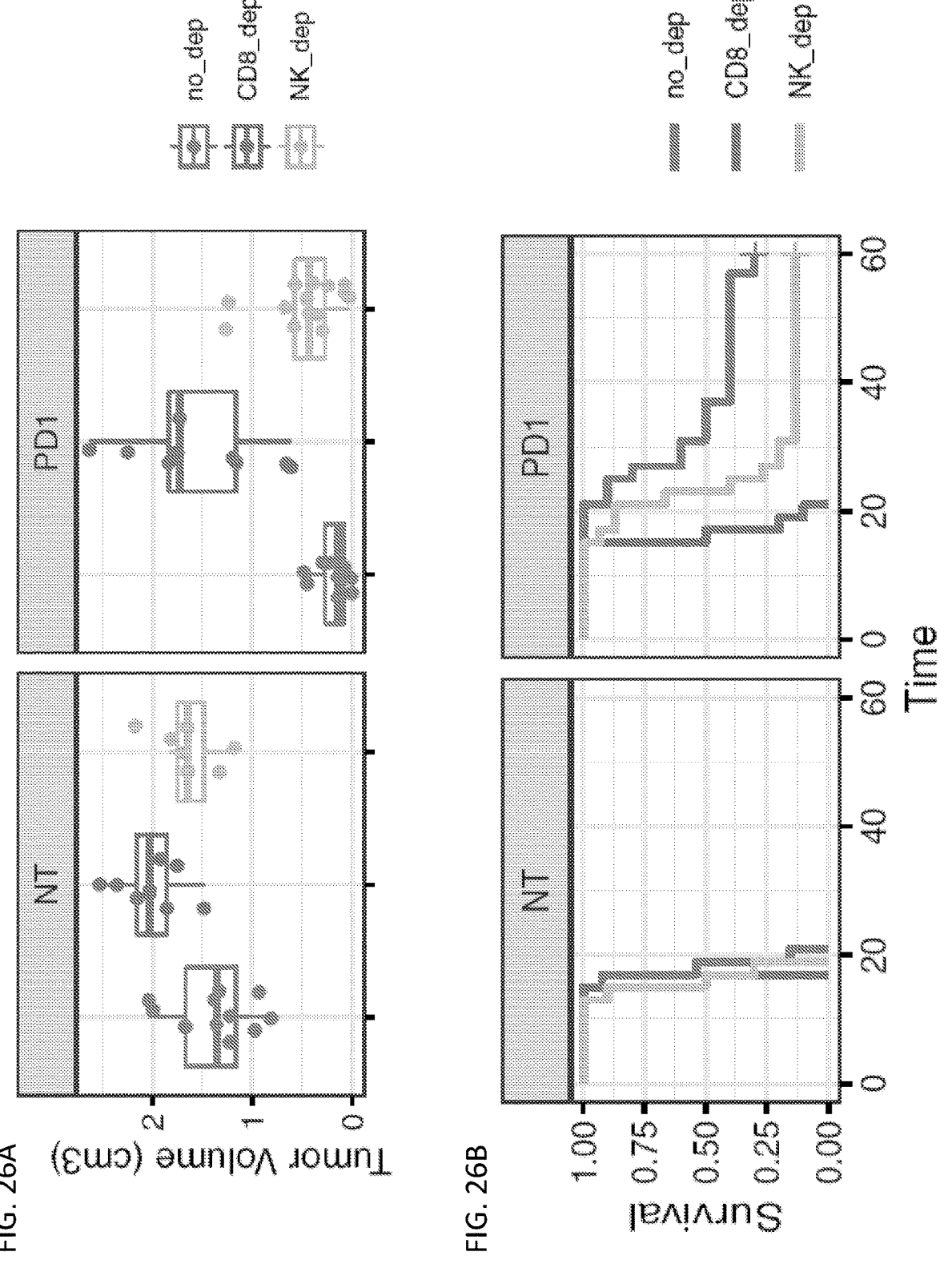
Figure 26F:
FIG. 26F is a series density plots of UMAP projection of CD8 T cell clusters by condition.
Figures 26G, 26H:
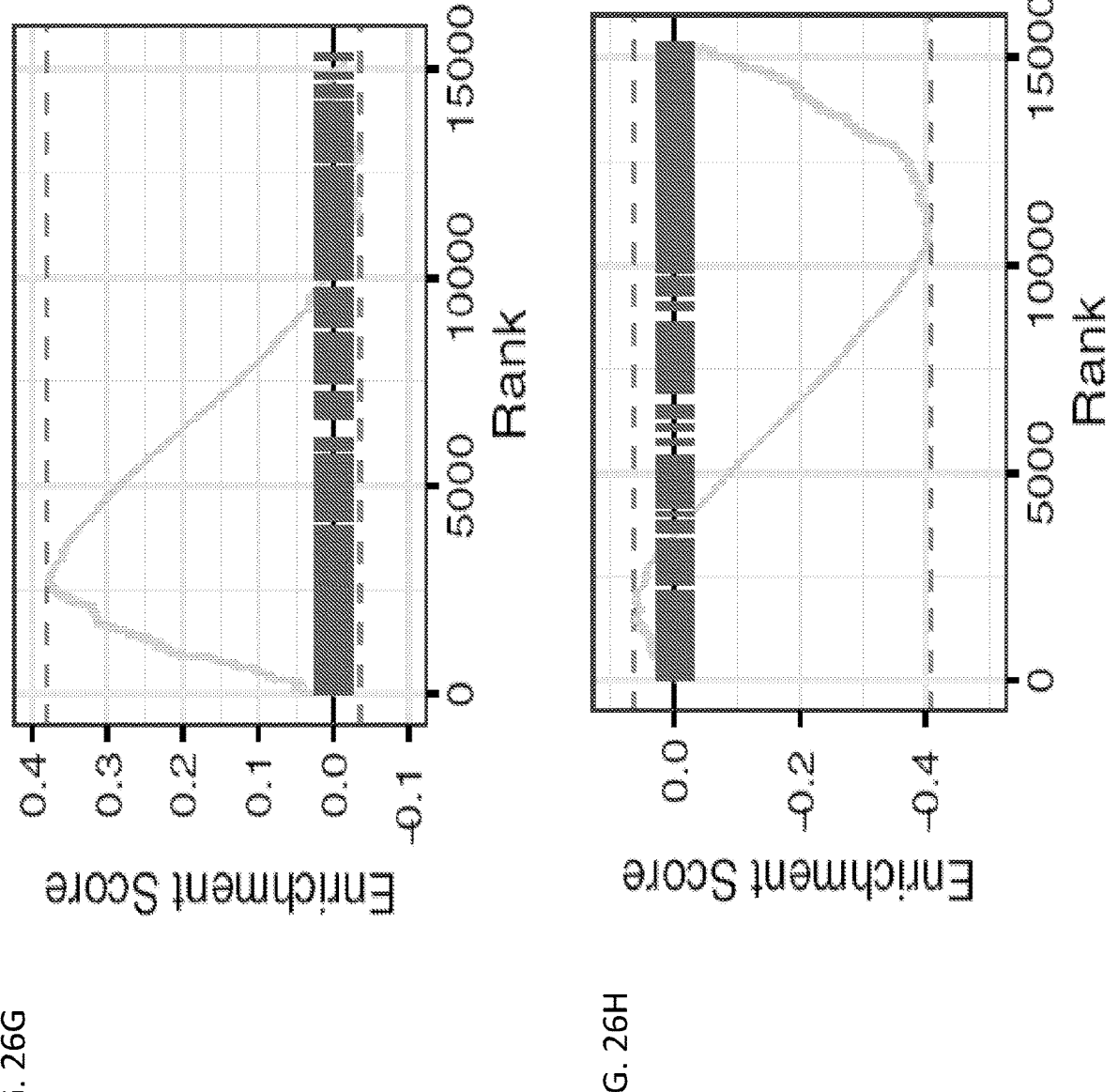
FIGS. 26G-26H illustrate GSEA of CD8 T cells from Res499 control or Ifnar knockout tumors treated with aPD1 using terminal (FIG. 26G) and progenitor (FIG. 26H) exhausted gene sets.
Figures 26I, 26J, 26K:
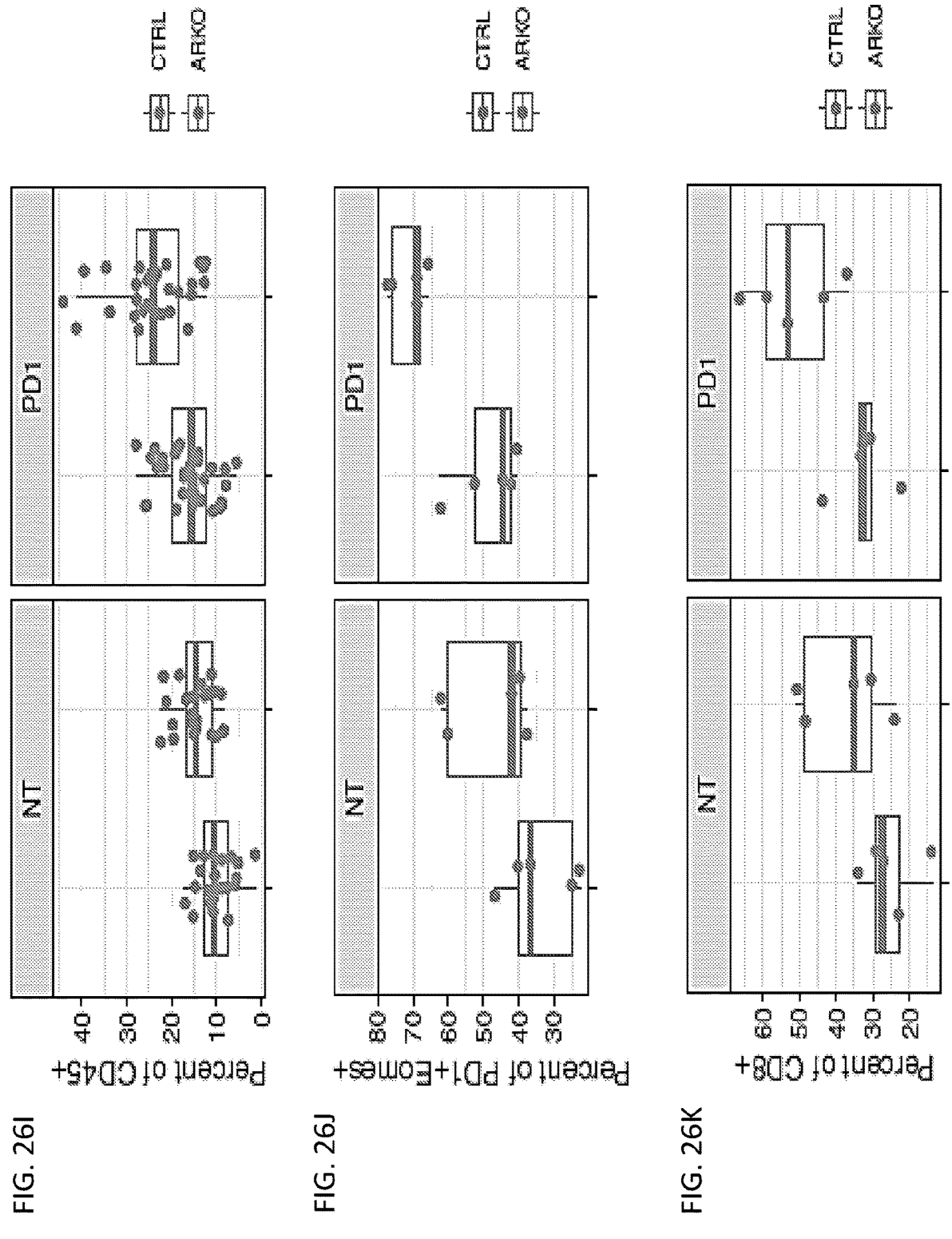
FIG. 26I shows percentage of CD8 T cells out of total CD45+ cells in Res499 control or Ifnar knockout tumors with or without aPD1 treatment.
FIG. 26J shows percentage of Ki67+/Gzmb+ in PD1+/Eomes+CD8 T cells by condition.
FIG. 26K shows percentage of perforin+ CD8 T cells by condition.

Example 18: Sensitization of Ifnar Knockout to aPD1 is Dependent on CD8 T Cells and DCs FIGS. 26A-26B illustrate day 15 tumor volumes of Res499 Ifnar knockout cell lines treated with or without aPD1, depleted with or without aCD8 or aNK1.1 antibody (FIG. 26A) and survival of mice (FIG. 26B) (n=7-15). FIG. 26C illustrates day 15 tumor volumes of Res499 Ifnar knockout cell line injected in WT or Perforin knockout mice treated with aPD1 (n=4 for Prf−/− and 9 for WT). FIG. 26D illustrates survival of mice injected with Res499 Ifnar knockout cell line injected in WT or Perforin knockout mice treated with or without aPD1 (n=2-4). FIG. 26E illustrates survival of mice injected with Res499 Ifnar/B2m double knockout cell line treated with or without aPD1 (n=5). FIG. 26F is a series density plots of UMAP projection of CD8 T cell clusters by condition. FIGS. 26G-26H illustrate GSEA of CD8 T cells from Res499 control or Ifnar knockout tumors treated with aPD1 using terminal (FIG. 26G) and progenitor (FIG. 26H) exhausted gene sets. FIG. 26I shows percentage of CD8 T cells out of total CD45+ cells in Res499 control or Ifnar knockout tumors with or without aPD1 treatment. FIG. 26J shows percentage of Ki67+/Gzmb+ in PD1+/Eomes+CD8 T cells by condition. FIG.

Figures 26L, 26M, 26N:
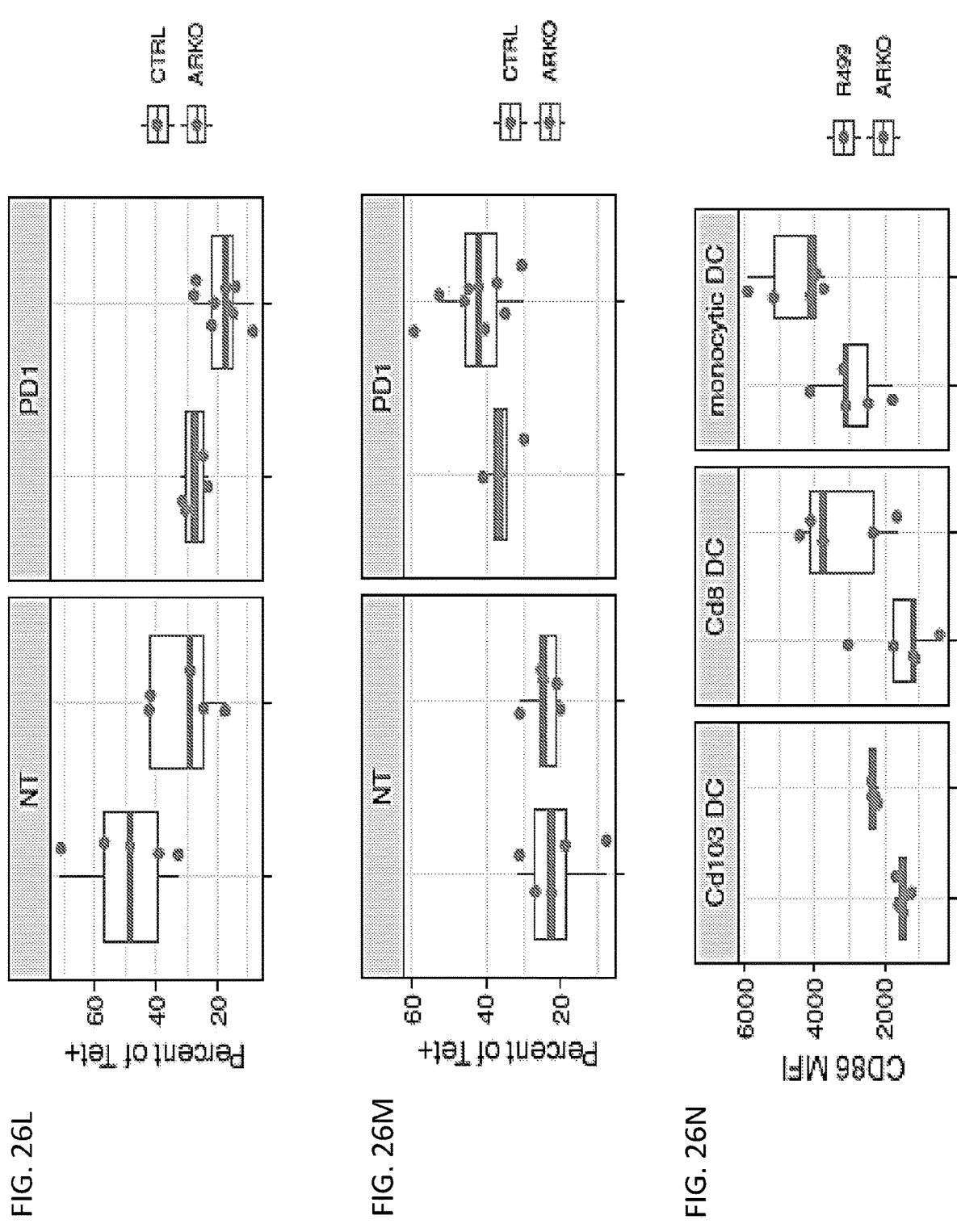
FIGS. 26L-26M show percentage of Slamf6+ Tim3− (FIG. 26L) and Slamf6-Tim3+(FIG. 26M) cells in tetramer positive CD8 T cells.
FIG. 26N shows mean fluorescence intensity of CD86 in subsets of dendritic cells in Res499 control or Ifnar knockout tumors.
Figure 26O:
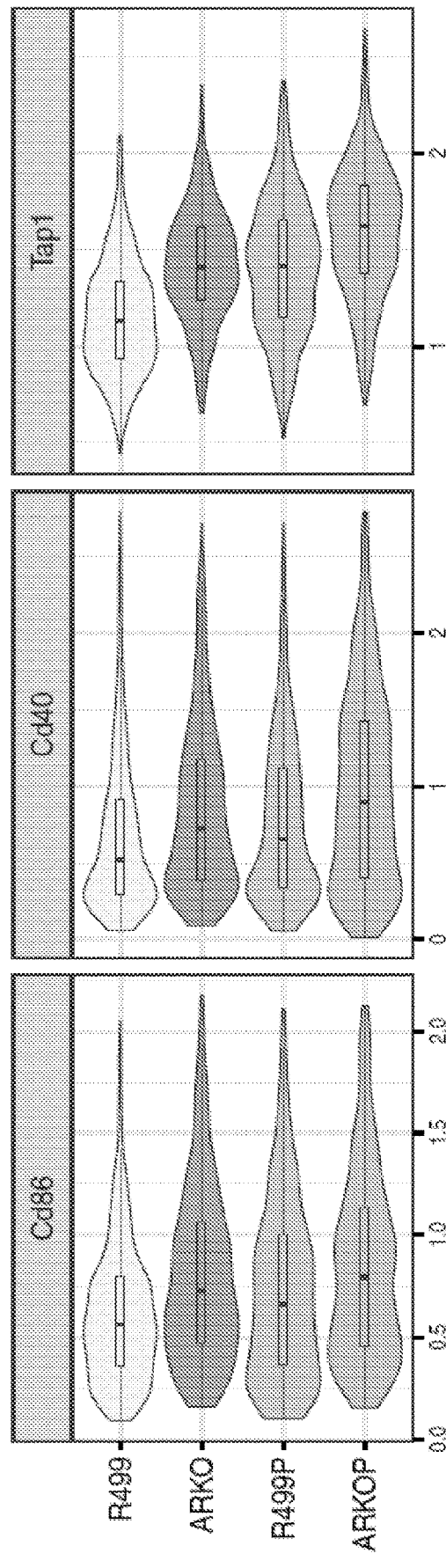

26K shows percentage of perforin+CD8 T cells by condition. FIGS. 26L-26M show percentage of Slamf6+ Tim3− (FIG. 26L) and Slamf6− Tim3+(FIG. 26M) cells in tetramer positive CD8 T cells. FIG. 26N shows mean fluorescence intensity of CD86 in subsets of dendritic cells in Res499 control or Ifnar knockout tumors. FIG. 26O illustrates expression of Cd86, Cd40 and Tap1 in dendritic cells subsetted on CD45+ single cells by condition.

Figure 27A:
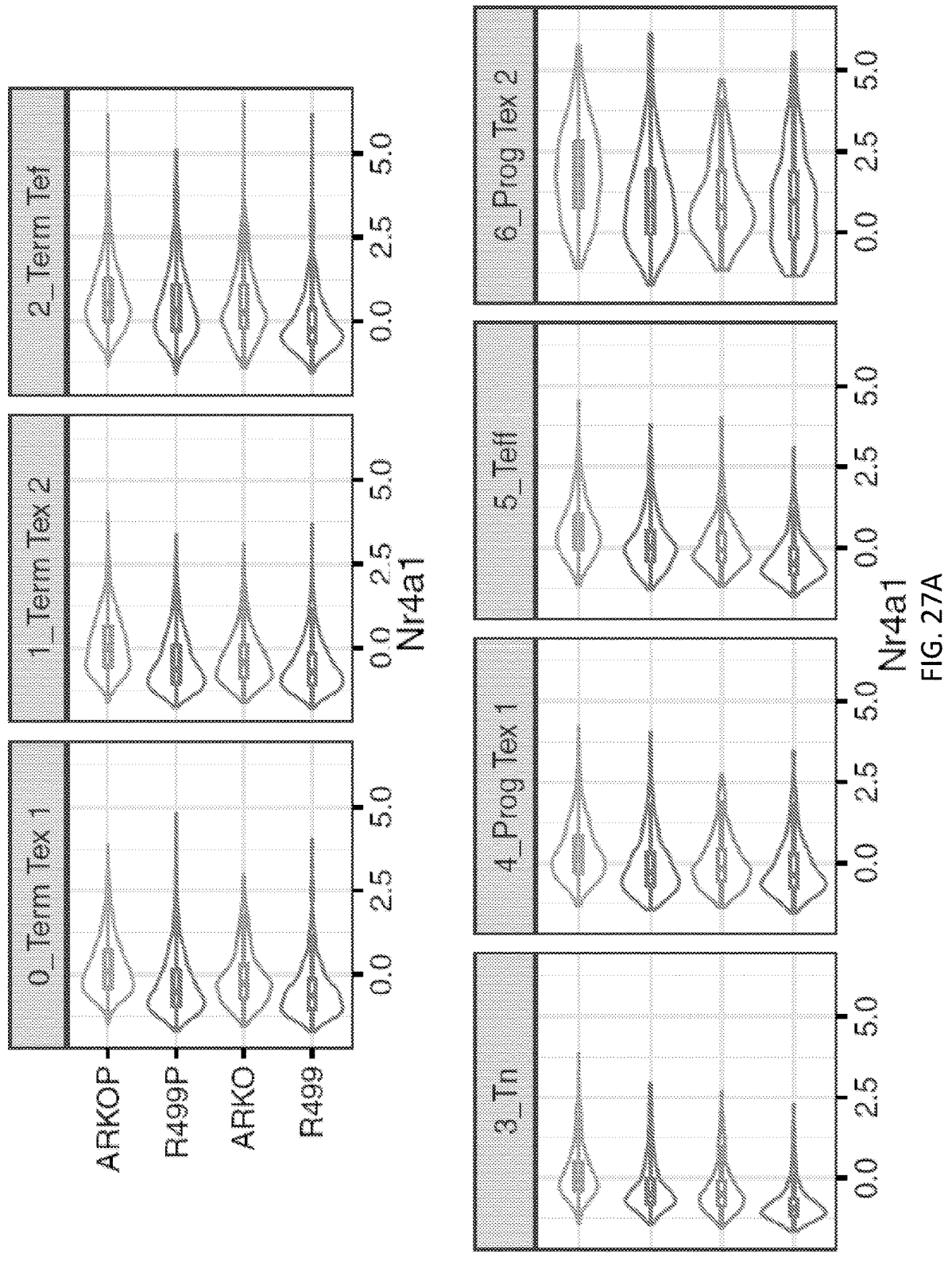
Figures 27B, 27C:
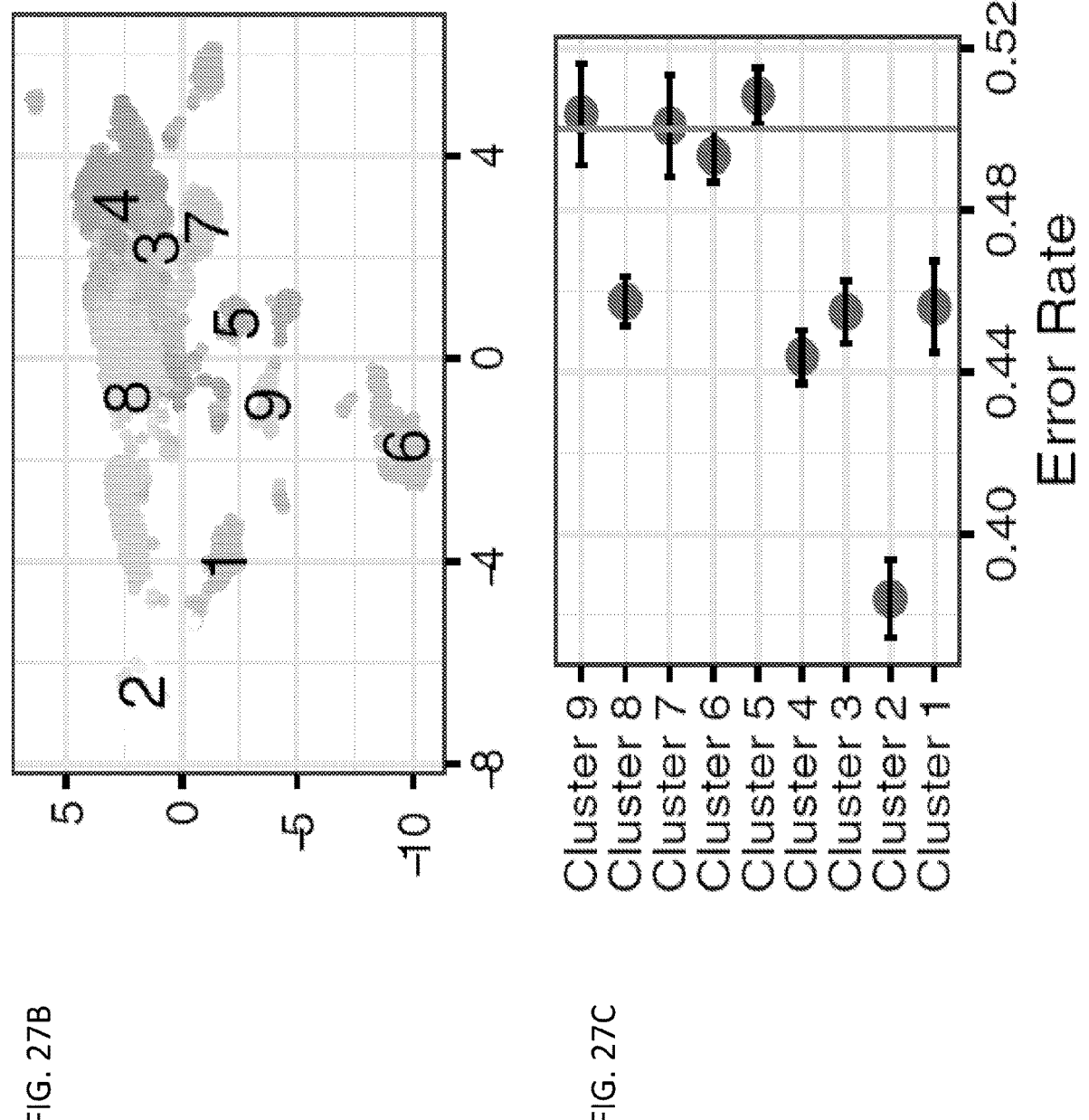
Figure 27D:
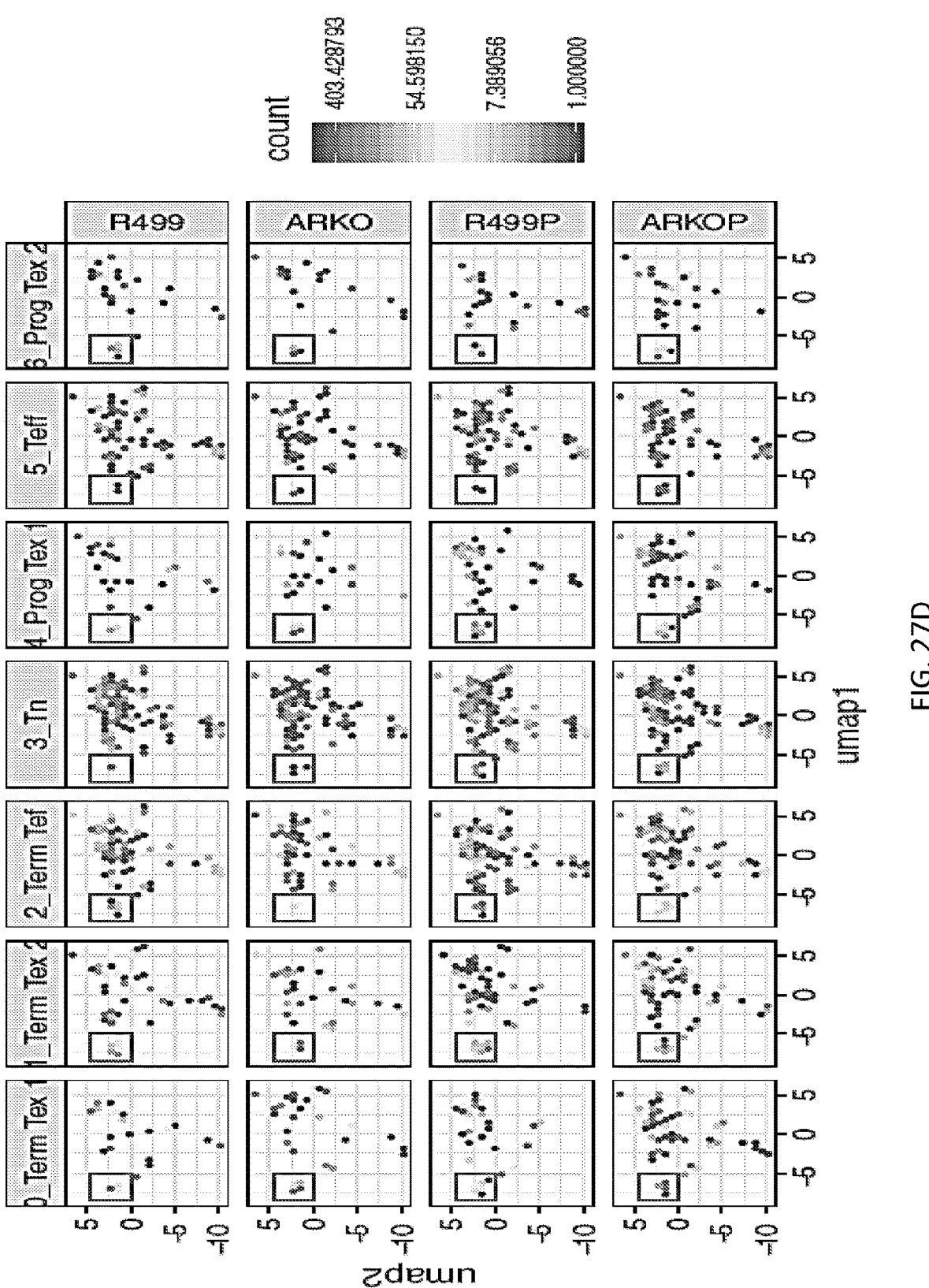
Figure 27E:
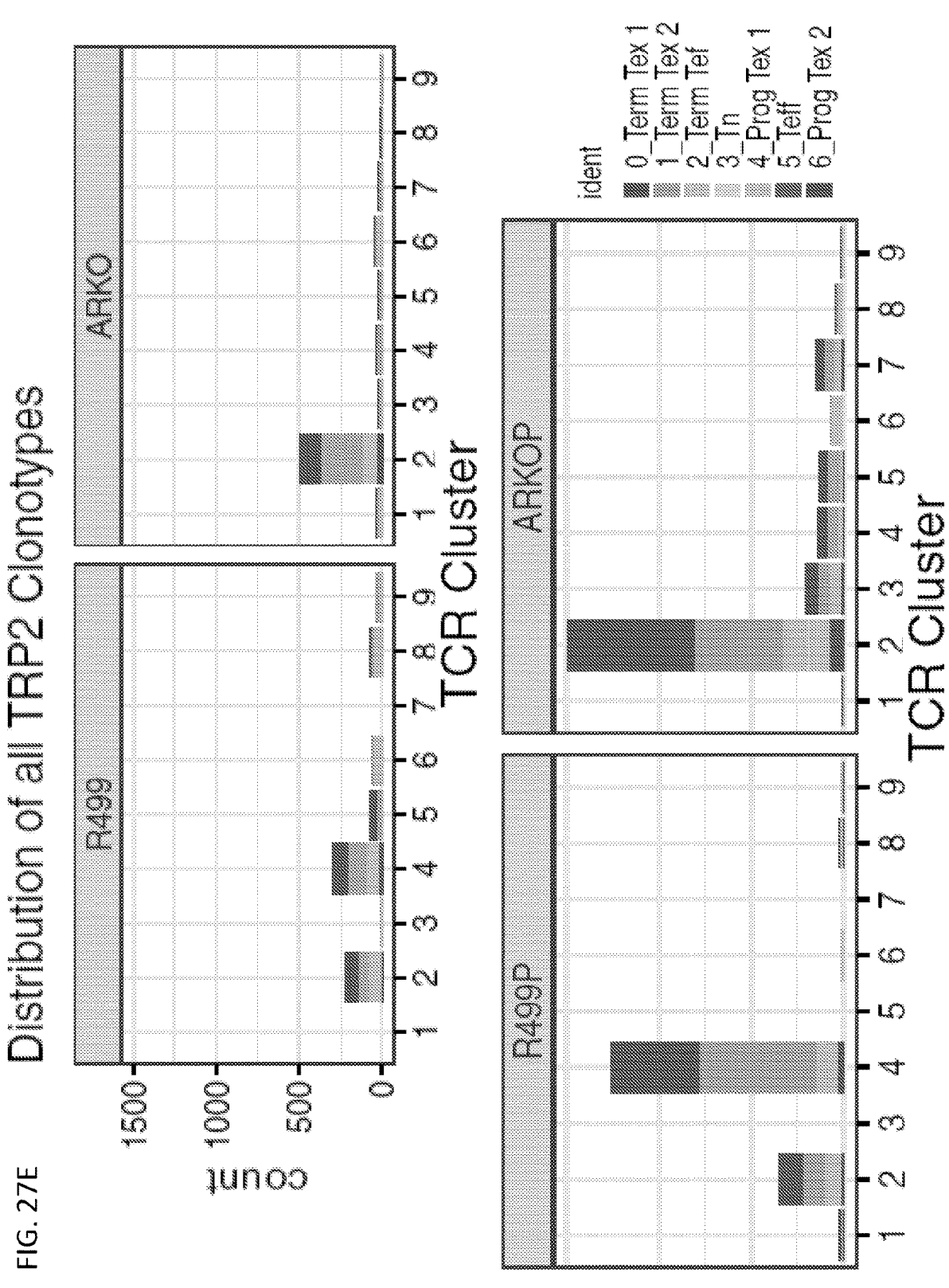
Figures 27F, 27G:
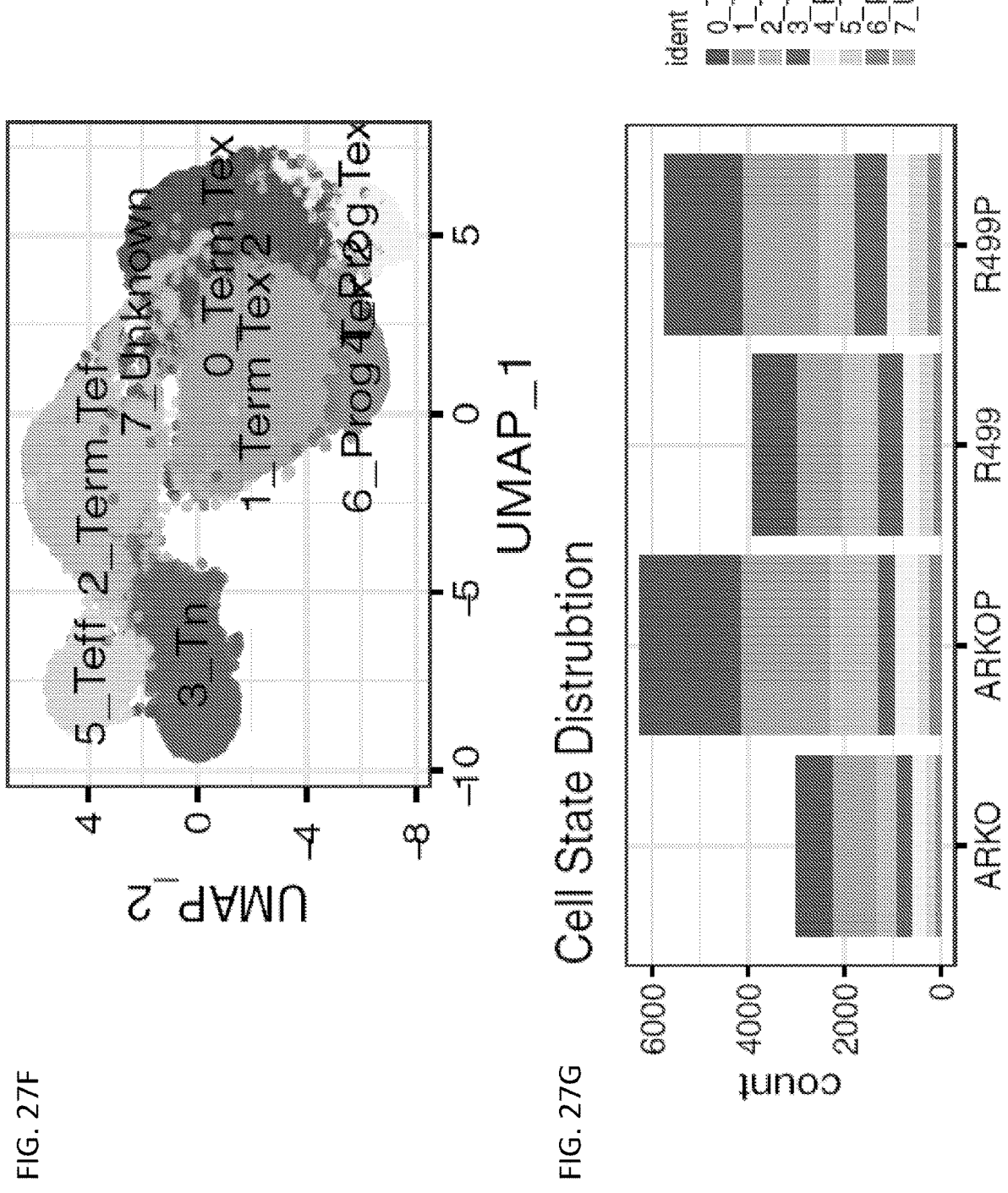
Figure 27H:
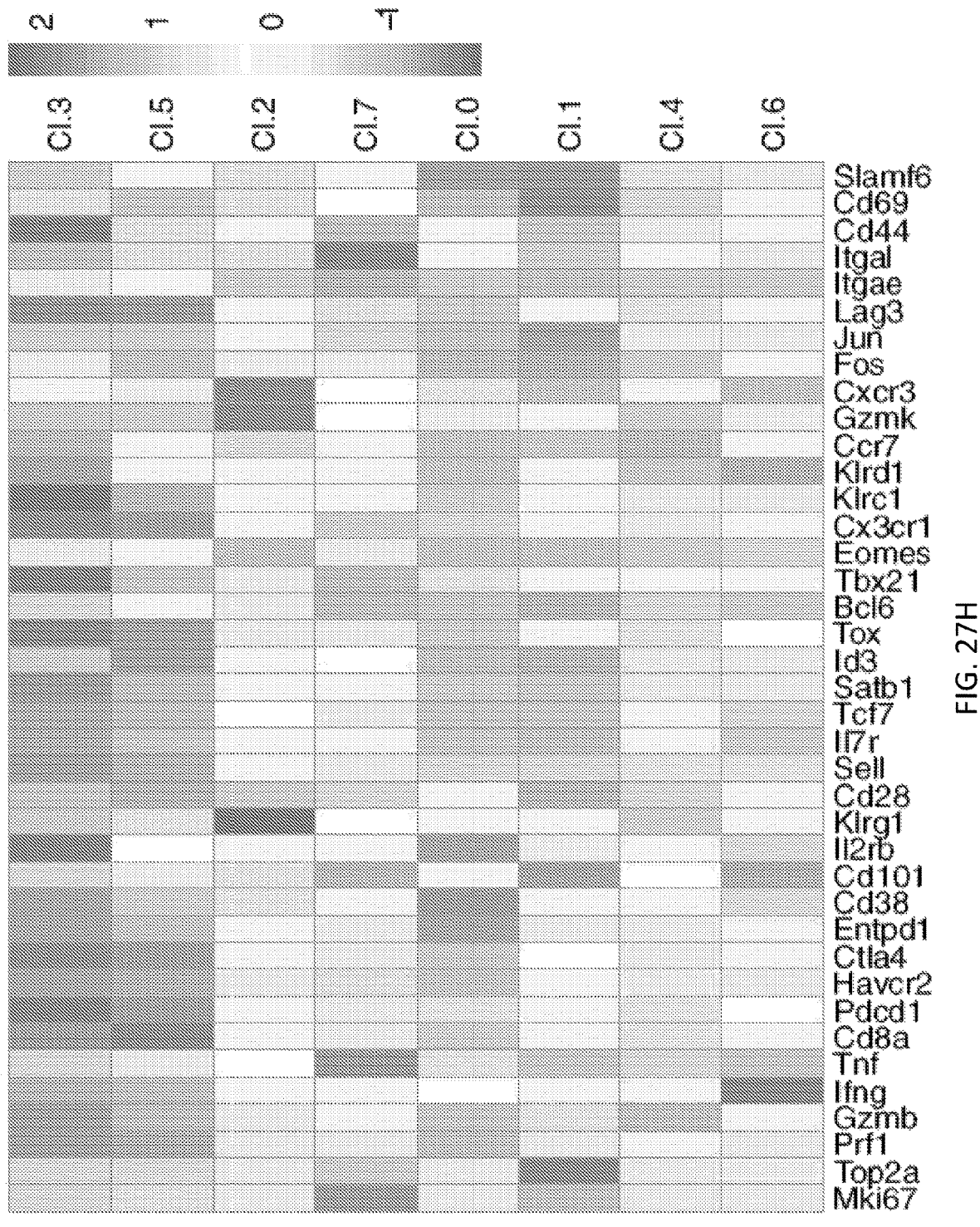
Figures 27I, 27J, 27K:
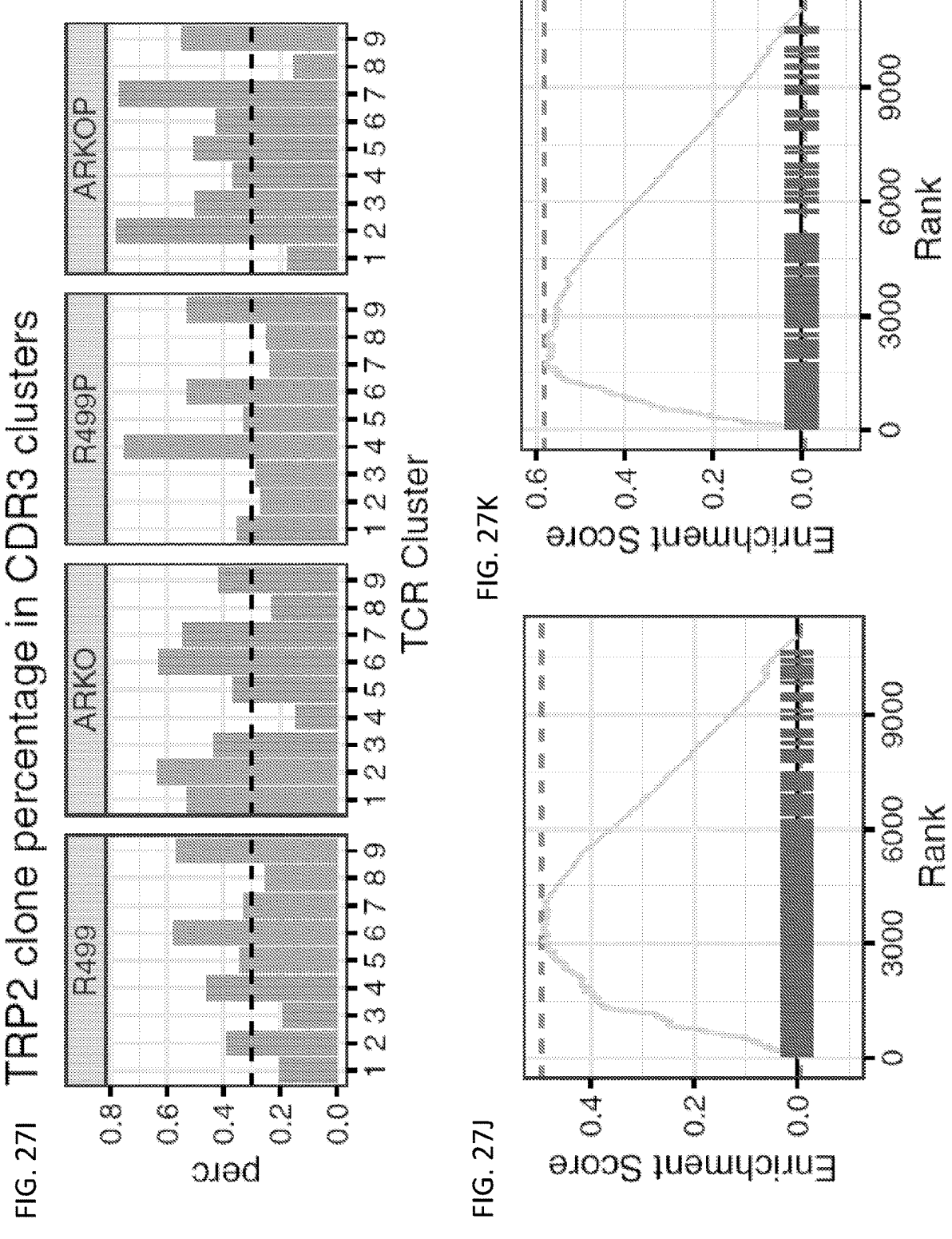

Example 19: The Quality of TCR in CD8 T Cells from Ifnar Knockout Tumors Differs from that in Res499 Control Tumors FIG. 27A shows Nr4a1 (Nur77) expression of single CD8 T cells across phenotype clusters by condition. FIG. 27B shows UMAP of CDR3 clusters as determined by amino acid properties from scTCR-seq TCRα and TCRβ pairs. FIG. 27C illustrates the random forest error rate of each CDR3 clusters classifying TCR coming from WT or Ifnar knockout tumors. FIG. 27D shows UMAP of CDR3 clusters that are predicted to recognize Trp2 arranged by conditions and phenotype clusters overlaid with number of clones. Box indicates CDR3 cluster 2. FIG. 27E shows the distribution of expanded TCR clones across CDR3 clusters as grouped by phenotype clusters across conditions. FIG. 27F shows a UMAP of CD8 T cell subsets. FIG. 27G shows the distribution of phenotype clusters in CD8 T cells from each condition. FIG. 27H is a heatmap of normalized expression of selected markers across CD8 T cell subsets. FIG. 27I shows the percentage of Trp2. Dashed line indicates the average number sampled against a known Trp2 library. FIGS. 27J-27K show GSEA of CDR3 cluster 2 from Ifnar knockout treated tumors vs CDR3 cluster 4 from Res499 control treated tumors using terminal exhausted signature (FIG. 27J) and Hallmark IFN gamma signature FIG. 27K.

Example 20: Phase II Study of Pembrolizumab and Itacitinib (INCB39110) for First Line Treatment of Metastatic Non-Small Cell Lung Cancer Expressing PD-L1

1.0 Trial Summary

| Title: | Phase II study of Pembrolizumab and Itacitinib (INCB039110) for First Line Treatment of Metastatic Non-Small Cell Lung Cancer Expressing PD-L1 |
|---|---|
| Abbreviated Title | Pembrolizumab and itacitinib (INCB039110) for NSCLC |
| Trial Phase | Phase II |
| Study Center(s) | University of Pennsylvania |
| Study Population | The first line treatment of patients with metastatic PD-L1 positive non-small cell lung cancer (NSCLC) |
| Methodology | This is a single center, single arm phase 2 study to establish the safety and efficacy of itacitinib (also known as INCB039110) administered in combination with pembrolizumab in patients with metastatic PD-L1 positive non-small cell lung cancer NSCLC). |
| Study Drugs, Dose and Regimen | Study Drug(s)<br>Itacitinib: a JAK 1 selective small molecule inhibitor; an investigational agent that is study supplied<br>Pembrolizumab: a highly selective humanized monoclonal antibody (mAb)<br>Dose and Route of Administration<br>Itacitinib: 200mg PO (extended release formulation)<br>Pembrolizumab: 200mg IV infusion over 30 minutes<br>Regimen<br>Treatment = 3 week (Q3W) dosing cycles<br>Itacitinib: Once daily for Cycle 3 and Cycle 4 (up to 6 weeks)<br>Pembrolizumab: Q3 week cycles of treatment beginning at Day 1; continued indefinitely as per clinician discretion |

-continued

| Number of trial subjects | Up to 48 evaluable subjects |
| Estimated duration of trial | Approximately 36 months |

1.0 Trial Design
1.1 Trial Design

Figure 28:
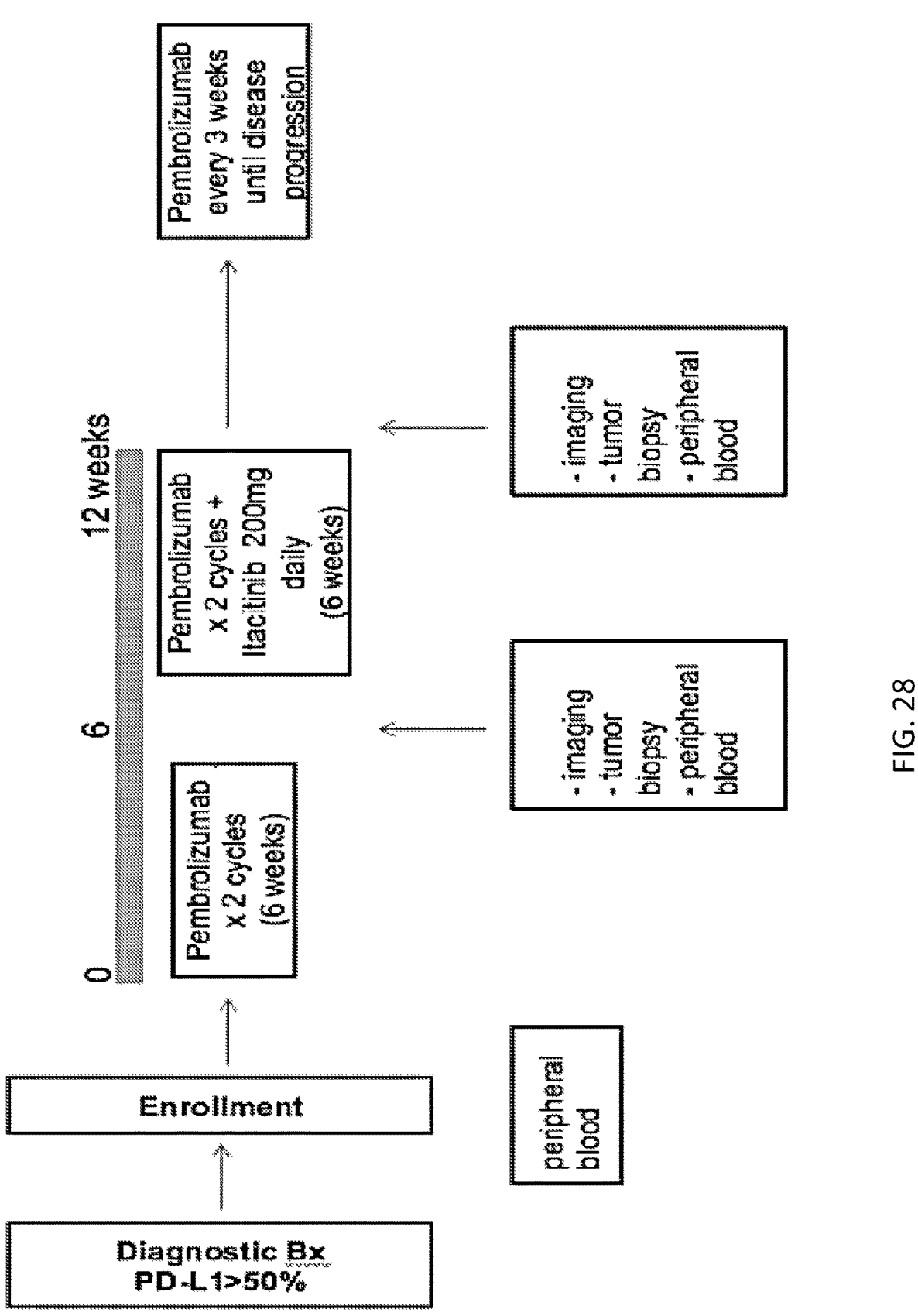
FIG. 28 is a schematic illustrating a clinical trial design for a Phase II clinical trail of pembrolizumab and itacitinib for first line treatment of metastatic non-small cell lung cancer expressing PD-L1.

An optimal 3-stage Phase II trial of trial of pembrolizumab and itacitinib for first line treatment of PD-L1 positive metastatic NSCLC is conducted. Up to 48 evaluable subjects are enrolled to examine the efficacy of adding itacitinib to pembrolizumab among patients with previously untreated metastatic NSCLC with tumor PD-L1 expression greater than or equal to 50%. Subjects receive 2 cycles of pembrolizumab (200 mg every 3 weeks), and then undergo repeat imaging and tumor biopsy. Beginning on the Day 1 of Cycle 3 the subject receives itacitinib (selective JAK1 inhibitor) 200 mg daily for 6 weeks. Pembrolizumab is continued at the same dose and frequency. After 6 weeks of treatment (week 12 of treatment overall) with itacitinib, repeat imaging and tumor biopsy are performed. The scan is purely for biopsy planning, and no treatment decisions are made based upon the results (FIG. 28). Objective response by RECIST 1.1 are determined based on the week 12 scan. Subjects who either experience documented progressive disease during the first 12 weeks of treatment or complete the first 12 weeks of treatment and undergo re-staging (i.e., PET/CT scan) are considered evaluable for objective response evaluation. Subjects who are withdrawn from study (due to toxicity or other reasons) in the first 12 weeks of treatment and who do not undergo re-staging are considered unevaluable for objective response evaluation are be included in the safety analyses. These subjects are replaced. Objective response rate (ORR) is defined as the proportion of evaluable subjects who achieve a complete or partial response according to RECIST 1.1 criteria.

The ORR for pembrolizumab in untreated PD-L1 positive advanced NSCLC was recently reported to be 45% (95% CI 37-53%) [1]. The 3-stage optimal design tests the null hypothesis that the ORR<35% (clearly inferior to pembrolizumab) versus the alternative that the ORR>55% (clearly superior to pembrolizumab) [2]. Eleven evaluable subjects are entered into the first stage of the study. If 2 or fewer of these 11 subjects respond, then the trial is terminated. If at least 3 of these subjects respond, then an additional 19 evaluable subjects are entered into the second stage of the study. If 12 or fewer of these 30 subjects respond, then the trial is terminated. If at least 13 of these subjects respond, then an additional 18 evaluable subjects are entered into the third stage of the study. If 20 or fewer of these 48 subjects respond, then it is concluded that the regimen does not merit further investigation. If at least 21 of these 48 subjects respond, then it is concluded that the regimen merits further investigation. If the true objective response rate is 35%, then the probability of recommending the regimen for further investigation (false positive error), is 0.100. If the true objective response rate is 55%, then the probability of recommending the regimen for further investigation (power), is 0.906. If the true objective response rate is 35%, then the probability of early termination of the trial by the end of the second stage is 0.786. The software program, PASS v14 was employed to define this 3-stage design.

Subjects that continue on study after 12 weeks are evaluated every 9 weeks (63±7 days) with radiographic imaging to assess disease status. If new signs or symptoms of progression occur between scheduled scans, directed imaging is obtained at the clinically appropriate time point to document disease status. Investigators make treatment-based decisions using RECIST 1.1. Adverse events are monitored throughout the subjects' participation in the trial and graded in severity according to the NCI Common Terminology Criteria for Adverse Events (CTCAE) version 5.0 per protocol section 10.1. Treatment with pembrolizumab continues indefinitely in the absence of (1), documented disease progression, (2) unacceptable adverse event(s), (3) intercurrent illness that prevents further administration of treatment, (4) investigator's decision to withdraw the subject, (5) subject withdrawal of consent, (6) pregnancy of the subject, (7) noncompliance with trial treatment or procedure requirements, (8) institution of alternative systemic treatment, or (9) other administrative reasons. Subjects have post-treatment follow-up for disease status until one of the following events: (1) disease progression; (2) initiation of non-study cancer treatment; (3) withdrawal of study consent; (4) loss to follow-up or (5) death. In addition, survival status beyond the establishment of PD or initiation of subsequent therapies is documented, as is all documented post-progression therapy, for up to 1 year after initiation of study treatment (Cycle 1/Day 1).

The primary objectives of the trial include determination of ORR per RECIST 1.1 for the combination of pembrolizumab and itacitinib and the safety of this combination, as assessed by CTCAE. Pre-specified adverse events of clinical interest include the following events: 1) Grade >3 diarrhea 2) Grade >2 colitis, 3) Grade >2 pneumonitis, 4) Grade >3 hypo—or hyperthyroidism, 5) Grade >2 hypophysitis, 6) Grade >2 uveitis, 7) Grade >2 nephritis, 8) Grade >3 anemia, 9) Grade >3 thrombocytopenia, and 10) Grade >3 neutropenia.

The secondary objective of this trial is to collect paired tumor biopsies and peripheral blood to characterize immune biomarkers of response to treatment with pembrolizumab and itacitinib. Additional secondary objectives include determination of progression free survival, duration of response and overall survival for up to 1 year after initiation of study treatment (Cycle 1/Day 1).

3.0 Objectives
3.1 Primary Objectives & Hypotheses

1) To determine the objective response rate at 12 weeks according to RECIST 1.1 for the combination of pembrolizumab and itacitinib among patients with previously untreated, PD-L1 positive metastatic NSCLC. Responses are compared to the subject's baseline assessment and historical controls using pembrolizumab monotherapy.

2) To evaluate toxicities (CTCAE v5.0 scoring) of pembrolizumab and itacitinib in patients with previously untreated, PD-L1 positive metastatic NSCLC 3.2 Secondary Objectives 1) To collect paired blood and tumor tissue samples in order to perform mechanistic studies on treatment-related changes in the subject and tumor immune profiles 2) To determine the median progression free survival (PFS), duration of response (DOR) and overall survival (OS) for subjects treated with pembrolizumab and itacitinib 3.3 Exploratory Objectives
    1) To perform analyses of tumor infiltrating lymphocytes (TILs) to identify changes in functional markers in response to the addition of itacitinib to pembrolizumab.
    2) To perform gene expression studies of tumor tissue using Nanostring to characterize genetic effects in response to immunotherapy.

4.0 Background & Rationale 4.1 Background

Non-small cell lung cancer (NSCLC) is the leading cause of cancer death in the United States [3]. More than half of patients present with metastatic disease, and are thus considered incurable [4]. Until very recently, the standard first-line treatment for NSCLC not harboring a targetable mutation was platinum doublet chemotherapy. While supportive care measures for patients receiving cytotoxic chemotherapy have improved markedly, the side effects of these agents can be substantial [5, 6]. Immunotherapy, most commonly using PD-1 inhibitors, is now known to have significant activity in NSCLC with a very favorable side effect profile [7-9]. Most recently, the KEYNOTE 024 study revealed that among patients with PD-L1 expression greater than or equal to 50%, pembrolizumab was associated with superior overall and progression free survival when compared with platinum doublet chemotherapy [1].

4.1.1 Pharmaceutical and Therapeutic Background

The importance of intact immune surveillance in controlling outgrowth of neoplastic transformation has been known for decades [10]. Accumulating evidence shows a correlation between tumor-infiltrating lymphocytes (TILs) in cancer tissue and favorable prognosis in various malignancies [11-15]. In particular, the presence of CD8+ T-cells and the ratio of CD8+ effector T-cells to FoxP3+ regulatory T-cells seems to correlate with improved prognosis and long-term survival in many solid tumors.

The PD-1 receptor-ligand interaction between tumor cells and the immune system is a major pathway hijacked by tumors to suppress immune control. The normal function of PD-1, expressed on the cell surface of activated T-cells under healthy conditions, is to down-modulate unwanted or excessive immune responses, including autoimmune reactions. PD-1 (encoded by the gene Pdcdl) is an Ig superfamily member related to CD28 and CTLA-4 which has been shown to negatively regulate antigen receptor signaling upon engagement of its ligands (PD-L1 and/or PD-L2) [16, 17]. The structure of murine PD-1 has been resolved [18]. PD-1 and family members are type I transmembrane glycoproteins containing an Ig Variable-type (V-type) domain responsible for ligand binding and a cytoplasmic tail which is responsible for the binding of signaling molecules. The cytoplasmic tail of PD-1 contains 2 tyrosine-based signaling motifs, an immunoreceptor tyrosine-based inhibition motif (ITIM) and an immunoreceptor tyrosine-based switch motif (ITSM). Following T-cell stimulation, PD-1 recruits the tyrosine phosphatases SHP-1 and SHP-2 to the ITSM motif within its cytoplasmic tail, leading to the dephosphorylation of effector molecules such as CD3Z, PKC0 and ZAP70 which are involved in the CD3 T-cell signaling cascade [19-22]. The mechanism by which PD-1 down modulates T-cell responses is similar to, but distinct from that of CTLA-4 as both molecules regulate an overlapping set of signaling proteins [23, 24]. PD-1 was shown to be expressed on activated lymphocytes including peripheral CD4+ and CD8+ T-cells, B-cells, T regs and Natural Killer cells [25, 26]. Expression has also been shown during thymic development on CD4−CD8− (double negative) T-cells as well as subsets of macrophages and dendritic cells [17]. The ligands for PD-1 (PD-L1 and PD-L2) are constitutively expressed or can be induced in a variety of cell types, including non-hematopoietic tissues as well as in various tumors [23, 27-29]. Both ligands are type I transmembrane receptors containing both IgV- and IgC-like domains in the extracellular region and contain short cytoplasmic regions with no known signaling motifs. Binding of either PD-1 ligand to PD-1 inhibits T-cell activation triggered through the T-cell receptor. PD-L1 is expressed at low levels on various non-hematopoietic tissues, most notably on vascular endothelium, whereas PD-L2 protein is only detectably expressed on antigen-presenting cells found in lymphoid tissue or chronic inflammatory environments. PD-L2 is thought to control immune T-cell activation in lymphoid organs, whereas PD-L1 serves to dampen unwarranted T-cell function in peripheral tissues [23]. Although healthy organs express little (if any) PD-L1, a variety of cancers have been demonstrated to express abundant levels of this T-cell inhibitor. PD-1 has been suggested to regulate tumor-specific T-cell expansion in subjects with melanoma (MEL) [30]. This suggests that the PD-1/PD-L1 pathway plays a critical role in tumor immune evasion and should be considered as an attractive target for therapeutic intervention.

Pembrolizumab (previously known as MK-3475 and SCH 900475) is a potent and highly selective humanized monoclonal antibody (mAb) of the IgG4/kappa isotype designed to directly block the interaction between PD-1 and its ligands, PD-L1 and PD-L2.

Interferons are known to have an important role early in generating anti-tumor T cell responses. However, interferons are also involved in the development of adaptive immune resistance [31, 32]. Signaling through the JAK-STAT pathway, interferons regulate PD-L1 expression as well as multiple other negative feedback effects on the immune response through pathways that would not be inhibited by PD-1 blockade alone [33]. Interferon signaling has been theorized as an explanation for the observation that elevated PD-L1 expression is not universally associated with response to pembrolizumab and may also be responsible for primary or secondary treatment resistance [1, 34]. JAK1 is a tyrosine kinase necessary for signaling downstream of both type I and II interferon receptors, as well as multiple other inflammatory cytokines. JAK/STAT signaling has been proposed to promote tumor growth in part by promoting an inflammatory microenvironment that limits CD8+ T cell activity [35].

Itacitinib is a potent JAK1 selective small molecule inhibitor (half maximal inhibitory concentration [IC50]=3.6 nM), with 22 to 500-fold greater selectivity for JAK1 compared to other JAK family members including JAK2, JAK3 and TYK2.

4.1.2 Preclinical and Clinical Trial Data

Previous work in a mouse melanoma model showed that tumor intrinsic interferon signaling promotes resistance to immune checkpoint blockade [36]. Knocking out type I and II interferon receptors on melanoma cells sensitizes them to immune checkpoint blockade, markedly improving treatment response and survival in pre-clinical models. T cells from these mice express higher proliferative and cytotoxic markers after immune checkpoint blockade.

Preclinical studies utilizing a JAK1/2 inhibitor to block interferon signaling revealed the following observations that can be translated to human trials:

JAK inhibition reduced tumor growth in response to immune checkpoint blockade and flow cytometry analysis of tumor cells demonstrated decreased surface expression of multiple inhibitory receptor ligands, which generally are associated with immune suppression.

As prolonged JAK inhibition can have side effects, a short course of JAK inhibitor therapy was tested. consistent improvements in tumor regression was observed.

When JAK inhibition began concurrently with checkpoint blockade, no improvement was seen in tumor regression relative to checkpoint blockade alone.

When JAK inhibition was started after an induction phase of checkpoint blockade, however, a marked increase in tumor regression was seen. The selective benefit of sequential, as opposed to concurrent therapy initiation is consistent with 1) the immunostimulatory role of interferon signaling in early events of dendritic cell activation and T cell priming, and 2) the feedback inhibition and immunosuppressive role that occurs with prolonged interferon signaling.

The importance of the timing of JAK inhibition is also implied by studies in chronic viral infections. Blocking interferon signaling late in infection improves viral control, while earlier inhibition is not beneficial[37, 38]. In this study, these findings are extended to patients by testing the addition of JAK inhibition to ongoing anti-PD-1 therapy. It is hypothesize that combined treatment with pembrolizumab and itacitinib are associated with an overall response rate of at least 55%. Moreover, using paired blood and tissue-based biomarkers during the course of treatment a better understanding of the dynamics of response to immunotherapy among patients with NSCLC is gained.

The combination of itacitinib and pembrolizumab is being evaluated in a phase I study in patients with advanced solid tumors. Data from this trial have not been presented or published. To date, 35 subjects have been treated in the dose escalation and expansion cohorts. No dose-limiting toxicities were noted. The risks of using itacitinib in combination with pembrolizumab are unknown at this time. The risk profile of these agents when given in combination is anticipated to be similar to that of the risk profile of each drug when given alone. Efficacy data is currently not available for this combination.

Refer to the Investigator's Brochure of itacitinib and the pembrolizumab package insert for additional Preclinical and Clinical data including information on potential toxicities.

4.2 Rationale 4.2.1 Rationale for the Trial and Selected Subject Population

The therapeutic benefit of immune checkpoint blockade has now been seen in multiple malignancies, with durable responses observed in a subset of patients [1, 9, 34, 39]. In spite of these exciting results, only a limited number of patients respond to PD-1 blockade, with response rates of approximately 20% in an unselected population. PD-L1 expression is the best-studied predictive biomarker for response to checkpoint blockade in NSCLC [40]. While PD-L1 is an imperfect biomarker, with significant dynamism and heterogeneity, a recent study of patients with tumors expressing a high level of PD-L1 (>50%) pembrolizumab was found to improve overall survival and progression free survival over platinum doublet chemotherapy in the first line treatment of NSCLC [1, 41] Even in this population enriched for patients likely to respond to PD-1 inhibition, the response rate to pembrolizumab was only 44.8%. While this is a great advance, there is clearly room for improvement as we attempt to extend the benefits of anti-PD-1 therapy to a larger patient population.

Patients with newly diagnosed stage IV or metastatic NSCLC with tumor PD-L1 expression greater than or equal to 50% are enrolled in this study prior to any systemic therapy for metastatic disease. This patient population is selected because 1) PD-L1 is itself upregulated by interferon signaling and could serve as a biomarker for JAK1 inhibition, and 2) it is hypothesize that in a proportion of patients with PD-L1+ tumors, feedback inhibition that occurs with prolonged interferon signaling limits response. Thus, patients with high levels of PD-L1 expression may be more likely to benefit from the combination of pembrolizumab and itacitinib.

4.2.2 Rationale for Dose Selection/Regimen/Modification

The currently approved dose for pembrolizumab in patients with NSCLC is 200 mg every 3 weeks. The 200 mg every 3 week dose was also shown to be safe and effective in a first line treatment trial for patients with PD-L1 positive NSCLC [1]. Pembrolizumab is continued in the absence of progression by irRECIST[42] or toxicity. At this time, the duration of treatment with pembrolizumab in patients with a clinical benefit is not clear but a standard practice is to continue treatment in the absence of adverse effects and/or clinical and radiographic disease progression.

In study INCB 39110-107, 35 subjects with advanced solid tumors have been treated with itacitinib in combination with pembrolizumab (8 subjects in Part 1a [dose escalation] and 27 subjects in Part 1b [dose expansion]). The most frequently reported treatment-emergent adverse events (TE-AEs) in Part 1a were anemia, fatigue, disease progression (50% each) and nausea, decreased appetite, and decreased weight (37.5% each). The most frequent TEAE in Part 1b were fatigue and nausea (37.0% each). There were no dose-limiting toxicities (DLTs) in Part 1a. The dose expansion cohort was treated with 300 mg daily of itacitinib. Serious adverse events (SAE) were reported in 6 subjects in the expansion cohort and include disease progression (2 subjects, 7.4%) and abdominal pain, gastric obstruction, pancreatitis, pyrexia, urinary tract infection and pulmonary embolism (1 subject each, 3.7%). Only pyrexia was considered to be a treatment-related SAE.

Itacitinib is also being evaluated in combination with other immunotherapies in research studies. In personal communications with Incyte (the sponsor of these trials), they decided that based upon proprietary information, the recommended phase 2 dose for future study is 200 mg/daily. As more precise data become available, the protocol and consent are updated to better characterize adverse events.

4.2.3 Rationale for Endpoints 4.2.3.1 Efficacy Endpoints 4.2.3.1.1 Primary

Objective response rate, defined as the percentage of evaluable subjects who achieve a complete or partial clinical response at 12 weeks, according to RECIST 1.1 is the primary endpoint of this study. Given that this is a first line study of a novel combination, ORR was chosen as an earlier indicator of efficacy of the combination and to limit the number of subjects exposed if improved efficacy is not observed. Moreover, based on the mechanism of action, JAK1 inhibition is predicted to improve the response rate in a population of patients with PD-L1 positive tumors by reducing the expression of additional immune inhibitory pathways in the tumor microenvironment. Responses are compared to the subject's baseline assessment and historical controls using pembrolizumab monotherapy.

4.2.3.1.2 Secondary

Peripheral blood immune profiling provides important mechanistic information on how PD-1 blockade and itacitinib function in human subjects. By studying treatment related changes in blood and tumor, and correlating these with response or resistance, superior and perhaps tailored combination treatment strategies could potentially be developed in the future. Correlative samples are banked upon receipt and correlative assays performed in the following priority order.

High Priority Assays:

1. Multiparametric flow cytometry analysis of peripheral blood mononuclear cells to analyze T cell subsets and markers of functionality. T cell subsets are determined using transcription factors and surface markers subsets. Functionality is measured by examining activation markers, cytokines, effector molecules, and proliferation markers.

2. Transcriptomic analyses of tumor specimens to identify changes in gene expression after the addition of itacitinib to pembrolizumab. In particular, a subset of interferon-stimulated genes (ISGs) associated with resistance to checkpoint blockade is examined in preclinical models.

3. Measurement of inflammatory cytokine or chemokine levels in subject serum. In particular, interferon levels and other cytokines regulated by the JAK1 pathway are examined as biomarkers for both on-target drug activity and response.

Second Priority Assays:

1. Measurement of inflammatory cytokine or chemokine levels in subject serum. Circulating tumor cell (CTC) and circulating tumor DNA (ctDNA) measurements and profiling.

Additional secondary endpoints include progression free survival (PFS), overall survival (OS) and duration of response (DOR). PFS is defined as days from initiation of study therapy to first documented disease progression, death due to any cause or last subject contact which documents progression-free status. DOR is defined as the time from first documentation of partial or complete response to first documented disease progression. OS is defined as days from initiation of study therapy to death due to any cause or last subject contact.

4.2.3.2 Exploratory Objectives

Perform analyses of tumor infiltrating lymphocytes (TILs) to identify changes in functional markers in response to the addition of itacitinib to pembrolizumab. This study is a pilot feasibility study of performing multiparametric analysis of TILs, particularly CD8+ T cells, from patients with metastatic NSCLC using approaches such as flow cytometry and multicolor immunohistochemistry.

Given the potential role for chronic interferon signaling as well as other inflammatory cytokines regulated by JAK/STAT signaling in impairing T cell function, it is anticipated that response to itacitinib and pembrolizumab is associated with 1) sustained activation of PD1+ T cells after an initial proliferative burst as measured by Ki67, 2) high pre-treatment interferon levels that is suppressed during treatment, and 3) high gene expression levels of resistance-associated ISGs. It is hypothesized that subjects failing to respond to treatment show initial proliferative burst in PD1+ T cells that is not sustained despite continued pembrolizumab, and 2) decreased expression of various other markers of T cell activation.

Additionally, deep sequencing of the T cell receptor (TCR) in tumor and blood is performed as feasible to identify clones that expand after treatment and their persistence is monitored over time. These are non-biased approaches to identify tumor reactive T cells in subjects where the specific neoantigen is not known.

5.0 Methodology 5.1 Entry Criteria 5.1.1 Inclusion Criteria

1. Stage IV or metastatic non-small cell lung cancer (NSCLC)
2. Provide written informed consent for the trial.
3. Patients >18 years of age
4. Tumor PD-L1>50% as assessed by the PD-L1 IHC 22C3 pharmDx assay (Dako North America).
5. Subject must have adequate tumor burden at a safely accessible site for biopsy. NOTE: If sites chosen for biopsy were previously irradiated, there must be evidence of tumor growth/viable tumor as assessed by the investigator.
6. At least one measurable lesion according to Response Evaluation Criteria in Solid Tumors (RECIST) v1.1
7. ECOG performance status 0 or 1
8. Adequate organ function as defined in Table 1
9. Subjects of reproductive potential must agree to use acceptable birth control methods as described in protocol section 5.5.2.

TABLE 1

| Adequate Organ Function Laboratory Values | |
|---|---|
| System | Laboratory Value |
| Hematological | |
| Absolute neutrophil count (ANC) | ≥1,250/mcL |
| Platelets | ≥100,000/mcL |
| Hemoglobin | ≥9 g/dL or ≥5.6 mmol/L |
| Renal | |
| Serum creatinine OR Measured or calculated[a] creatinine clearance (GFR can also be used in place of creatinine or CrC1) | ≤1.5 × upper limit of normal (ULN) OR ≥50 mL/min for subject with creatinine levels > 1.5 × institutional ULN |
| Hepatic | |
| Serum total bilirubin | ≤1.5 × ULN OR Direct bilirubin ≤ULN for subjects with total bilirubin levels > 1.5 ULN |
| AST (SGOT) and ALT (SGPT) | ≤2.5 × ULN OR 5 × ULN for subjects with liver metastases |

[a]Creatinine clearance calculated per institutional standard.

5.1.2 Exclusion Criteria

1. Sensitizing mutations in Epidermal growth factor receptor (EGFR) or anaplastic lymphoma kinase (ALK) or ROS1 proto-oncogene receptor tyrosine kinase (ROS1) translocations.
2. Currently participating in or has participated in a study of an investigational agent or anticipated use of an investigational device within 4 weeks of the first dose of study treatment.
3. Untreated symptomatic central nervous system (CNS) metastases and/or carcinomatous meningitis.
4. Received prior systemic cytotoxic chemotherapy, biologic therapy, targeted therapy or immunotherapy for incurable (metastatic) NSCLC.
5. Diagnosis of immunodeficiency within 7 days prior to eligibility confirmation by the physician-investigator.
6. Prior monoclonal antibody within 4 weeks prior to eligibility confirmation by the physician-investigator, or individuals who have not recovered (i.e., <Grade 1 or at baseline) from adverse events due to agents administered more than 4 weeks earlier.
7. Known additional malignancy that is progressing or requires active treatment. Exceptions include basal cell carcinoma of the skin, squamous cell carcinoma of the skin, non-invasive bladder tumors, or in situ cervical cancer.

8. Active autoimmune disease requiring systemic immunosuppressive treatment within the past 3 months prior to eligibility confirmation by the physician-investigator. Subjects that require intermittent use of steroid-containing bronchodilators or local steroid injections or topical steroid medications are not excluded from the study. Subjects with hypothyroidism stable on hormone replacement or Sjogren's syndrome are not excluded from the study.

9. Interstitial lung disease or history of pneumonitis that has required oral or IV steroids.

10. Active infection requiring systemic therapy with IV antibiotics.

11. History or current evidence of any condition, therapy, or laboratory abnormality that might confound the results of the trial, interfere with the subject's participation for the full duration of the trial, or is not in the best interest of the subject to participate, in the opinion of the treating investigator.

12. Known psychiatric or substance abuse disorders that would interfere with cooperation with the requirements of the trial.

13. Pregnant or breastfeeding women.

14. Prior therapy with an anti-PD-1, anti-PD-L1, anti-PD-L2, anti-CD137, or anti-Cytotoxic T-lymphocyte-associated antigen-4 (CTLA-4).

15. Known history of Human Immunodeficiency Virus (HIV) (HIV 1/2 antibodies).

16. Known active Hepatitis B (e.g., HBsAg positive or HBV DNA detectable) or Hepatitis C (e.g., HCV RNA [qualitative] is detected).

17. Anticipated receipt of any live vaccine within 30 days prior to the first dose of trial treatment.

Note: For the purposes of determining eligibility above, enrollment is defined as the date of subject consent.

5.2 Enrollment

The Subject Number consists of the Protocol Number with a sequential subject number affixed to it. Assignment of subject numbers occur at the time of consent and occur in ascending order (i.e. 09517-01, 09517-02, etc). No numbers are omitted. Subject numbers are thereafter used on all study documentation.

At the time a subject consents to participate in this study, a Consent Notification Form should is completed. When eligibility of the subject is confirmed by a physician-investigator, an Enrollment Notification is completed.

5.3 Study Drugs

The treatments to be used in this trial are outlined below in Table 2.

| Drug | Dose/ Potency | Dose Frequency | Route of Administration | Regimen | Use |
|---|---|---|---|---|---|
| Pembrolizumab | 200 mg | Q3W | IV infusion | Day 1 of each 3-week cycle | Per label- with the exception of the drug being administered with itacitinib |
| Itacitinib (INCB039110) | 200 mg | Once Daily | Oral | Daily for cycles 3-4 (q3 weeks); up to 42 days of therapy | Investigational |

The pembrolizumab dosing interval may be modified as per package insert.

5.3.1 Dose Selection/Modification 5.3.1.1 Dose Selection

The rationale for selection of doses to be used in this trial is provided in Section 4.0—Background and Rationale.

5.3.1.2 Dose Modifications

Pembrolizumab

Please refer to the pembrolizumab package insert.

Itacitinib

TABLE 3

| Dose modification guidelines for itacitinib-related adverse events. |||||| 
|---|---|---|---|---|---|
| Toxicity | Grade | Hold Treatment (Y/N) | Timing for restarting treatment[1] | Dose/Schedule for restarting treatment | Discontinue itacitinib (after consultation with the Sponsor Medical Director)[2] |
| Hematological Toxicity | 1, 2 | No | N/A | N/A | N/A |
| | 3, 4 | Yes | Toxicity improves to Grade 02 or baseline | Reduce itacitinib by 1 dose level (100 mg daily) If second dose reduction is necessary subject will be discontinued from itacitinib treatment. | Toxicity does not resolve within 2 weeks of last dose. If second dose reduction is necessary subject will be discontinued from itacitinib treatment. |

TABLE 3-continued

Dose modification guidelines for itacitinib-related adverse events.

| Toxicity | Grade | Hold Treatment (Y/N) | Timing for restarting treatment[1] | Dose/Schedule for restarting treatment | Discontinue itacitinib (after consultation with the Sponsor Medical Director)[2] |
|---|---|---|---|---|---|
| Thrombocytopenia with bleeding | 1, 2 | No- but dose reduce | N/A | Reduce itacitinib by 1 dose level (100 mg daily) If second dose reduction is necessary subject will be discontinued from itacitinib treatment. | If second dose reduction is necessary subject will be discontinued from itacitinib treatment. |
| | 3, 4 | Yes | Toxicity improves to Grade 02 or baseline | Hold itacitinib until count recovery. If second dose hold is necessary subject will be discontinued from itacitinib treatment. | Toxicity does not resolve within 2 weeks of last dose. If second dose hold is necessary subject will be discontinued from itacitinib treatment. |
| Febrile neutropenia | 3 | Yes | N/A | N/A | Discontinue itacitinib |
| Infection | 3, 4 | Yes | Completion of IV antibiotics | Reduce itacitinib by 1 dose level (100 mg daily) | Toxicity does not resolve with typical antibiotic course |
| Non- hematological toxicity | 1 | No | N/A | N/A | N/A |
| Note: Exceptions to be treated similar to grade 1 toxicity Grade 2 alopecia Grade 2 fatigue | 2 | Consider withholding for clinically significant symptoms | improves to Toxicity Grade 01 or baseline | Same dose and schedule | N/A |
| | 3, 4 | Yes | Toxicity improves to Grade 01 or baseline | Reduce itacitinib by 1 dose level (100 mg daily) If second dose reduction is necessary subject will be discontinued from itacitinib treatment. | Toxicity does not resolve within 2 weeks of last dose. If second dose reduction is necessary subject will be discontinued from itacitinib treatment. |
| Hepatic Toxicity | Bilirubin >2 × ULN AND Grade 3 AST/ALT (>3 × ULN) | Yes | N/A | N/A | Discontinue itacitinib |

*N/A = Not applicable
[1]Missed doses will not be made up. The subject may receive up to 42 days of itacitinib therapy.
[2]If a subject discontinues itacitinib therapy, they may continue on pembrolizumab treatment and may remain on study.

5.3.2 Timing of Dose Administration

Trial treatment is administered on Day 1 of each cycle after all procedures/assessments have been completed as detailed on the Trial Flow Chart (Section 6.0). Trial treatment is administered up to 3 days before or after the scheduled Day 1 of each cycle due to administrative reasons.

All trial treatments are administered on an outpatient basis.

Pembrolizumab is administered as a 30 minute IV infusion. Pembrolizumab treatment cycle intervals may be increased due to toxicity as per package insert. Sites should make every effort to target infusion timing to be as close to 30 minutes a possible. However, given the variability of infusion pumps, a window of +/−10 minutes is permitted.

Itacitinib is administered daily starting at Cycle 3/Day 1 and continue for a total of 6 weeks (42 days). Itacitinib is taken orally by the subject at the prescribed dose—200 mg QD (2×100 mg tablets). If dose reductions are required due to toxicity, the prescribed dose is reduced to 100 mg QD (1×100 mg tablet). Itacitinib is taken with water, and may be taken without regard to food. If itacitinib doses are missed due to toxicity (per Table 3) or if vomiting occurs, these missed doses are be made up.

5.4 Concomitant Medications

All concomitant medications received within 28 days before the first dose of trial treatment and 30 days after the last dose of trial treatment (End of Treatment Visit) are recorded. Anticancer therapies administered after 30 days after the End of Treatment Visit continue to be recorded until the subject is discontinued from study follow-up. Medications or vaccinations specifically prohibited in the exclusion criteria are not allowed during the ongoing trial. If there is a clinical indication for one of these or other medications or vaccinations specifically prohibited during the trial, discontinuation from trial therapy may be required. The investigator should discuss any questions regarding this with the Sponsor. The final decision on any supportive therapy or vaccination rests with the investigator and/or the subject's primary physician. However, the decision to continue the subject on trial therapy rests with the Sponsor.

5.4.1 Acceptable Concomitant Medications

All treatments that the investigator considers necessary for a subject's welfare are administered at the discretion of the investigator in keeping with the community standards of medical care. All concomitant medications are recorded on the case report form (CRF) including all prescription, over-the-counter (OTC), herbal supplements, and IV medications and fluids. Subjects may receive other medications that the investigator deems to be medically necessary unless specified in Section 5.4.2 below.

5.4.2 Prohibited Concomitant Medications

Subjects are prohibited from receiving the following therapies during the Screening and Treatment Phase (including retreatment for post-complete response relapse) of this trial:

Systemic corticosteroid therapy or any other form of immunosuppressive therapy is prohibited within 7 days prior to study treatment. (Nasal or oral inhalers are permissible). Physiologic replacement doses of steroids (mineralocorticoid or less than or equal to a prednisone 10 mg daily dose) are be permitted.

Anti-cancer systemic chemotherapy or biological therapy

Immunotherapy not specified in this protocol

Investigational agents other than pembrolizumab and itacitinib

Radiation therapy

Note: Radiation therapy to a symptomatic solitary lesion or to the brain may be allowed after consultation with Sponsor, but is regarded as a disease progression event for the primary outcome.

Live vaccines within 30 days prior to the first dose of trial treatment and while participating in the trial. Examples of live vaccines include, but are not limited to, the following: measles, mumps, rubella, chicken pox, yellow fever, rabies, BCG, and typhoid (oral) vaccine. Seasonal influenza vaccines for injection are generally killed virus vaccines and are allowed; however intranasal influenza vaccines (e.g. Flu-Mist®) are live attenuated vaccines and are not allowed.

Glucocorticoids, in excess of physiologic doses (prednisone >10 mg per day equivalent), for any purpose other than an abbreviated course to modulate symptoms from an event of clinical interest of suspected immunologic etiology.

CYP3A4 inhibitors and dual CYP3A4/2C9

Fluconazole (>200 mg doses) There are no prohibited therapies during the Post-Treatment Follow-up Phase.

5.5 Rescue Medications & Supportive Care 5.5.1 Supportive Care Guidelines

Subjects receive appropriate supportive care measures as deemed necessary by the treating investigator. Please refer to the pembrolizumab package insert for supportive care guidelines related to pembrolizumab administration.

Toxicity management considerations for itacitinib are outlined below.

Nausea/vomiting: Nausea and vomiting are treated aggressively, and consideration is given in subsequent cycles to the administration of prophylactic antiemetic therapy according to standard institutional practice. Subjects are strongly encouraged to maintain liberal oral fluid intake.

Anti-infectives: Subjects with a documented infectious complication receive oral or IV antibiotics or other anti-infective agents as considered appropriate by the treating investigator for a given infectious condition, according to standard institutional practice.

5.6 Diet/Activity/Other Considerations 5.6.1 Diet

Subjects maintain a normal diet unless modifications are required to manage an AE such as diarrhea, nausea or vomiting.

5.6.2 Contraception

Pembrolizumab and/or itacitinib may have adverse effects on a fetus in utero. Furthermore, it is not known if pembrolizumab and/or itacitinib have transient adverse effects on the composition of sperm. Therefore while enrolled, all subjects must agree not to participate in a conception process (i.e. active attempt to become pregnant or to impregnate, sperm donation, in vitro fertilization, etc).

Female subjects of reproductive potential (women who have reached menarche or women who have not been post-menopausal for at least 24 consecutive months, i.e., who have had menses within the preceding 24 months, or have not undergone a sterilization procedure [hysterectomy or bilateral oophorectomy]) must have a negative serum or urine pregnancy test performed within 72 hours of Cycle 1/Day 1 as per the Trial Flow Chart.

All participants participating in sexual activity that could lead to pregnancy must agree to use two methods of birth control. The two birth control methods can be either two barrier methods or a barrier method plus a hormonal method to prevent pregnancy. Subjects should start using birth control from screening throughout the study period up to 120 days after the last dose of study therapy.

The following are considered adequate barrier methods of contraception: diaphragm, condom (by the partner), copper intrauterine device, sponge, or spermicide. Appropriate hormonal contraceptives include any registered and marketed contraceptive agent that contains an estrogen and/or a progestational agent (including oral, subcutaneous, intrauterine, or intramuscular agents). Male sterilization (i.e. vasectomy) is also considered an acceptable method of birth control as long as a barrier method is also utilized.

Subjects should be informed that taking the study medication may involve unknown risks to the fetus (unborn baby) if pregnancy were to occur during the study. In order to participate in the study they must adhere to the contraception requirement above. If there is any question that a subject does not reliably comply with the requirements for contraception, that subject is not entered into the study.

5.6.3 Use in Nursing Women

It is unknown whether the study drugs are excreted in human milk. Since many drugs are excreted in human milk, and because of the potential for serious adverse reactions in the nursing infant, subjects who are breast-feeding are not eligible for enrollment.

5.7 Subject Withdrawal/Discontinuation

A subject must be discontinued from study treatment for any of the following reasons:

Withdrawal of consent

Confirmed radiographic disease progression; (as per standard of care, a patient receiving pembrolizumab who experiences asymptomatic progression of disease may be continued on therapy until progression is confirmed with a subsequent scan).

Unacceptable adverse experiences or toxicities (see section 5.3.1.2)

Intercurrent illness that prevents further administration of treatment

Investigator's decision to withdraw the subject

Confirmed positive serum pregnancy test

Noncompliance with trial treatment or procedure requirements

Loss to follow-up

Other Administrative reasons

Subjects who discontinue from study treatment have an End of Treatment Visit and remain in study follow-up per the Trial Flow Chart in section 6.0. Subjects are discontinued from study follow-up at the end of the study, or if they are lost to follow-up or withdraw consent.

5.8 Subject Replacement Strategy

Subjects who either experience documented progressive disease during the first 12 weeks of treatment or complete the first 12 weeks of treatment and undergo re-staging are considered evaluable and are not replaced. Subjects who complete study treatments but are unable to complete planned biopsies are also considered evaluable for response and adverse events. All other subjects are considered non-evaluable and are replaced.

5.9 Clinical Criteria for Early Trial Termination

The 3-stage optimal design tests the null hypothesis that the ORR<35% (clearly inferior to pembrolizumab) versus the alternative that the ORR>55% (clearly superior to pembrolizumab) [2]. ORR includes both subjects with partial responses and complete responses, per RECIST 1.1. Stable disease is not considered a response. Eleven evaluable subjects are entered into the first stage of the study. If 2 or fewer of these 11 subjects respond, then the trial is terminated. If at least 3 of these subjects respond, then an additional 19 evaluable subjects are entered into the second stage of the study. If 12 or fewer of these 30 subjects respond, then the trial is terminated. If at least 13 of these subjects respond, then an additional 18 evaluable subjects are entered into the third stage of the study. If 20 or fewer of these 48 subjects respond, then it is concluded that the regimen does not merit further investigation. If at least 21 of these 48 subjects respond, then it is concluded that the regimen merits further investigation. If the true objective response rate is 35%, then the probability of recommending the regimen for further investigation (false positive error), is 0.100. While if the true objective response rate is 55%, then the probability of recommending the regimen for further investigation (power), is 0.906. If the true objective response rate is 35%, then the probability of early termination of the trial by the end of the second stage is 0.786. The software program, PASS v14 was employed to define this 3-stage design.

A Bayesian termination rule for unacceptable toxicity (to be defined in protocol) is employed to monitor safety. Assuming a minimally informative beta (1,5) prior, which is information equivalent to 1 of 6 treated subjects with unacceptable toxicity. If the number of subjects with unacceptable toxicity in the first stage of 2-stage design is: >2 in first 3 subjects, >3 in first 6, >4 in first 9, or in the second stage of the design is: >5 in first 12, >6 in first 15, >7 in first 18, >9 in first 25 subjects, >10 in first 30 or in the third stage of the design is: >12 in first 35, >13 in first 40 and >14 in first 45, then termination is considered as it is likely that the rate of unacceptable toxicity is >25%.

5.10 Clinical Criteria for Early Trial Termination due to Trial Conduct or Other Factors Early trial termination occurs for any of the following:

1. Incidence or severity of adverse drug reaction in this or other studies indicates a potential health hazard to subjects 2. Plans to modify or discontinue the development of the study drug 6.0 Trial Flow Chart 6.1 the Study Flow Chart is Depicted in FIGS. 29A-29B. Denoted in the Flow Chart:

1. The order of preference for biopsy site, if safely accessible, is primary tumor>solid organ metastasis (including thoracentesis)>lymph node metastasis. Preference is made to biopsy the same site for both biopsies, if safe and feasible.

2. Up to 78 mL of blood is collected for research studies. Please refer to the Study Laboratory Manual for additional details related to sample collection and handling.

3. Female subjects of reproductive potential only. A negative pregnancy test is required within 72 hours of Cycle 1/Day 1.

4. Directed physical examinations are symptom and disease driven based on physician discretion.

5. Required q12 weeks (i.e. approximately every 4 cycles).

6. Subjects who discontinue study treatment in the absence of disease progression have post-treatment follow-up q8 weeks for disease status until one of the following events: (1) disease progression; (2) initiation of non-study cancer treatment; (3) withdrawal of study consent; (4) loss to follow-up; or (5) death. The subject then enters into survival follow-up. Subjects who discontinue study treatment due to disease progression or initiation of a new anti-cancer therapy enter survival follow-up directly. Survival follow-up continues up to 1 year from initiation of study treatment (Cycle 1/Day 1).

7. RECIST 1.1 is used in this study for assessment of tumor response. While either CT or MRI may be utilized, as per RECIST 1.1, CT is the preferred imaging technique in this study.

8. The 30 day Safety Follow-up Visit must occur prior to the first dose of any new anti-cancer therapy.

9. Baseline tumor imaging is performed within 30 days prior to Cycle 1/Day 1. A PET/CT may be used to fulfill baseline imaging requirements, however a PET/CT cannot be substituted for post-infusion imaging. Please refer to Section 7.1.2.6 for additional information.

10. Tumor imaging to be performed q9 weeks (approximately every 3 cycles). Tumor imaging timing should follow calendar days and should not be adjusted for delays in cycle starts or extension of pembrolizumab cycle duration.

11. Please refer to Table 4 for additional information. After Cycle 1, pre-dose laboratory procedures are conducted up to 72 hours prior to dosing. Results must be reviewed by the investigator or qualified designee and found to be acceptable prior to each dose of trial treatment.

12. Screening laboratory tests are performed within 10 days prior to Cycle 1/Day 1.

13. Treatment with pembrolizumab continues indefinitely in the absence of (1) documented disease progression, (2) unacceptable adverse event(s), (3) intercurrent illness that prevents further administration of treatment, (4) investigator's decision to withdraw the subject, (5) subject withdrawal of consent, (6) pregnancy of the subject, (7) noncompliance with trial treatment or procedure requirements, (8) institution of alternative systemic treatment, or (9) other administrative reasons.

14. Tumor imaging in post-treatment follow-up is performed per routine care and at the discretion of the treating investigator.

15. Performed 7-14 days after Cycle 2 of pembrolizumab. Tumor imaging is used for biopsy planning only, and no treatment decisions are made based upon the results.

16. Performed at the end of Cycle 4 prior to Cycle 5/Day 1, approximately Day 14-21. Imaging performed at this timepoint is used to evaluate objective response by RECIST 1.1.

17. An archived tumor tissue sample is collected for exploratory analysis if available. Subjects do not undergo an additional procedure to obtain this sample. Please refer to the Lab Manual for additional instructions.

7.0 Trial Procedures 7.1 Trial Procedures

The Trial Flow Chart—Section 6.0 summarizes the trial procedures performed at each visit. Individual trial procedures are described in detail below. It may be necessary to perform these procedures at unscheduled time points if deemed clinically necessary by the investigator.

Furthermore, additional evaluations/testing may be deemed necessary by the Sponsor for reasons related to subject safety. In these cases, such evaluations/testing is performed in accordance with those regulations.

7.1.1 Administrative Procedures 7.1.1.1 Informed Consent

The Investigator obtains documented consent from each potential subject prior to participating in a clinical trial. Copies of the informed consent form are placed in the electronic medical record as well as study folder.

7.1.1.1.1 General Informed Consent

Consent is documented by the subject's dated signature or by the subject's legally acceptable representative's dated signature on a consent form along with the dated signature of the person conducting the consent discussion.

A copy of the signed and dated consent form is given to the subject before participation in the trial. The initial informed consent form, any subsequent revised written informed consent form and any written information provided to the subject receives the IRB/ERC's approval/favorable opinion in advance of use. The subject or his/her legally acceptable representative is informed in a timely manner if new information becomes available that may be relevant to the subject's willingness to continue participation in the trial. The communication of this information is provided and documented via a revised consent form or addendum to the original consent form that captures the subject's dated signature or by the subject's legally acceptable representative's dated signature.

The informed consent adheres to IRB/ERC requirements, applicable laws and regulations and Sponsor requirements.

7.1.1.2 Inclusion/Exclusion Criteria

All inclusion and exclusion criteria are reviewed by the physician-investigator to ensure that the subject qualifies for the trial.

7.1.1.3 Medical History

A medical history is obtained by the investigator or qualified designee. Medical history includes all active conditions, and any condition diagnosed within the prior 10 years that are considered to be clinically significant by the Investigator. Details regarding the disease for which the subject has enrolled in this study are recorded separately and not listed as medical history.

7.1.1.4 Prior and Concomitant Medications Review 7.1.1.4.1 Prior Medications

The investigator or qualified designee reviews prior medication use, including any protocol-specified washout requirement, and records prior medication taken by the subject within 28 days before starting the trial. Treatment for the disease for which the subject has enrolled in this study is recorded separately and not listed as a prior medication.

7.1.1.4.2 Concomitant Medications

The investigator or qualified designee records medications, if any, taken by the subject during the trial.

7.1.1.5 Disease Details and Treatments 7.1.1.5.1 Disease Details

The investigator or qualified designee obtained prior and current details regarding disease status.

7.1.1.5.2 Prior Treatment Details

The investigator or qualified designee reviews all prior cancer treatments including systemic treatments, radiation and surgeries.

7.1.1.5.3 Subsequent Anti-Cancer Therapy Status

The investigator or qualified designee reviews all new anti-neoplastic therapy initiated after the last dose of trial treatment. If a subject initiates a new anti-cancer therapy within 30 days after the last dose of trial treatment, the 30 day Safety Follow-up visit occurs before the first dose of the new therapy. Once new anti-cancer therapy is initiated the subject moves into survival follow-up.

7.1.1.6 Trial Compliance (Medication/Diet/Activity/Other)

Please refer to Table 3 for additional information on dose modification guidelines for itacitinib-related adverse events.

7.1.2 Clinical Procedures/Assessments 7.1.2.1 Adverse Event (AE) Monitoring

The investigator or qualified designee assesses each subject to evaluate for potential new or worsening AEs as specified in the Trial Flow Chart and more frequently if clinically indicated. Adverse experiences are graded and recorded throughout the study and during the follow-up period according to NCI CTCAE Version 5.0. Toxicities are characterized in terms regarding seriousness, causality, toxicity grading, and action taken with regard to trial treatment. Please refer to Section 10 for additional information on the assessment and recording of adverse events.

7.1.2.2 Full Physical Exam

The investigator or licensed medical professional performs a complete physical exam during the screening period. Clinically significant abnormal findings are recorded as medical history. A full physical exam is performed during screening, 7.1.2.3 Directed Physical Exam For cycles that do not require a full physical exam per the Trial Flow Chart, the investigator or qualified designee performs a directed physical exam as clinically indicated prior to trial treatment administration. Directed physical examinations are symptoms and disease driven based on physician discretion.

7.1.2.4 Vital Signs

The investigator or qualified designee takes vital signs at screening, prior to beginning each treatment cycle and at treatment discontinuation as specified in the Trial Flow Chart (Section 6.0). Vital signs include temperature, pulse, weight and blood pressure. Height is measured at screening only.

7.1.2.5 Eastern Cooperative Oncology Group (ECOG) Performance Scale

The investigator or qualified designee assesses ECOG status (see Section 16.1) as specified in the Trial Flow Chart.

7.1.2.6 Tumor Imaging and Assessment of Disease

The initial tumor imaging is performed within 30 days prior to the first dose of trial treatment. Scans performed as part of routine clinical management are acceptable for use as the screening scan if they are of diagnostic quality and performed within 30 days prior to the first dose of trial treatment. A PET/CT is used to fulfill baseline imaging requirements; however a PET/CT cannot be substituted for post-infusion imaging.

As responses to immunotherapy may be delayed, no subjects has treatment decisions modified by the week 6 scan (42±7 days) alone—this is intended as a research scan to guide biopsies. A repeat scan at 12 weeks (performed at the end of Cycle 4 prior to Cycle 5/Day 1, approximately Day 14-21) is intended for the primary outcome and clinical decision-making. For subjects with stable disease or objective response who remain on study beyond 12 weeks, imaging is performed every 9 weeks. Tumor imaging timing follows calendar days and is not adjusted for delays in cycle starts or extension of pembrolizumab cycle duration.

After the first documentation of radiographic progression, it is at the discretion of the investigator either to verify true PD, to keep a clinically stable subject on trial treatment or to stop trial treatment until repeat imaging performed at least 28 days later confirms progression. Clinical Stability is defined as:

1) Absence of symptoms and signs indicating clinical significant progression of disease (including worsening of laboratory values) indicating disease progression.
2) No decline in ECOG performance status.
3) Absence of rapid progression of disease or progressive tumor at critical anatomical sites (e.g., cord compression) requiring urgent alternative medical intervention.

Subjects who are deemed clinically unstable and/or progressing are not required to have repeat imaging for confirmation. If progression is confirmed, then the subject is discontinued from trial treatment. If progression is not confirmed, then the subjects resumes/continues trial treatment and has their next scan as per protocol. When feasible, subjects are not discontinued until progression is confirmed.

The same imaging techniques are used to follow a subject throughout the trial. For subjects with brain metastases, MRI brain is included in the imaging follow up prior to treatment and at any time when a subject develops new neurologic symptoms.

7.1.3 Archived Tumor Tissue Sample

If available, an archived tumor tissue sample is requested for exploratory analysis after informed consent is obtained. Subjects are not asked to undergo an additional procedure to obtain this sample.

7.1.4 Unscheduled Research Sample Collections

Beyond the research sample collections scheduled for specific time points, up to 30 mL (2 tablespoons) of additional peripheral blood may be drawn once per week to better characterize correlates of clinical events. In addition, samples obtained during procedures performed for standard clinical indications (e.g., clinical tumor biopsies, etc) may be diverted for research use if such diversion does not substantially increase the risk of the procedure or compromise standard clinical diagnostic studies.

7.1.5 Laboratory Procedures/Assessments

Details regarding specific laboratory procedures/assessments performed in this trial are provided in FIG. 30. The total amount of blood/tissue to be drawn/collected over the course of the trial (from pre-trial to post-trial visits), including approximate blood/tissue volumes drawn/collected by visit and by sample type per subject may vary depending upon clinical course of the subject and length of time on trial.

7.1.6 Other Procedures 7.1.6.1 Withdrawal/Discontinuation

When a subject discontinues/withdraws prior to trial completion, all applicable activities scheduled for the final trial visit are performed at the time of discontinuation. Any adverse events which are present at the time of discontinuation/withdrawal are followed in accordance with the safety requirements outlined in Section 10. After discontinuing treatment, these subjects return to the site for a Safety Follow-up Visit and then proceed to the Follow-Up Period of the study as per the Trial Flow Chart in Section 6.

7.1.6.2 Blinding/Unblinding

Study treatment is open label for this study.

7.1.7 Visit Requirements

Visit requirements are outlined in Section 6.0—Trial Flow Chart. Specific procedure-related details are provided above in Section 7.1—Trial Procedures.

7.1.7.1 Screening

Visit requirements are outlined in Section 6.0—Trial Flow Chart. Specific procedure-related details are provided above in Section 7.1—Trial Procedures.

Prior to treatment initiation, potential subjects are evaluated to determine that they fulfill the entry requirements as set forth in Section 5.1. Screening procedures may be repeated. Written informed consent is obtained prior to performing any tests/procedures for research purposes. Results of a test performed prior to the subject signing consent as part of routine clinical management are acceptable in lieu of a screening test if performed within the specified time frame.

7.1.7.2 Treatment Period

Visit requirements are outlined in Section 6.0—Trial Flow Chart. Specific procedure-related details are provided above in Section 7.1—Trial Procedures.

7.1.7.3 Post-Treatment Visits

Visit requirements are outlined in Section 6.0—Trial Flow Chart. Specific procedure-related details are provided above in Section 7.1—Trial Procedures.

7.1.5.3.1 Safety Follow-Up Visit

The mandatory Safety Follow-Up Visit is conducted approximately 30 days after the last dose of trial treatment or before the initiation of a new anti-cancer treatment, whichever comes first. All AEs that occur prior to the Safety Follow-Up. Visit is recorded. Any SAEs experienced after this 30 day period are reported to the sponsor if the investigator suspects a causal relationship to the study treatment. Once an adverse event is detected, it is followed until its resolution or until it is judged to be permanent.

7.1.7.4 Post-Treatment Follow-Up Visits

Subjects who discontinue trial treatment for a reason other than disease progression move into the Post-Treatment Follow-Up Phase and are assessed every 8 weeks (56±7 days) for disease status until one of the following events: (1) disease progression; (2) initiation of non-study cancer treatment; (3) withdrawal of study consent; (4) loss to follow-up; or (5) death.

7.1.7.4.1 Survival Follow-Up

Once a subject experiences confirmed disease progression or starts a new anti-cancer therapy, the subject moves into the survival follow-up phase and is contacted by telephone every 12 weeks to assess for survival status. Survival follow-up continues up to 1 year from initiation of study treatment (Cycle 1/Day 1).

7.1.8 Definition of an Overdose for This Protocol and Reporting of Overdose to the Sponsor Pembrolizumab: Please refer to package insert.

Itacitinib: For purposes of this trial, an overdose is defined as any dose exceeding the prescribed dose of itacitinib. There is no clinical experience with overdosage of itacitinib. In clinical studies, the highest total daily dose was 1200 mg and no adverse events were associated with this dose. Treatment of overdose includes supportive care.

All reports of overdose with and without an adverse event are reported within 24 hours to the Sponsor.

8.0 Statistical Analysis Plan 8.1 Statistical Design 3-stage optimal design. The ORR for pembrolizumab in untreated PD-L1 positive advanced NSCLC was recently reported (Reck NEJM October 2016) to be 45% (95% CI 37-53%). The 3-stage optimal design (TT Chen, Statistics in Medicine 16:2701-2711, 1997) tests the null hypothesis that the ORR<35% (clearly inferior to pembrolizumab) versus the alternative that the ORR>55% (clearly superior to pembrolizumab). Eleven evaluable subjects are entered into the first stage of the study. If 2 or fewer of these 11 subjects respond, then the trial is terminated. If at least 3 of these subjects respond, then an additional 19 evaluable subjects are entered into the second stage of the study. If 12 or fewer of these 30 subjects respond, then the trial is terminated. If at least 13 of these subjects respond, then an additional 18 evaluable subjects are entered into the third stage of the study. If 20 or fewer of these 48 subjects respond, then it is concluded that the regimen does not merit further investigation. If at least 21 of these 48 subjects respond, then it is concluded that the regimen merits further investigation. If the true objective response rate is 35%, then the probability of recommending the regimen for further investigation (false positive error), is 0.100. While if the true objective response rate is 55%, then the probability of recommending the regimen for further investigation (power), is 0.906. If the true objective response rate is 35%, then the probability of early termination of the trial by the end of the second stage is 0.786. The software program, PASS v14 was employed to define this 3-stage design.

8.2 Statistical Analysis Plan

Based on evaluable subjects, the objective response rate and 95% confidence interval is calculated. Duration of remission, progression-free survival and overall survival are estimated by the method of Kaplan and Meier. Median values and 95% confidence intervals will be calculated. All observed toxicities will be graded and tabled. Toxicity tables will be separately constructed for cycles with pembrolizumab alone (cycles 1-2 and cycle>5) or pembrolizumab and itacitinib (cycles 3-4). Changes in immune pharmacodynamic biomarkers will be examined with scatter plots and summary statistics. Fold changes from baseline values will be estimated and summarized. Sample Size: The required sample size ranges from 11 to 48 evaluable subjects. In the event that 5% of subjects are not evaluable for objective response evaluation, the maximum sample size is 50 subjects. Study Duration: With an estimated accrual of 2 patients per month, it is anticipated that accrual will continue for approximately 24 months and subject follow-up will continue for up to year post Cycle 1/Day 1 (initiation of study treatment) for a total study duration of up to 36 months.

8.2.1 Hypothesis/Evaluation

Study Objectives are stated in Section 3.

Hypotheses

Pembrolizumab and itacitinib are associated with an ORR of at least 55% among patients with previously untreated, PD-L1 positive metastatic NSCLC.

Pembrolizumab and itacitinib are well tolerated among patients with previously untreated, PD-L1 positive metastatic NSCLC.

The addition of itacitinib to pembrolizumab results in increased T cell activation in the peripheral blood and decreased interferon signaling in tumor tissue in the week 12 biopsy, compared to the week 6 biopsy.

Analysis Endpoints Primary

There are two primary endpoints of this study: objective response rate (ORR) and tolerability of therapy.

Objective response rate: Objective response rate (ORR) is defined as the percentage of evaluable subjects who achieve a complete or partial clinical response according to RECIST criteria Tolerability of Therapy: Tolerability of therapy is determined on the basis of CTCAE adverse event reporting.

Secondary

Immune Biomarkers

Priority assays for research blood collection is multiparametric flow cytometry analysis of T cell subsets for changes in markers of exhaustion/activation. Additional assays include measurement of serum cytokines, circulating tumor cells and circulating DNA.

Tumor tissue is analyzed by immunohistochemical, transcriptomic and genomic approaches.

Overall Survival

Overall Survival (OS) is defined as the time from initiation of study therapy to death due to any cause or last subject contact. Subjects without documented death at the time of the final analysis are censored at the date of the last follow-up.

Progression Free Survival (PFS)

Progression-free survival (PFS) is defined as days from initiation of study therapy to first documented disease progression, death due to any cause or last subject contact which documents progression-free status Duration of Response (DOR)

Duration of response (DOR) is defined as days from first documented complete or partial clinical response to first documented disease progression.

8.2.2 Analysis Populations 8.2.2.1 Efficacy Analysis Populations

Subjects who either experience documented progressive disease during the first 12 weeks of treatment or complete the first 12 weeks of treatment and undergo re-staging are considered evaluable for objective response evaluation. Subjects who are withdrawn from study (due to toxicity or other reasons) in the first 12 weeks of treatment and who do not undergo re-staging are considered unevaluable for objective response evaluation but will be included in the safety analyses. The All Patients as Treated population is used for estimation of PFS and OS.

8.2.2.2 Safety Analysis Populations

The All Patients as Treated (APaT) population is used for the analysis of safety data in this study. The APaT population consists of all enrolled subjects who received at least one dose of study treatment with either itacitinib or pembrolizumab. At least one laboratory or vital sign measurement obtained subsequent to at least one dose of trial treatment is required for inclusion in the analysis of each specific parameter. To assess change from baseline, a baseline measurement is also required.

8.2.3 Statistical Methods Primary Objectives

1. Based on evaluable subjects, the objective response rate and 95% confidence interval is calculated.

2. Toxicities are graded, categorized and tabled. Toxicity tables are separately constructed for cycles with pembrolizumab alone (cycles 1-2 and cycle>5) or pembrolizumab and itacitinib (cycles 3-4).

Secondary Objectives

1. Changes in immune pharmacodynamic biomarkers are examined with scatter plots and summary statistics. Fold changes from baseline values are estimated and summarized.

2. Duration of response, progression-free survival and overall survival are estimated by the method of Kaplan and Meier. Median values and 95% confidence intervals will be calculated.

8.3 Sample Size

The required sample size ranges from 11 to 48 evaluable subjects. In the event that 5% of subjects are not evaluable for objective response evaluation, the maximum sample size is 50 subjects.

9.0 Labeling, Packaging, Storage and Return of Study Drugs 9.1 Itacitinib 9.1.1 Availability Study drug supplied by Incyte. Provided as 100 mg (free base equivalent) sustained-release tablets.

9.1.2 Preparation None 9.1.3 Storage and Stability

Itacitinib is stored in a secure, limited-access location at ambient conditions (15° C. to 30° C., or 59° F. to 86° F.).

9.1.4 Product Handling and Labeling

The investigator takes responsibility for and takes all steps to maintain appropriate records and ensure appropriate supply, storage, handling, distribution and usage of investigational product in accordance with the protocol and any applicable laws and regulations. Receipt and dispensing of trial medication are recorded by an authorized person at the trial site. All study drug dispensed are affixed with a clinical label in accordance with regulatory requirements. Subjects are instructed to bring all used/unused study medications to the site at each study visit. Subjects are asked to document administration on a study-supplied pill diary. Clinical supplies are not used for any purpose other than that stated in the protocol.

9.1.5 Potential Toxicities

Please refer to the itacitinib Investigator Brochure.

9.2 Pembrolizumab

Commercially available and administered per package insert with the exception of the drug is administered with another drug, itacitinib. Please refer to the pembrolizumab package insert for additional information.

9.3 Returns and Reconciliation (Itacitinib)

The investigator is responsible for keeping accurate records of the clinical supplies received from Incyte, the amount dispensed to and returned by the subjects, and the amount remaining at the conclusion of the trial. Upon completion or termination of the study, all unused and/or partially used investigational product is destroyed and/or returned as per instructions from the sponsor. It is the Investigator's responsibility to arrange for appropriate disposal according to applicable federal, state, local and institutional guidelines and procedures, and maintain appropriate records of disposal.

10.0 Safety and Adverse Events 10.1 Definitions Adverse Event

An adverse event (AE) is any untoward medical occurrence associated with the use of a drug in humans, whether or not considered drug related. Intercurrent illnesses or injuries should be regarded as adverse events.

Serious Adverse Event:

Adverse events are classified as serious or non-serious. A serious adverse event is any AE that is:

fatal life-threatening requires or prolongs hospital stay leads to a persistent or significant disability or incapacity or substantial disruption of the ability to conduct normal life functions a congenital anomaly or birth defect an important medical event Note that hospitalizations that meet the following criteria are not reported as serious adverse events:

Routine treatment or monitoring of the studied indication, not associated with any deterioration in condition, such as preplanned study visits and preplanned hospitalizations for study procedures or treatment administration Elective or pre-planned treatment for a pre-existing condition that is unrelated to the indication under study and has not worsened since signing the informed consent Social reasons and respite care in the absence of any deterioration in the patient's general condition Note that treatment on an emergency outpatient basis that does not result in hospital admission and involves an event not fulfilling any of the definitions of a SAE given above is not a serious adverse event.

Important medical events are those that may not be immediately life threatening, but are clearly of major clinical significance. They may jeopardize the subject, and may require intervention to prevent one of the other serious outcomes noted above. For example, drug overdose or abuse, a seizure that did not result in in-patient hospitalization, or intensive treatment of bronchospasm in an emergency department would typically be considered serious.

All adverse events that do not meet any of the criteria for serious should be regarded as non-serious adverse events.

Unexpected Adverse Events:

An adverse event is considered unexpected if the event severity and/or frequency is not described in the investigator brochure, package insert, or protocol. Please refer to the itacitinib investigator brochure and pembrolizumab package insert for additional detail related to severity and/or frequency of a particular event.

Related Adverse Events:

An adverse event is considered related to participation in the research if there is a reasonable possibility that an event was caused by an investigational product, intervention, or research-required procedures. For the purposes of this study, "reasonable possibility" means there is evidence to suggest a causal relationship.

Adverse Event Reporting Period:

Collection of adverse events begin at the time of consent and continue through the Safety Follow-up Visit. After the Safety Follow-up Visit, any SAE that the investigator becomes aware of should be reported to the sponsor if the investigator suspects the event may reasonably be related to the study treatment.

Preexisting Condition/General Physical Examination Findings:

A preexisting condition is one that is present prior to the start of the Adverse Event Reporting Period. At screening, any clinically significant abnormality is recorded as a preexisting condition on the medical history eCRF. During the course of the study, a preexisting condition is recorded as an adverse event if the frequency, intensity, or the character of the condition worsens. Preexisting conditions that improve are recorded appropriately.

Abnormal Laboratory Values:

A clinical laboratory abnormality is documented as an adverse event if any one of the following conditions is met:

The laboratory abnormality is not otherwise refuted by a repeat test to confirm the abnormality The abnormality suggests a disease and/or organ toxicity The abnormality is of a degree that requires active management; e.g. change of dose, discontinuation of the drug, more frequent follow-up assessments, further diagnostic investigation, etc.

Laboratory abnormalities that meet the criteria for Adverse Events are followed until they have returned to normal or an adequate explanation of the abnormality is found. When an abnormal laboratory or test result corresponds to a sign/symptom of an already reported adverse event, it is not necessary to separately record the lab/test result as an additional event. Laboratory abnormalities that do not meet the definition of an adverse event, should are not reported as adverse events. A Grade 3 or 4 event (severe) as per CTCAE does not automatically indicate a SAE unless it meets the definition of serious defined above and/or as per investigator's discretion. Whenever possible, a diagnosis, rather than a symptom is provided (i.e. anemia instead of low hemoglobin).

10.2 Recording of Adverse Events

Safety is assessed by monitoring and recording potential adverse effects of the treatment using the Common Terminology Criteria version 5.0 at each study visit.

Patients are monitored by medical histories, physical examinations, and blood studies to detect potential toxicities from the treatment. If CTCAE grading does not exist for an adverse event, the severity of mild, moderate, severe, life-threatening, and death, corresponding to Grades 1-5, are used whenever possible. Subjects are monitored by medical histories, physical examinations, and blood studies to detect potential toxicities from the treatment.

At each contact with the subject, the investigator seeks information on adverse events by non-directive questioning and, as appropriate, by examination. Adverse events also are detected when they are volunteered by the subject during the screening process or between visits, or through physical examination, laboratory test, or other assessments. Information on all adverse events are recorded in the source documentation. All clearly related signs, symptoms, and abnormal diagnostic procedures results are recorded in the source document, though are grouped under one diagnosis. To the extent possible, adverse events are recorded as a diagnosis and symptoms used to make the diagnosis recorded within the diagnosis event. Symptoms are not listed separately if a diagnosis can be assigned.

All adverse events occurring during the adverse event reporting period (defined in Section 10.1 above) are recorded.

As much as possible, each adverse event is evaluated to determine:

1. The severity grade (CTCAE Grade 1-5)
2. Its duration (Start and end dates)
3. Its relationship to the study treatment—[Reasonable possibility that AE is related: No (unrelated/not suspected) or Yes (a suspected adverse reaction)]. If yes (suspected)—is the event possibly, probably or definitely related to the investigational treatment?
4. Expectedness to study treatment—[Unexpected—if the event severity and/or frequency is not described in the investigator brochure (if applicable) or protocol].
5. Action taken with respect to study or investigational treatment (none, dose adjusted, temporarily interrupted, permanently discontinued, unknown, not applicable)
6. Whether medication or therapy taken (no concomitant medication/non-drug therapy, concomitant medication/non-drug therapy)
7. Whether it is serious, where a serious adverse event (SAE) is defined as in Section 10.1.

All adverse events are treated appropriately. If a concomitant medication or non-drug therapy is given, this action is recorded. Once an adverse event is detected, it is followed until its resolution or until it is judged to be permanent, and assessment is made at each visit (or more frequently, if necessary) of any changes in severity, the suspected relationship to the study treatment, the interventions required to treat it, and the outcome.

Adverse events that occur concurrently with the progression of malignancy but that are not related to disease progression (i.e. deep vein thrombosis or hemoptysis) are reported as an adverse event as described above. Progression of malignancy resulting in death should is reported as a serious adverse event.

Serious adverse events that are still ongoing at the end of the adverse event reporting period are followed to determine the final outcome. Any serious adverse event that occurs after the adverse event reporting period and is considered to be possibly related to the study treatment or study participation, is recorded and reported.

10.3 Reporting of Serious Adverse Events

Every SAE, regardless of suspected causality, occurring during the adverse event reporting period defined in Section 10.1 is reported to the sponsor within 24 hours of learning of its occurrence. The original SAE notification may take place by email to meet the 24 hour reporting window. However within 3 business days of knowledge of the event, the investigator submits a complete SAE form to the Sponsor along with any other diagnostic information that will assist the understanding of the event. The Investigator keeps a copy of this SAE Form on file at the study site.

Follow-up information on SAEs are reported when updates are available, as a follow-up to the initial SAE form, and include both the follow-up number and report date. New information on ongoing serious adverse events are provided promptly to the sponsor. The follow-up information describes whether the event has resolved or continues, if there are any changes in assessment, if and how it was treated, and whether the subject continued or withdrew from study participation.

At the time of the initial report, the following information is provided: Study identifier, subject number, a description of the event, date of onset, current status, whether study treatment was discontinued, a description of the event, date of onset, current status, the reason the event is classified as serious, investigator assessment of the association between the event and study treatment, and expectedness relative to investigational product(s). The Sponsor Team will communicate all SAEs to Incyte per the terms of the research agreement.

10.3.1 Investigator Reporting: Local Regulatory Review Committees

Report events to local regulatory review committees per institutional policy.

10.3.2 Pregnancies

To ensure patient safety, each pregnancy occurring while the patient is on study treatment must be reported to protocol sponsor within 24 hours of learning of its occurrence. The pregnancy should be followed up to determine outcome, including spontaneous or voluntary termination, details of the birth, and the presence or absence of any birth defects, congenital abnormalities, or maternal and/or newborn complications.

Pregnancy should be recorded on a Clinical Trial Pregnancy Form and reported by the investigator to the protocol sponsor Pregnancy follow-up should be recorded on the same form and should include an assessment of the possible relationship to the study drug for any pregnancy outcome. Any SAE experienced during pregnancy must be reported on the SAE Report Form. Pregnancy outcomes must be collected for the female partners of any males who took study treatment in this study. Consent to report information regarding these pregnancy outcomes should be obtained from the mother.

10.4 Protocol Exceptions and Deviations

Exception: A one time, intentional action or process that departs from the approved study protocol, intended for one occurrence. If the action disrupts the study progress, such that the study design or outcome (endpoints) may be compromised, or the action compromises the safety and welfare of study subjects, advance documented approval from the Regulatory Sponsor and local regulatory review committees per institutional guidelines is required. Approval from the Regulatory Sponsor must be received prior to submission to local regulatory review committees for approval. However, the departure is intended to eliminate an apparent immediate hazard to subjects may be implemented immediately provided the Sponsor is subsequently notified immediately.

Deviation: A one time, unintentional action or process that departs from the approved study protocol, involving one incident and identified retrospectively, after the event occurred. If the impact on the protocol disrupts the study design, may affect the outcome (endpoints) or compromises the safety and welfare of the subjects, the deviation must be reported to the Regulatory Sponsor within 10 business days of PI knowledge, and to local regulatory review committees per institutional guidelines. Acknowledgement from the Regulatory Sponsor must be received prior to submission to local regulatory review committees.

Other deviations are appropriately documented per site policies/procedures (such as a subject missing a visit is not an issue unless a critical/important treatment or procedure was missed and must have been done at that specific time). The following information is included on the Sponsor supplied exception/deviation form: protocol number, subject study number, description of the exception/deviation from the protocol, and rationale. All completed exception/deviation forms are signed by the Principal Investigator (or sub-investigator) and submitted to the Sponsor Project Manager for review. Once approval of the exception request or acknowledgement of the deviation has been granted by the Regulatory Sponsor, the exception or deviation is submitted to all applicable committees for review and approval.

11.0 Data Handling and Recordkeeping 11.1 Confidentiality

Information about study subjects is kept confidential and managed according to the requirements of the Health Insurance Portability and Accountability Act (HIPAA) of 1996. Those regulations require a signed subject authorization informing the subject of the following:

What protected health information (PHI) will be collected from subjects in this study Who will have access to that information and why Who will use or disclose that information The rights of a research subject to revoke their authorization for use of their PHI In the event that the subject revokes authorization to collect or use PHI, the investigator, by regulation, retains the ability to use all information collected prior to the revocation of subject authorization. For subjects that have revoked authorization to collect or use PHI, attempts should be made to obtain permission to collect at least vital status (i.e. that the subject is alive) at the end of their scheduled study period.

11.2 Source Documents

Source data is all information, original records of clinical findings, observations, or other activities in a clinical trial necessary for the reconstruction and evaluation of the trial.

Source data are contained in source documents Examples of these original documents, and data records include: hospital records, clinical and office charts, laboratory notes, memoranda, subjects' diaries or evaluation checklists, pharmacy dispensing records, recorded data from automated instruments, copies or transcriptions certified after verification as being accurate and complete, microfiches, photographic negatives, microfilm or magnetic media, x-rays, subject files, and records kept at the pharmacy, at the laboratories, and at medico-technical departments involved in the clinical trial.

11.3 Case Report Forms

The study case report form (CRF) is the primary data collection instrument for the study. All data requested on the CRF are recorded. All entries are entered into an electronic data capture system (EDC) via PennCTMS/VELOS. The Principal Investigator is responsible for assuring that the data entered into eCRF is complete, accurate, and that entry and updates are performed in a timely manner.

11.4 Records Retention

It is the investigator's responsibility to retain study essential documents for at least 2 years after the last approval of a marketing application in their country and until there are no pending or contemplated marketing applications in their country or at least 2 years have elapsed since the formal discontinuation of clinical development of the investigational product. These documents are retained for a longer period if required by an agreement with the sponsor. In such an instance, it is the responsibility of the sponsor to inform the investigator/institution as to when these documents no longer need to be retained.

12.0 Study Monitoring, Auditing, and Inspecting 12.1 Study Monitoring Plan

This study is monitored according to the Sponsor Data and Safety Monitoring Plan. Interim Monitoring Visits are conducted during the course of the study. The Monitors assure that submitted data are accurate and in agreement with source documentation; verify that investigational products are properly stored and accounted for, verify that subjects' consent for study participation has been properly obtained and documented, confirm that research subjects entered into the study meet inclusion and exclusion criteria, and assure that all essential documentation required by Good Clinical Practices (GCP) guidelines are appropriately filed.

At the end of the study, Monitors conduct a close-out visit and will advise on storage of study records and disposition of unused study drug. The investigator allocates adequate time for such monitoring activities. The Investigator also ensures that the monitor or other compliance reviewer is given access to all the above noted study-related documents and study related facilities (e.g. pharmacy, diagnostic laboratory, etc.), and has adequate space to conduct the monitoring visit.

12.2 Auditing and Inspecting

The investigator permits study-related monitoring, audits, and inspections by the IRB, the sponsor, government regulatory bodies, and University compliance groups of all study related documents (e.g. source documents, regulatory documents, data collection instruments, study data etc.). The investigator ensures the capability for inspections of applicable study-related facilities (e.g. pharmacy, diagnostic laboratory, etc.).

Participation as an investigator in this study implies acceptance of potential inspection by government regulatory authorities and applicable University compliance offices. The Principal Investigator must notify the Sponsor in real-time if an audit/inspection notification is received.

US 12,662,705 B2

83                                           84

13.0 Ethical Considerations

This study is conducted according to US and international standards of Good Clinical Practice (FDA Title 21 part 312 and International Conference on Harmonization guidelines), applicable government regulations and Institutional research policies and procedures.

This protocol and any amendments are submitted to a properly constituted independent Institutional Review Board (IRB), in agreement with local legal prescriptions, for formal approval of the study conduct. The decision of the IRB concerning the conduct of the study is made in writing to the investigator and a copy of this decision is provided to the sponsor before commencement of this study.

All subjects for this study are provided a consent form describing this study and providing sufficient information for subjects to make an informed decision about their participation in this study. This consent form is submitted with the protocol for review and approval by the IRB for the study. The formal consent of a subject, using the IRB-approved consent form, is obtained before that subject is submitted to any study procedure. This consent form is signed by the subject and the physician-investigator obtaining the consent. The protocol is listed under clinicaltrials.gov.

14.0 Appendices 16.1 ECOG Performance Status

| Grade | Description |
|---|---|
| 0 | Normal activity. Fully active, able to carry on all pre-disease performance without restriction. |
| 1 | Symptoms, but ambulatory. Restricted in physically strenuous activity, but ambulatory and able to carry out work of a light or sedentary nature (e.g. light housework office work) |
| 2 | In bed <50% of the time. Ambulatory and capable of all self-care, but unable to carry out any work activities. Up and about more than 50% of waking hours |
| 3 | In bed >50% of the time. Capable of only limited self-care, confined to bed or chair more than 50% of waking hours. |
| 4 | 100% bedridden. Completely disabled. Cannot carry on any self- care. Totally confined to bed or chair |
| 5 | Dead. |

*As published in *Am. J. Clin. Oncol.*: Oken, M.M., Creech, R.H., Tormey, D.C., Horton, J., Davis, T.E., McFadden, E.T., Carbone, P.P.: Toxicity And Response Criteria Of The Eastern Cooperative Oncology Group. Am J Clin Oncol 5:649-655, 1982. The Eastern Cooperative Oncology Group, Robert Comis M.D., Group Chair.

16.2 Response Evaluation Criteria in Solid Tumors (RE-CIST) 1.1—Criteria for Evaluating Response in Solid Tumors RECIST version 1.1 [44] is used in this study for assessment of tumor response.

While either CT or MRI may be utilized, as per RECIST 1.1, CT is the preferred imaging technique in this study.

References Cited in Example 20

1. Reck, M., et al., Pembrolizumab versus Chemotherapy for P D-L1-Positive Non-Small-Cell Lung Cancer. N Engl J Med, 2016.
2. Chen, T. T., Optimal three-stage designs for phase II cancer clinical trials. Stat Med, 1997. 16(23): p. 2701-11.
3. Siegel, R. L., K. D. Miller, and A. Jemal, Cancer statistics, 2015. CA Cancer J Clin, 2015. 65(1): p. 5-29.
4. Ettinger, D. S., et al., Non-small cell lung cancer, version 1.2015, in Journal of the National Comprehensive Cancer Network: JNCCN2013. p. 645-53—quiz 653.
5. Scagliotti, G. V., et al., Phase III Study Comparing Cisplatin Plus Gemcitabine With Cisplatin Plus Pemetrexed in Chemotherapy-Naive Patients With Advanced- Stage Non-Small-Cell Lung Cancer. Journal of clinical oncology: official journal of the American Society of Clinical Oncology, 2008. 26(21): p. 3543-3551.
6. Morabito, A., et al., Randomized phase III trial of gemcitabine and cisplatin vs. gemcitabine alone in patients with advanced non-small cell lung cancer and a performance status of 2: the CAPPA-2 study. Lung cancer (Amsterdam, Netherlands), 2013. 81(1): p. 77-83.
7. Herbst, R. S., et al., Pembrolizumab versus docetaxel for previously treated, PD-L1-positive, advanced non-small-cell lung cancer (KEYNOTE-010): a randomised controlled trial. The Lancet, 2015.
8. Borghaei, H., et al., Nivolumab versus Docetaxel in Advanced Nonsquamous Non-Small-Cell Lung Cancer. The New England journal of medicine, 2015.
9. Brahmer, J., et al., Nivolumab versus Docetaxel in Advanced Squamous-Cell Non-Small-Cell Lung Cancer. N Engl J Med, 2015. 373(2): p. 123-35.
10. Disis, M. L., Immune regulation of cancer. J Clin Oncol, 2010. 28(29): p. 4531-8.
11. Dong, H., et al., Tumor-associated B7-H1 promotes T-cell apoptosis: a potential mechanism of immune evasion. Nat Med, 2002. 8(8): p. 793-800.
12. Sharpe, A. H. and G. J. Freeman, The B7-CD28 superfamily. Nat Rev Immunol, 2002. 2(2): p. 116-26.
13. Brown, J. A., et al., Blockade of programmed death-1 ligands on dendritic cells enhances T cell activation and cytokine production. J Immunol, 2003. 170(3): p. 1257-66.
14. Francisco, L. M., P. T. Sage, and A. H. Sharpe, The PD-1 pathway in tolerance and autoimmunity. Immunol Rev, 2010. 236: p. 219-42.
15. Thompson, R. H., et al., PD-1 is expressed by tumor-infiltrating immune cells and is associated with poor outcome for patients with renal cell carcinoma. Clin Cancer Res, 2007. 13(6): p. 1757-61.
16. Hino, R., et al., Tumor cell expression of programmed cell death-1 ligand 1 is a prognostic factor for malignant melanoma. Cancer, 2010. 116(7): p. 1757-66.
17. Nomi, T., et al., Clinical significance and therapeutic potential of the programmed death-1 ligand/programmed death-1 pathway in human pancreatic cancer. Clin Cancer Res, 2007. 13(7): p. 2151-7.
18. Al-Shibli, K. I., et al., Prognostic effect of epithelial and stromal lymphocyte infiltration in non-small cell lung cancer. Clin Cancer Res, 2008. 14(16): p. 5220-7.

19. Talmadge, J. E., M. Donkor, and E. Scholar, Inflammatory cell infiltration of tumors: Jekyll or Hyde. Cancer Metastasis Rev, 2007. 26(3-4): p. 373-400.
20. Deschoolmeester, V., et al., Tumor infiltrating lymphocytes: an intriguing player in the survival of colorectal cancer patients. BMC Immunol, 2010. 11: p. 19.
21. Diez, M., et al., Histopathologic prognostic score in colorectal adenocarcinomas. Anticancer Res, 1998. 18(1B): p. 689-94.
22. Galon, J., et al., Type, density, and location of immune cells within human colorectal tumors predict clinical outcome. Science, 2006. 313(5795): p. 1960-4.
23. Hiraoka, N., Tumor-infiltrating lymphocytes and hepatocellular carcinoma: molecular biology. Int J Clin Oncol, 2010. 15(6): p. 544-51.
24. Nobili, C., et al., Prolonged survival of a patient affected by pancreatic adenocarcinoma with massive lymphocyte and dendritic cell infiltration after interleukin-2 immunotherapy. Report of a case. Tumori, 2008. 94(3): p. 426-30.
25. Hodi, F. S. and G. Dranoff, The biologic importance of tumor-infiltrating lymphocytes. J Cutan Pathol, 2010. 37 Suppl 1: p. 48-53.
26. Kloor, M., Lymphocyte infiltration and prognosis in colorectal cancer. Lancet Oncol, 2009. 10(9): p. 840-1.
27. Lee, H. E., et al., Prognostic implications of type and density of tumour-infiltrating lymphocytes in gastric cancer. Br J Cancer, 2008. 99(10): p. 1704-11.
28. Leffers, N., et al., Prognostic significance of tumor-infiltrating T-lymphocytes in primary and metastatic lesions of advanced stage ovarian cancer. Cancer Immunol Immunother, 2009. 58(3): p. 449-59.
29. Nishimura, H., T. Honjo, and N. Minato, Facilitation of beta selection and modification of positive selection in the thymus of PD-1-deficient mice. J Exp Med, 2000. 191(5): p. 891-8.
30. Liotta, F., et al., Frequency of regulatory T cells in peripheral blood and in tumour-infiltrating lymphocytes correlates with poor prognosis in renal cell carcinoma. BJU Int, 2011. 107(9): p. 1500-6.
31. Topalian, S. L., C. G. Drake, and D. M. Pardoll, Immune checkpoint blockade: a common denominator approach to cancer therapy. Cancer Cell, 2015. 27(4): p. 450-61.
32. Diamond, M. S., et al., Type I interferon is selectively required by dendritic cells for immune rejection of tumors. J Exp Med, 2011. 208(10): p. 1989-2003.
33. Minn, A. J., Interferons and the Immunogenic Effects of Cancer Therapy. Trends Immunol, 2015. 36(11): p. 725-37.
34. Garon, E. B., et al., Pembrolizumab for the treatment of non-small-cell lung cancer. N Engl J Med, 2015. 372(21): p. 2018-28.
35. Caetano, M. S., et al., IL6 Blockade Reprograms the Lung Tumor Microenvironment to Limit the Development and Progression of K-ras-Mutant Lung Cancer. Cancer Res, 2016. 76(11): p. 3189-99.
36. Benci, J. L., et al., Tumor Interferon Signaling Regulates a Multigenic Resistance Program to Immune Checkpoint Blockade. Cell, 2016. 167(6): p. 1540-1554 e12.
37. Teijaro, J. R., et al., Persistent LCMV infection is controlled by blockade of type I interferon signaling. Science, 2013. 340(6129): p. 207-11.
38. Wilson, E. B., et al., Blockade of chronic type I interferon signaling to control persistent LCMV infection. Science, 2013. 340(6129): p. 202-7.
39. Borghaei, H., et al., Nivolumab versus Docetaxel in Advanced Nonsquamous Non-Small-Cell Lung Cancer. N Engl J Med, 2015. 373(17): p. 1627-39.
40. Topalian, S. L., et al., Mechanism-driven biomarkers to guide immune checkpoint blockade in cancer therapy. Nat Rev Cancer, 2016. 16(5): p. 275-87.
41. McLaughlin, J., et al., Quantitative Assessment of the Heterogeneity of P D-L1 Expression in Non-Small-Cell Lung Cancer. JAMA Oncol, 2016. 2(1): p. 46-54.
42. Wolchok, J. D., et al., Guidelines for the evaluation of immune therapy activity in solid tumors: immune-related response criteria. Clin Cancer Res, 2009. 15(23): p. 7412-20.
43. Mascarenhas, J. O., et al., Primary analysis of a phase II open-label trial of INCB039110, a selective JAK1 inhibitor, in patients with myelofibrosis. Haematologica, 2016.
44. E. A. Eisenhauer, P. Therasse, J. Bogaerts, L. H. Schwartz, D. Sargent, R. Ford, J. Dancey, S. Arbuck, S. Gwyther, M. Mooney, L. Rubinstein, L. Shankar, L. Dodd, R. Kaplan, D. Lacombe, J. Verweij. New response evaluation criteria in solid tumors: Revised RECIST guideline (version 1.1). Eur J Cancer. 2009 January; 45(2):228-47.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating cancer in a subject in need thereof, the method comprising:

measuring expression level of an interferon stimulating genes resistance signature (ISG.RS) metagene in a tumor from the subject and/or in a cancer cell from the subject;

measuring expression level of an interferon gene signature (IFNG.GS) metagene in a tumor from the subject and/or in an intratumoral immune cell from the subject; and administering an immunotherapy comprising an immune checkpoint blockade (ICB) to the subject when the measured expression level of the IFNG.GS metagene is greater than the measured expression level of the ISG.RS metagene, or administering an alternative cancer treatment to the subject when the measured expression level of the ISG.RS metagene is greater than the measured expression level of the IFNG.GS metagene, wherein the subject is not administered the immunotherapy, thereby treating the cancer in the subject; wherein:

the cancer is melanoma;

the ISG.RS metagene comprises IFI27, IRF7, USP18, BST2, CXCL10, DDX60, HERC6, HLA-B, HLA-G, IFI35, IFI44, IFI44L, IFIT1, IFIT3, ISG15, LGALS3BP, LY6E, MX1, MX2, OAS3, OASL, PLSCR1, STAT1, TRIM14, HSD17B1, OAS1, CA2, CCNA1, CXCL1, GALC, IFI6, IFITM1, LAMP3, MCL1, ROBO1, SLC6A15, THBS1, and TIMP3; and the IFNG.GS metagene comprises TNFSF10, IRF9, EPSTI1, PARP12, TRIM25, CASP7, UPP1, B2M, IRF4, SRI, NFKBIA, OAS2, RSAD2, XAF1, SP110, IFITM3, GBP4, IRF8, IFIH1, UBE2L6, ADAR, STAT2, CXCL9, IL10RA, PLA2G4A, TRIM21, PTGS2, DDX58, IL15, NLRC5, NMI, IDO1, PSMB10, CXCL11, SAMD9L, RTP4, PTPN2, TNFAIP2, IFITM2, SOCS1, CASP1, ICAM1, WARS, PSME1, ISG20, FCGR1A, SOCS3, HLA-DMA, TNFAIP6, TRIM26, VCAM1, CD274, CIITA, NAMPT, GPR18, FPR1, PRIC285, PSME2, SERPING1, CCL5, RNF31, SOD2, PSMA3, RNF213, PELI1, CFB, CD86, HLA-DQA1, GCH1, PNP, CCL7, PTPN6, SPPL2A, IL4R, DHX58, CASP8, IFI30, CCL2, FGL2, SECTM1, IL15RA, CD40, HLA-DRB1, GBP6, LCP2, MT2A, RIPK1, PSMB2, TDRD7, HIF1A, PFKP, ZBP1, PDE4B, IL7, BPGM, FTSJD2, AUTS2, RIPK2, MYD88, PSMA2, NOD1, TAPBP, SLC25A28, PTPN1, SSPN, NUP93, MTHFD2, CDKN1A, NFKB1, BATF2, LATS2, IRF5, SLAMF7, ISOC1, P2RY14, STAT3, NCOA3, GZMA, IFNAR2, CD74, RAPGEF6, CASP4, OGFR, ARL4A, LYSMD2, CSF2RB, C1R, METTL7B, ST8SIA4, CD38, PSMB9, BANK1, TOR1B, ITGB7, RBCK1, FAS, LAP3, SAMHD1, CMPK2, MVP, TXNIP, ST3GAL5, PARP14, CASP3, IFIT2, CD69, CMKLR1, TAP1, EIF2AK2, PIM1, XCL1, IL2RB, IRF1, BTG1, CFH, VAMP5, IL18BP, IRF2, ZNFX1, PSMB8, ARID5B, MARCH1, TNFAIP3, APOL6, STAT4, JAK2, PML, TRAFD1, SELP, KLRK1, CIS, EIF4E3, HLA-A, PNPT1, VAMP8, and IL6.

2. The method of claim 1, wherein the ICB is selected from the group consisting of anti-CTLA4, anti-PD1, anti-PDL1, and any combination thereof, and/or the immunotherapy further comprises adoptive cell therapy comprising CAR T cell therapy or TCR engineered T cell therapy.

3. The method of claim 2, wherein the ICB comprises anti-PD1 and anti-CTLA4.

4. The method of claim 1, wherein:

(a) the alternative treatment comprises one or more selected from the group consisting of chemotherapy, radiation, surgery, an alternative immune checkpoint blockade (ICB), an alternative adoptive cell therapy, an alternative immunotherapy, and any combination thereof, and/or (b) the alternative treatment comprises a treatment that increases the IFNG.GS metagene expression level and/or decreases the ISG.RS metagene expression level.

5. The method of claim 4, wherein:

(a) the treatment that decreases the ISG.RS metagene expression level comprises one or more selected from the group consisting of an IFN blocking agent, an IFN receptor blocking agent, a JAK inhibitor, a STAT inhibitor, an alternative adoptive cell therapy, a small molecule, and any combination thereof; and/or (b) the treatment that increases the IFNG.GS metagene expression level comprises one or more selected from the group consisting of anti-CTLA4, anti-PDL1, anti-TIM3, anti-LAG3, anti-2B4, anti-4-1BB, anti-GITR, anti-VISTA, anti-CD40, cGAS/STING agonists, RIG-I agonists, TLR agonists, MDA5 agonists, radiation, chemotherapy, molecularly targeted agents, epigenetic therapies, and any combination thereof.

6. The method of claim 1, wherein the intratumoral immune cell is selected from the group consisting of a T cell, a natural killer (NK) cell, a macrophage, a dendritic cell, a myeloid cell, an innate lymphoid cell (ILC), and a CD8+ cell.

7. The method of claim 1, wherein measuring the expression level comprises at least one method selected from the group consisting of RNA-Seq, q-PCR, RT-PCR, sequencing, transcriptomics, and microarray.

8. A method for treating cancer in a subject in need thereof, the method comprising:

measuring expression level of an interferon stimulating genes resistance signature (ISG.RS) metagene in a tumor from the subject and/or in a cancer cell from the subject;

measuring expression level of an interferon gene signature (IFNG.GS) metagene in a tumor from the subject and/or in an intratumoral immune cell from the subject;

calculating a ratio of the expression level of the IFNG.GS metagene over the expression level of the ISG.RS metagene; and administering an immunotherapy comprising an immune checkpoint blockade (ICB) to the subject when the ratio is increased in comparison to that of a reference sample; or administering an alternative cancer treatment to the subject when the ratio is not increased in comparison to that of a reference sample, wherein the subject is not administered the immunotherapy, thereby treating the cancer in the subject; wherein:

the cancer is melanoma;

the ISG.RS metagene comprises IFI27, IRF7, USP18, BST2, CXCL10, DDX60, HERC6, HLA-B, HLA-G, IFI35, IFI44, IFI44L, IFIT1, IFIT3, ISG15, LGALS3BP, LY6E, MX1, MX2, OAS3, OASL, PLSCR1, STAT1, TRIM14, HSD17B1, OAS1, CA2, CCNA1, CXCL1, GALC, IFI6, IFITM1, LAMP3, MCL1, ROBO1, SLC6A15, THBS1, and TIMP3; and the IFNG.GS metagene comprises TNFSF10, IRF9, EPSTI1, PARP12, TRIM25, CASP7, UPP1, B2M, IRF4, SRI, NFKBIA, OAS2, RSAD2, XAF1, SP110, IFITM3, GBP4, IRF8, IFIH1, UBE2L6, ADAR, STAT2, CXCL9, IL10RA, PLA2G4A, TRIM21, PTGS2, DDX58, IL15, NLRC5, NMI, IDO1, PSMB10, CXCL11, SAMD9L, RTP4, PTPN2, TNFAIP2, IFITM2, SOCS1, CASP1, ICAM1, WARS, PSME1, ISG20, FCGR1A, SOCS3, HLA-DMA, TNFAIP6, TRIM26, VCAM1, CD274, CIITA, NAMPT, GPR18, FPR1, PRIC285, PSME2, SERP-ING1, CCL5, RNF31, SOD2, PSMA3, RNF213, PELI1, CFB, CD86, HLA-DQA1, GCH1, PNP, CCL7, PTPN6, SPPL2A, IL4R, DHX58, CASP8, IFI30, CCL2, FGL2, SECTM1, IL15RA, CD40, HLA-DRB1, GBP6, LCP2, MT2A, RIPK1, PSMB2, TDRD7, HIF1A, PFKP, ZBP1, PDE4B, IL7, BPGM, FTSJD2, AUTS2, RIPK2, MYD88, PSMA2, NOD1, TAPBP, SLC25A28, PTPN1, SSPN, NUP93, MTHFD2, CDKN1A, NFKB1, BATF2, LATS2, IRF5, SLAMF7, ISOC1, P2RY14, STAT3, NCOA3, GZMA, IFNAR2, CD74, RAPGEF6, CASP4, OGFR, ARL4A, LYSMD2, CSF2RB, C1R, METTL7B, ST8SIA4, CD38, PSMB9, BANK1, TOR1B, ITGB7, RBCK1, FAS, LAP3, SAMHD1, CMPK2, MVP, TXNIP, ST3GAL5, PARP14, CASP3, IFIT2, CD69, CMKLR1, TAP1, EIF2AK2, PIM1, XCL1, IL2RB, IRF1, BTG1, CFH, VAMP5, IL18BP, IRF2, ZNFX1, PSMB8, ARID5B, MARCH1, TNFAIP3, APOL6, STAT4, JAK2, PML, TRAFD1, SELP, KLRK1, CIS, EIF4E3, HLA-A, PNPT1, VAMP8, and IL6.

9. The method of claim 8, wherein the ICB is selected from the group consisting of anti-CTLA4, anti-PD1, anti-PDL1, and any combination thereof, and/or the immunotherapy further comprises adoptive cell therapy comprising CAR T cell therapy or TCR engineered T cell therapy.

10. The method of claim 8, wherein the ICB comprises anti-PD1 and anti-CTLA4.

11. The method of claim 8, wherein:

(a) the alternative treatment comprises one or more selected from the group consisting of chemotherapy, radiation, surgery, an alternative immune checkpoint blockade (ICB), an alternative adoptive cell therapy, an alternative immunotherapy, and any combination thereof; and/or (b) the alternative treatment comprises a treatment that increases the IFNG.GS metagene expression level and/or decreases the ISG.RS metagene expression level.

12. The method of claim 11, wherein:

(a) the treatment that decreases the ISG.RS metagene expression level comprises one or more selected from the group consisting of an IFN blocking agent, an IFN receptor blocking agent, a JAK inhibitor, a STAT inhibitor, an alternative adoptive cell therapy, a small molecule, and any combination thereof; and/or (b) the treatment that increases the IFNG.GS metagene expression level comprises one or more selected from the group consisting of anti-CTLA4, anti-PDL1, anti-TIM3, anti-LAG3, anti-2B4, anti-4-1BB, anti-GITR, anti-VISTA, anti-CD40, cGAS/STING agonists, RIG-I agonists, TLR agonists, MDA5 agonists, radiation, chemotherapy, molecularly targeted agents, epigenetic therapies, and any combination thereof.

13. The method of claim 8, wherein the intratumoral immune cell is selected from the group consisting of a T cell, a natural killer (NK) cell, a macrophage, a dendritic cell, a myeloid cell, an innate lymphoid cell (LC), and a CD8+ cell.

14. The method of claim 8, wherein measuring the expression level comprises at least one method selected from the group consisting of RNA-Seq, q-PCR, RT-PCR, sequencing, transcriptomics, and microarray.

* * * * *

SEQUENCE LISTING

```
<160> NUMBER OF SEQ ID NOS: 8

<210> SEQ ID NO 1
<211> LENGTH: 455
<212> TYPE: DNA
<213> ORGANISM: Artificial Sequence
<220> FEATURE:
<223> OTHER INFORMATION: common gene block sequence
<220> FEATURE:
<221> NAME/KEY: misc_feature
<222> LOCATION: (320)..(338)
```

-continued

```
<223> OTHER INFORMATION: n is a, c, g, or t

<400> SEQUENCE: 1
tgtacaaaaa agcaggcttt aaaggaacca attcagtcga ctggatccgg taccaaggtc      60
gggcaggaag agggcctatt tcccatgatt ccttcatatt tgcatatacg atacaaggct     120
gttagagaga taattagaat taatttgact gtaaacacaa agatattagt acaaaatacg     180
tgacgtagaa agtaataatt tcttgggtag tttgcagttt taaaattatg ttttaaaatg     240
gactatcata tgcttaccgt aacttgaaag tatttcgatt tcttggcttt atatatcttg     300
tggaaaggac gaaacaccgn nnnnnnnnnn nnnnnnnngt tttagagcta gaaatagcaa     360
gttaaaataa ggctagtccg ttatcaactt gaaaaagtgg caccgagtcg gtgctttttt     420
tctagaccca gctttcttgt acaaagttgg catta                                455

<210> SEQ ID NO 2
<211> LENGTH: 20
<212> TYPE: DNA
<213> ORGANISM: Artificial Sequence
<220> FEATURE:
<223> OTHER INFORMATION: gRNA

<400> SEQUENCE: 2
gactccaagt tcctggagcg                                                   20

<210> SEQ ID NO 3
<211> LENGTH: 20
<212> TYPE: DNA
<213> ORGANISM: Artificial Sequence
<220> FEATURE:
<223> OTHER INFORMATION: gRNA

<400> SEQUENCE: 3
cagctggact ccaagttccg                                                   20

<210> SEQ ID NO 4
<211> LENGTH: 20
<212> TYPE: DNA
<213> ORGANISM: Artificial Sequence
<220> FEATURE:
<223> OTHER INFORMATION: gRNA

<400> SEQUENCE: 4
tacgatgaca gtttccccag                                                   20

<210> SEQ ID NO 5
<211> LENGTH: 20
<212> TYPE: DNA
<213> ORGANISM: Artificial Sequence
<220> FEATURE:
<223> OTHER INFORMATION: gRNA

<400> SEQUENCE: 5
gacaagcacc agaaagacca                                                   20

<210> SEQ ID NO 6
<211> LENGTH: 20
<212> TYPE: DNA
<213> ORGANISM: Artificial Sequence
<220> FEATURE:
<223> OTHER INFORMATION: gRNA

<400> SEQUENCE: 6
gtgagtatac ttgaatttga                                                   20
```

-continued

```
<210> SEQ ID NO 7
<211> LENGTH: 20
<212> TYPE: DNA
<213> ORGANISM: Artificial Sequence
<220> FEATURE:
<223> OTHER INFORMATION: gRNA

<400> SEQUENCE: 7
gtgggcgtgc tgggtcctgg                                              20

<210> SEQ ID NO 8
<211> LENGTH: 20
<212> TYPE: DNA
<213> ORGANISM: Artificial Sequence
<220> FEATURE:
<223> OTHER INFORMATION: gRNA

<400> SEQUENCE: 8
atcgtccagc tggcctacag                                              20
```